United States Patent [19]
Evers et al.

[11] Patent Number: 5,558,638
[45] Date of Patent: Sep. 24, 1996

[54] PATIENT MONITOR AND SUPPORT SYSTEM

[75] Inventors: David C. Evers, Acworth; A. Darrell Lindsey, Marrietta; Marcus Finch, Atlanta, all of Ga.; Reynolds G. F. Gorsuch, Yountville, Calif.

[73] Assignee: Healthdyne, Inc., Marietta, Ga.

[21] Appl. No.: 55,987

[22] Filed: Apr. 30, 1993

[51] Int. Cl.⁶ .................................................. A61M 1/00
[52] U.S. Cl. ............................................................ 604/66
[58] Field of Search ................................. 604/67, 30, 31, 604/49–53, 65, 66; 128/900, 903, 904, 905

[56] References Cited

U.S. PATENT DOCUMENTS

| | | |
|---|---|---|
| 4,004,577 | 1/1977 | Sarnoff . |
| 4,086,917 | 2/1978 | Burks et al. . |
| 4,838,275 | 6/1989 | Lee . |
| 4,950,224 | 8/1990 | Gorsuch et al. . |
| 5,151,082 | 9/1992 | Gorsuch et al. . |
| 5,182,707 | 1/1993 | Cooper et al. . |

*Primary Examiner*—Manuel Mendez
*Attorney, Agent, or Firm*—Jerry R. Seiler, Esq.

[57] ABSTRACT

A system for monitoring the health and medical requirements of a plurality of patients located at remote sites and providing these requirements to a care center. At the patient site, there is a base unit, which can be connected to a number of sensors and/or recorders with sensors. The sensors are for monitoring the patient's medical state and the recorders are for recording the medical data. The base unit stores the data and transfers the data to a care center, where the data is stored and analyzed. The care center may likewise communicate with the base unit and may reconfigure the base unit based on the data analyzed. The data retrieved from the base units is accessible on a local area network and care providers of the patients may monitor their patients by accessing the local area network.

99 Claims, 102 Drawing Sheets

Microfiche Appendix Included
(13 Microfiche, 684 Pages)

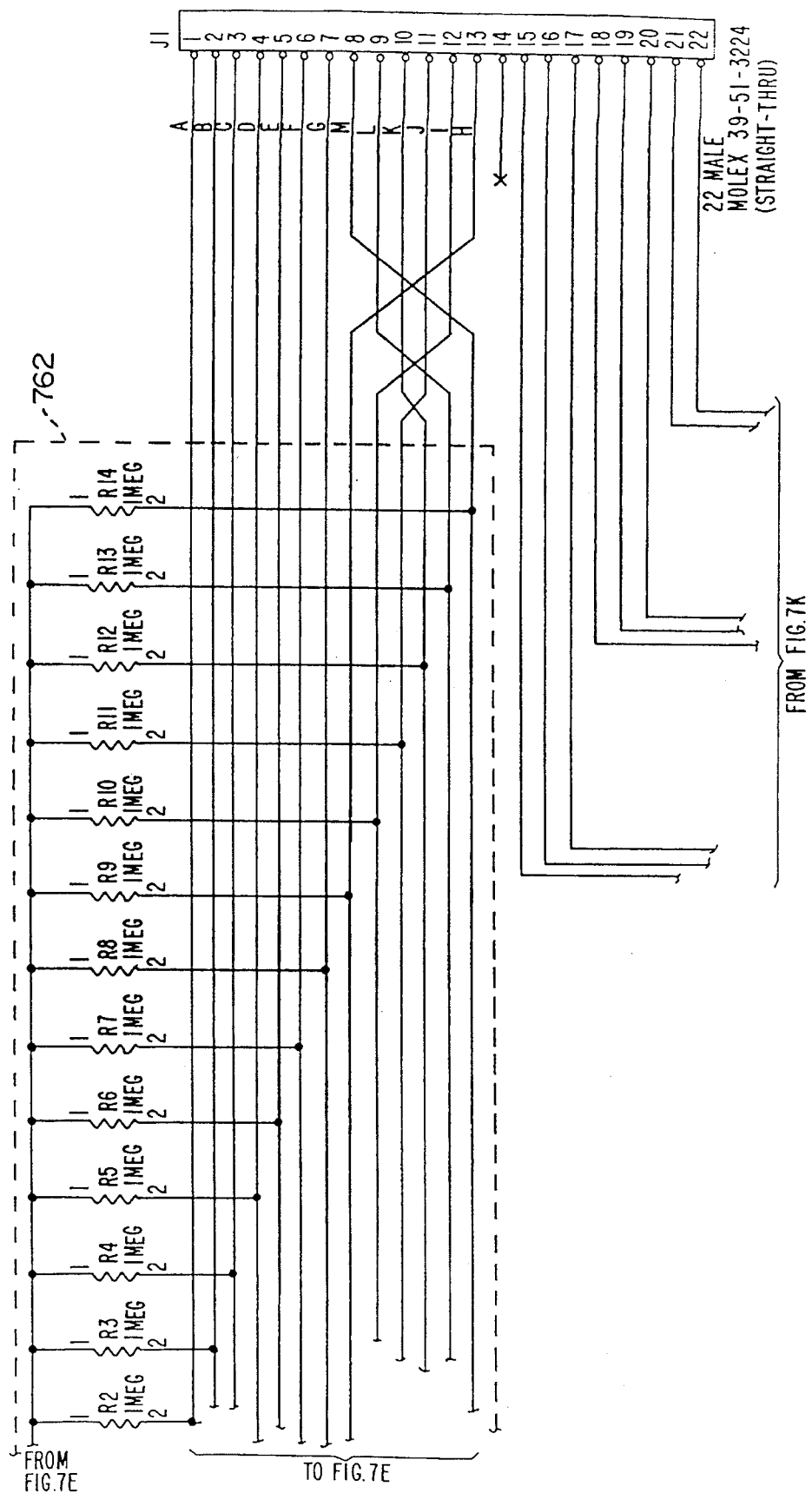

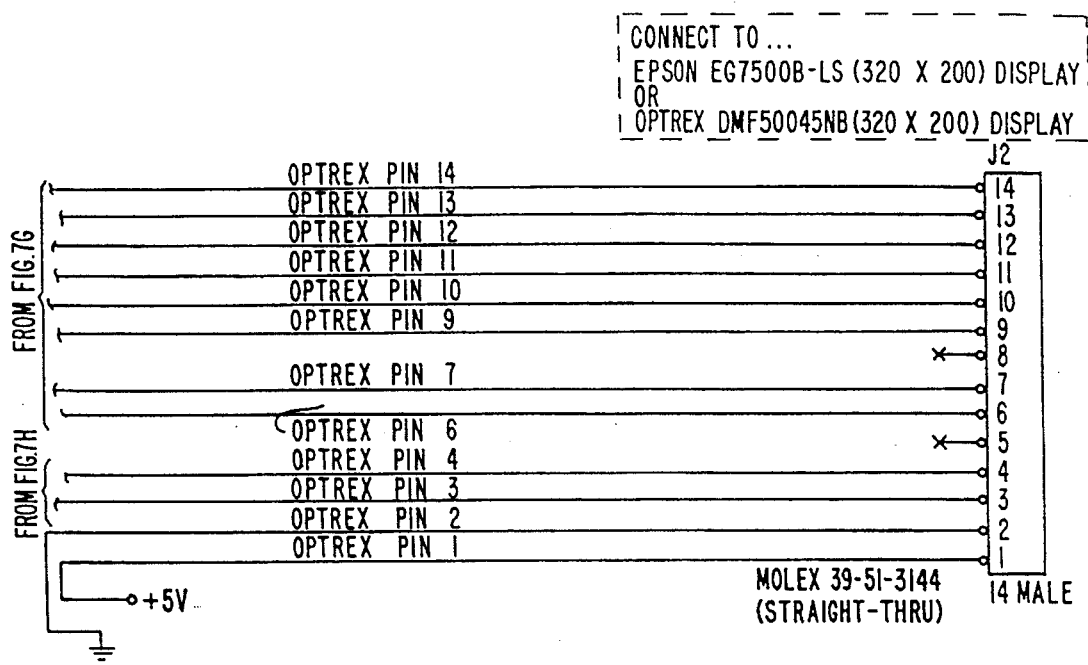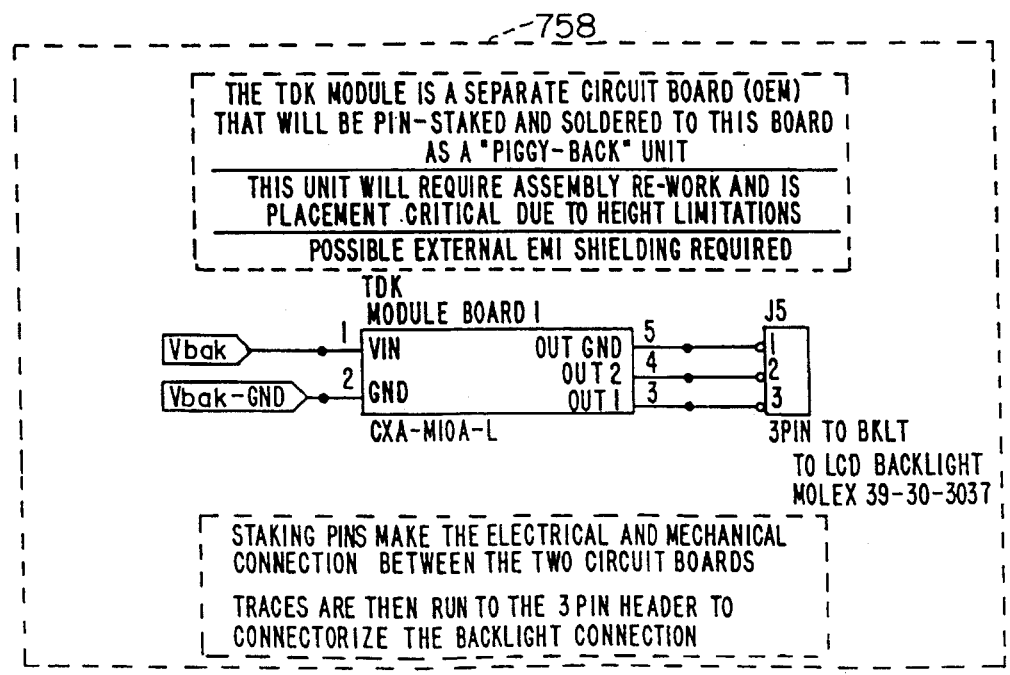
FIG. 7L

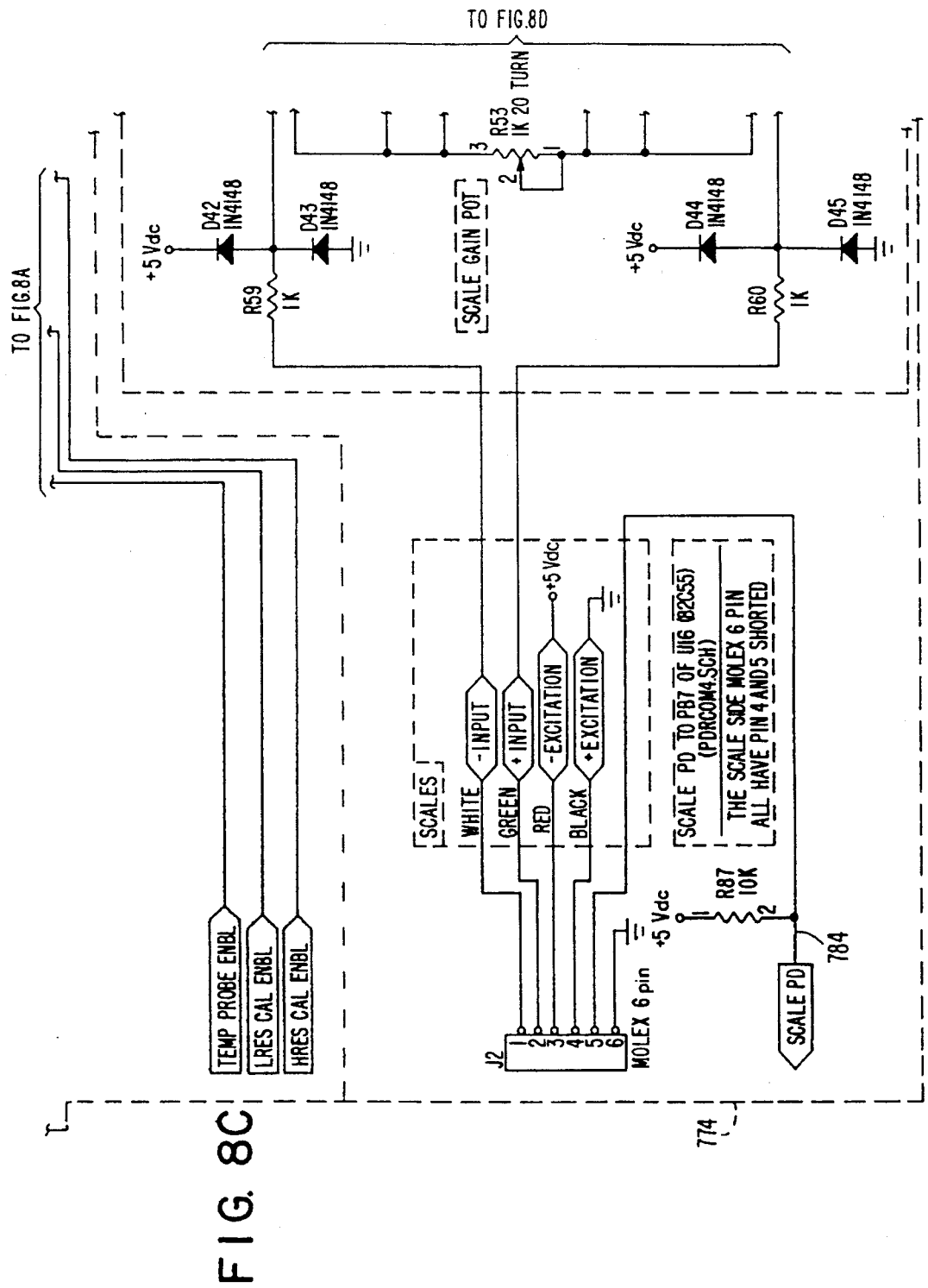

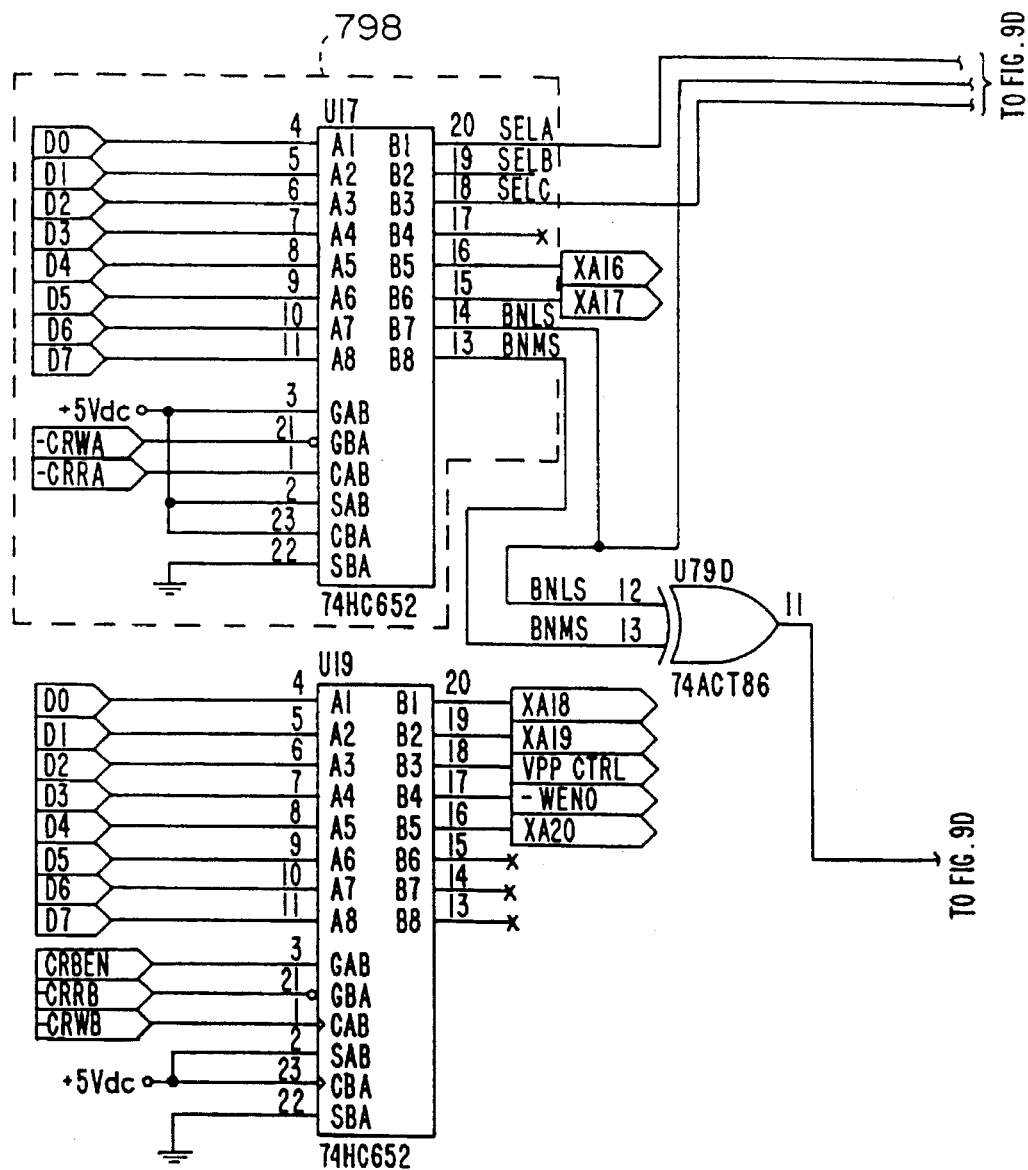
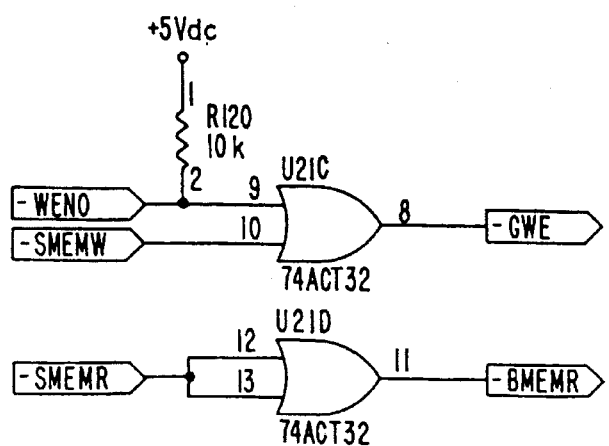
FIG. 9A

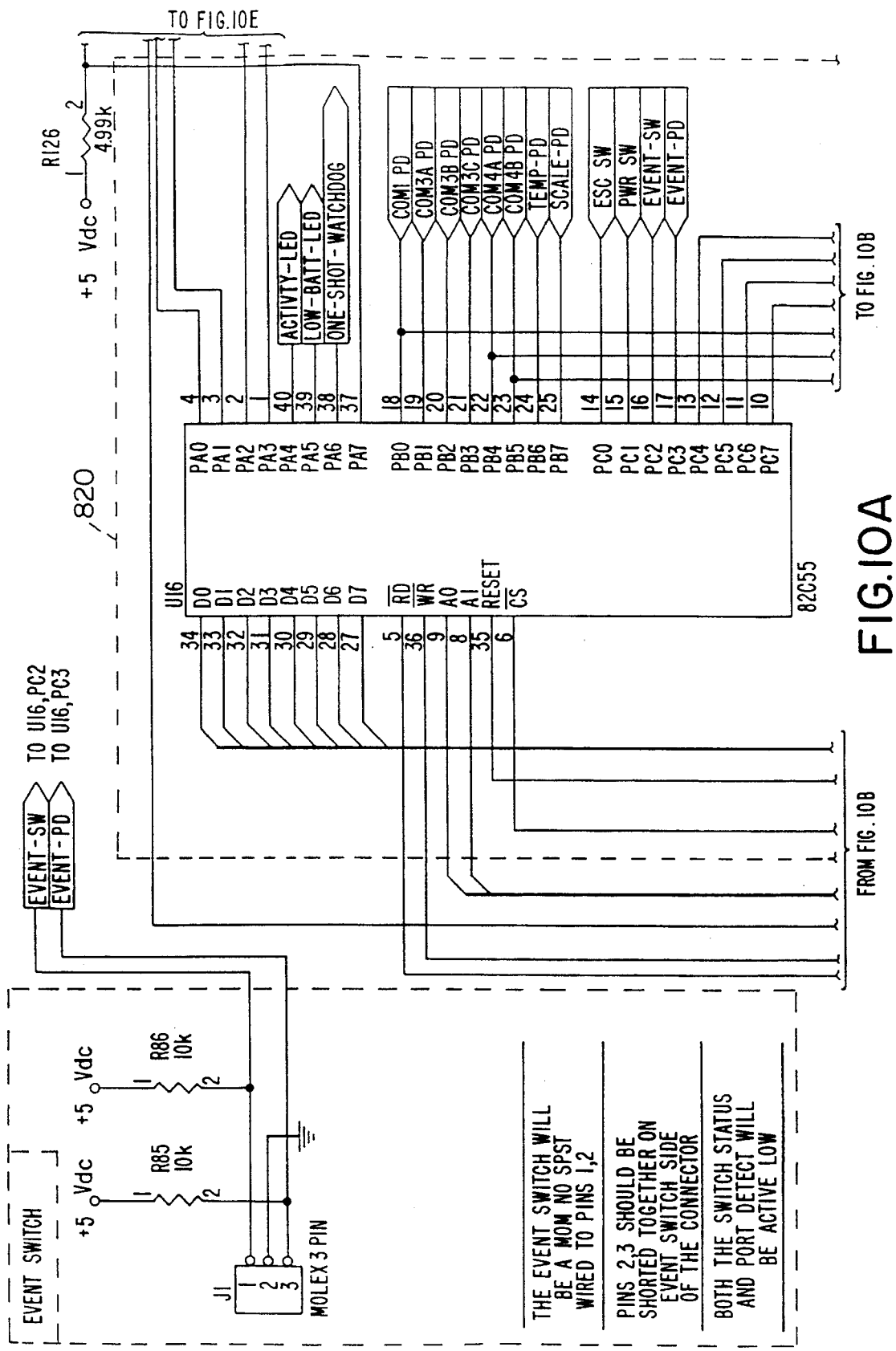

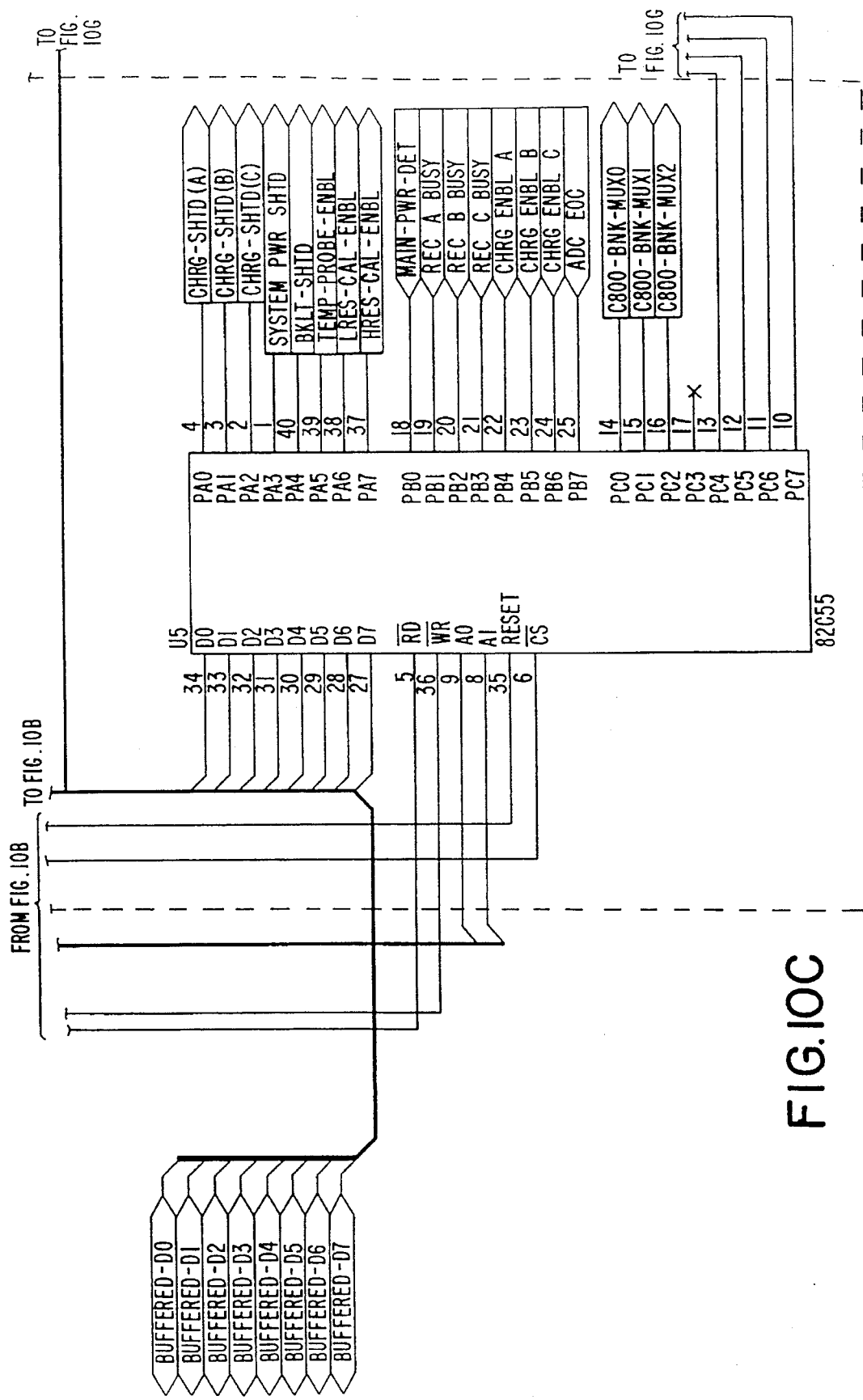

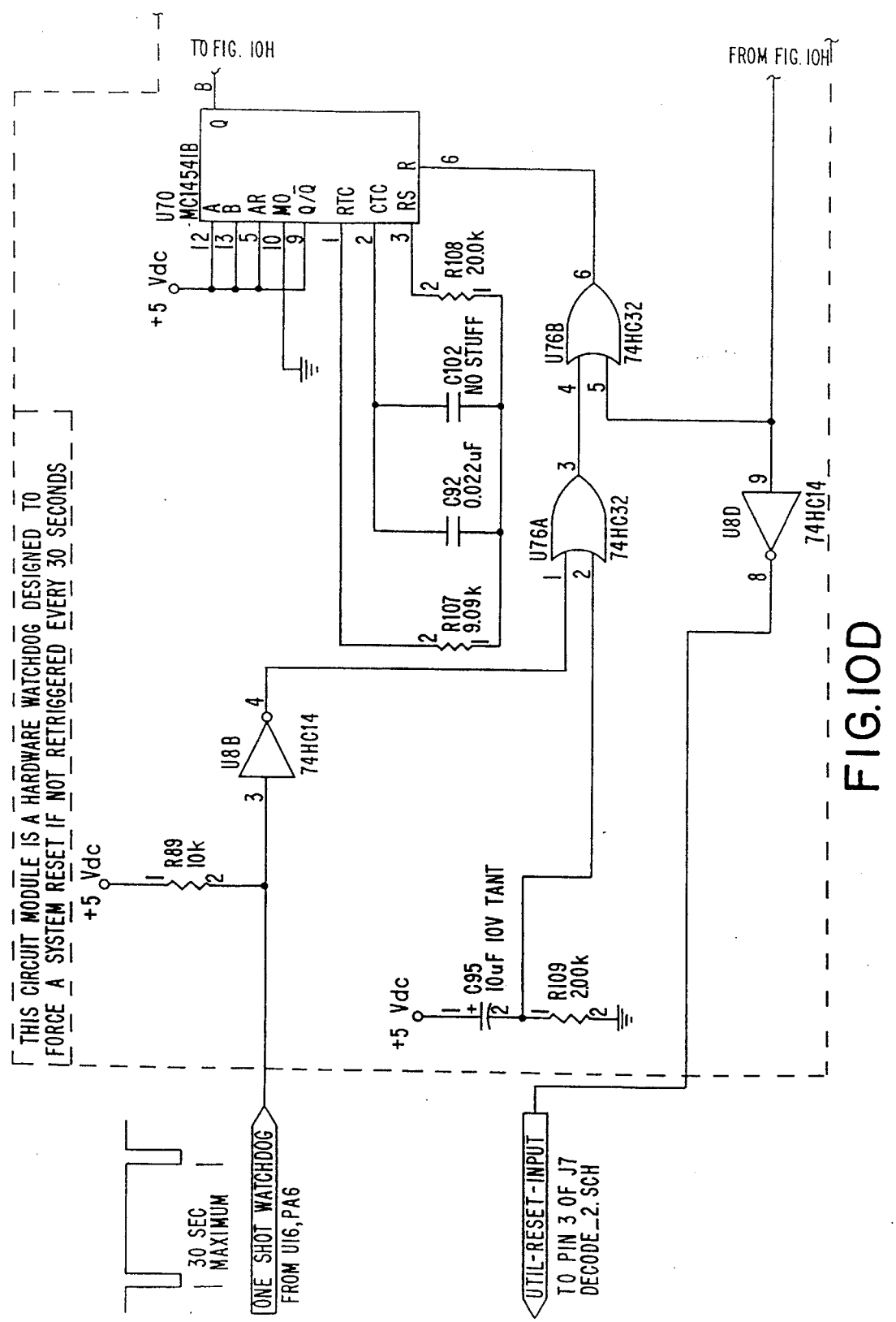

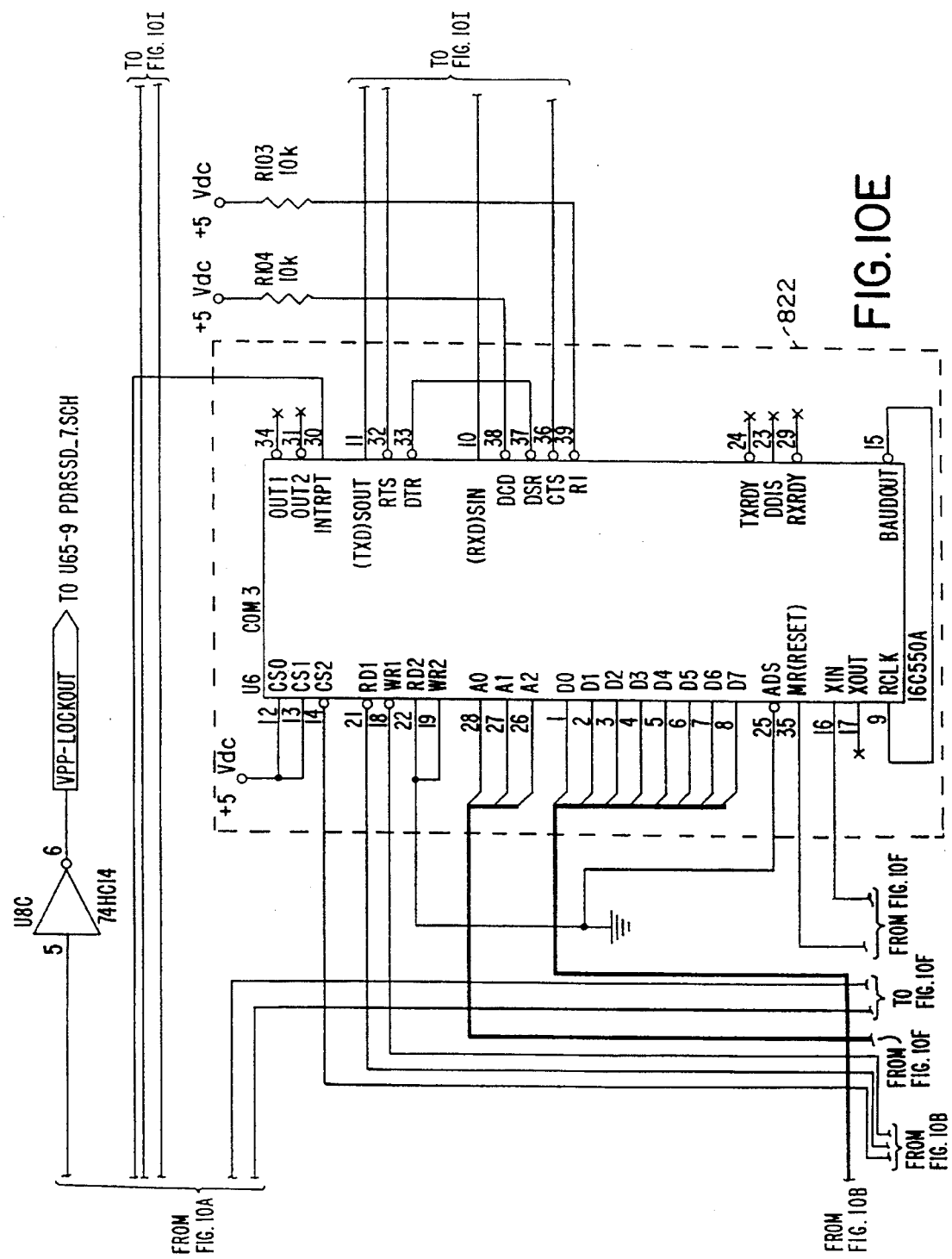

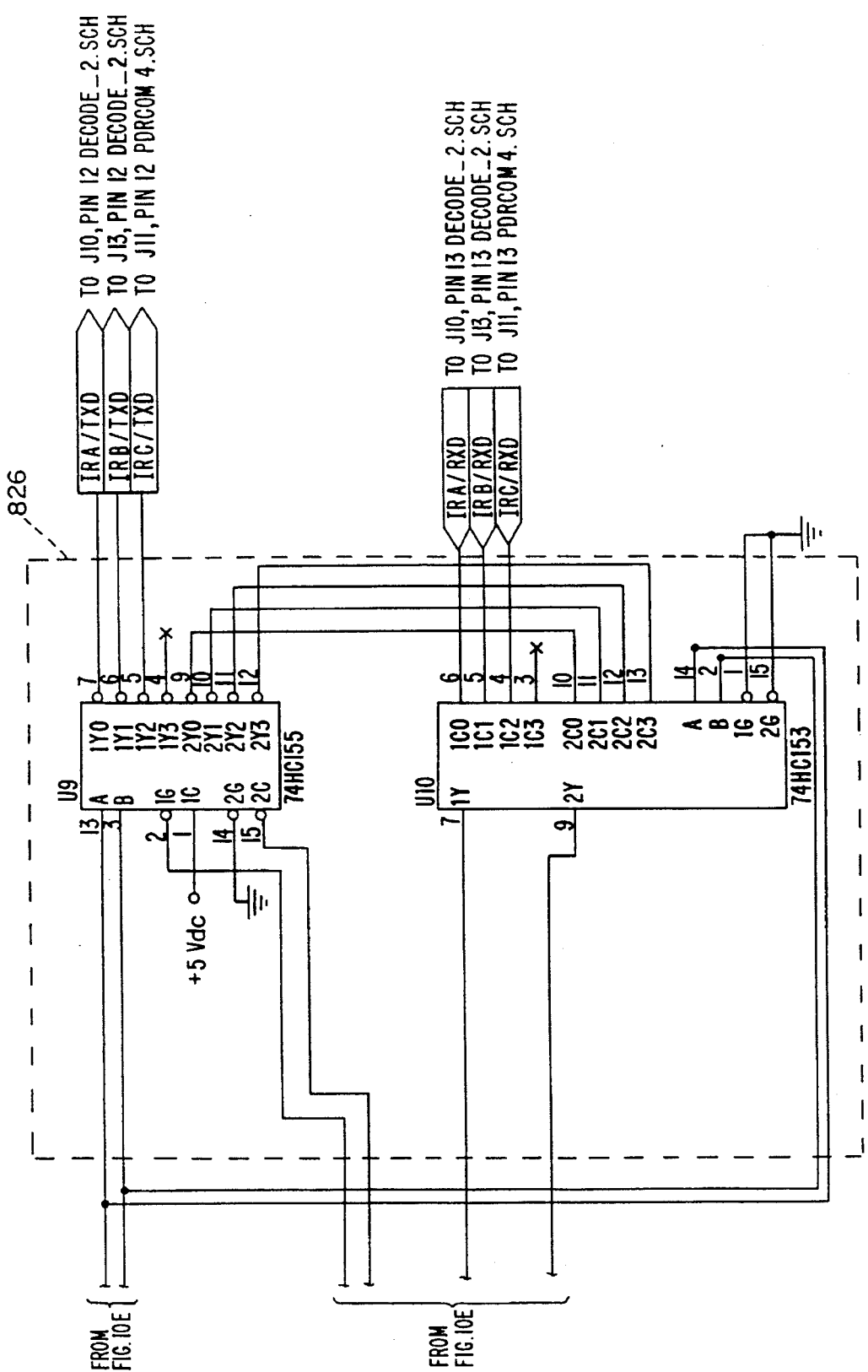

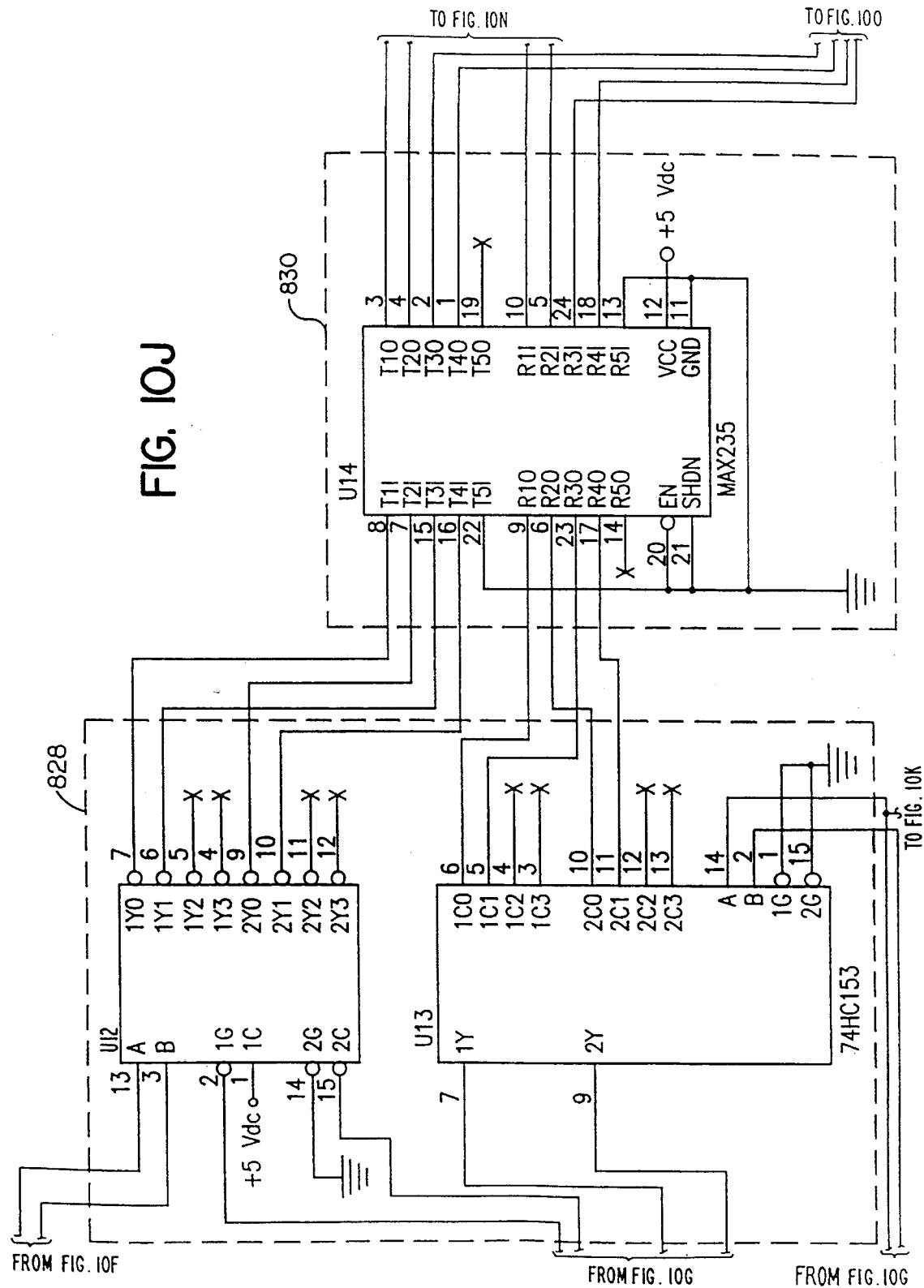

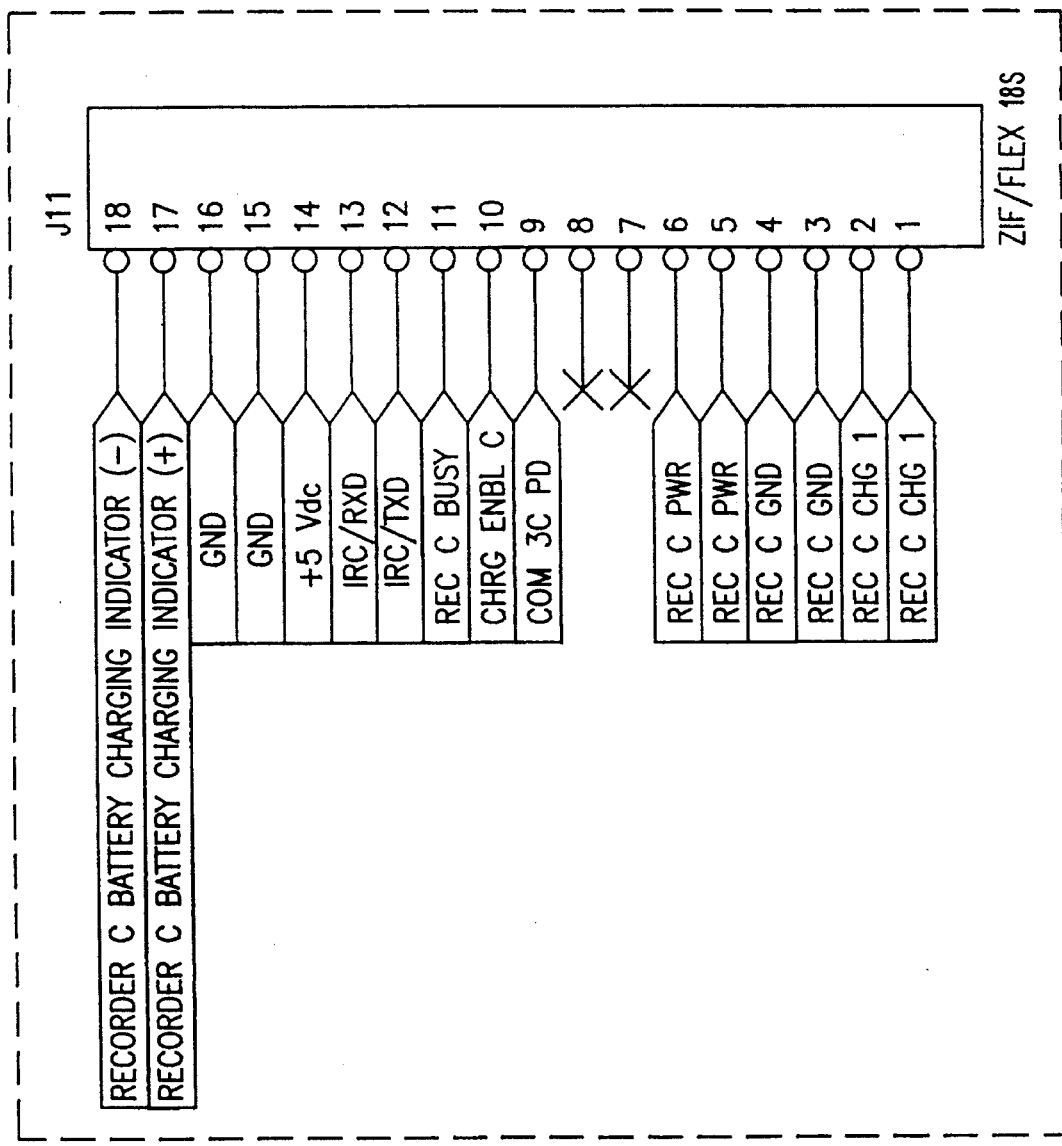
FIG. IOM

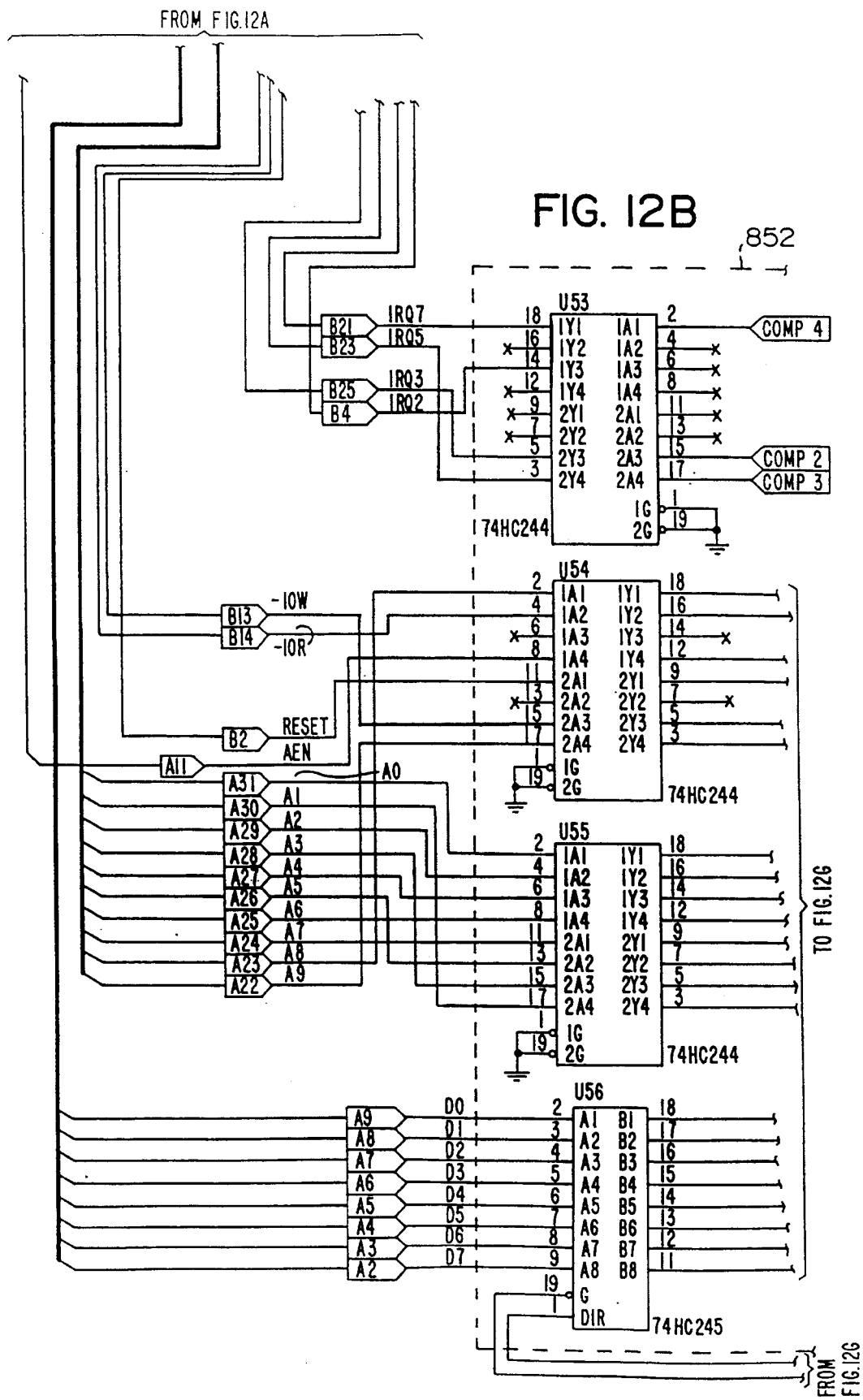

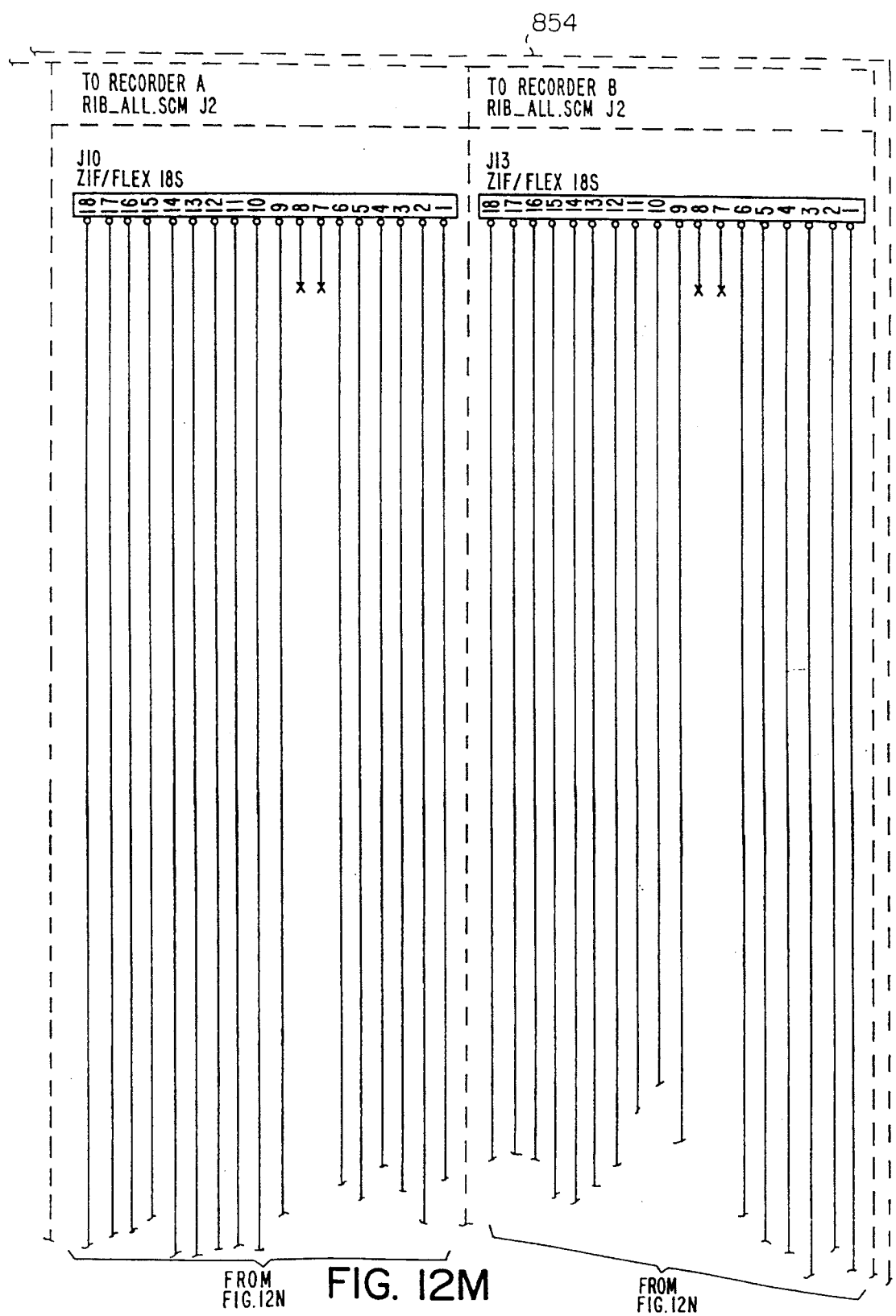

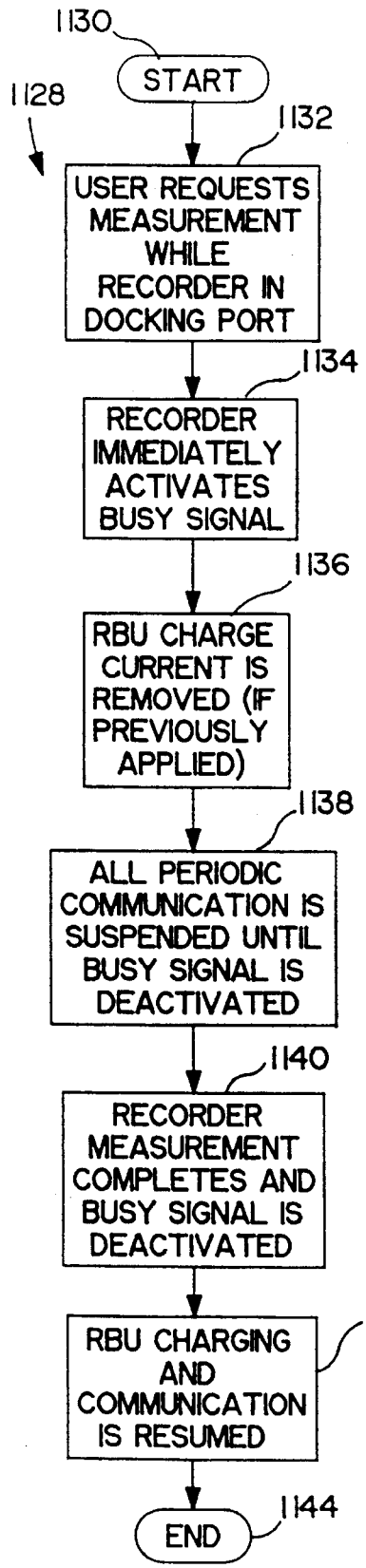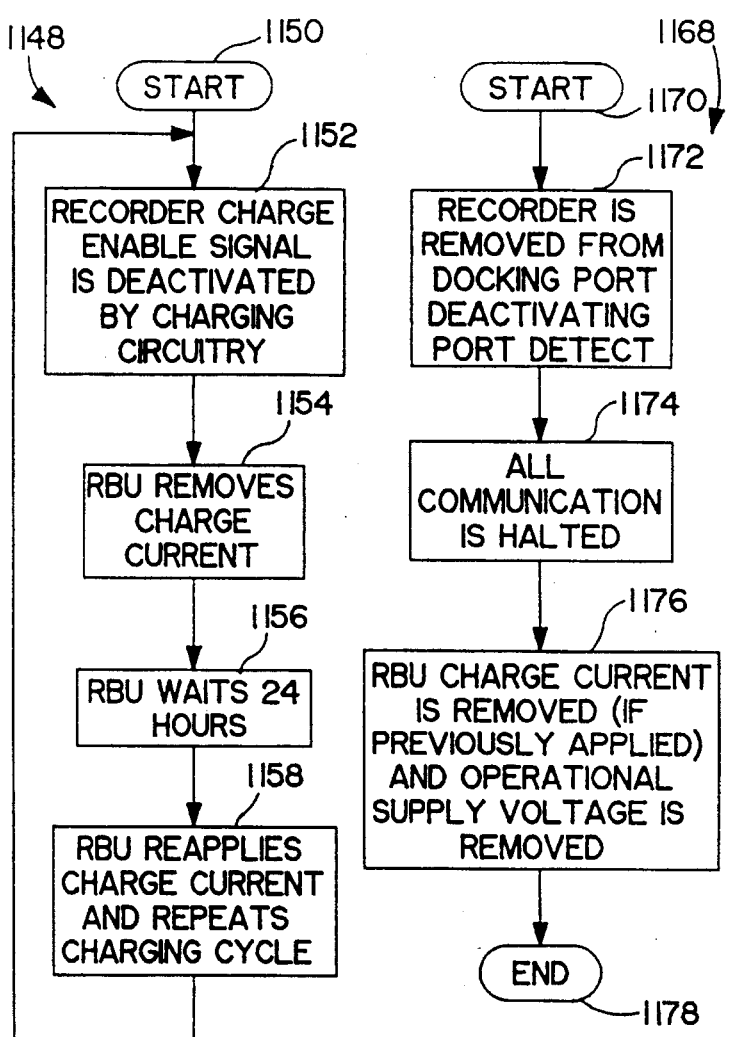
FIG. 18B
FIG. 18C
FIG. 18D

PATIENT MONITOR AND SUPPORT SYSTEM

MICROFICHE APPENDIX

A microfiche appendix containing computer source code is attached. The microfiche appendix comprises 13 sheets of microfiche having 684 frames, including one title frame. This microfiche appendix contains material which is subject to copyright protection. The copyright owner has no objection to the reproduction of such material, as it appears in the files of the Patent and Trademark Office, but otherwise reserves all copyright rights whatsoever.

BACKGROUND OF THE INVENTION

1. Field of the Invention

The present invention relates generally to medical electronics and, more specifically, to a system for monitoring the medical status of patients at home from a care center.

2. Description of the Related Technology

Modern medical technology is used to monitor a variety of medical conditions, medical risks and disease states such as high blood pressure (hypertension), at-risk pregnancies, AIDS, cancer and kidney failure. Patients having such medical conditions are often required to make frequent visits to physicians' offices or medical institutions. Moreover, patients having chronic conditions often are institutionalized in a hospital, convalescent home or the like. The cost of providing medical care to patients using conventional methods can be unimaginably expensive. This has been due largely to the low ratio of patient to medical care personnel required under the existing medical care infrastructure.

Patients who are unable to gain access to hospitals or are not inclined to be treated in medical institutions are generally unable to effectively and adequately monitor their own medical condition or treatment. Field nurses assigned to monitor these patients may spend many hours traveling from each patient site, significantly reducing their productivity. Moreover, patients may not be able to gain access to trained medical staff who can continuously monitor their treatment or medical conditions either due to distance, lack of available funds or lack of trained personnel. Furthermore, patients who attempt to monitor their own medical conditions may actually complicate their conditions through lack of training or the absence of proper medical equipment programmed to assist them in monitoring and supporting their conditions and medical treatment. For instance, the monitoring of certain medical conditions, like blood pressure, may be required of a patient who has selected home care.

In the past, such information would either be recorded manually by the patient, or stored in a device. However, such information may not be conveyed in a timely manner to a health care provider such as a doctor or nurse. Alternative, such information may not be conveyed to a health care provider at all, due to negligence or miscommunications. Patients who have difficulty in using the equipment may require the attention of a field nurse. Monitoring patients from home to home drastically decreases the productivity of such medical personnel.

At present, there are few provisions for a centrally stored medical data. There is also no easy access to such medical information. The lack of such pooled medical data is a significant loss to researchers, and the gathering of such medical data is both time consuming and expensive. Since it may take a significant amount of time to gather information, it will take an even longer period of time to develop treatment of medical conditions.

Consequently, a need arises for providing quality medical care to a plurality of patients through more cost effective means. There also exists a need to increase the productivity of medical and paramedical personnel such that more patients per medical care infrastructure unit can be treated without jeopardy or degradation of the quality of care. There is the additional need of providing a central source of medical data, including patient information, so as to facilitate medical research. Finally, there is the need to provide quality medical care to patients who, due to the remote sites they are located in or, physical disabilities or inconveniences, are unable to make the required and/or frequent visits to their physicians or health care institutions to monitor their medical conditions or disease states.

SUMMARY OF THE INVENTION

The present invention satisfies these needs by providing adequate care in the home while maintaining low cost through use of a patient monitor and support system. It also provides increased productivity of medical and paramedical personnel by providing monitoring of a plurality of patients by a care center without jeopardy or degradation of the quality of care.

The present invention also provides a central source of medical data, including patient information, so as to facilitate medical research. Finally, the present invention provides quality medical care to patients who, due to the remote sites they are located in or, physical disabilities or inconveniences, are unable to make the required and/or frequent visits to their physicians or health care institutions to monitor their medical conditions or disease states.

The present invention is a system for monitoring the health and medical requirements of a plurality of patients suffering from a variety of medical conditions, risks or disease states from a remote location.

The system comprises a sensor for monitoring the patient's medical state, the sensor generating a parameter indicative of the patient's medical state; a data base located at a remote location from the sensor for storing the patient's medical state; a means for communicating the parameter to the data base; a means for retrieving the parameter from the data base; and a means for providing medical procedure to the patient in response to the retrieved parameter.

BRIEF DESCRIPTION OF THE DRAWINGS

FIGS. 18A, 18B, 180 and 18D are flow diagrams of the data communications between the remote base unit and one of the recorders shown in FIG. 4;

DETAILED DESCRIPTION OF THE PREFERRED EMBODIMENTS

The description of the presently preferred patient monitor and support system is presented in the following sections: I. System Overview; II. Structure and Operation of the Remote Base Units; III. Functional Modules Used in Monitoring of At-Risk Pregnancy; IV. Functional Modules Used in Monitoring of Other Disease States; V. System Process Flow; VI. Process Flow for Monitoring At-Risk Pregnancy; VII. Data Flow between the Remote Base Unit and the Care Center; VIII. Data Flow between the Remote Base Unit and the Recorders; IX. Human Interface Process Flow; and X. Exemplary Demonstration Sequence.

I. System Overview

Figure 1:
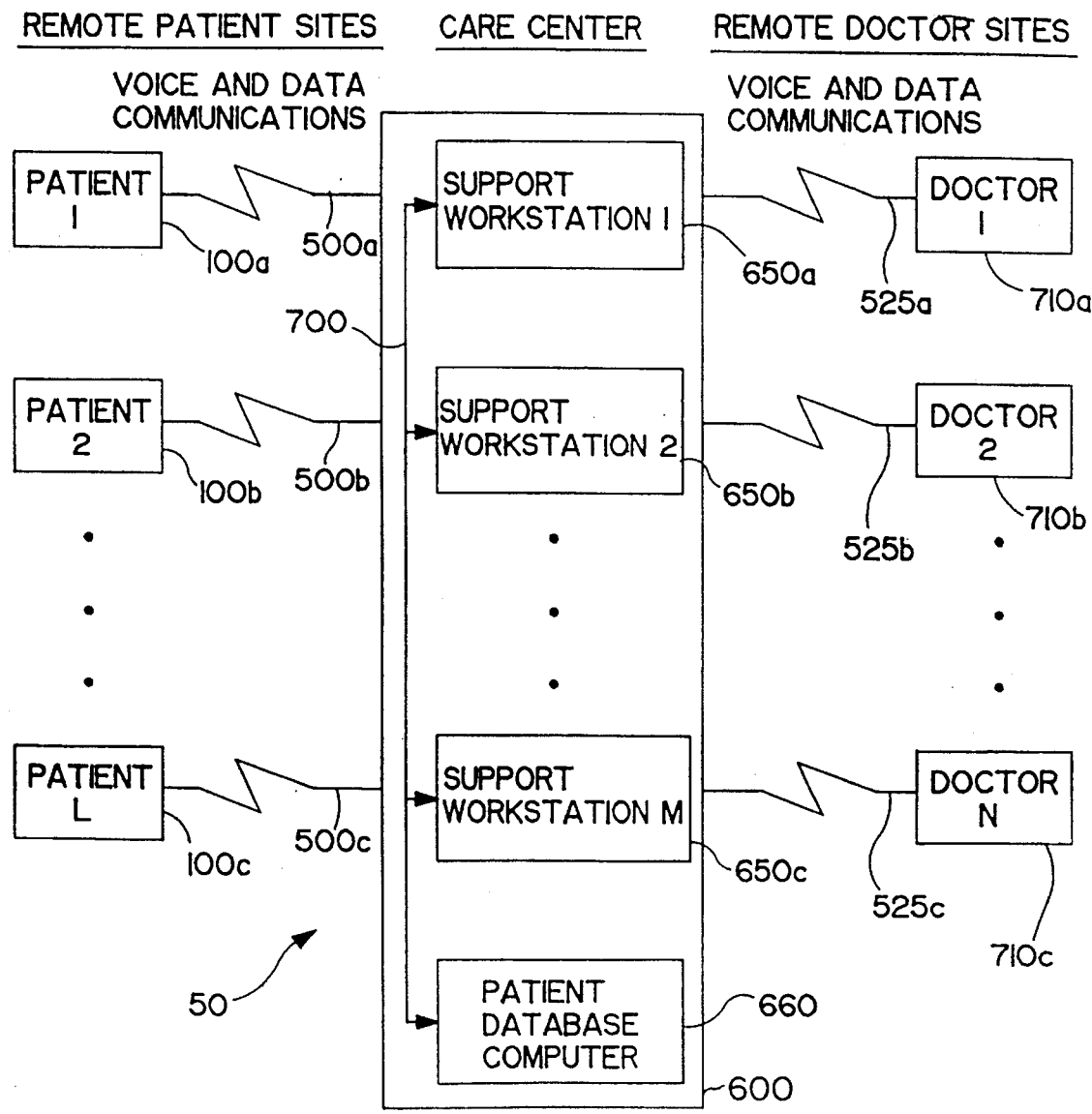
FIG. 1 is a block diagram of remote patient sites, a care center and doctor sites communicating via a patient monitoring and support system of the present invention.

FIG. 1 depicts a site block diagram wherein a patient monitor and support system 50 of the present invention is configured. The patient monitor and support system 50 includes a number of patient sites 100 a, 100 b, 100c the total number indicated by L), which are individually connected via a set of communications links 500a, 500b, 500c to a care center 600.

A subsystem at each of the patient sites 100 has control and data acquisition capabilities and may be configured to automatically transfer patient communications and data to the care center 600 and to receive nursing communications, instructions and prompts from the care center 600. The care center 600 comprises a plurality of support workstations 650a, 650b and 650c (the total number indicated by M) and a Central Database on a database computer 660. In the present preferred embodiment, the workstations 650 is an IBM compatible personal computer using one of the 80×86 family of microprocessors.

In the present embodiment, each patient site 100 communicates with one of the workstations 650 over a communications link 500. The communications link 500 may be any communications system such as a radio communications link, a modem/telephone line link, a fiber optic link or any other communications link. In the present embodiment, a dial-up or leased telephone line switched across the public telephone network is used and communications is established via a modem at the patient site 100 and the care center 600. The patients at sites 100 may also communicate by voice with the workstation 650.

The data received by the workstation 650 is ultimately stored in the patient database computer 660. The care center 600 is typically connected to the facility's existing Local Area Network ("LAN") 700. Thus, the information collected by the care center 600 is accessible from any computer on the LAN 700 and may be assimilated by existing database management software. In this configuration, the primary care physician sites 710a, 710b, 710c (the total number indicated by N) can access information collected on each patient monitored by the care center 600 via communications link 525. In addition, the primary care physicians at sites 710 may communicate by voice with the staff monitoring the care center 600 and with the patients at the sites 100.

The care center 600 is staffed by a medical team comprising a case nurse, a field nurse, a pharmacist, a therapist and a nutritionist. Additional medical personnel is added as required. The care center 600 also has the ability to download settings and instructions to the subsystem located at each patient site 100. The subsystem may also be configured to alert the patient when it is time to take measurements and/or medication. It will also prompt the patient and guide them through the procedure through visual displays.

II. Structure and Operation of the Remote Base Units

Figure 2:
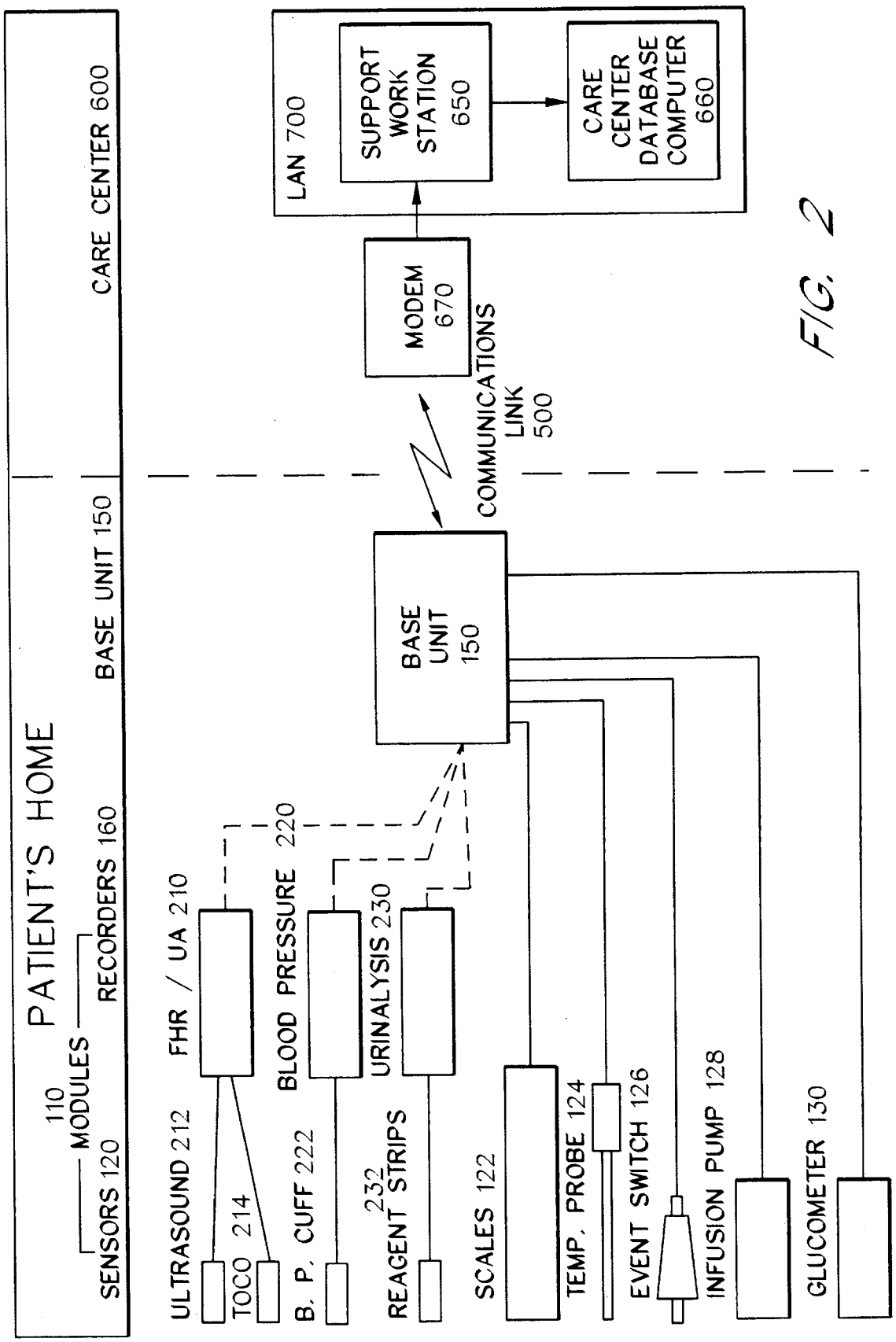
FIG. 2 is a block diagram of a preferred embodiment of the patient monitoring and support system configured to monitor at-risk pregnancy.

The subsystem located at each patient site 100 is controlled by a base unit 150 as shown in FIG. 2. The base unit 150 is a self-contained system configured to monitor and support a specific disease state or medical condition.

FIG. 2 is a block diagram of a preferred embodiment of the patient monitoring and support system 50 of FIG. 1 configured to monitor at-risk pregnancy. As illustrated in FIG. 2, the base unit 150 is connected to a set of modules 110 which provide measurements of a patient's medical status. The base unit 150 is also connected via the communications link 500 to the care center 600. As previously described, the communications link 500 may comprise any communications system such as a radio communications link, a modem/telephone line link, a fiber optic link or any other communications link. In the present embodiment, a dial-up or leased telephone line is used and communications is established via a modem 670 at the care center 600.

Two types of functional modules 110 may be connected to the base unit 150: sensors 120, which are directly connected to the base unit 150, and recorders 160, which receive inputs from sensors 120, record the sensor information, and transmit the recorded data to the base unit 150. The recorders 160 are completely portable and may be used remotely by the patient. The recorders 160 must, however, be periodically docked in the base unit 150 so as to upload or download data or instructions and to charge its batteries.

In one of the presently preferred embodiments, the base unit 150 may be provided with three recorders 160 for monitoring and supporting the treatment of at-risk pregnancy. A combined fetal heart rate/uterine activity recorder 210, a blood pressure recorder 220 and a urinalysis recorder 230 provide measurements of fetal heart rate and uterine activity, blood pressure and urinalysis test data respectively to the base unit 150.

The sensors associated with the recorders 160 are as follows. An ultrasound transducer 212 provides the means for monitoring the fetal heart rate and provides signals indicative of the fetal heart rate, to the fetal heart rate/uterine activity recorder 210. Likewise, a tokodynamometer 214 provides the means for monitoring uterine activity and provides signals indicative of uterine activity to the fetal heart rate/uterine activity recorder 210. Similarly, a blood pressure cuff 222 provides the means for monitoring blood pressure and provides signals indicative of the blood pressure of a patient to the blood pressure recorder 220. Reagent strips 232 provided to the urinalysis recorder 230 provide the required urinalysis test data.

In the illustrated embodiment, five types of sensors 120 may be directly connected to the base unit 150. These sensors 120 are: weight scale 122, a temperature probe 124, an event switch 126, an infusion pump 128 and a glucometer 130. The weight scale 122 provides a signal indicative of the patient's weight to the base unit 150; the temperature probe 124 provides a signal indicate of the patient's temperature; the event switch 126 is a manual switch provided to the patient to monitor contractions; the infusion pump 128 infuses medicine into the patient's bloodstream and provides signals of the quality and quantity of medicine infused into the patient's system; and the glucometer provides signals indicative of the glucose levels in a patient's system. The base unit 150 may also provide signals to the infusion pump 128 to reconfigure the amount and frequency of medicine which is supplied to a patient's system. The sensors 120 and recorders 160 will be described in greater detail in the following sections.

Figure 3A:
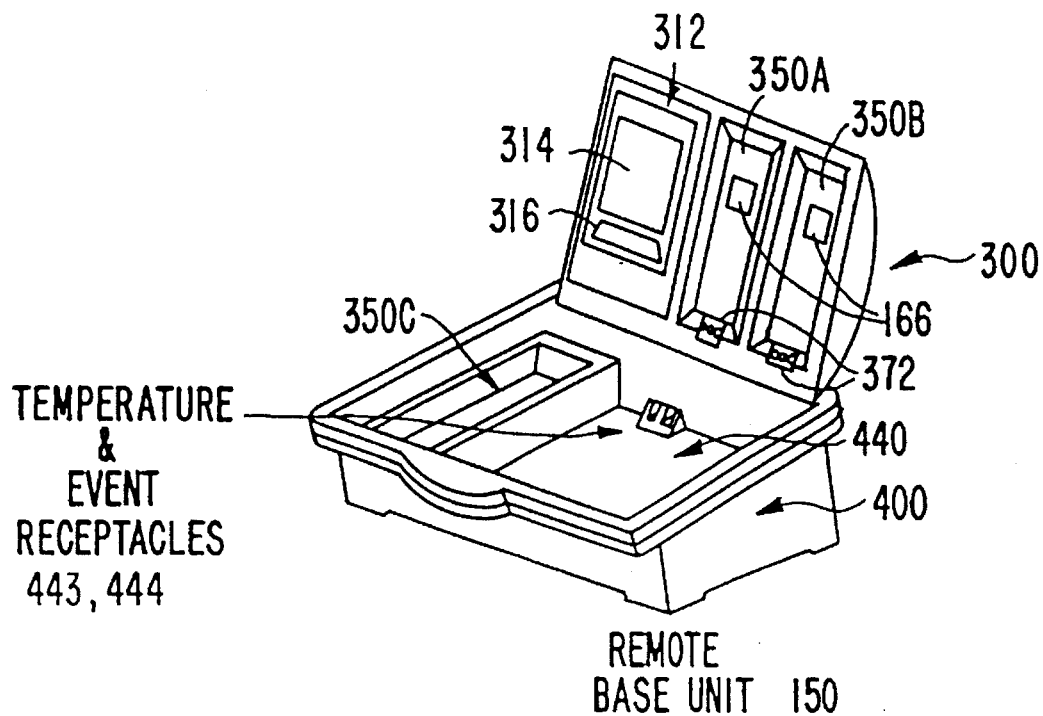
FIG. 3A is a perspective view of a preferred embodiment of the remote base unit (RBU) of the system shown in FIG. 2.
Figure 3B:
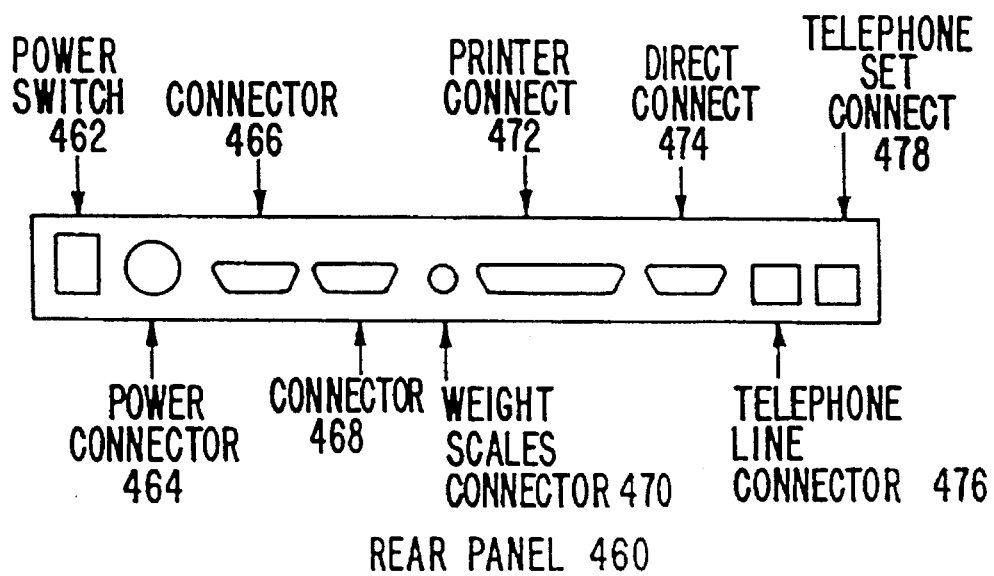
FIG. 3B illustrates the rear panel of the remote base unit of FIG. 3A.

FIG. 3A is a perspective view of a preferred embodiment of the base unit 150. FIG. 3B illustrates the rear panel of the remote base unit of FIG. 3A. The unit is small and portable such that it may be placed on a table next to the patient's bed.

As illustrated in FIG. 3A, the base unit 150 comprises a lid assembly 300 and a base assembly 400. The lid assembly 300 comprises a display assembly 310, a lid assembly board 340 (shown in FIG. 4) and two recorder docking ports 350a, 350b. The base assembly 400 comprises a system board 410 (shown in FIG. 4), a third recorder docking port 350c, a storage bay 440 and a rear panel 460. The lid assembly board 340 and the system board 410 provide the circuitry for the base unit 150 and will be described below.

Figure 3C:
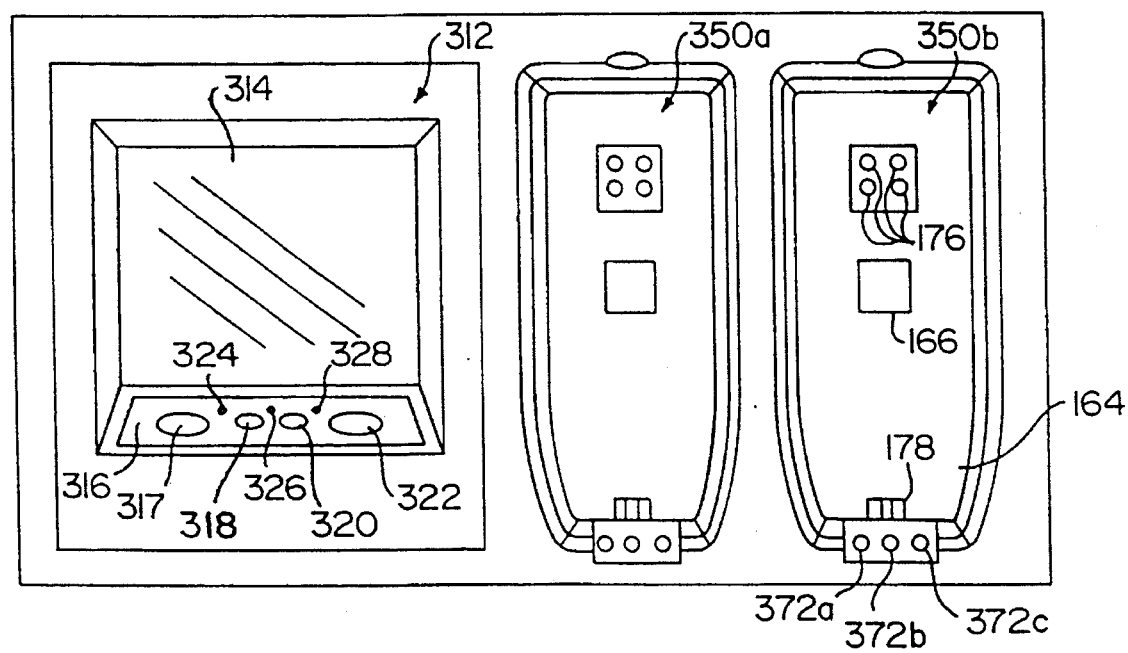
FIG. 3C is a front view of the liquid crystal display and the docking ports of the remote base unit of FIG. 3A.

As depicted in FIG. 3C, the display assembly 310 comprises a Liquid Crystal Display ("LCD") 312 with backlight 313 capability, a touch-sensitive screen 314, a control panel 316 and three indicator lights 324, 326, 328. In the present embodiment, the LCD display 312 is a graphics display with a CGA resolution of 320×200 pixels and a viewing area of 5.04 inches×4.33 inches. The touch sensitive screen 314 is capable of displaying a set of function keys (not shown), generated through software, for user selection. The function keys are generic and reconfigurable in software, may be selected by touching the screen 314. Up to 24 keys may be generated by software.

The control panel 316 comprises four buttons. The leftmost button 317 controls power from the fluorescent backlight. The next button 318 controls the up contrast voltage to the LCD display 312. The third button 320 from the left controls the down contrast voltage to the LCD display 312. This second and third buttons 318, 320 are used to provide compensation for different light levels and angles. The rightmost button 322 is the Enter key. It is used for returning to a previous screen. The three indicator lights indicate the status of system. The leftmost indicator light 324 indicates the start of a session, the middle indicator light 326 indicates if the power is on, and the rightmost indicator light 328 is a low battery warning indicator alarm.

The lid assembly board 340 comprises integrated circuits for the control of the LCD 312 and touchscreen 314 of the display assembly 310. The components of the board will be discussed in greater detail in the following sections.

The docking ports 350a, 350b, 350c on the lid assembly 300 and the base assembly 400 provide for mechanical docking of the recorders 160. The docking reports 350a, 350b and 350c are identical and can receive any one of the recorders 160. Data transfer to and from the recorders 160 and battery charging of the recorders 160 are provided through electrical and optical interfaces with the base unit 150.

Figure 3E:
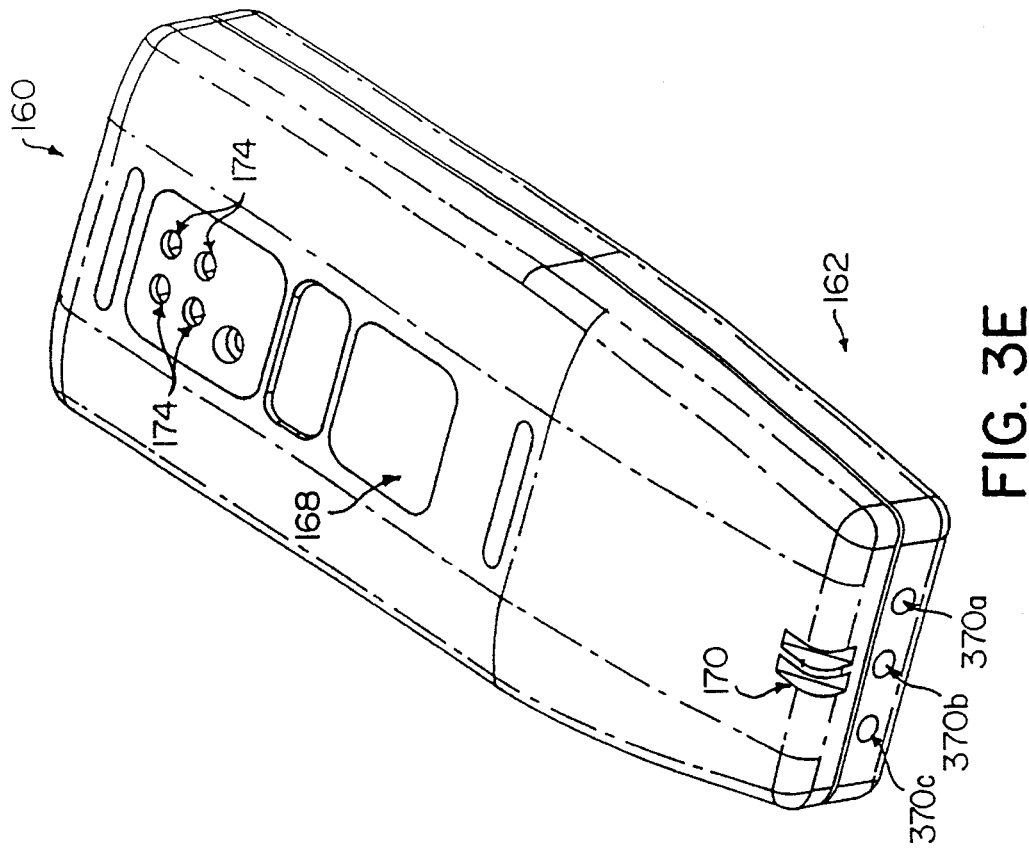
FIG. 3E is a rear, perspective view of a preferred embodiment of the recorder of FIG. 3D.
Figure 3D:
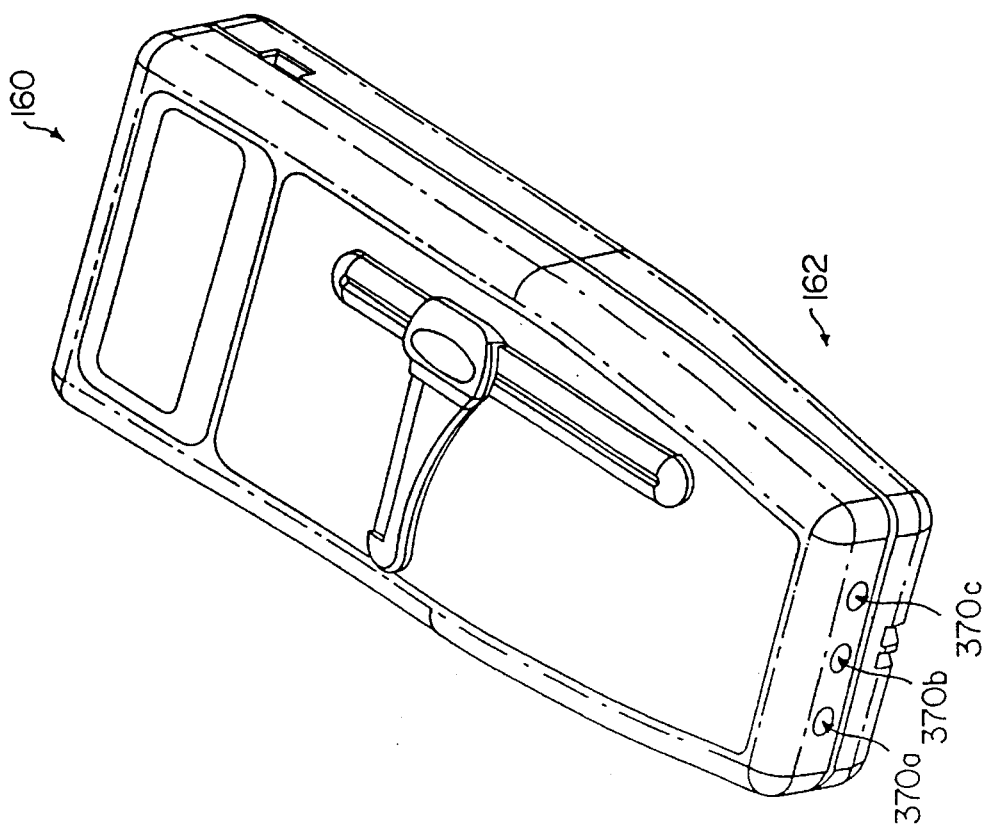
FIG. 3D is a front, perspective view of a preferred embodiment of a recorder which docks to the docking port of the remote base unit of FIG. 3A.

In the present embodiment and as shown in FIGS. 3B and 3C, the docking port 350 is molded to accept the shape of the recorder 160, illustrated in FIGS. 3D and 3E, which is similar to that of a cordless phone cradle. The narrow end 162 of the recorder 160 fits into the cradle 164 of the docking port 350 and a magnet 166 in the base will contact a metal plate 168 in the middle of the recorder 160 to retain it during charging and data exchange. Three spring-loaded contacts 370a, 370b, 370c, at the bottom of the cradle 164 in the docking ports 350 provide the electrical and optical interface with the base unit 150. The contacts 370 connect to corresponding contacts 372 on the end of the recorder 160 for charging of the battery and powering the recorder 160 while the recorder 160 is docked. A molded projection 170 on the narrow end 162 of the recorder 160 presses against an interlock switch 178 in the base of the docking port 350 to indicate that a recorder 160 is docked.

Four infrared components 174 at the top end of the recorder 160 allow the transmitting and receiving of data, and two of the infrared components 174 are flag channels for indicating the recorder is busy and the battery charging state. Four infrared components 176 in the docking port 350 correspond to and communicate with the four infrared components 174 in the recorder 160 via the infrared and power link 415 (shown in FIG. 4). When the recorder 160 is removed from the docking port 350, all power is removed from the accessible metal contacts 370, 372.

The storage bay 440 is a cavity located in the right side of the base assembly 400. It provides storage space for sensors 120 and associated accessories required for measuring a variety of parameters. Two communications ports 443, 444 for receiving the temperature probe 124 and the event switch 126 are located in the storage bay 440.

As shown in FIG. 3B, the rear panel 460 is an input/output interface which provides further monitoring and control capabilities for the base unit 150. In the preferred embodiment, the rear panel 460 comprises a power switch 462 and a plurality of connectors. The power switch 462 permits the powering on and off of the base unit 150. The first connector 466 provides for connection from an external 16 volt DC supply. The second connector 468 provides connection to a sensor. Preferably, a DB-9 connector is used, which accepts bi-directional data from the infusion pump 128. The third connector 466 provides connection to a second sensor. The connector is preferably a DB-9 connector which accepts data from a glucometer 130. The fourth connector 470 accepts an analog signal from the weight scale sensor 122 and provides power to the load cells in the scale 122. The fifth connector 472 is provided for connection to a printer 136 which prints fetal heart rate/uterine activity charts. The sixth connector 474 is a direct connect port 474. The port is preferably a conventional RS-232 type port, provided to permit the base unit 150 to be connected directly to another personal computer 138 for testing and data retrieval. The seventh connector 476 provides for connection to a telephone line 134. Preferably, the connector is an RJ-11 jack, which provides for direction connection to the public switched telephone network. The eighth connector 478 provides for connection to a telephone line 134. Preferably, a RJ-11 connector is used, which accepts a standard telephone and provides a connection to the telephone line 134 when the modem 670 is not on-line.

Figure 4A:
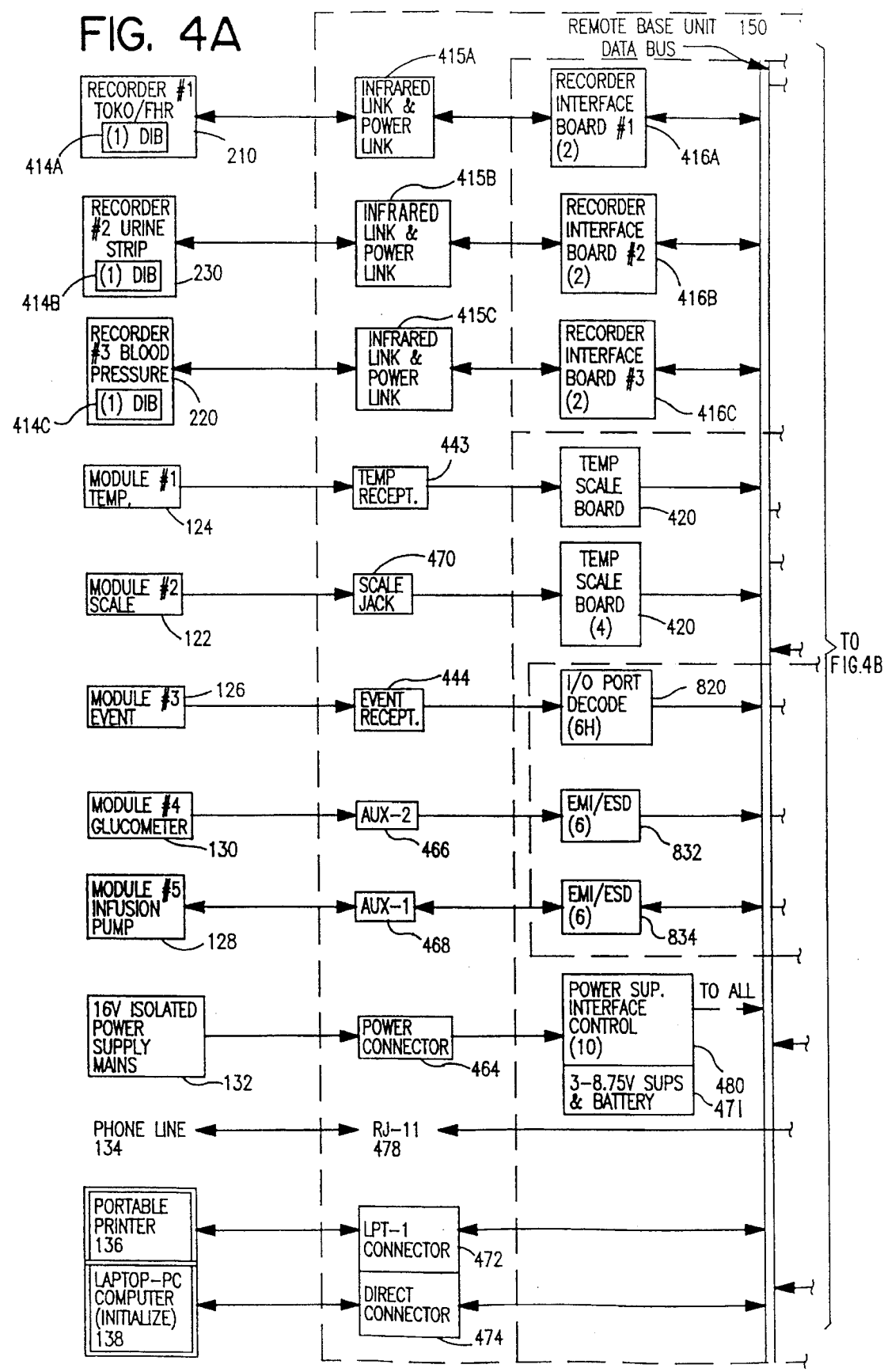
FIG. 4 is a functional block diagram of one preferred remote base unit including its external interfaces.
Figure 4B:
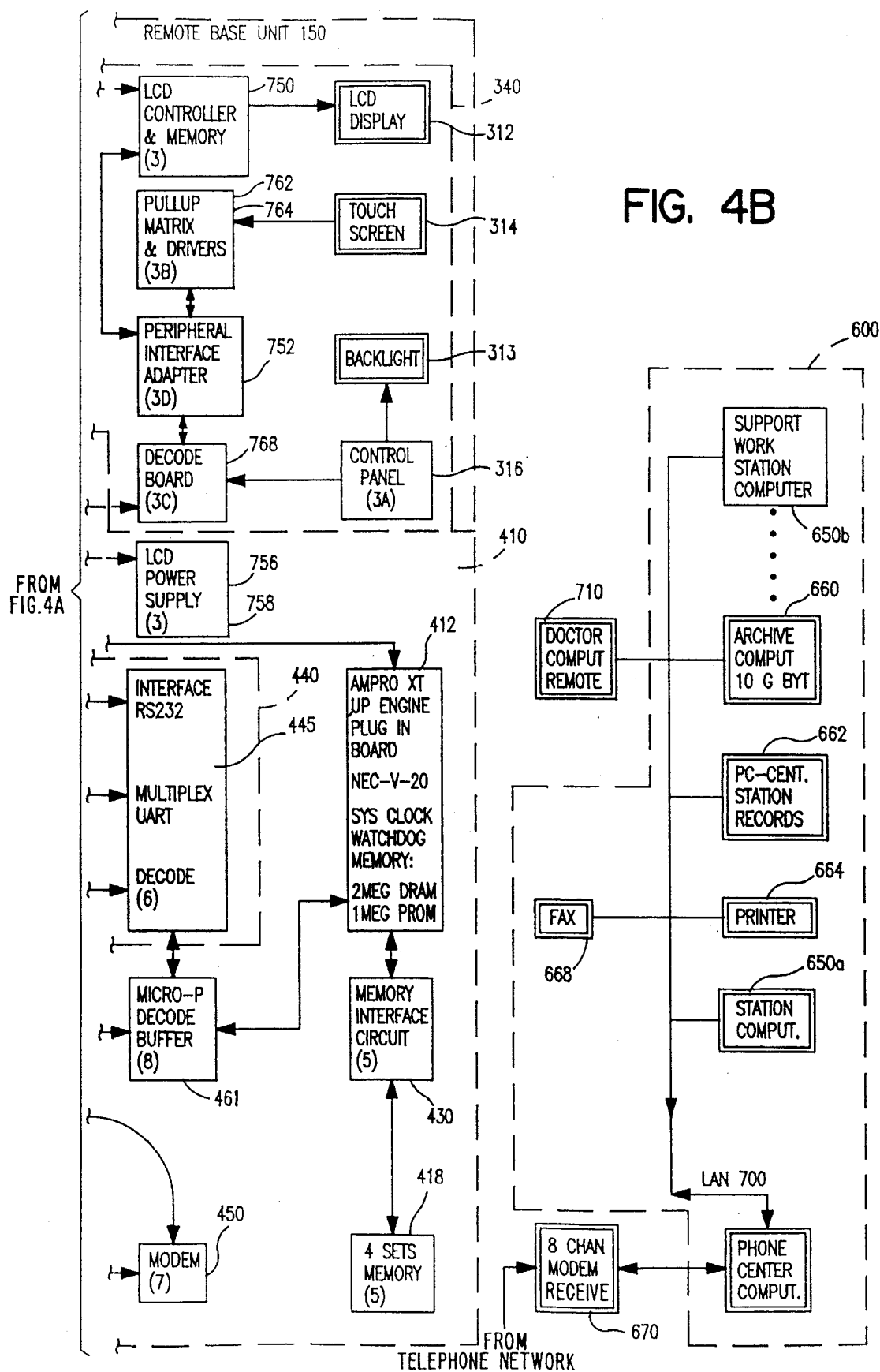
Figure 5A:
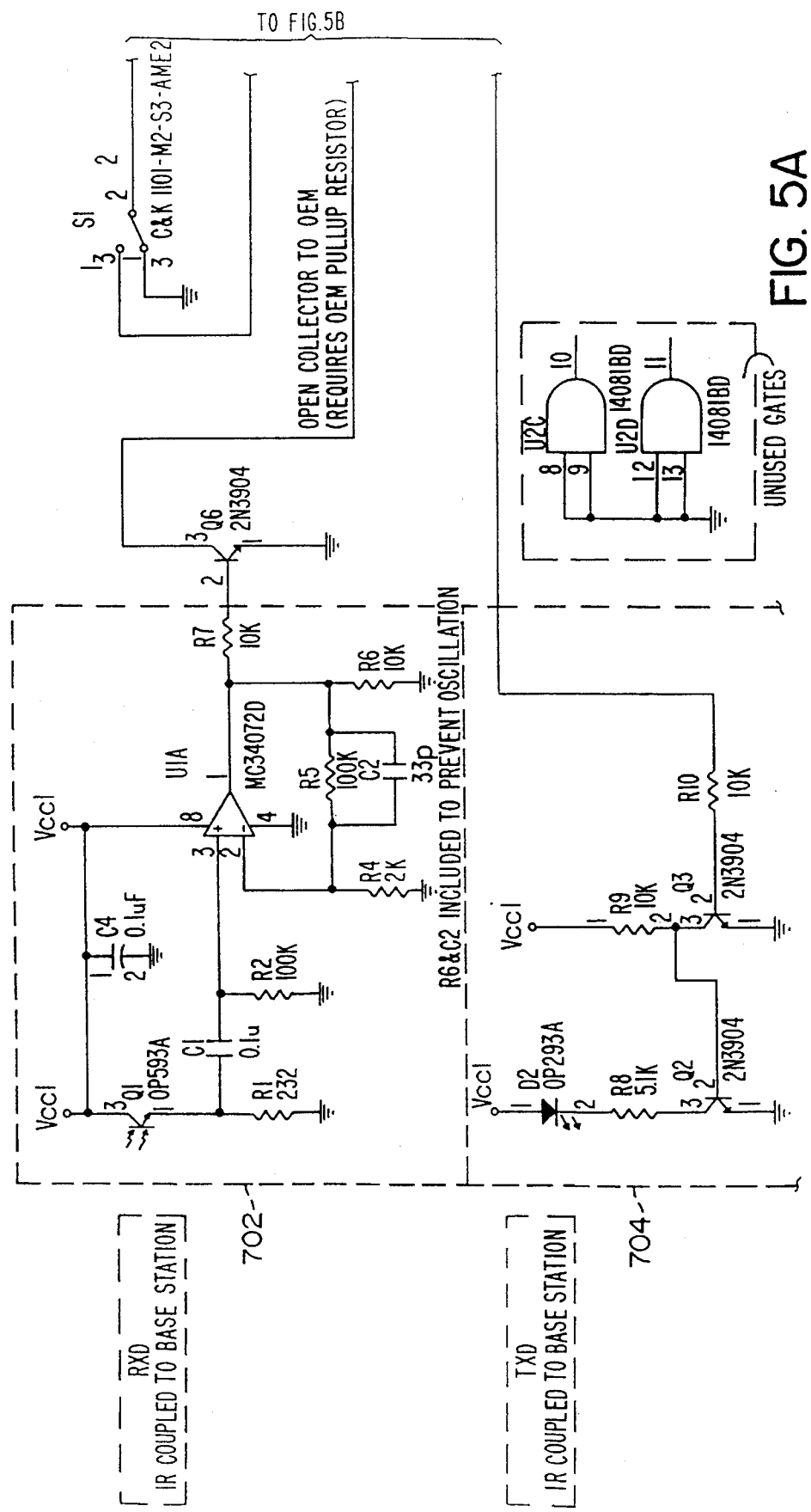
FIG. 5 is a schematic diagram of an exemplary Docking Interface Board of the remote base unit of FIG. 4.
Figure 5B:
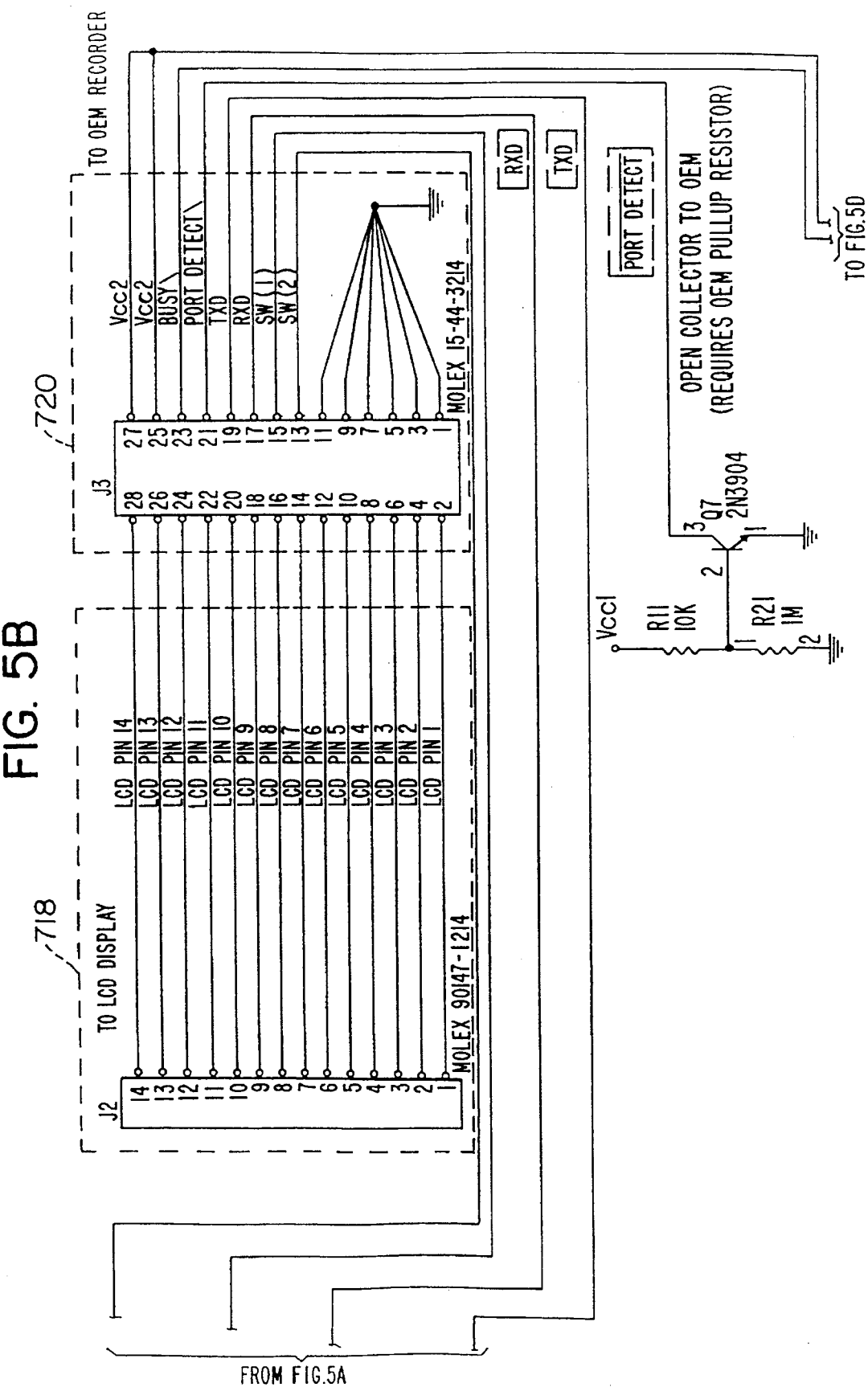
Figure 5C:
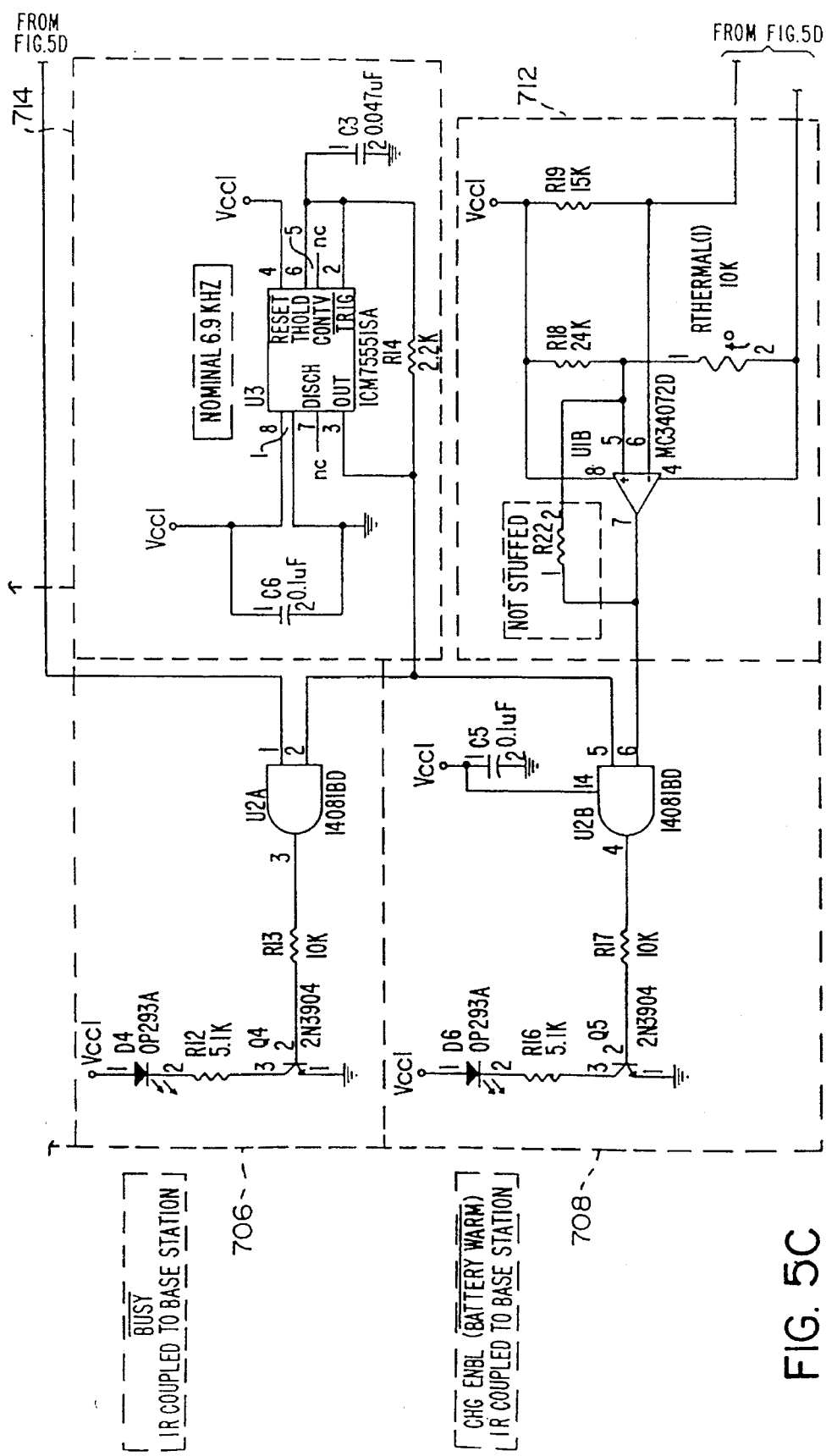
Figure 5D:
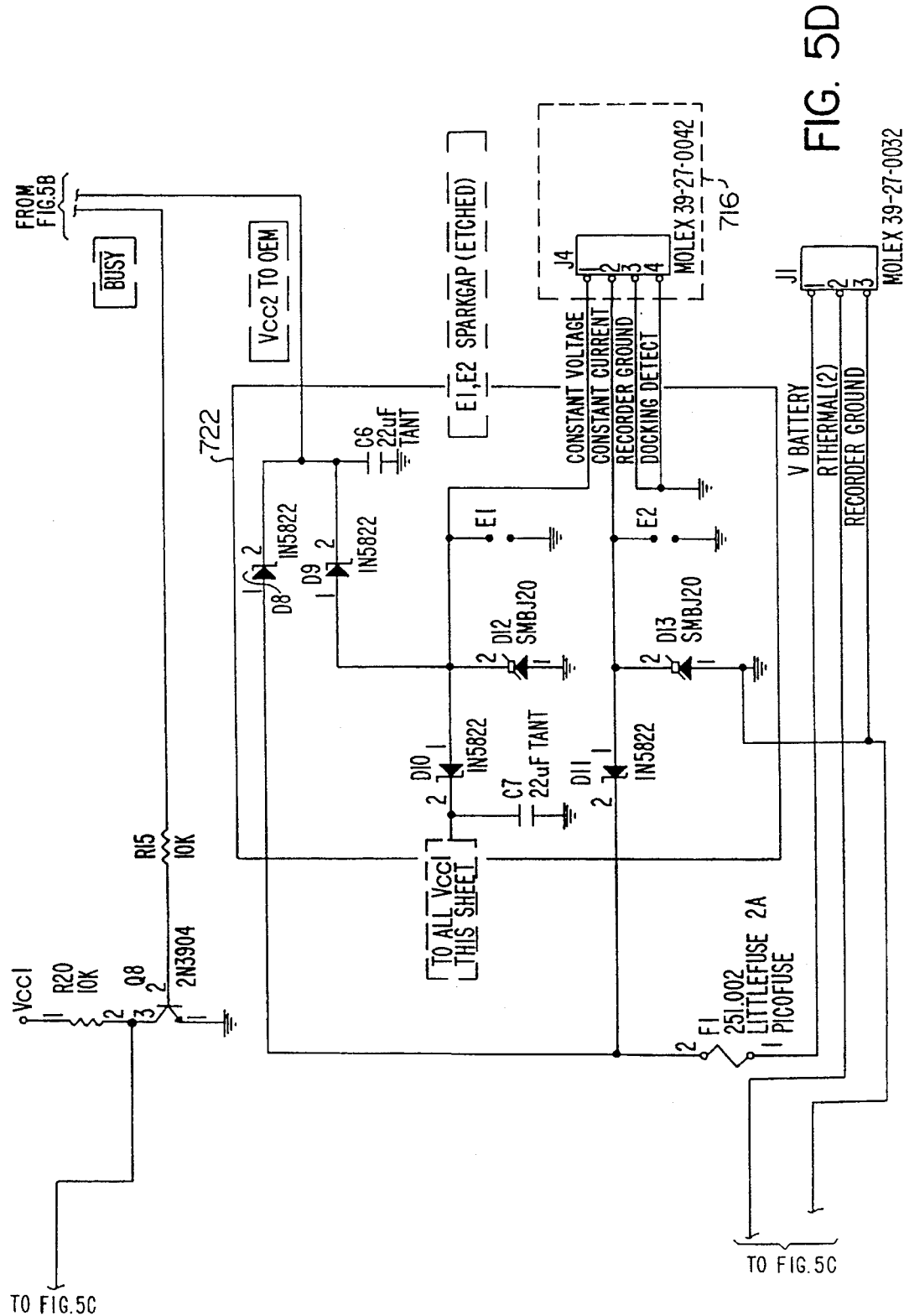

FIG. 4 is a functional block diagram of an exemplary base unit 150 and the modules 110 (sensors 120 and recorders 160) and care center 600 with which it interfaces. As depicted in FIG. 4, the base unit 150 communicates with the care center 600 from remote sites 100. As illustrated, the sensors 120 are connected to the remote base unit (RBU) 150 via connectors 464, 466, 468, 470, 472, 474, 476 and 478 on the rear panel 460 of the RBU 150 and via connectors 443 and 444 located within the storage bay 440 of the RBU 150. The recorders 160 communicate with the RBU 150 via infrared and power links 415. These connectors 443, 444, 464, 466, 468, 470, 472, 474, 476 and 478 and infrared links 415 provide the signals from the sensors 120 and recorders 160 to the electronics circuitry in the RBU 150.

As previously discussed, the RBU 150 comprises a lid assembly 300 (shown in FIG. 3) and a base assembly 400 (shown in FIG. 3). The lid assembly 300 comprises a display assembly 310, a lid assembly board 340 and two recorder docking ports 350a, 350b. The base assembly 400 comprises a system board 410, a third recorder docking port 350c, a storage bay 440 and a rear panel 460.

As shown in FIG. 4, the lid assembly board 340 comprises integrated circuits for the control of the LCD 312 and touchscreen 314 and two recorder interface boards 416a, 416b.

The system board 410 comprises a recorder interface board 416c, a microprocessor-based central processing unit (CPU) 412, a memory module 418, a temperature/scale board 420, a memory interface circuit 430, a communications interface circuit 440, a modem board 450, a microprocessor decode buffer circuit 461, three power supplies 471a, 471b, 471c and a power interface and control circuit 480.

The memory module 418, connected to the CPU 412 via a conventional data bus, comprises 64 Kbytes of Read Only Memory (ROM) used for the Basic I/O System (BIOS), 1 Megabyte of ROM used for the operating system and applications software and up to 32 Megabytes of Random Access Memory (RAM).

As illustrated in FIG. 4, the fetal heart rate/uterine activity recorder 210, the blood pressure recorder 220 and the urinalysis recorder 230 are each connected using infrared and power links 415a, 415b, 415c via the docking interface boards 414a, 414b, 414c in each recorder 210, 220, 230 to one of two recorder interface boards (RIBs) 416 on the Lid Assembly 300 or to the recorder interface board 416 on the base assembly 400. Information previously recorded by the recorders 210, 220, 230 are then transferred to the CPU 412. Alternatively, when a session is scheduled, the patient takes the required measurements and the recorders 210, 220, 230 store the information, which is transferred to the CPU 412.

The five directly connected sensors are connected to the RBU as follows. The weight scale sensor 122 is plugged into connector 470 in the rear panel 460 of the RBU 150. Likewise, the infusion pump 128 and the glucometer 130 are plugged into either connector 466 or connector 468 on the rear panel 460 of the RBU 150. The temperature probe 124 and the event switch 126 are plugged into the receptacles 443 and 444 located within the storage bay 440 of the base assembly 400.

The measurements monitored by the temperature probe 124 and weight scales 122 are provided to the temperature/scale board 420, which processes the signals provided by the temperature probe 124 and weight scales 122. The resultant signals are provided via the communications interface circuit 440 to the CPU 412.

Signals provided by the event switch 126 via event receptacle 444 are provided to an I/O port decode circuit 820, in the communications interface circuit 440 which provides proper selection of the I/O ports to be read. Similarly, signals provided by the glucometer 130 and infusion pump 128 via connectors 466, 468 are first provided to electromagnetic interference/electromagnetic static discharge (EMI/ESD) circuits 832, 834 which filter the signals from extraneous electromagnetic radiation. The signals from the I/O port decode circuit 820 and the EMI/ESD circuits 832, 834 are provided to the interface circuit 445, which permits the CPU 412 to select the device it communicates with. Here, the device is either the event switch 126, glucometer 130 or infusion pump 128. The resultant signals are provided to the microprocessor decode buffer circuit 461, which then provides the signals to the CPU 412.

The external power supply 132 is provided to the power supply interface and control circuitry 480 via power connector 464. The power is provided via the microprocessor decode buffer circuitry 461 to the other elements in the RBU 150.

The telephone line 134 is provided via an RJ-11 connector 478 to the internal modem circuitry 450 of the RBU 150. A portable printer 136 for printing fetal heart rate/uterine activity charts, is connected via connector 472 to the CPU 412 and then to the modem 450. A computer 138 for testing and data retrieval may be connected via a direct connector 474 to the CPU 412 and then to the modem 450.

FIG. 5 is a schematic diagram of an exemplary docking interface board (DIB) 414 in each of the recorders 160. The DIB 414 comprises four infrared circuits 702, 704, 706, 708, a battery charge control circuit 712, and a battery charge ESD protection circuit 714. Of the four infrared circuits, two circuits 702, 704 are dedicated for receiving and transmitting data, respectively. The other two circuits provide two flag channels 706, 708 used for indicating that the recorder 160 is busy and for indicating the battery charging state of the recorder 160 and docking port 350, respectively.

As discussed earlier, three spring-loaded contacts at the bottom of the cradle in the docking ports 416 provide the electrical and optical interface with the RBU 150. The contacts connect to corresponding contacts on the end of the recorder case for charging of the battery and powering the recorder 160 while the recorder 160 is docked. A molded projection 178 (FIGS. 3D and 3E) on the narrow end 164 of the recorder 160 presses against an interlock switch 176 (FIG. 3C) in the docking port 350 to indicate that a recorder 160 is docked. The battery charge controller 706 coordinates the charging of the battery in the recorder 160. The battery charge ESD protection circuit 722 isolates the board from extraneous ESD. The battery cells in the DIB 414 are charged by a battery pack in the RBU 150 via connector 716. The battery cells permit the recorder to record measurements remote from the RBU 150. Connector 718 provides for connection to the LCD 312. A second connector 720 provides a means for supplying power to the components on the DIB 414. Preferably, these connectors are Molex connectors. An ambient light chopper and controller 722 ensures that ambient light does not interfere with the functioning of the infrared sensors.

Figure 6A:
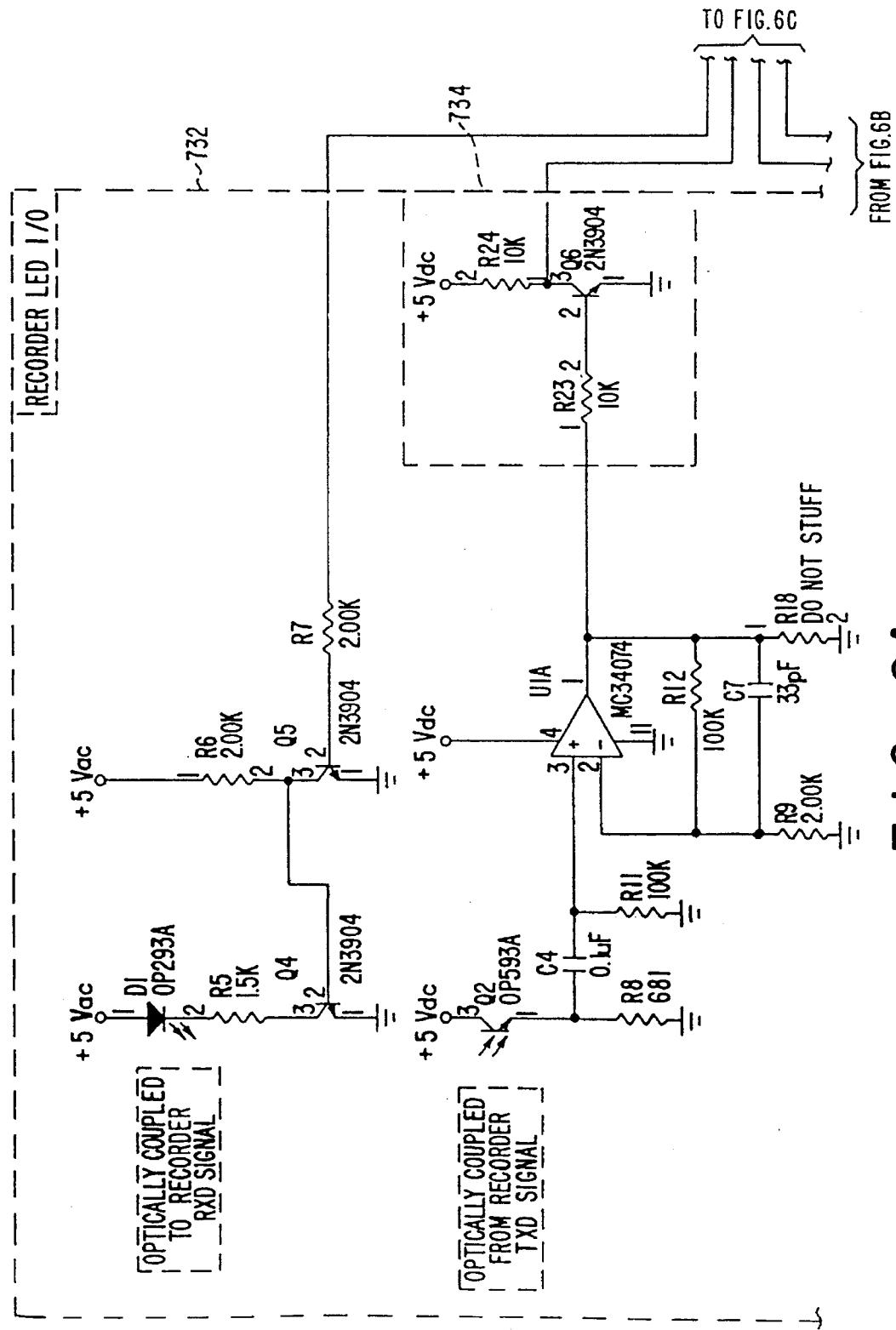
FIG. 6 is a schematic diagram of an exemplary Recorder Interface Board of the remote base unit of FIG. 4.
Figure 6B:
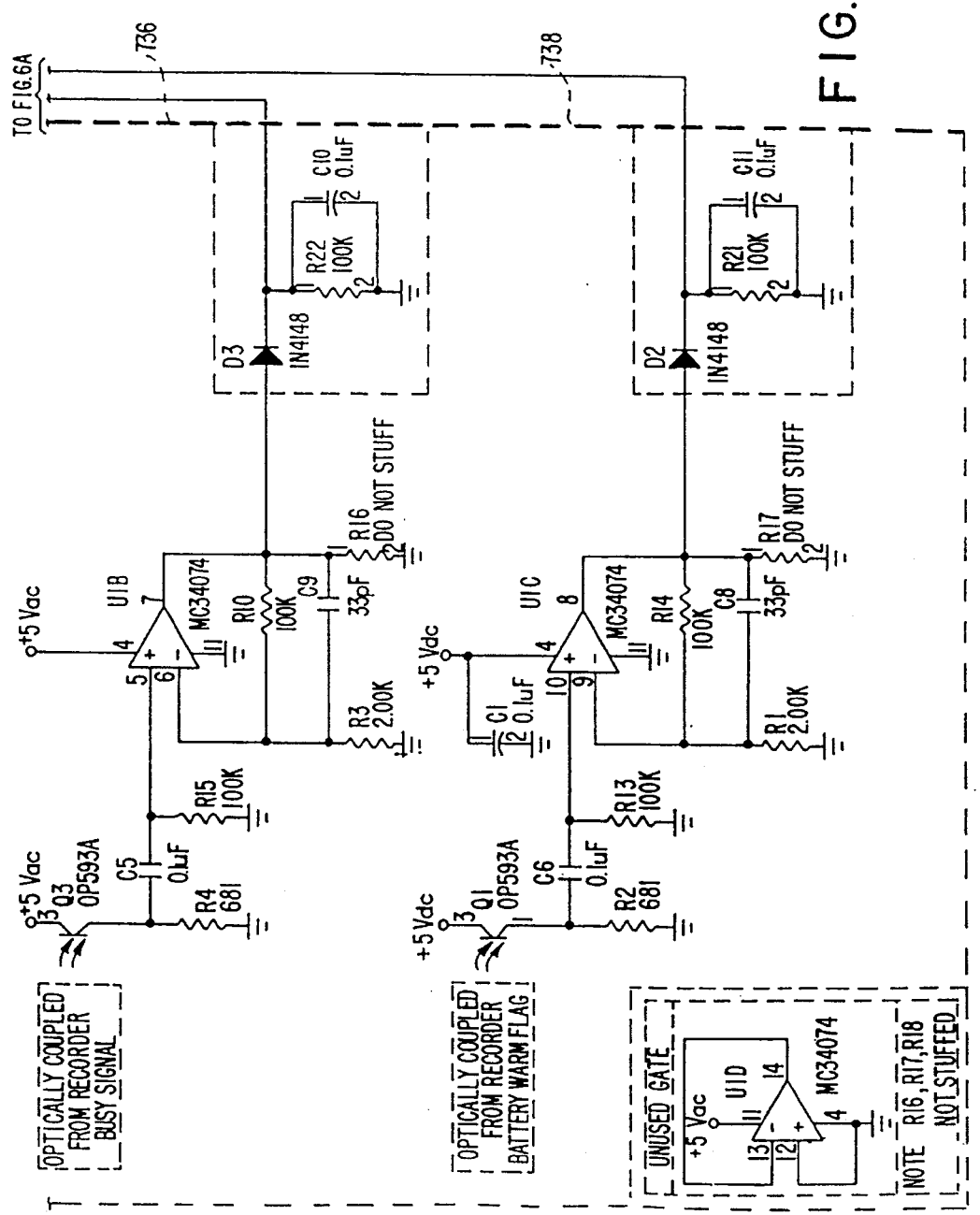
Figure 6C:
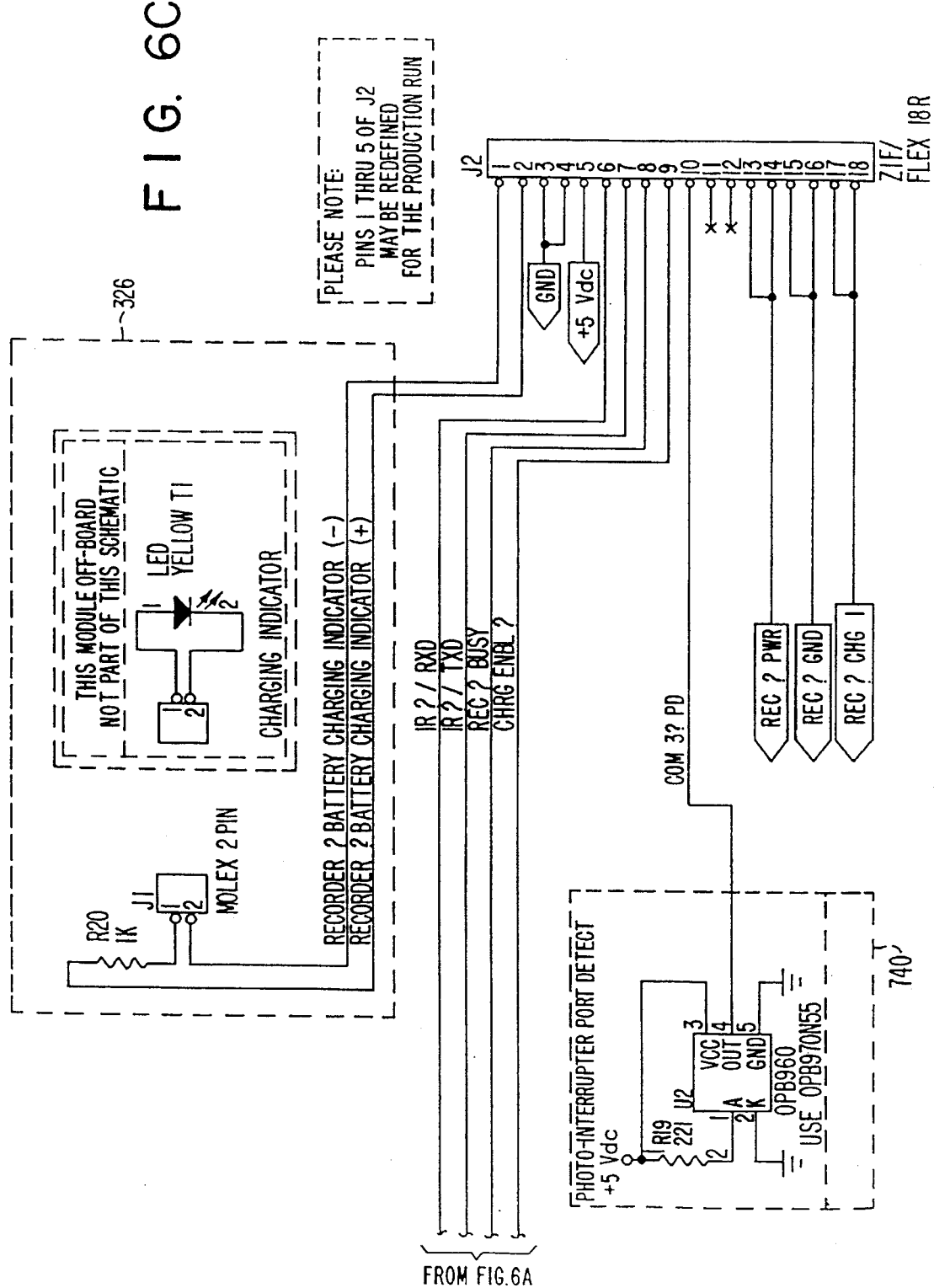
Figure 7A:
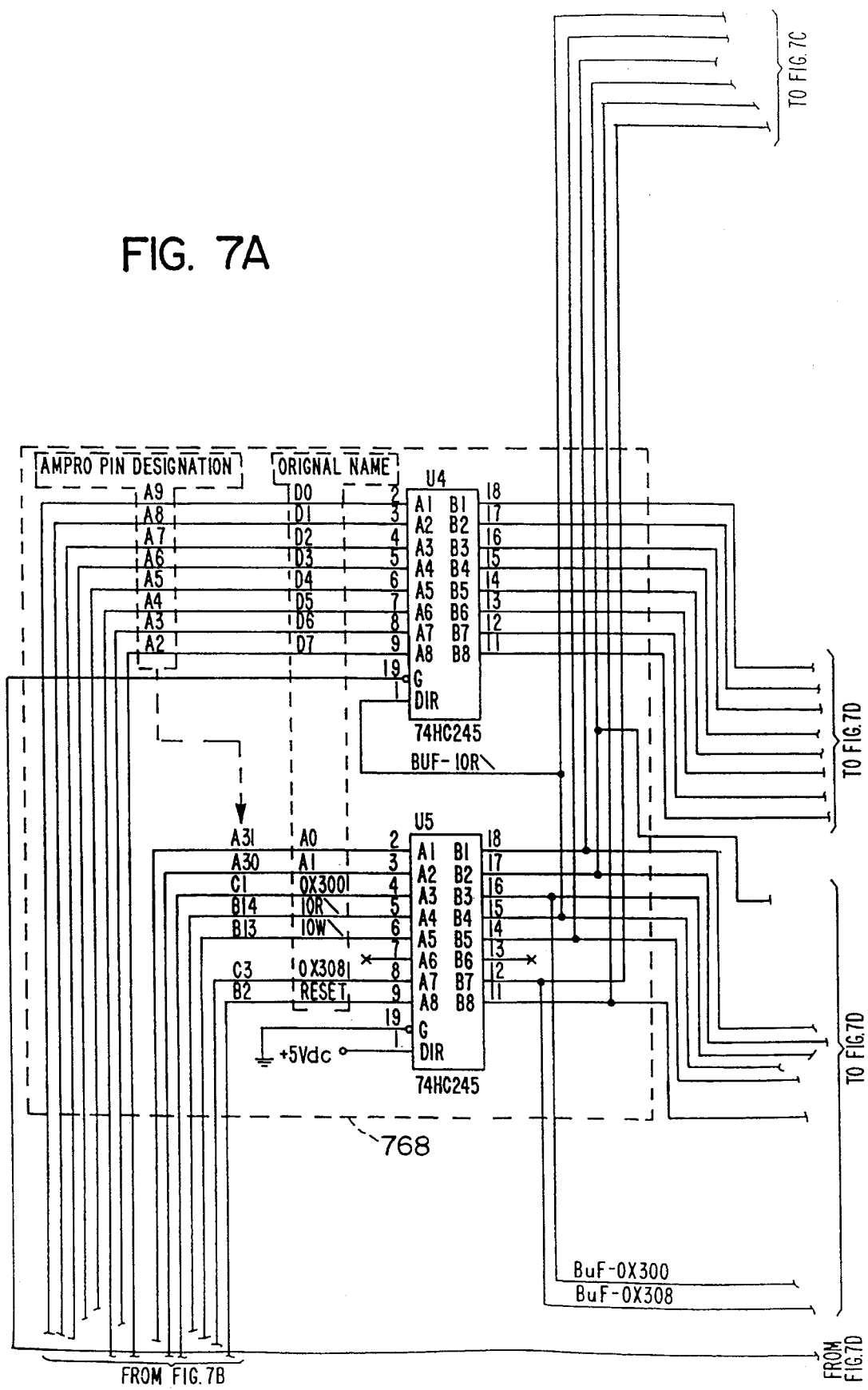
FIG. 7 is a schematic diagram of an exemplary circuit for Liquid Crystal Display of the remote base unit of FIG. 4.
Figure 7B:
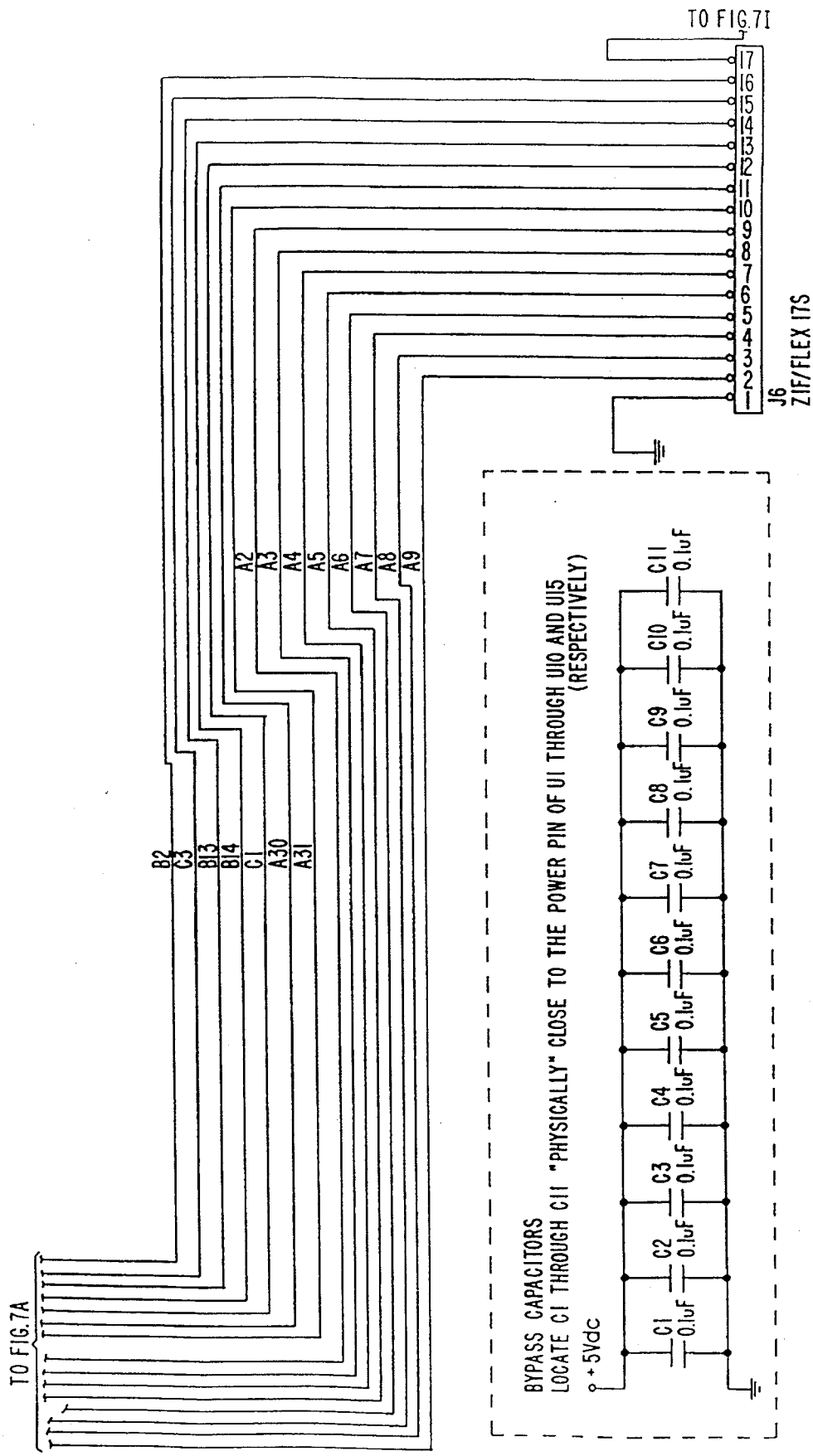
Figure 7C:
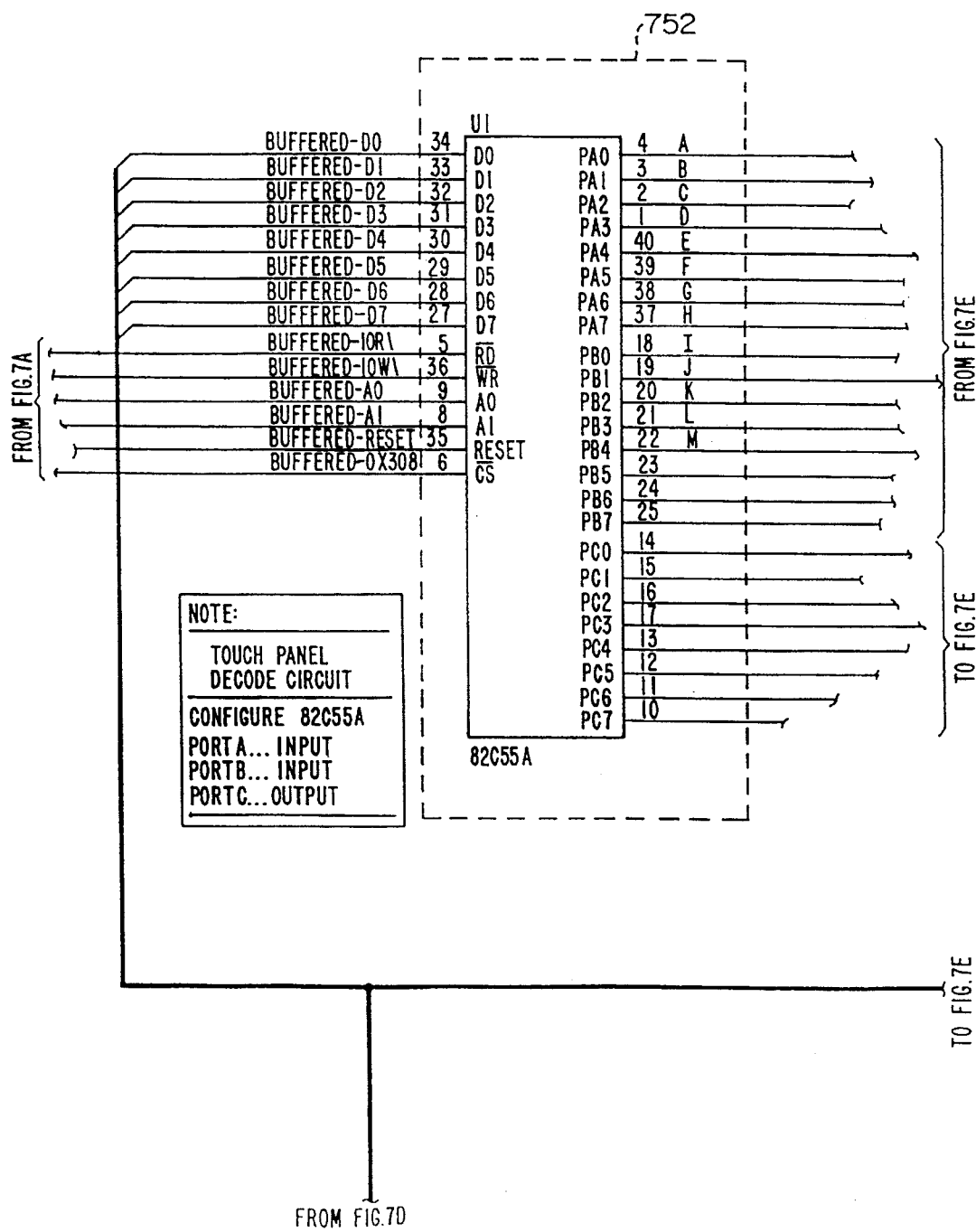
Figure 7D:
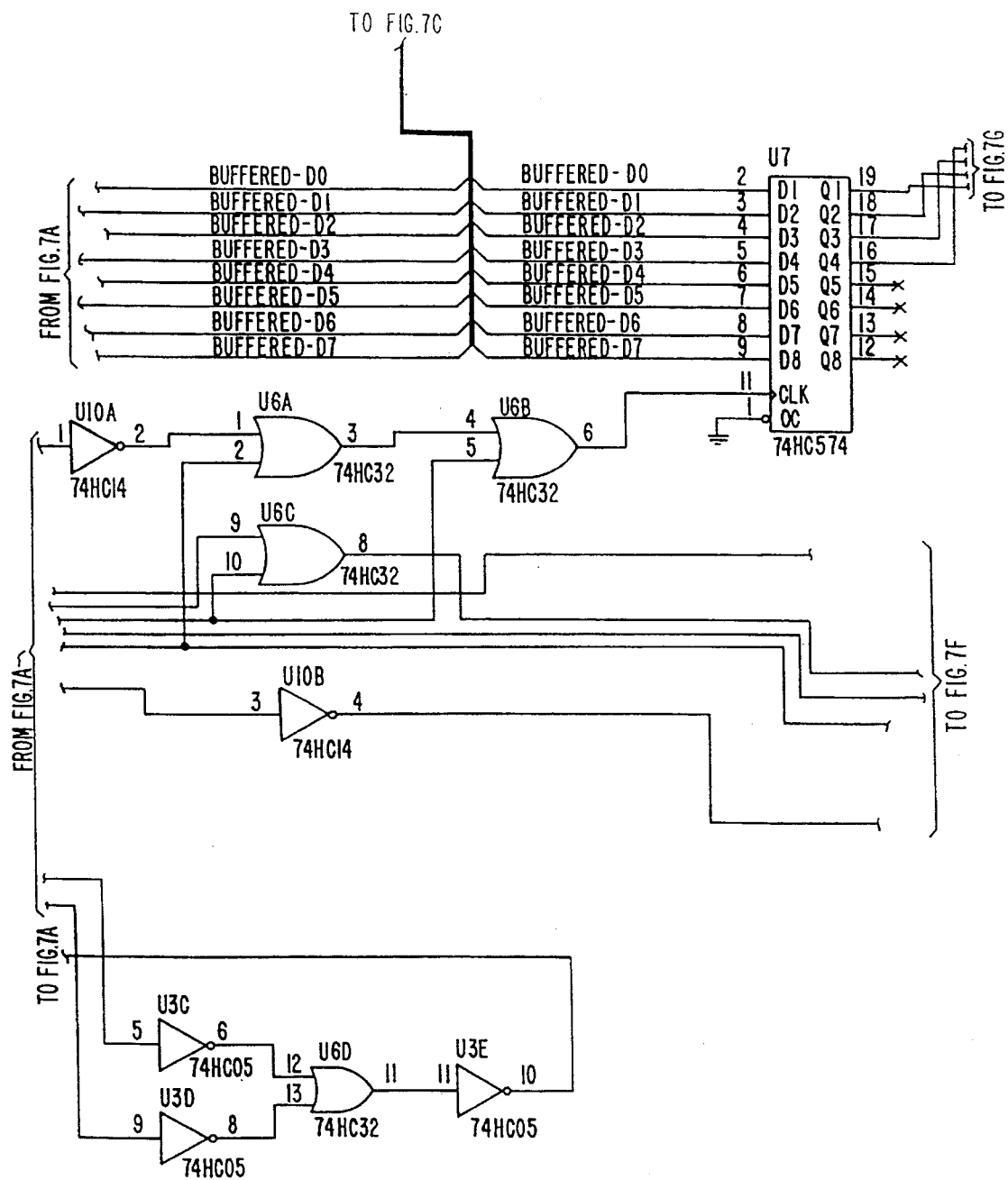
Figure 7E:
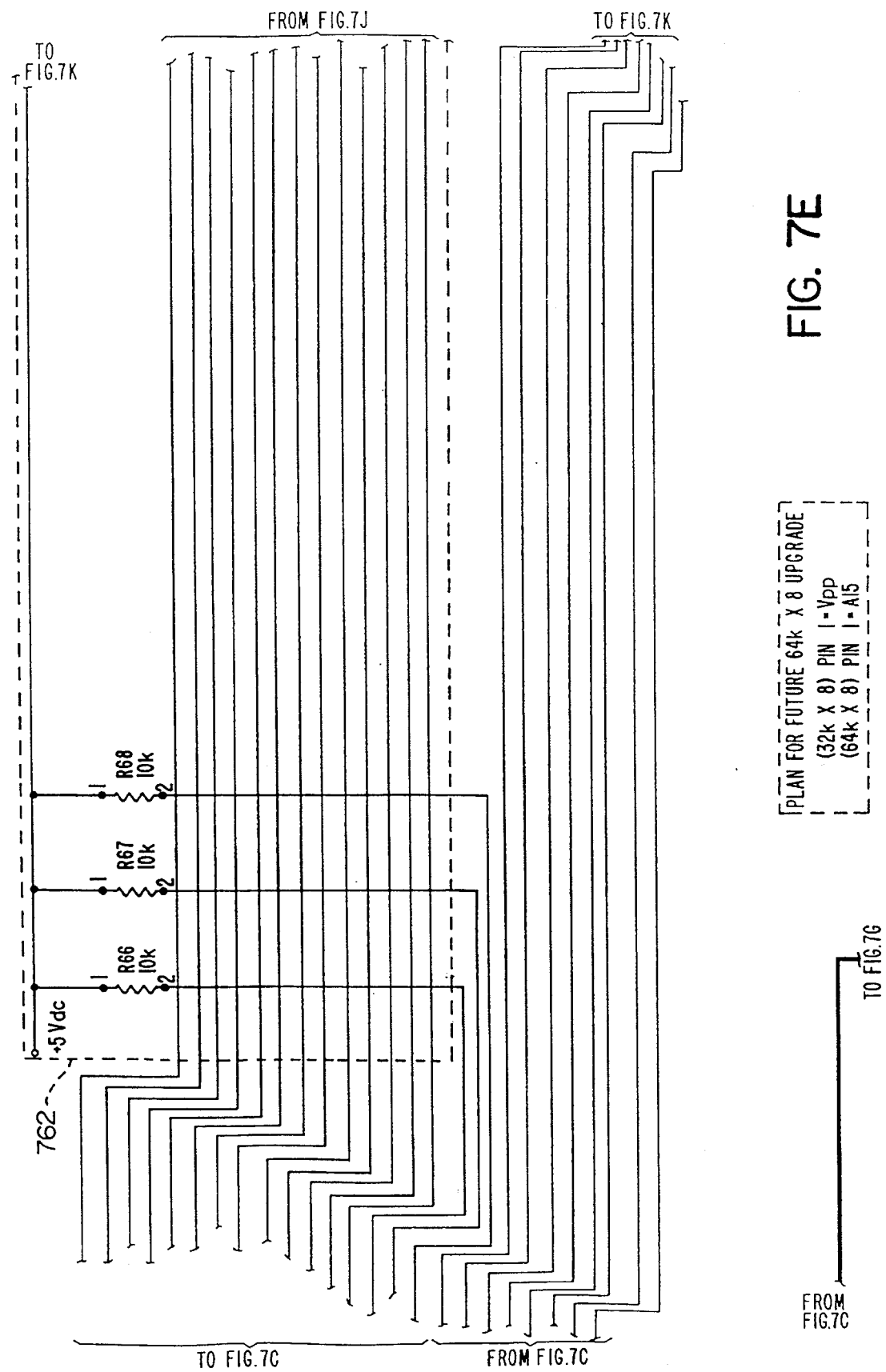
Figure 7F:
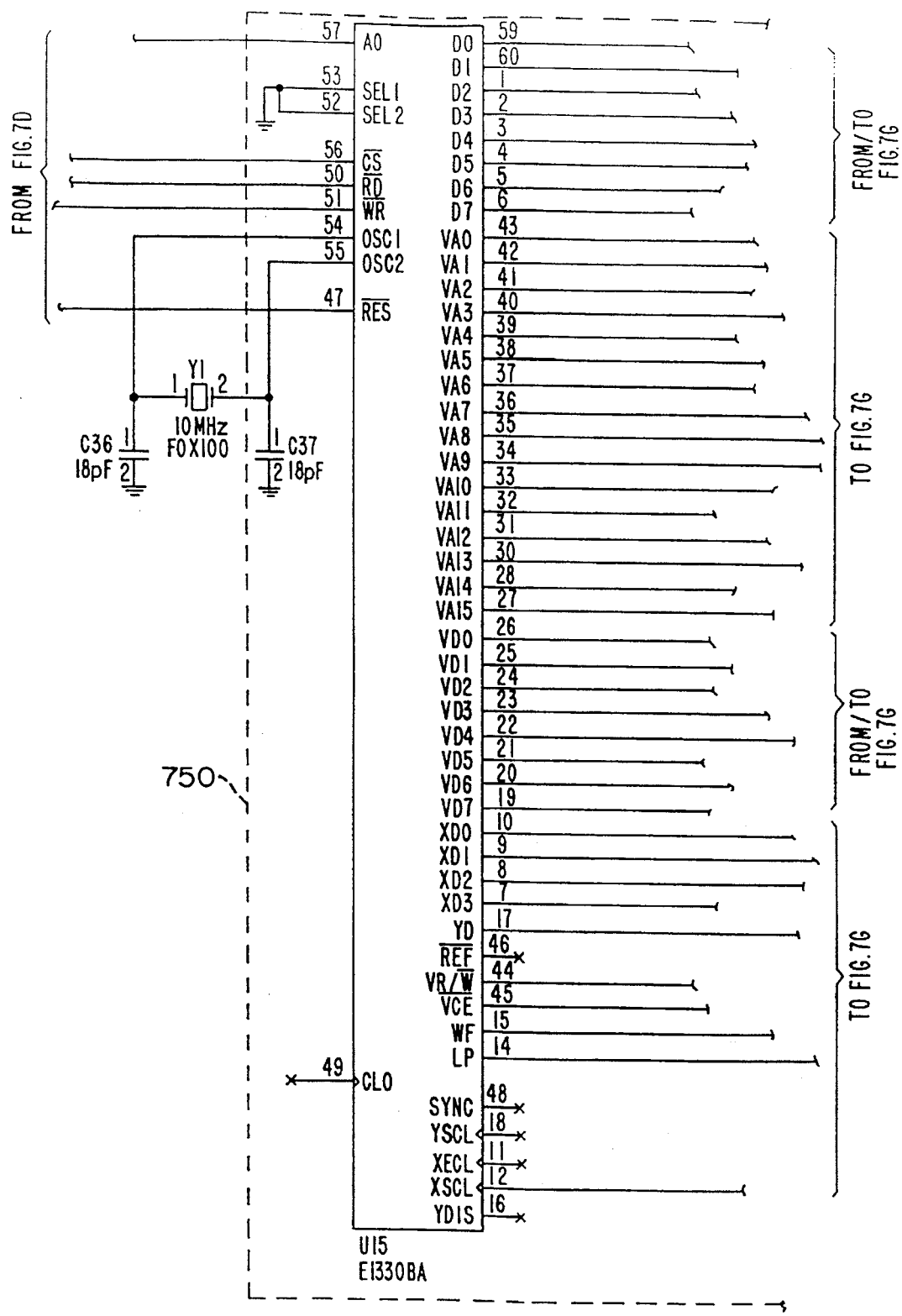
Figure 7G:
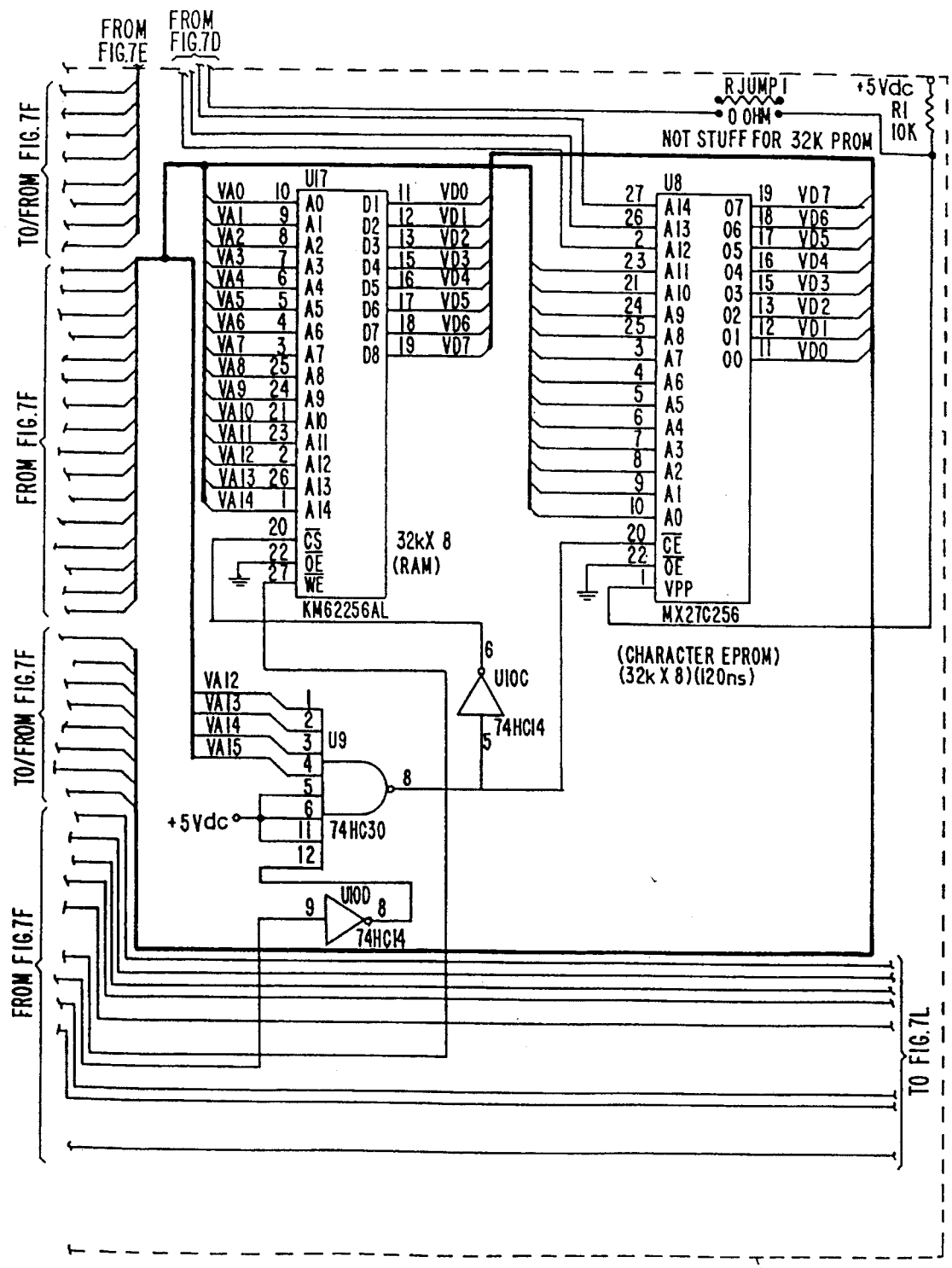
Figure 7H:
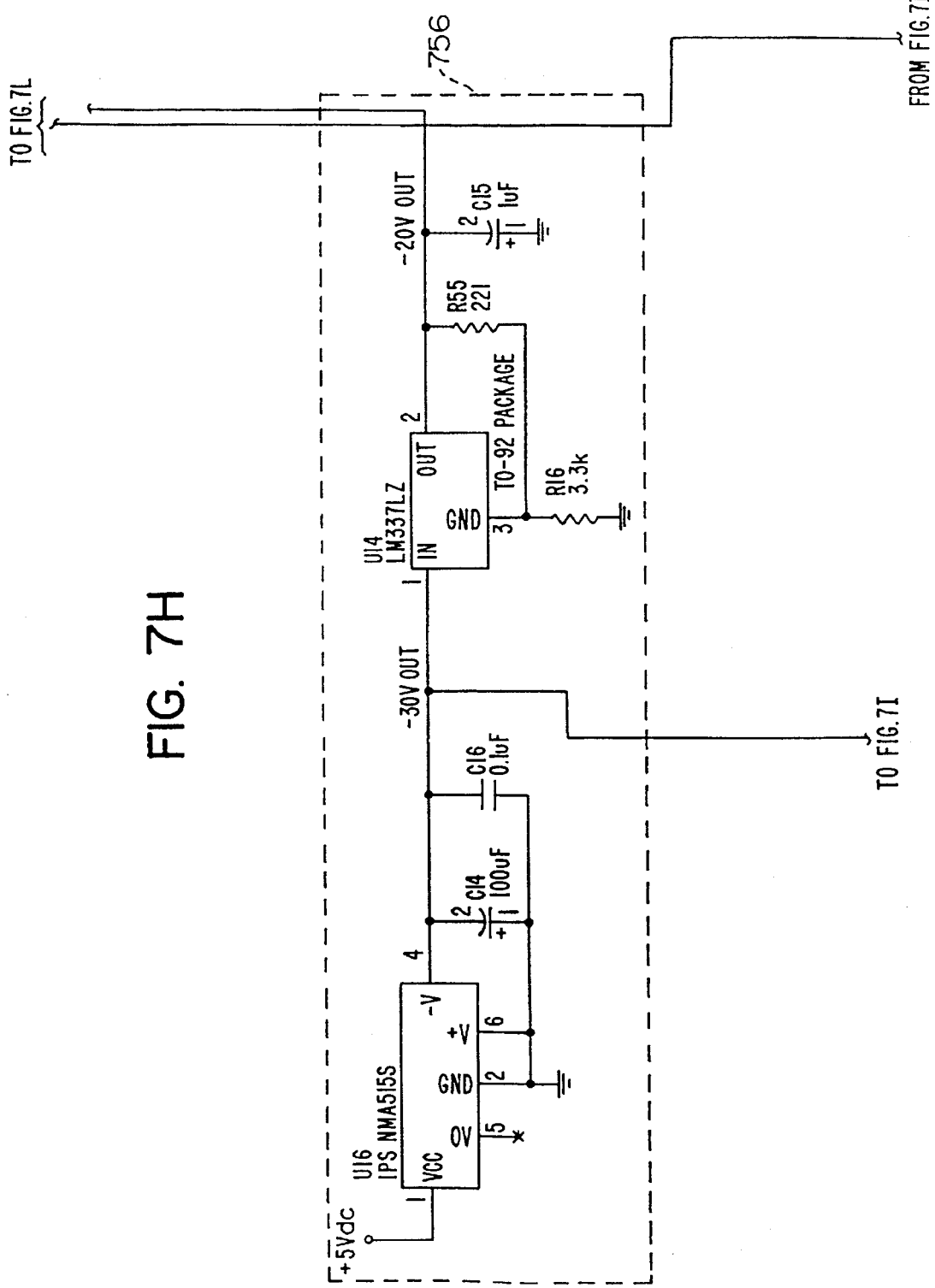
Figure 7I:
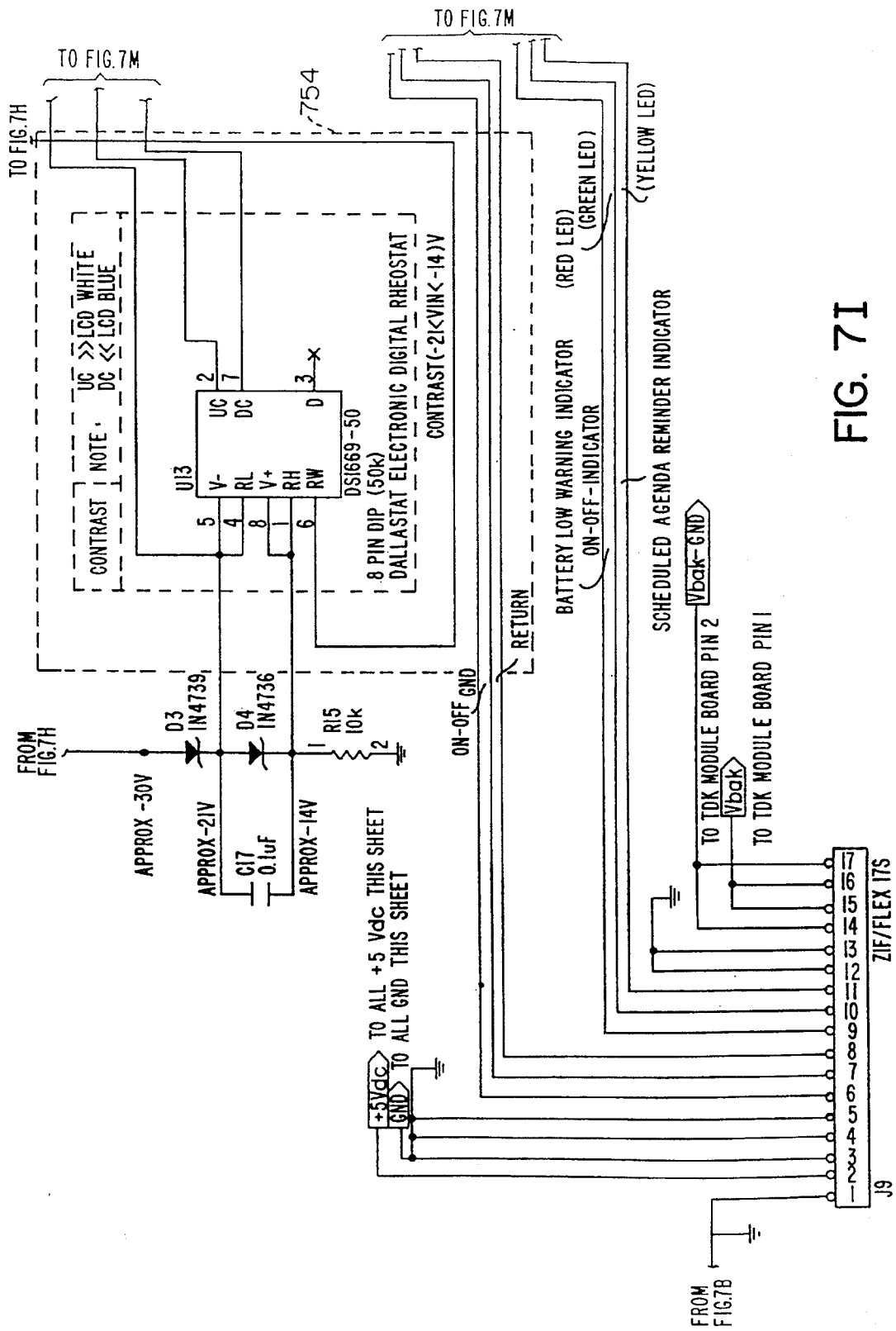
Figure 7K:
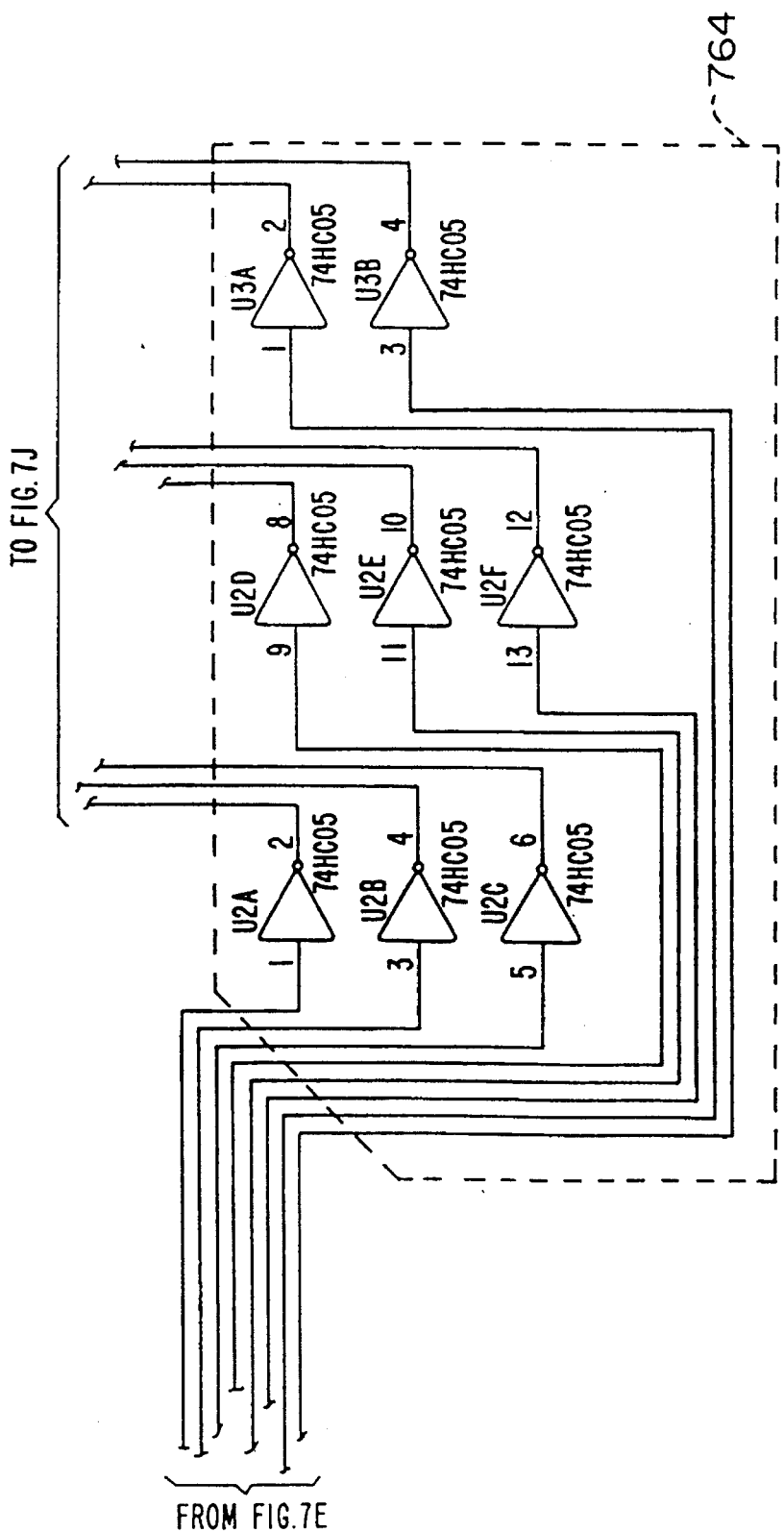
Figure 7M:
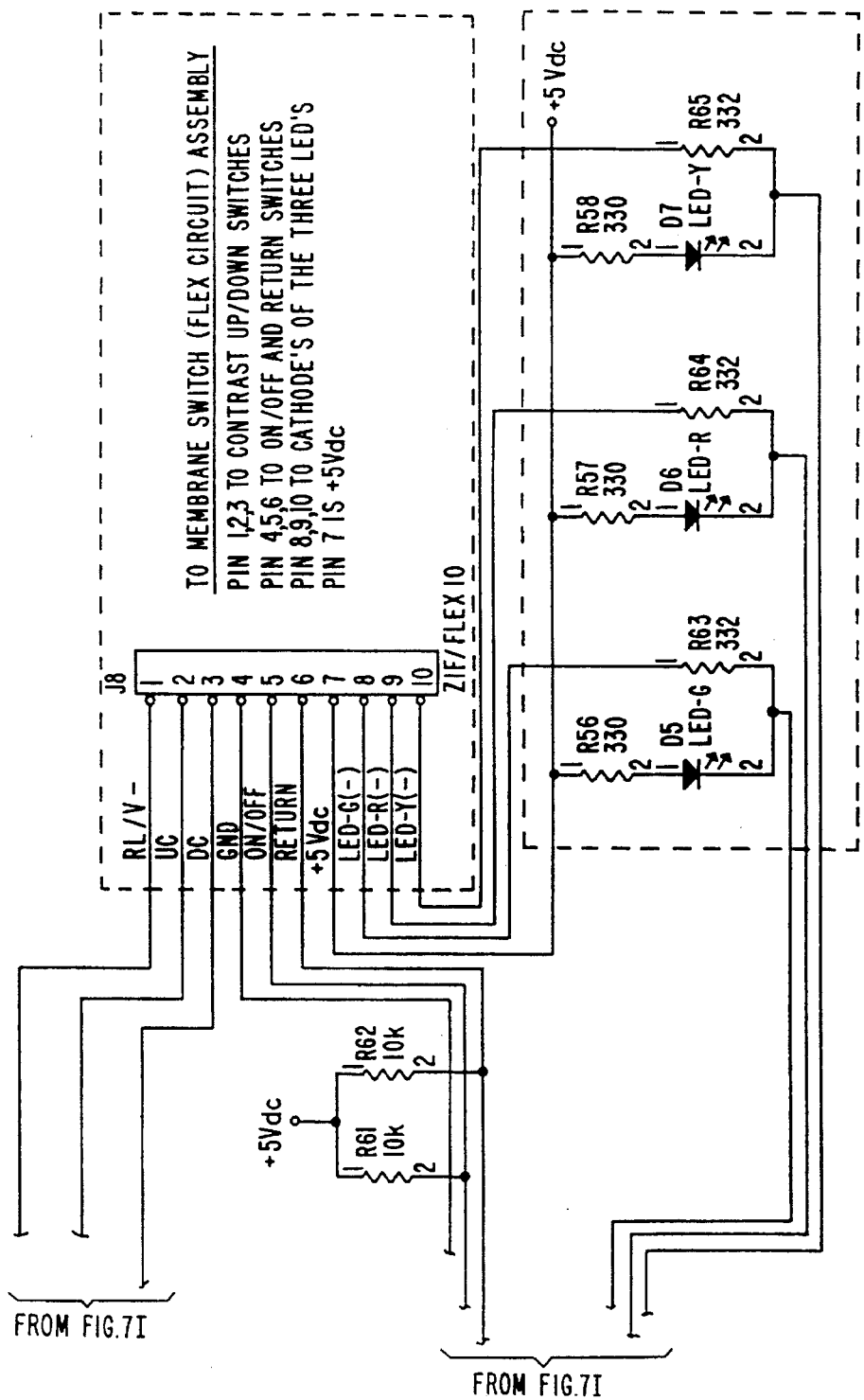
Figure 7N:
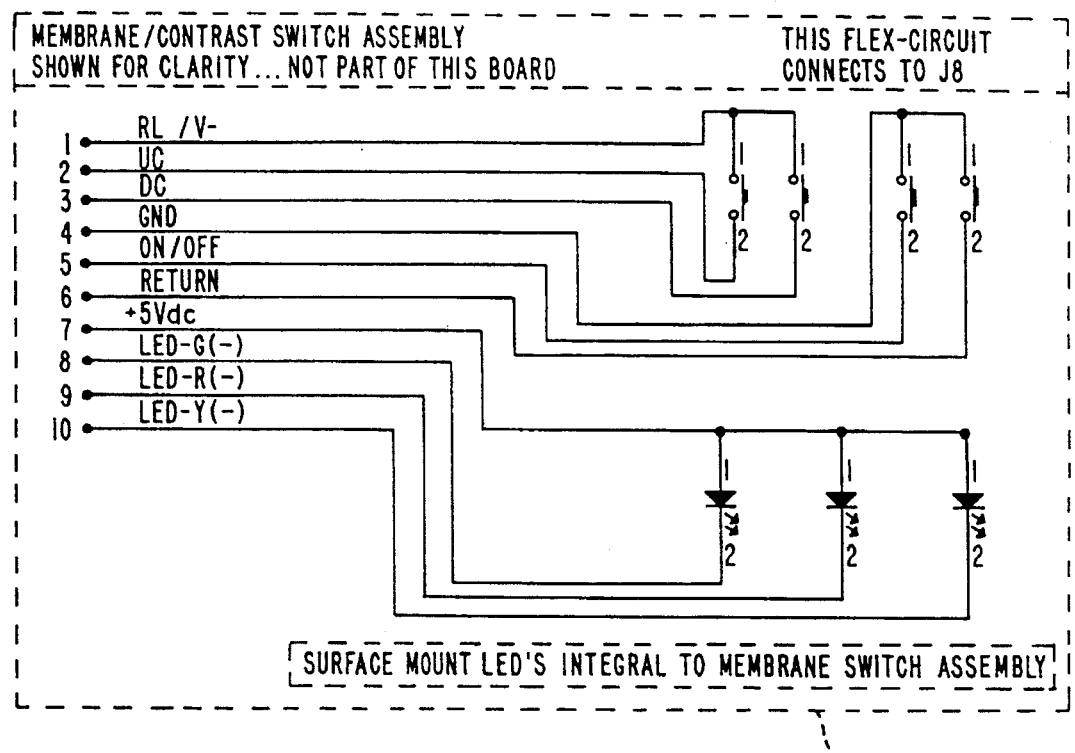

FIG. 6 is a schematic diagram of an exemplary recorder interface board ("RIB") 416 of the RBU 150 diagrammed in FIG. 4. The RIB 416 comprises four infrared circuits 732, 734, 736, 738, a light beam interrupt sensor 740 and an LED power charge indicator 326. Two of the circuits 732, 734 provide channels for transmitting and receiving data, respectively, from the recorders 160 and two flag channels 736, 738, for indicating the RBU 160 is busy and in a battery charging state, respectively. These four channels correspond to the four infrared channels on the DIB 414 (FIG. 5). The LED 326 on the RIB 416 provides indication of the power charging state of the RBU 150 and a light beam interrupt sensor 740 indicates the presence of a docked recorder 160.

FIG. 7 is a schematic diagram of an exemplary Lid Assembly Board 340 of RBU 150 diagrammed in FIG. 4. The LCD Assembly Board 340 comprises an EPSON E 1330DA LCD display controller chip 750 which controls the LCD display 312 and touch screen 314 decoding functions, as well known in the art. The LCD controller 750 is provided with volatile Random Access Memory ("RAM") 750 for screen bit mapping and a Read Only Memory ("ROM") 750 for character generation. A Peripheral Interface Adapter (PIA) 752, connected to the controller chip 750, is used to provide the interface with the touch sensitive screen 314. These components are well known in the art.

In the present embodiment, the LCD screen brightness and contrast control voltages are provided by a digital rheostat 754 which is controlled by a pair of switches 318, 320 mounted on the front control panel 316 of the lid assembly 300. Preferably, the rheostat 754 is a DS 1669-50 digital rheostat. The lid assembly board 340 also has an LED power supply 756 which supplies power for the up/down contrast voltage controlled by buttons 318, 320 on the control panel 316 and a backlight power supply 758 controlled by the button 317. The lid assembly board 340 also provides connectors 760 for the system board's input/output (I/O) bus and annunciator signals (power on, low battery and Scheduled Appointment Reminder Indicator (SARI)). Electrical signals from the lid assembly board are routed to and from the base assembly flex cables (not shown). The matrix pullups circuit 762 and the matrix drivers circuit 764 identify the area of the touch screen 314 the area has selected, as known in the art. A decode latches circuit 768 enables data to be saved, as known in the art.

Figure 8A:
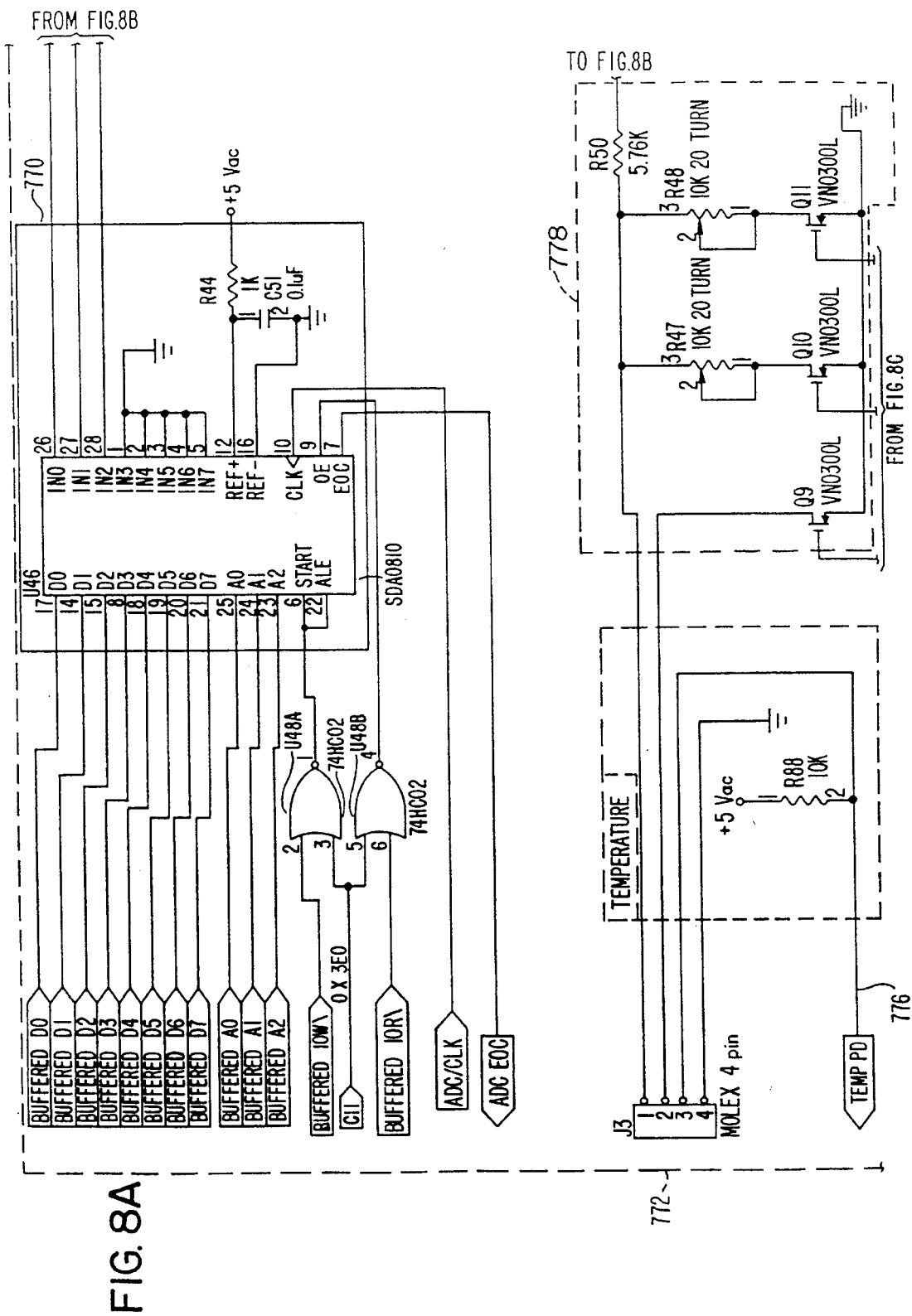
FIG. 8 is a schematic diagram of an exemplary Temperature and Scale Board of the remote base unit of FIG. 4.
Figure 8B:
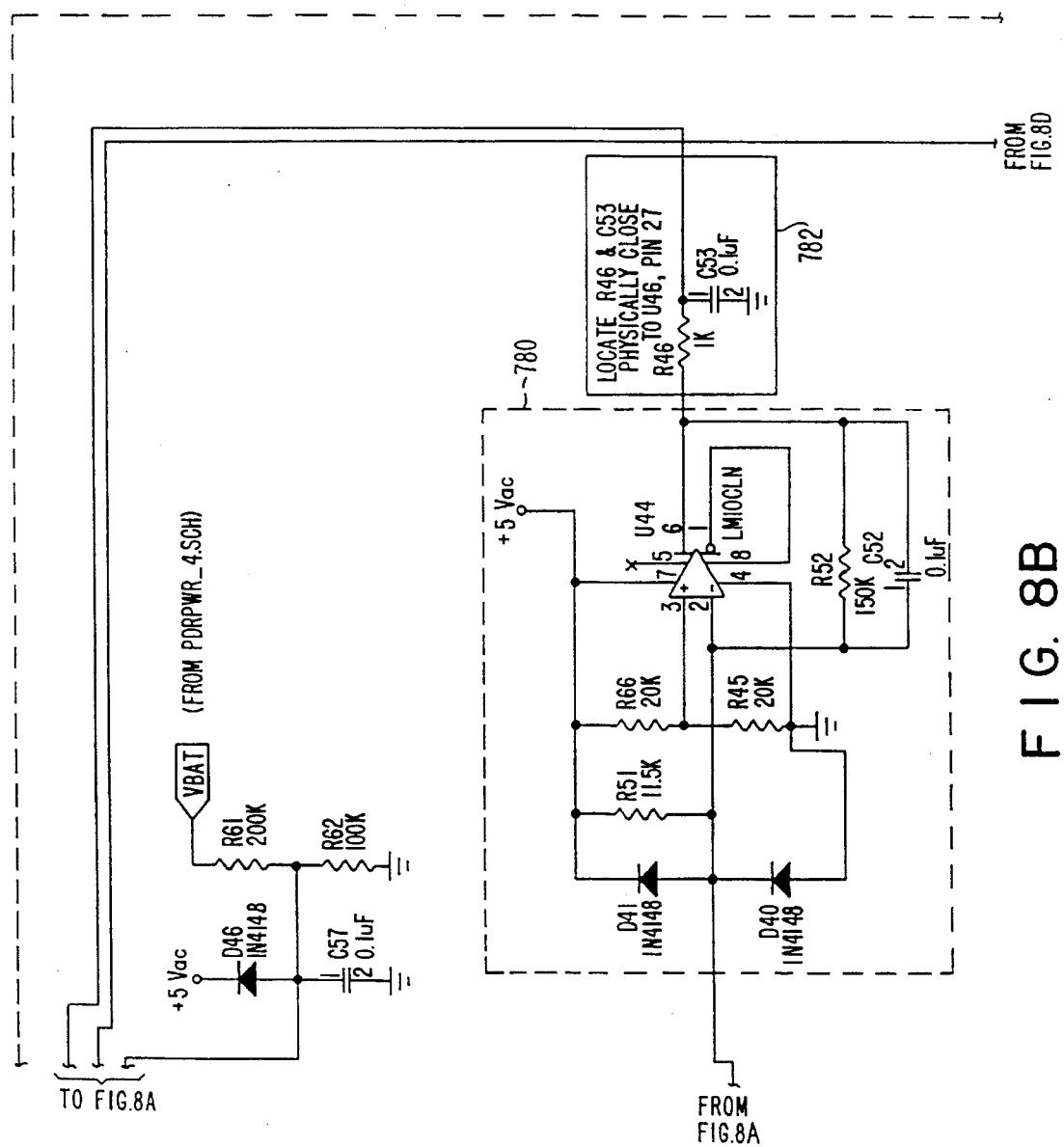
Figure 8D:
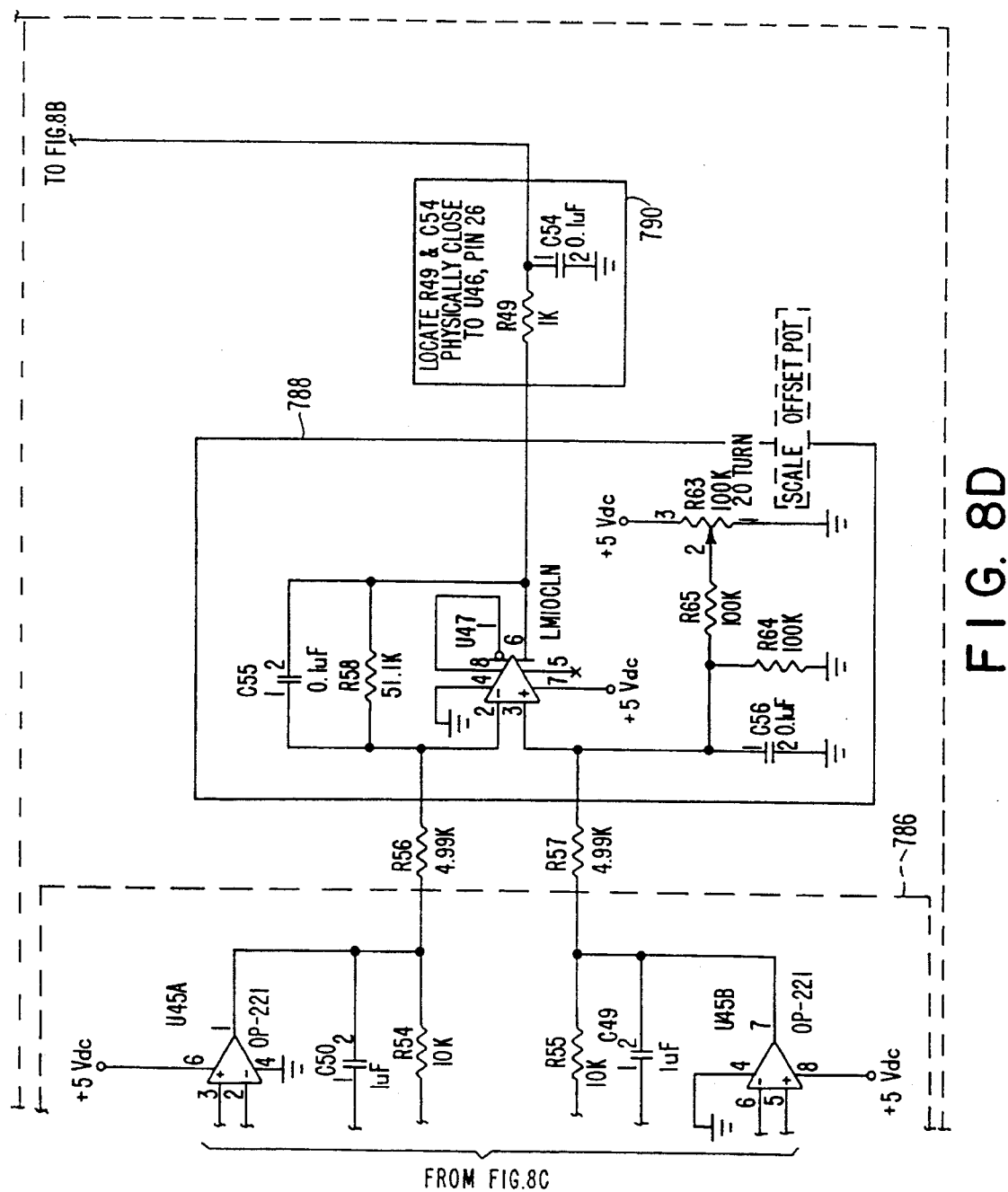
Figure 9B:
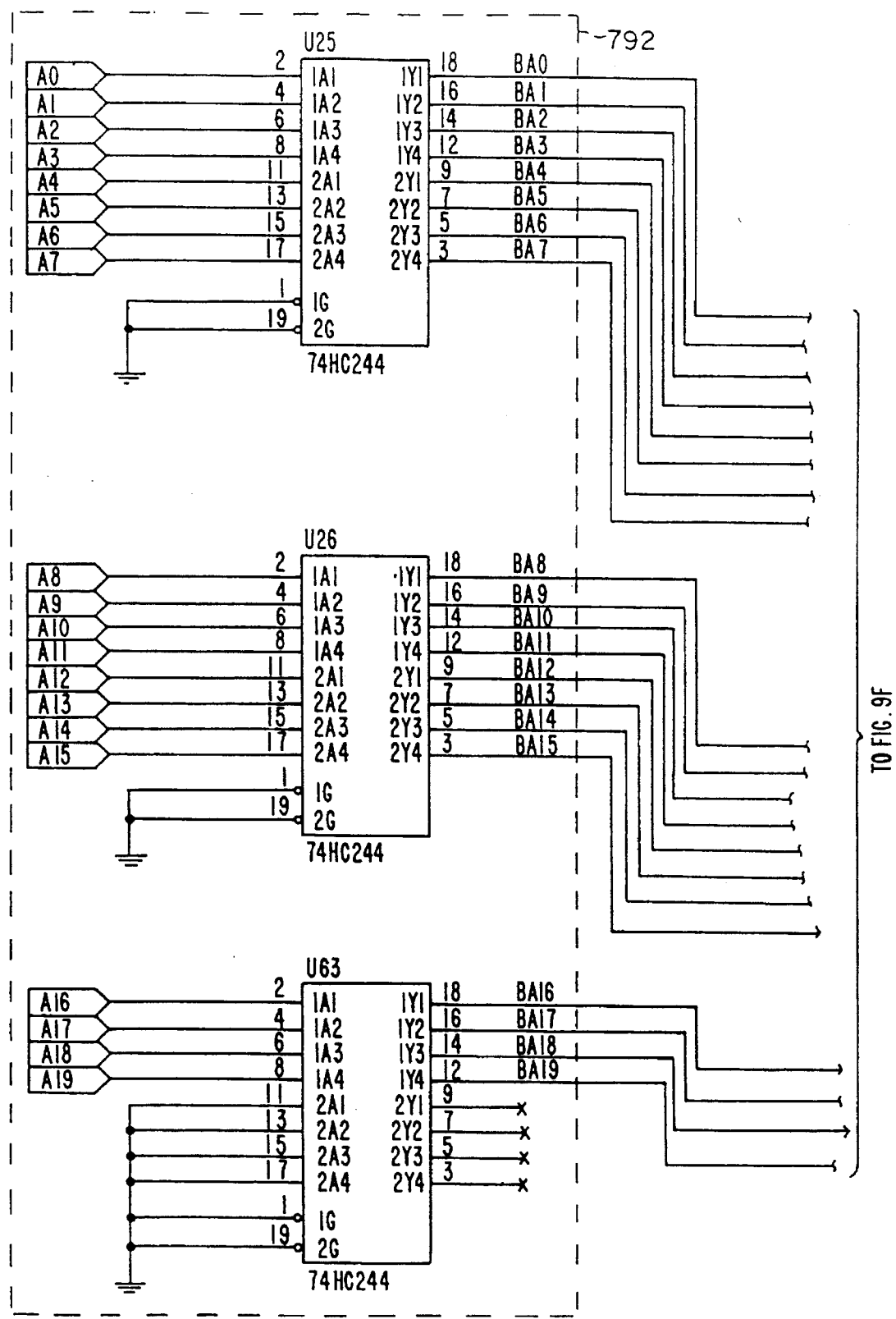
FIG. 9 is a schematic diagram of an exemplary Memory Interface Circuit of the remote base unit of FIG. 4.
Figure 9C:
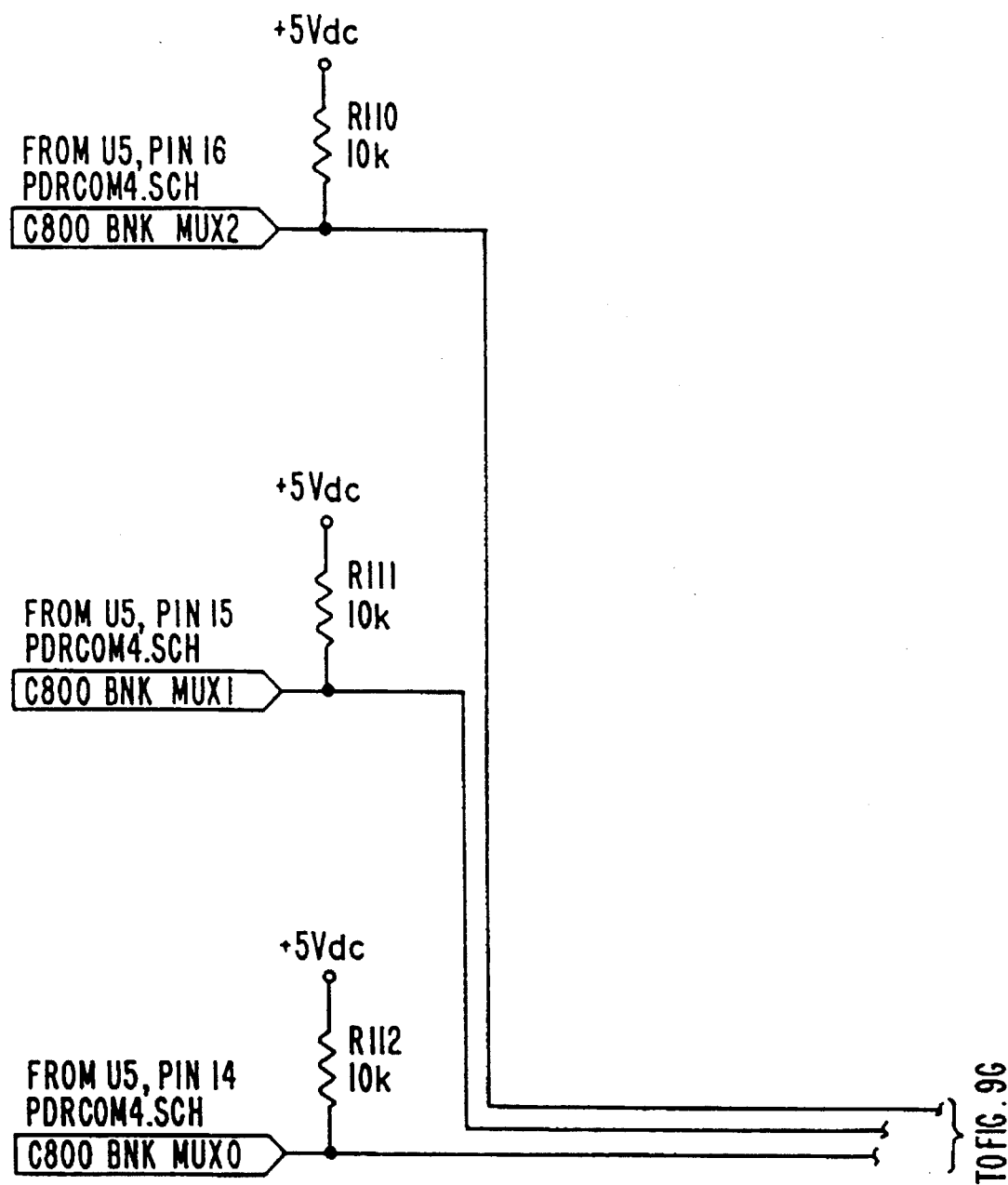
Figure 9D:
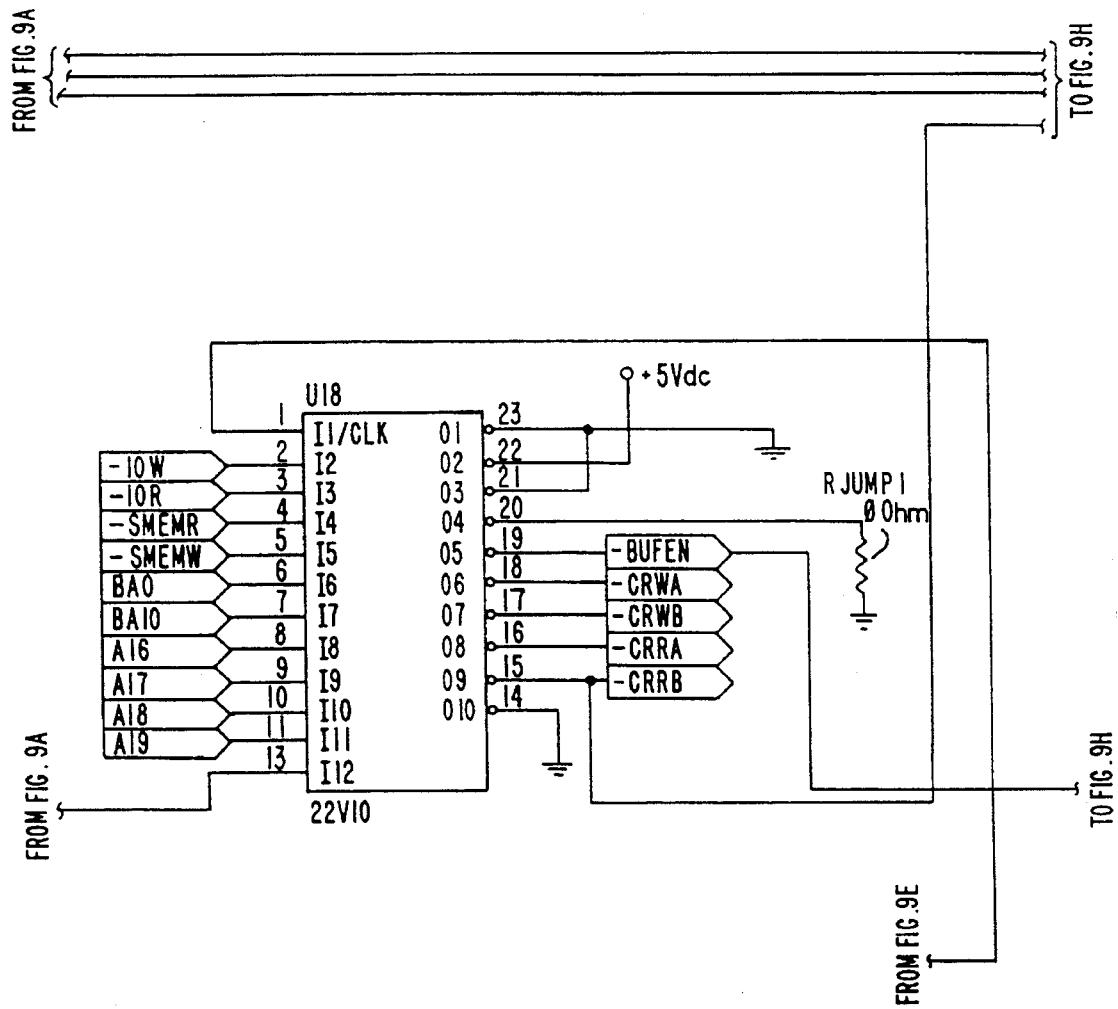
Figure 9E:
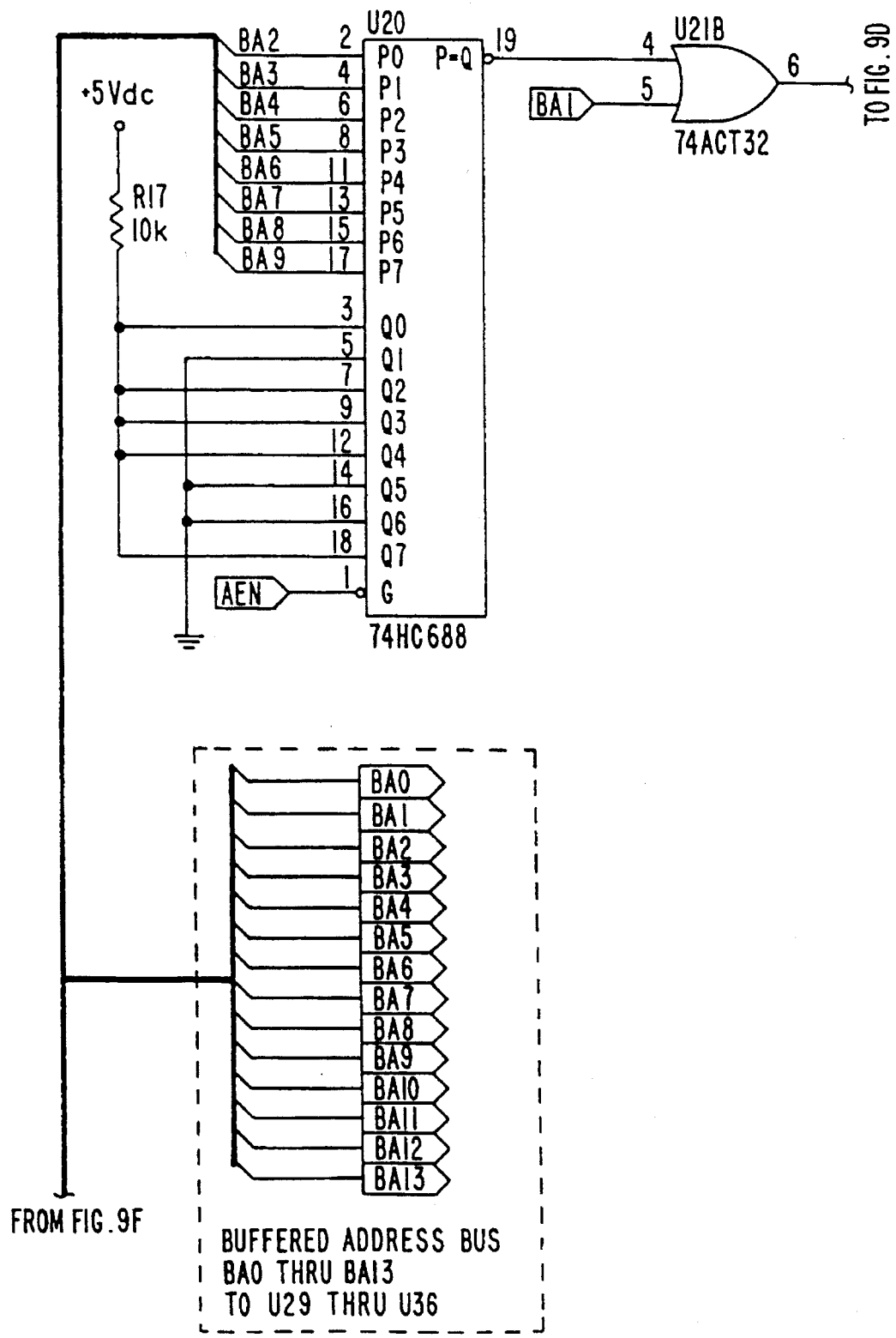
Figure 9F:
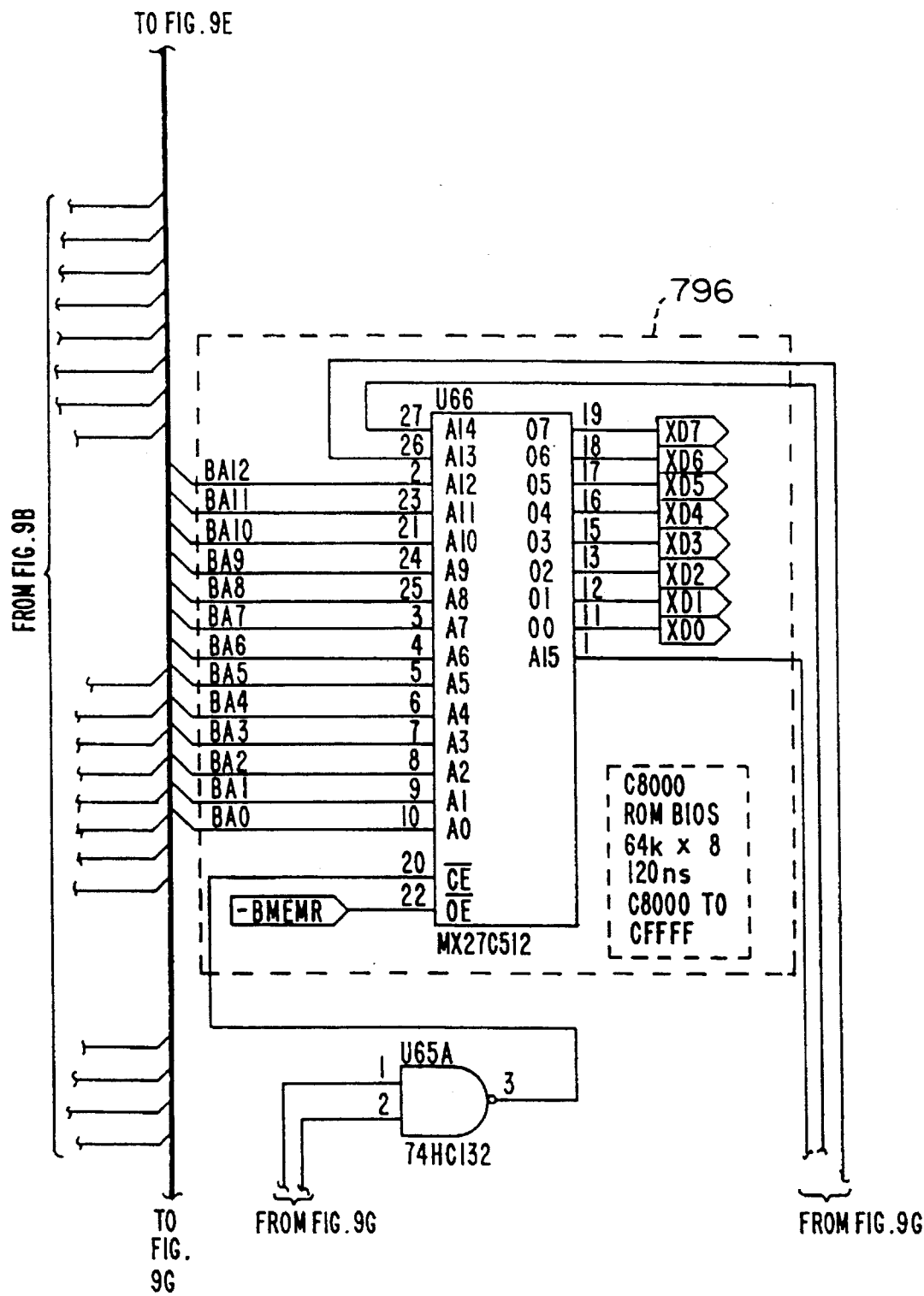
Figure 9G:
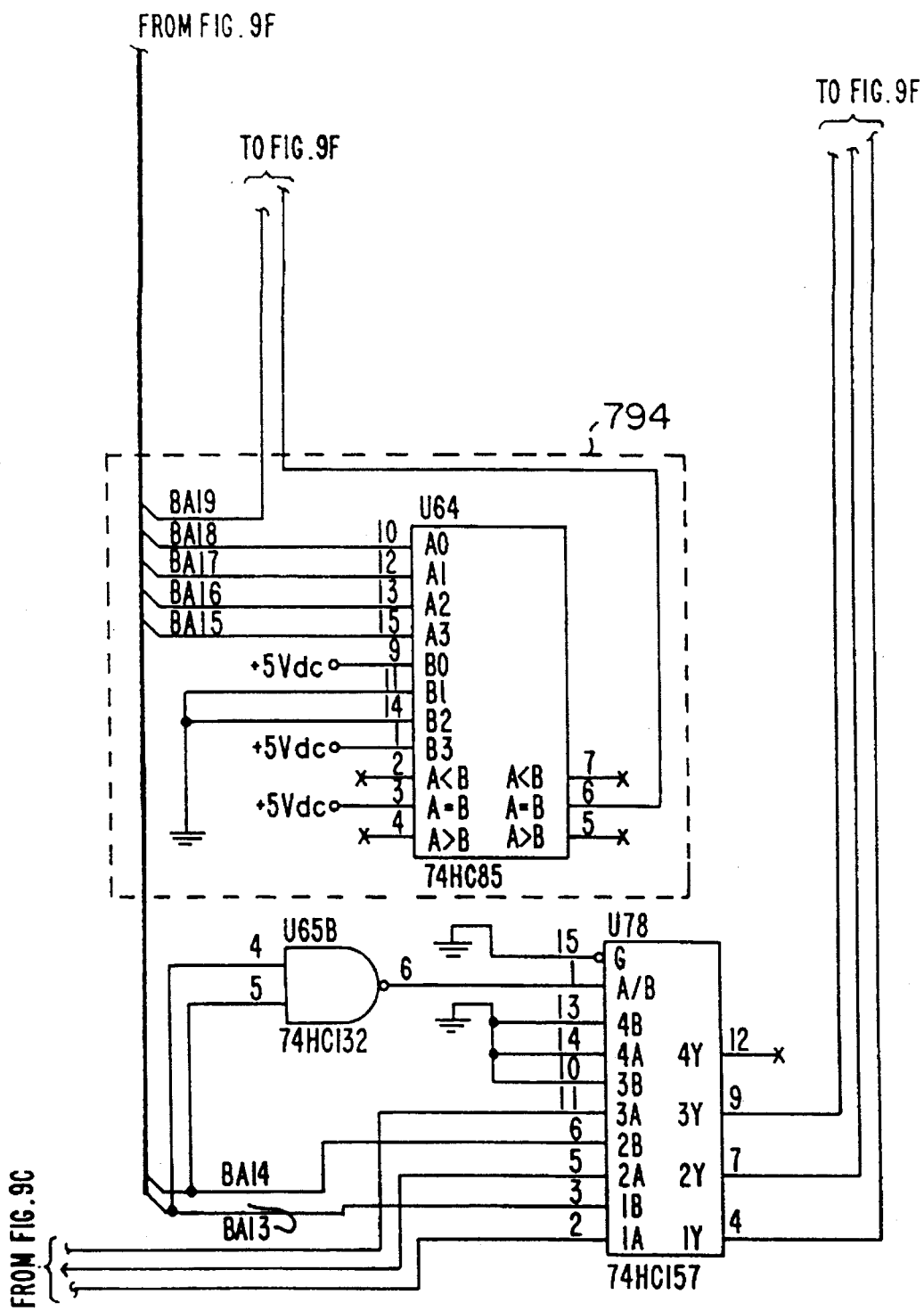
Figure 9H:
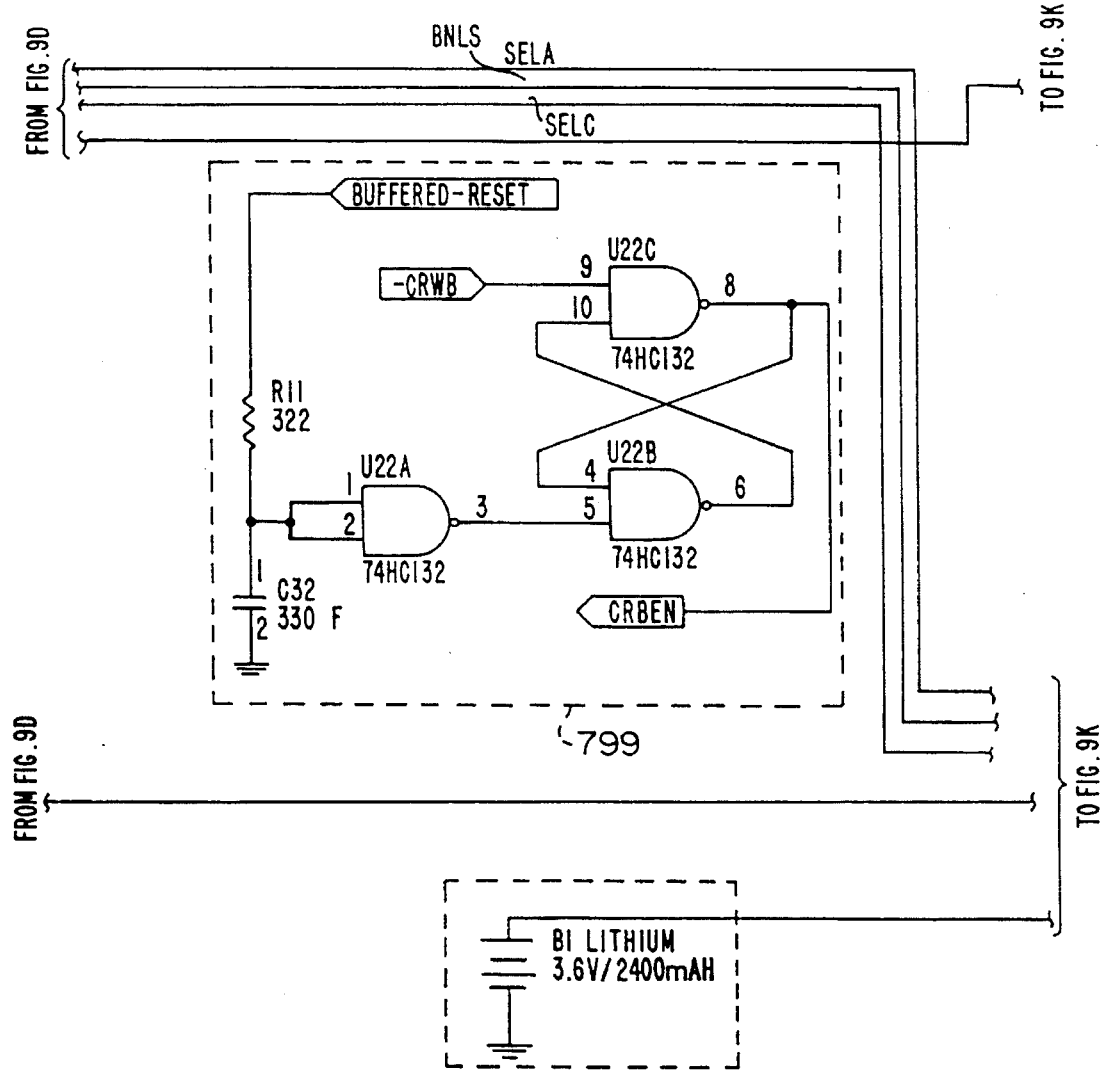
Figure 9I:
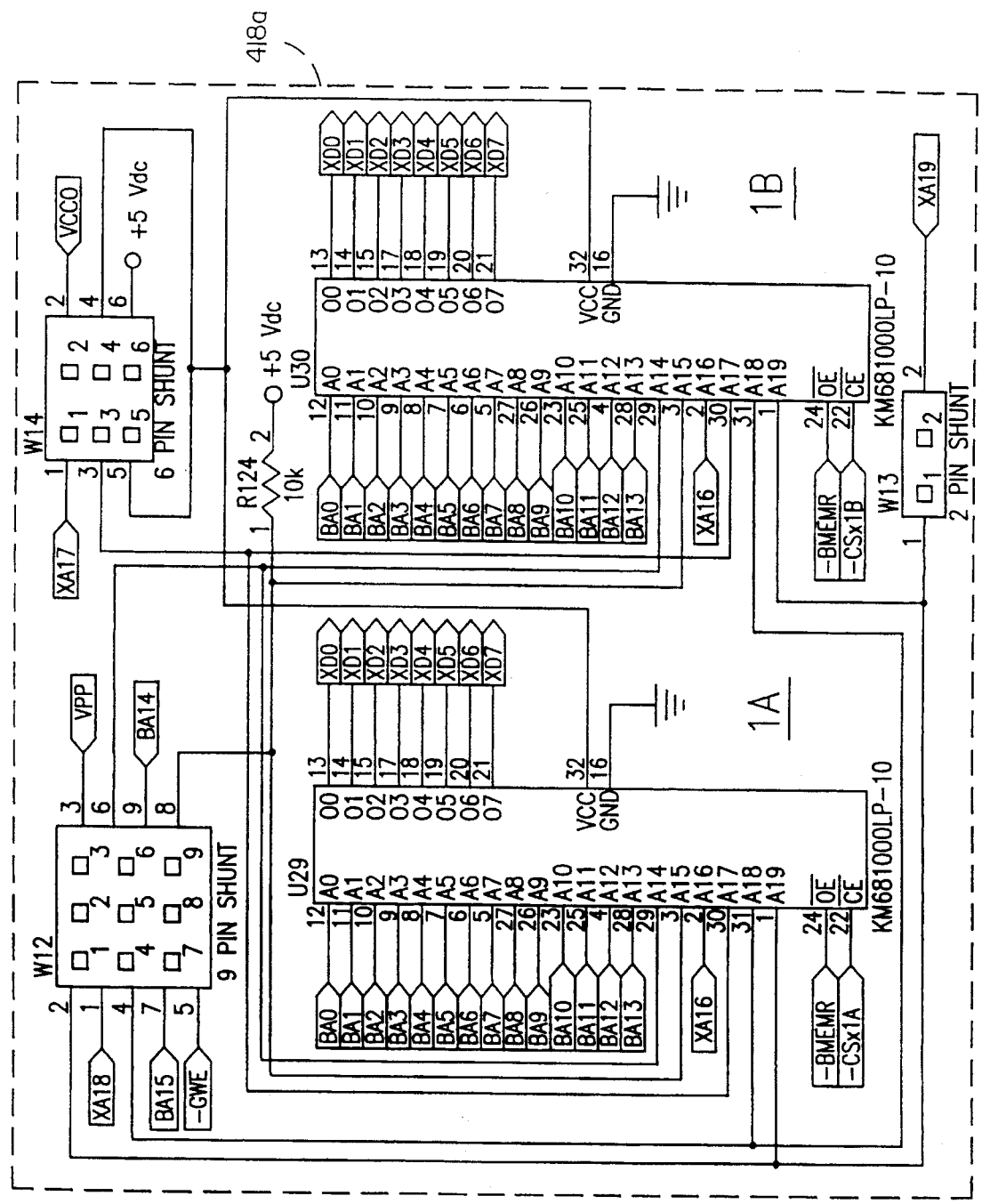
Figure 9J:
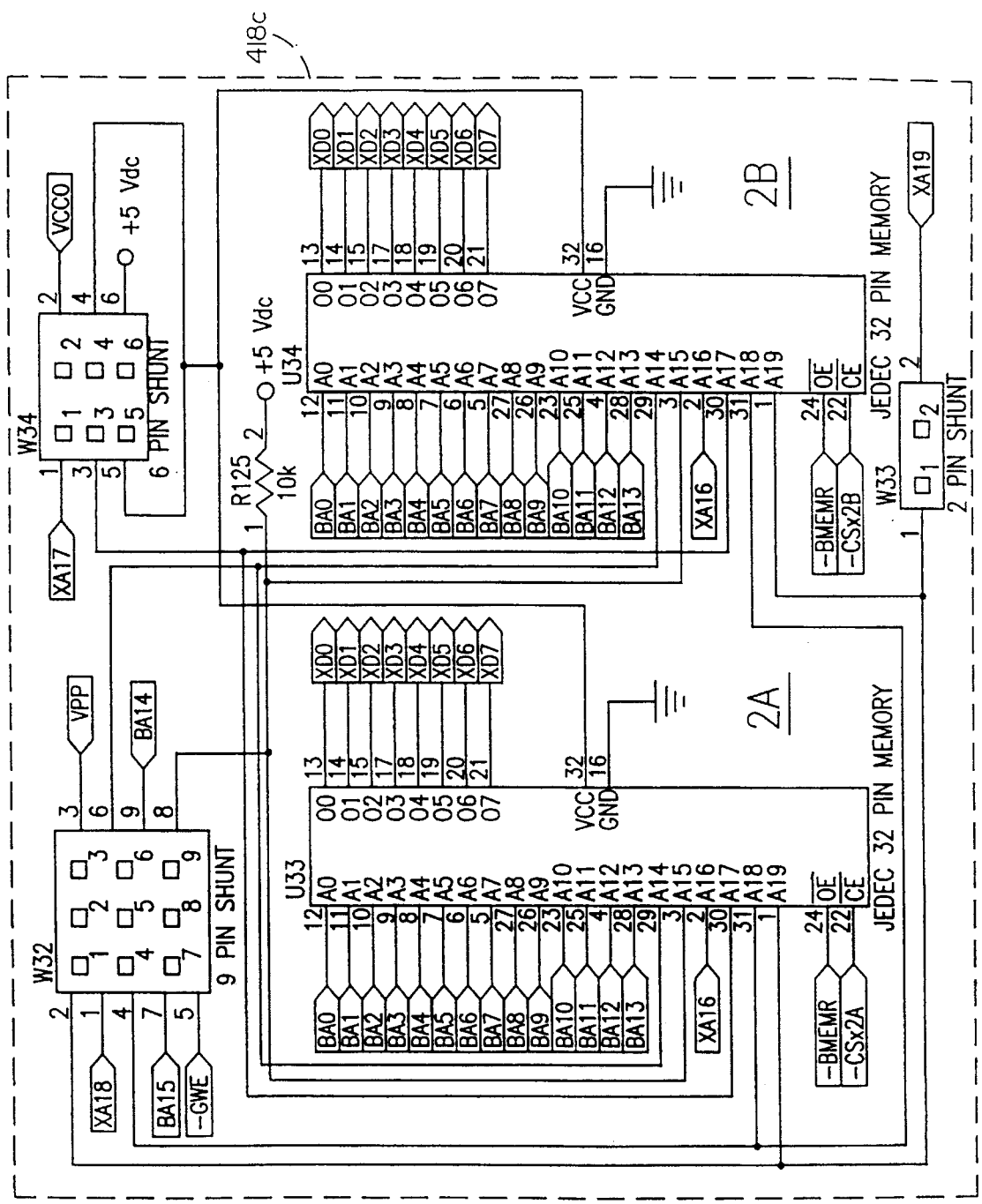
Figure 9K:
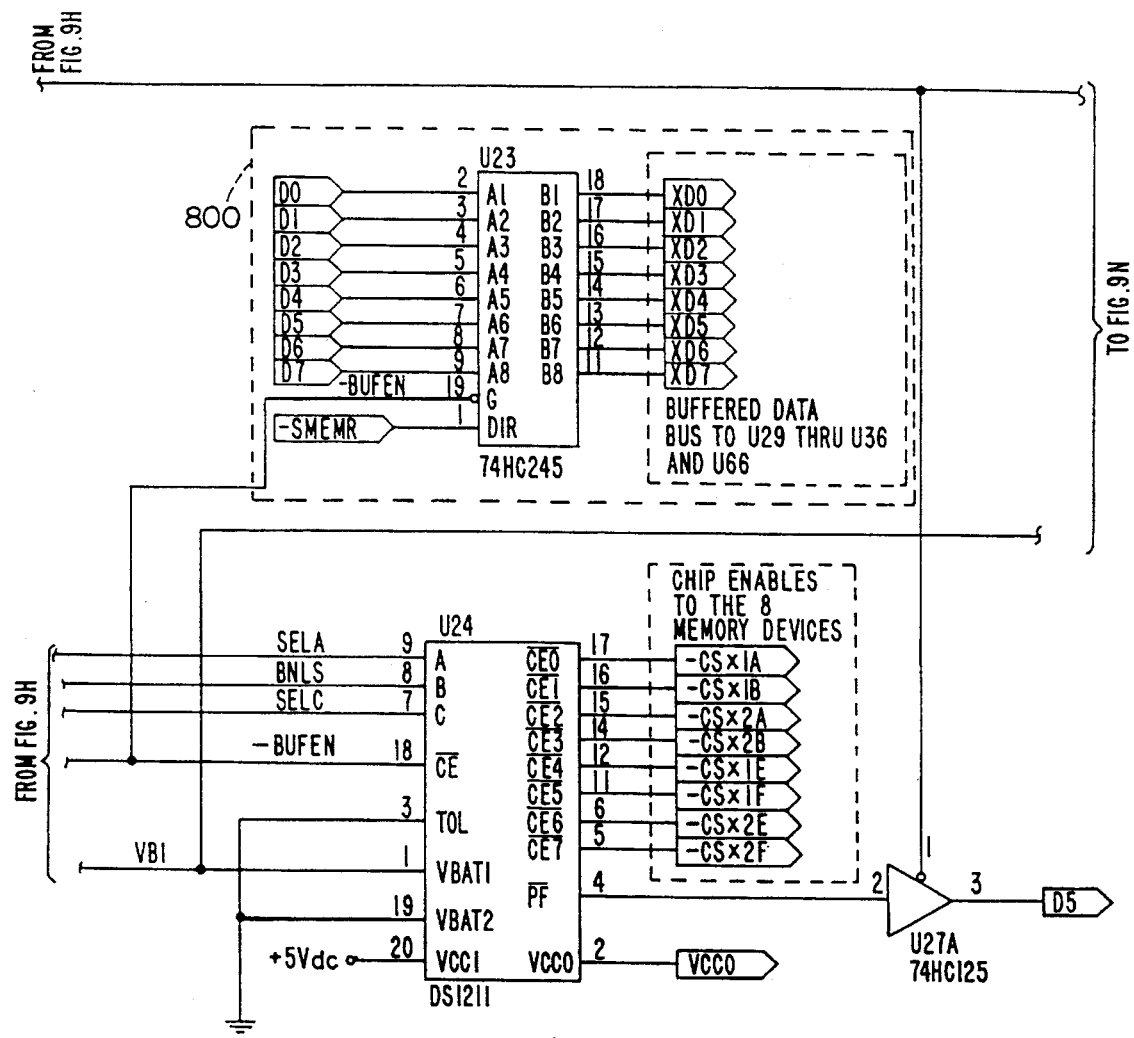
Figure 9L:
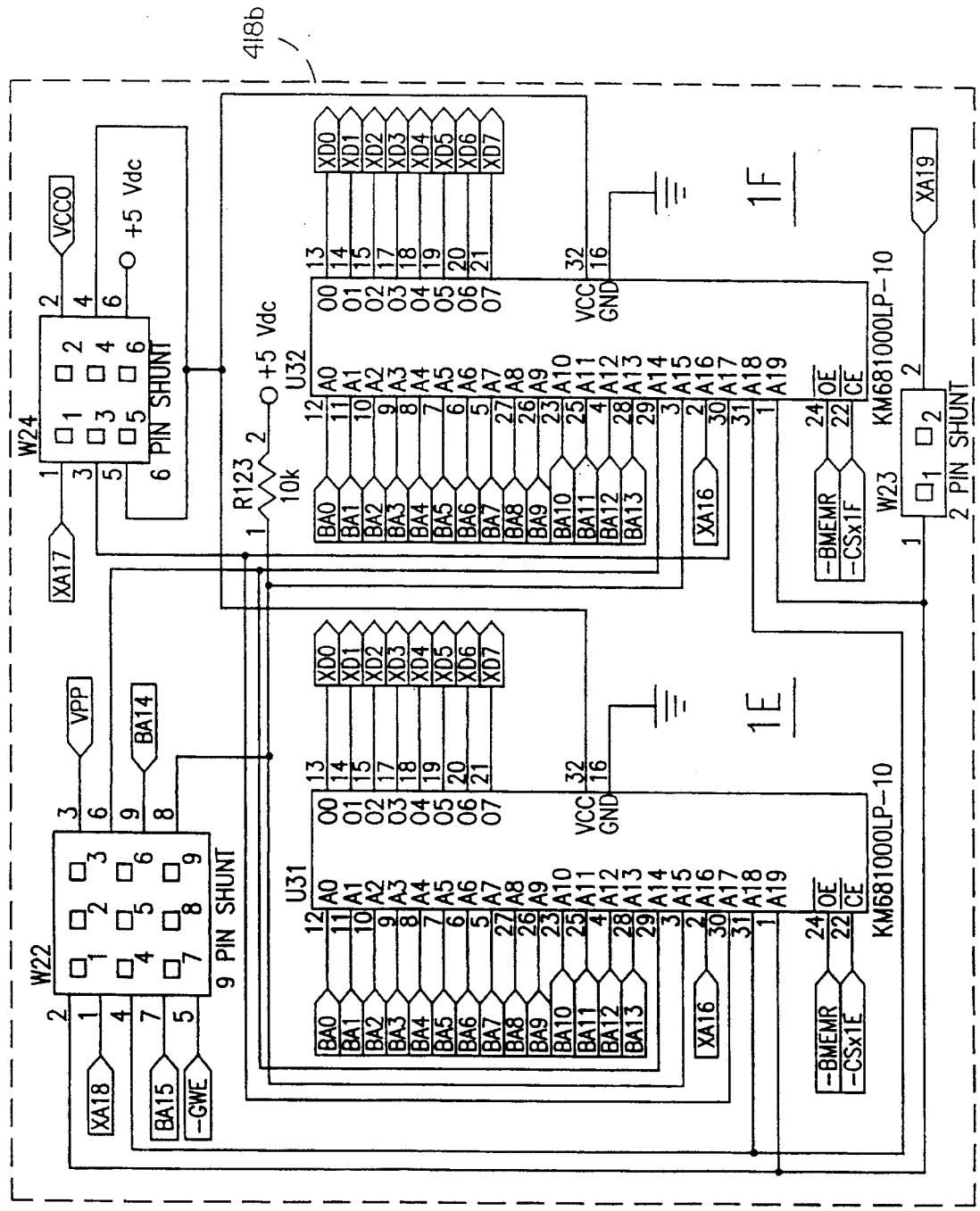
Figure 9M:
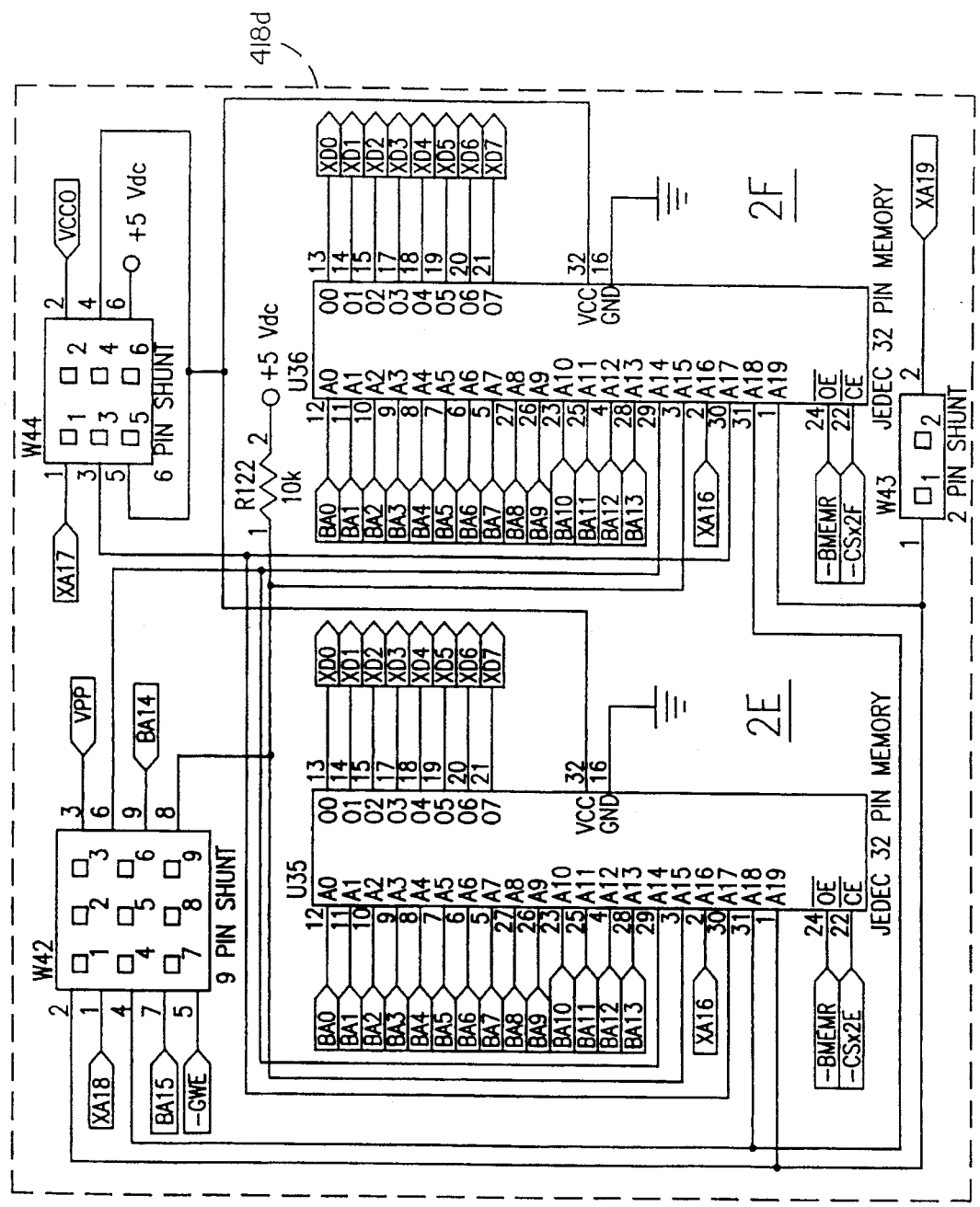
Figure 9N:
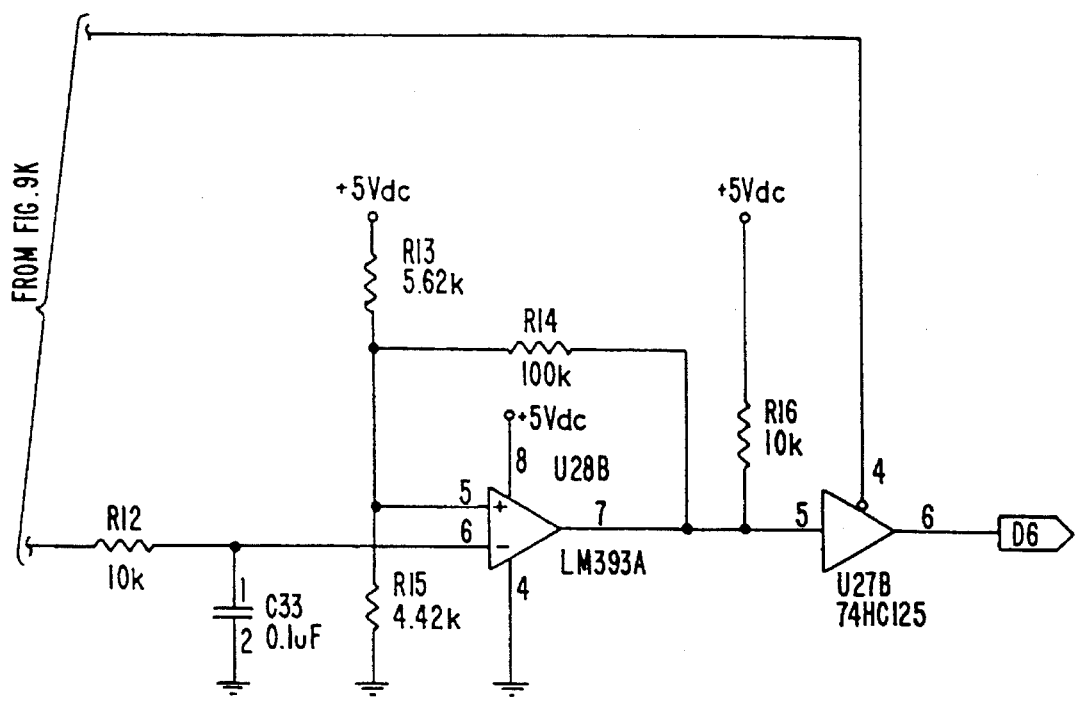
Figure 90:
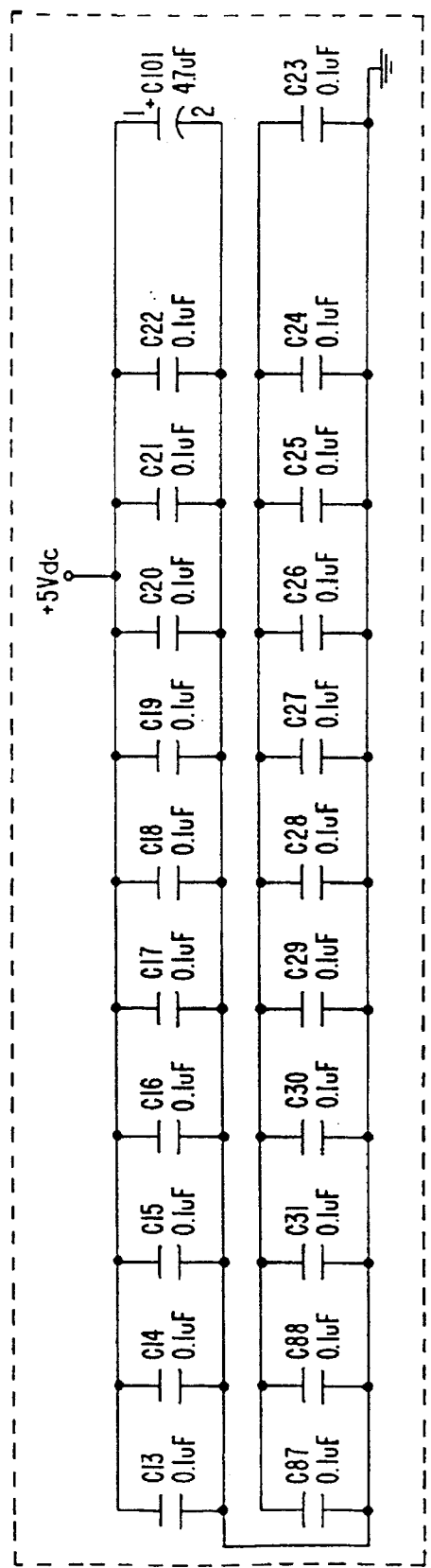
Figure 9P:
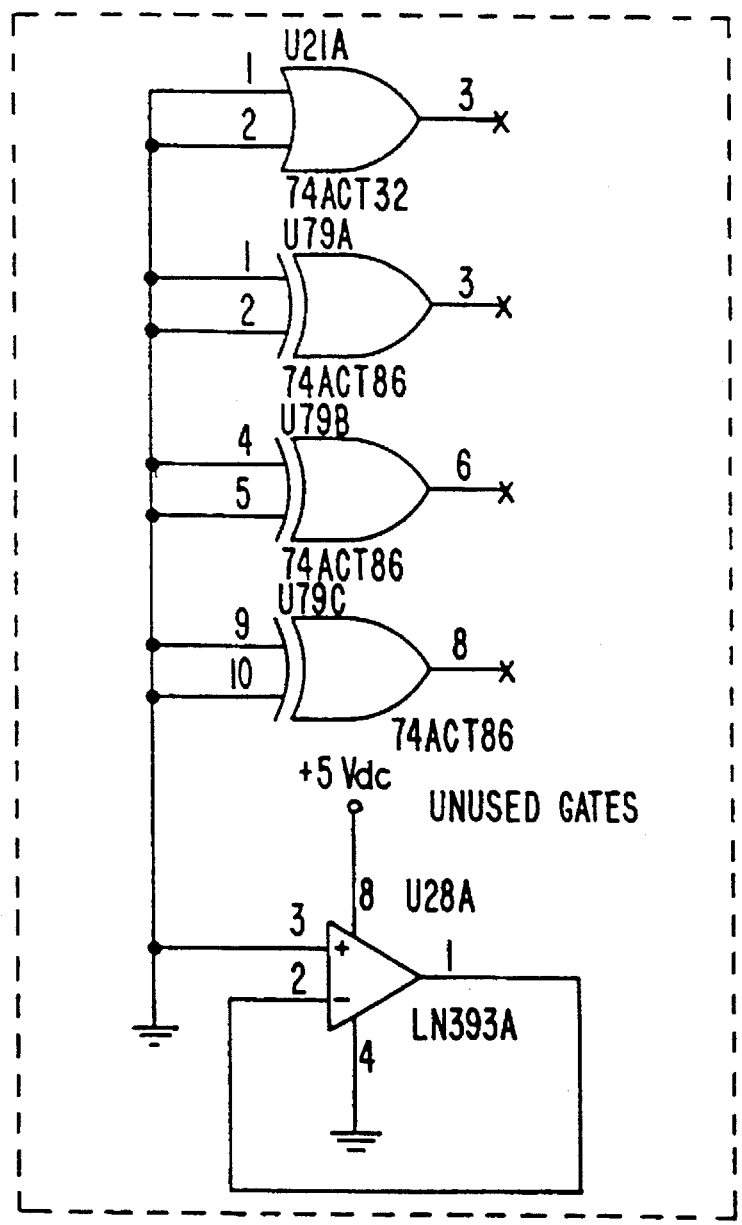
Figure 9Q:
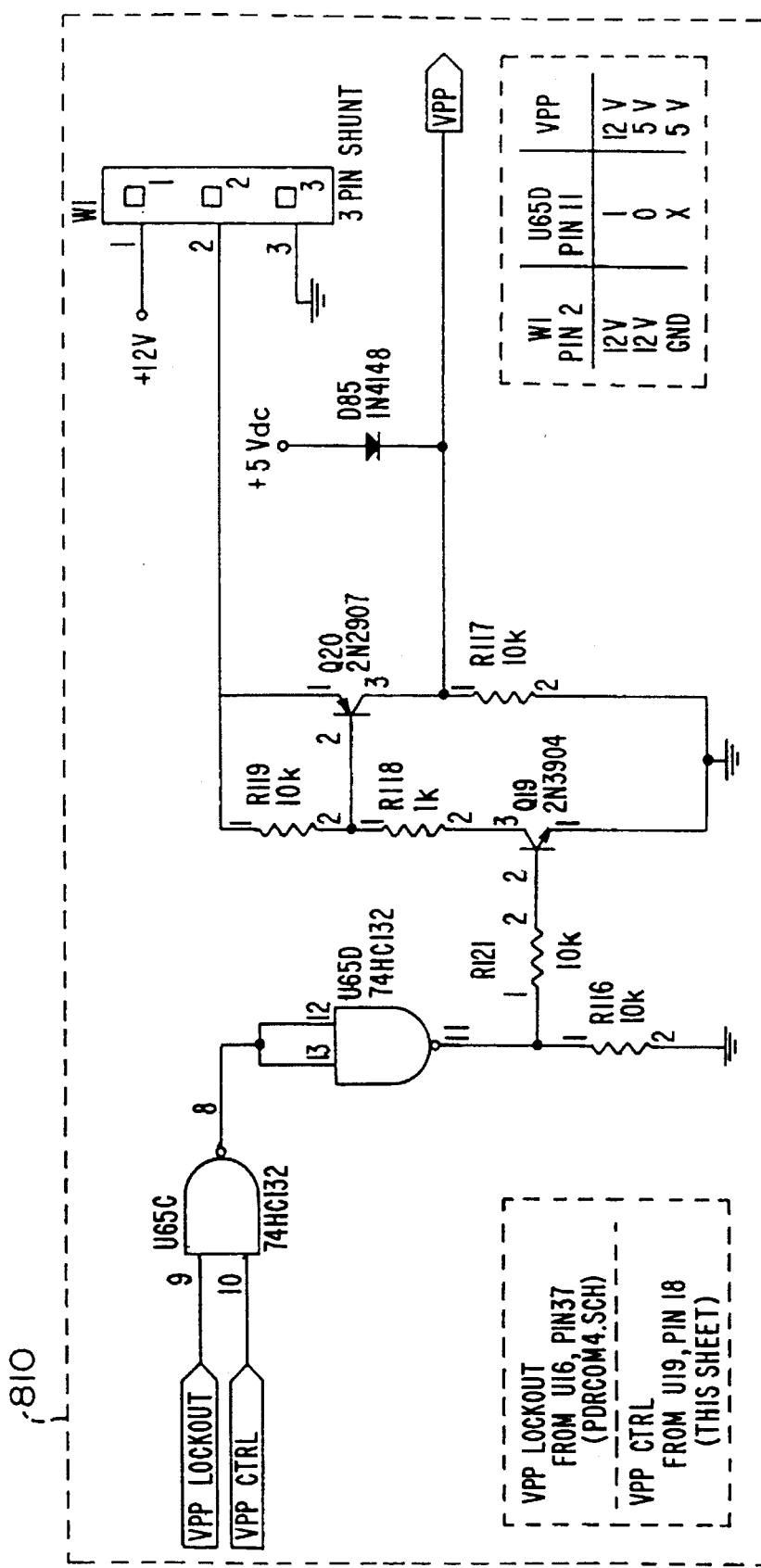
Figure 10B:
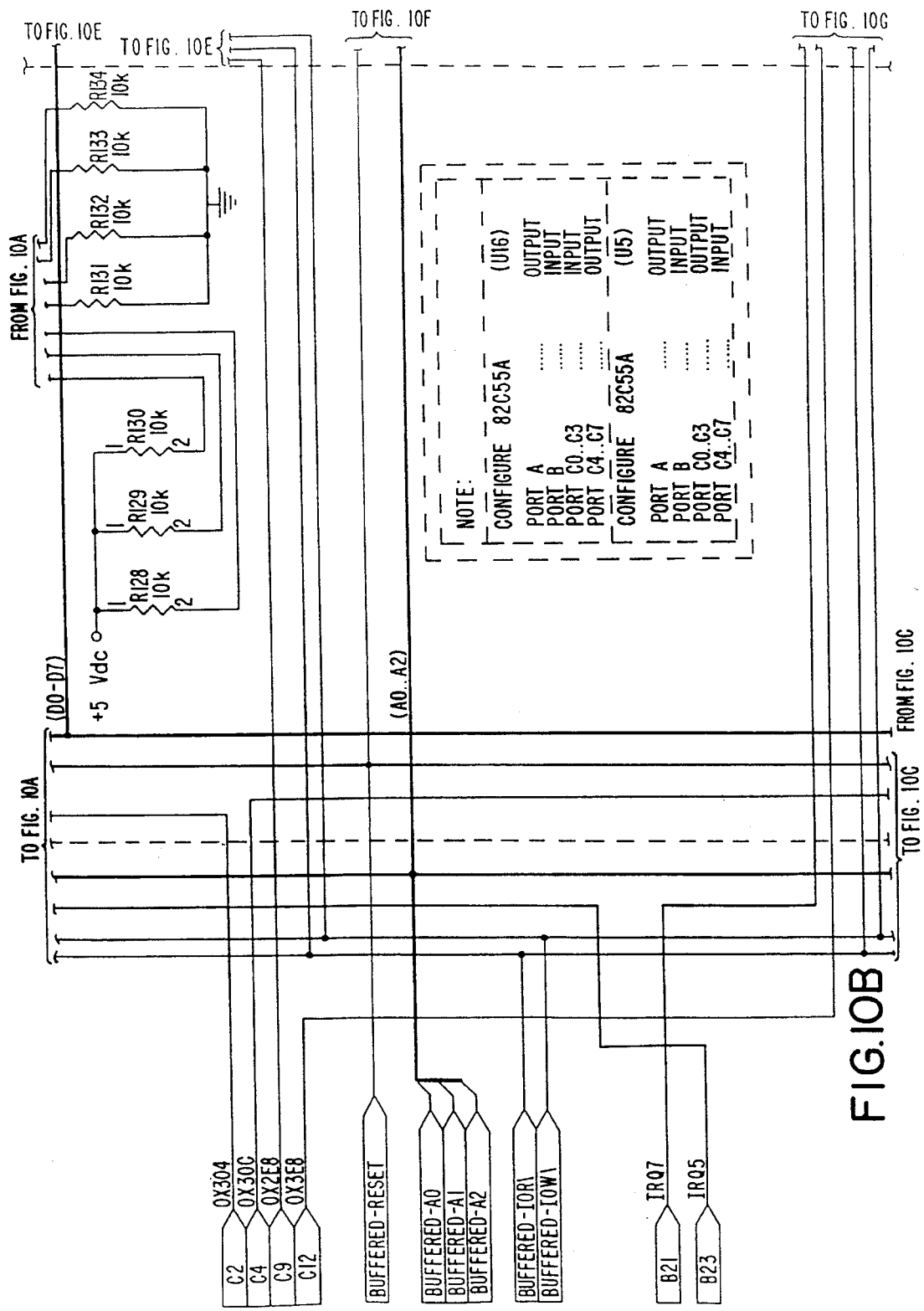
FIG. 10 is a schematic diagram of an exemplary Communications Section Circuit of the remote base unit of FIG. 4.
Figure 10F:
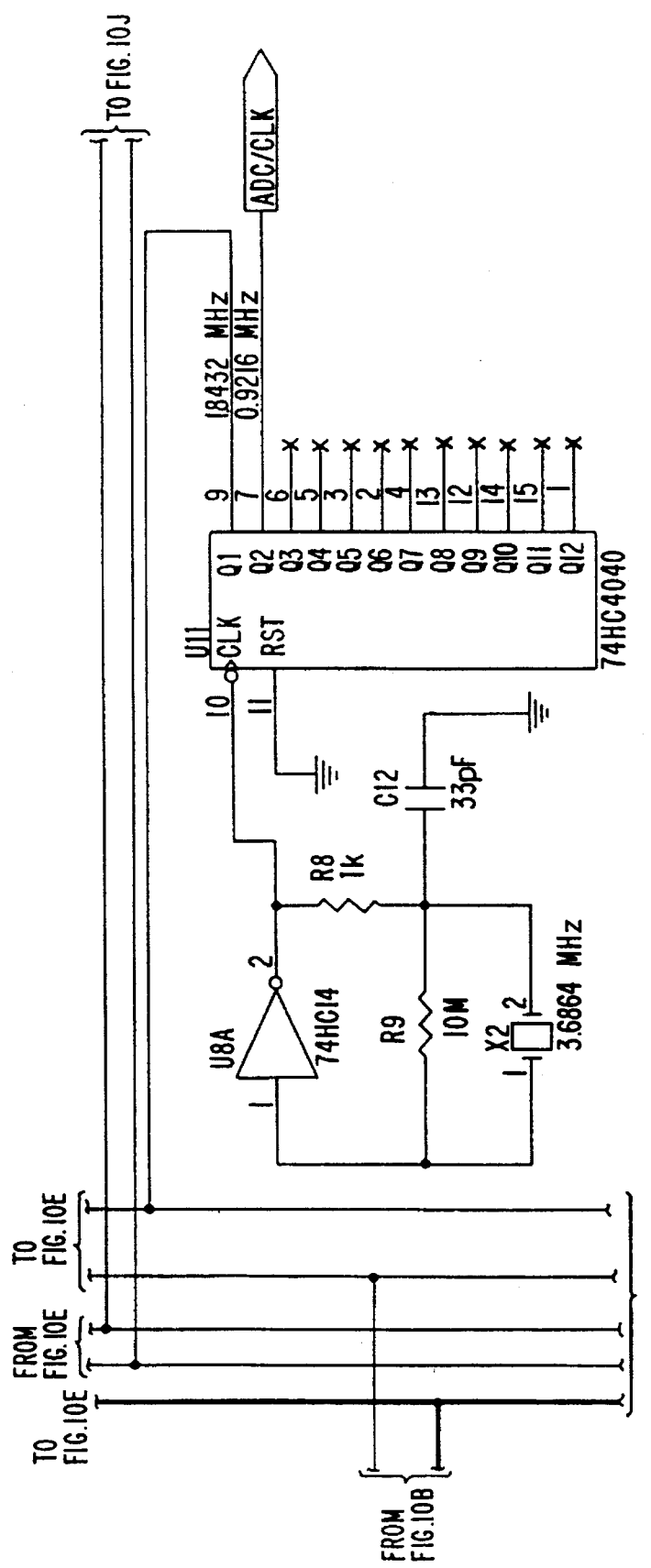
Figure 10G:
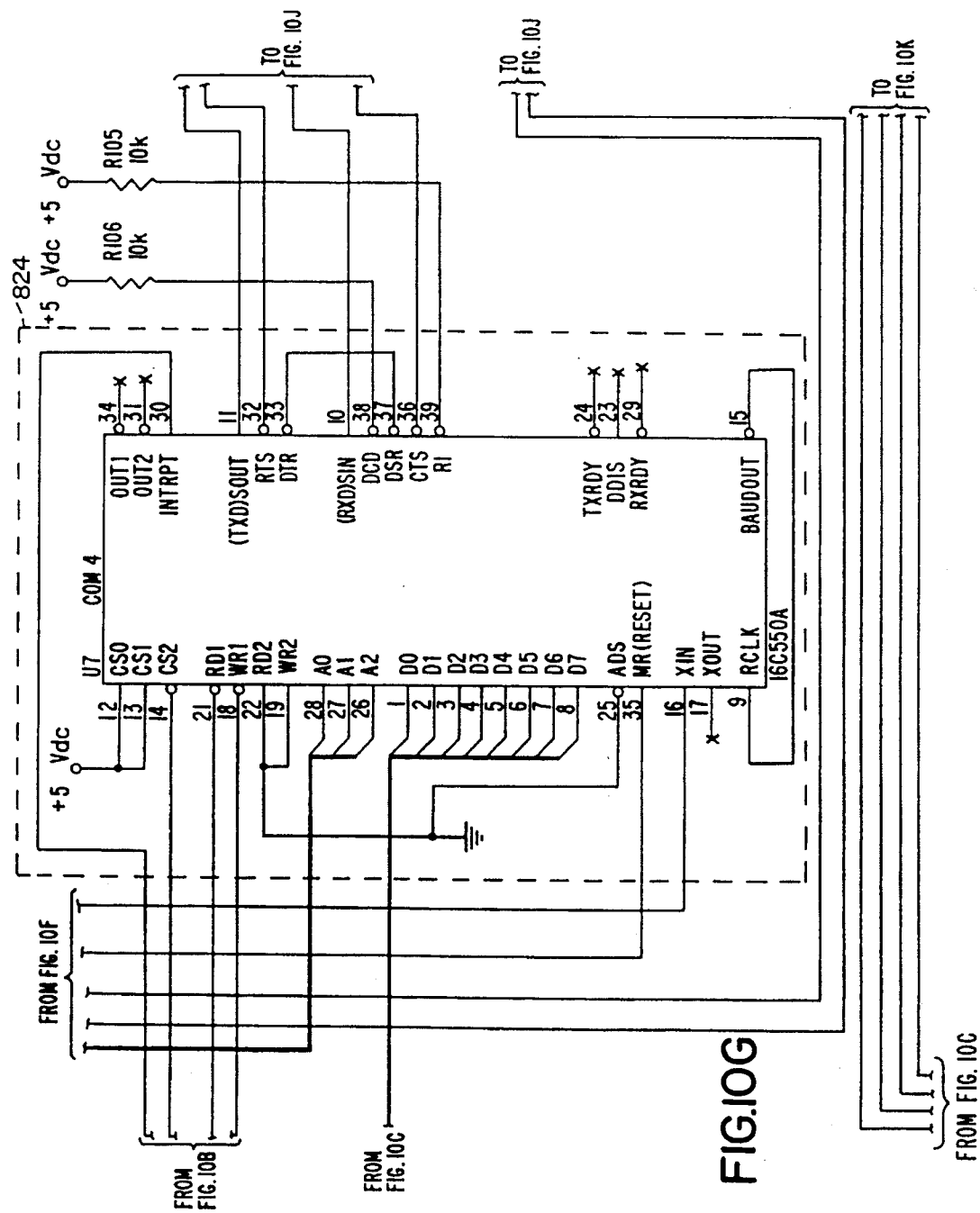
Figure 10H:
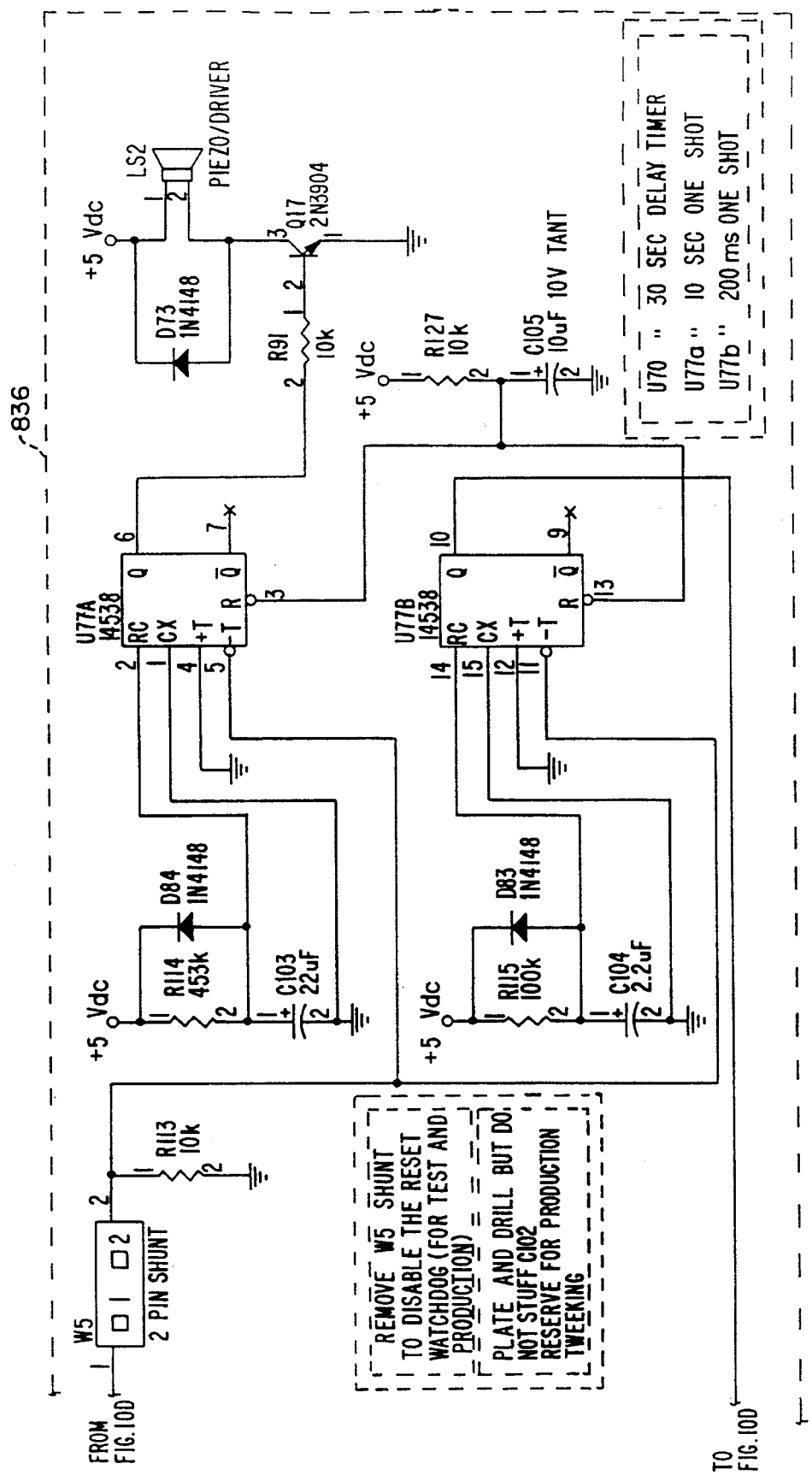
Figure 10K:
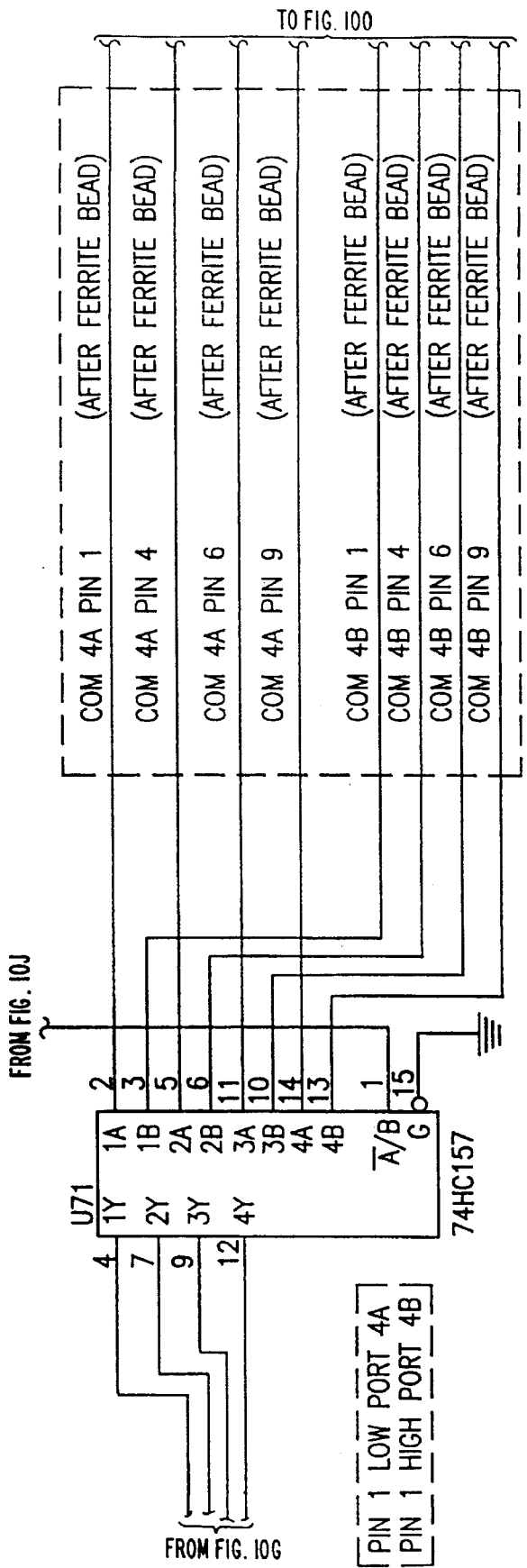
Figure 10L:
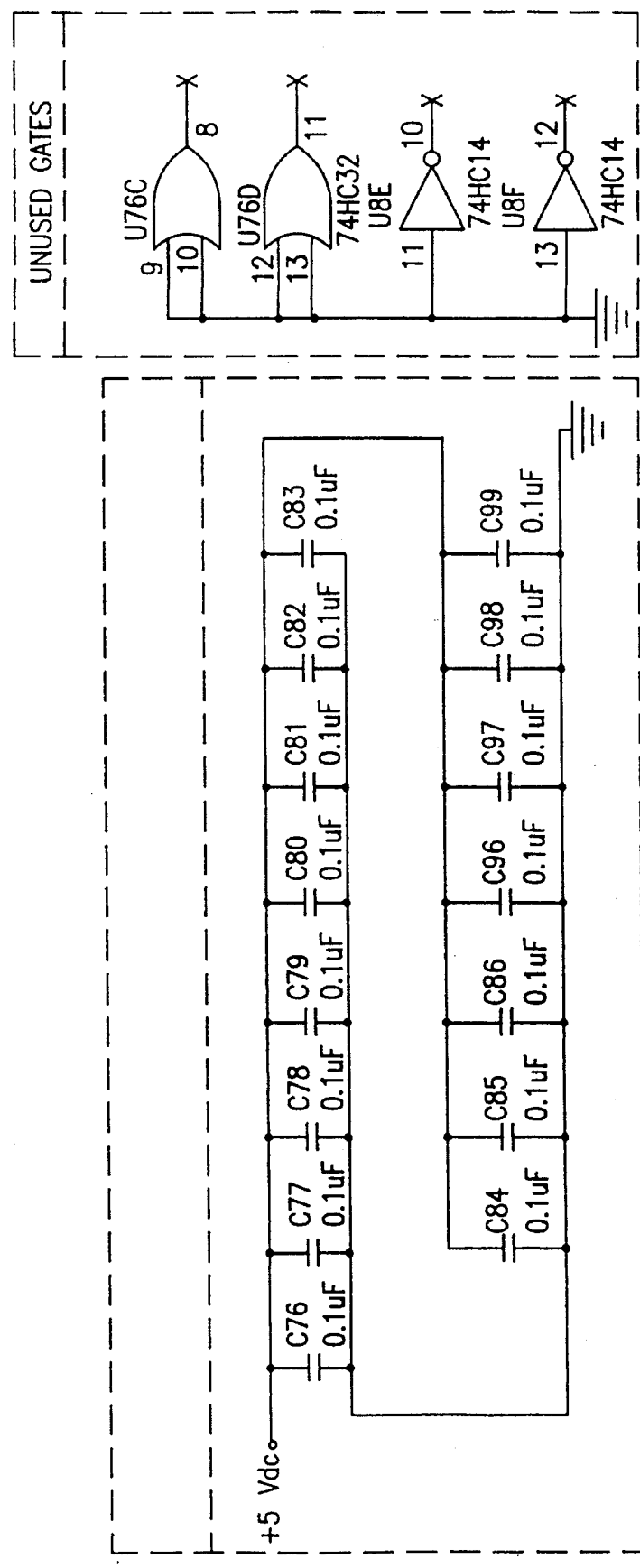
Figure 10N:
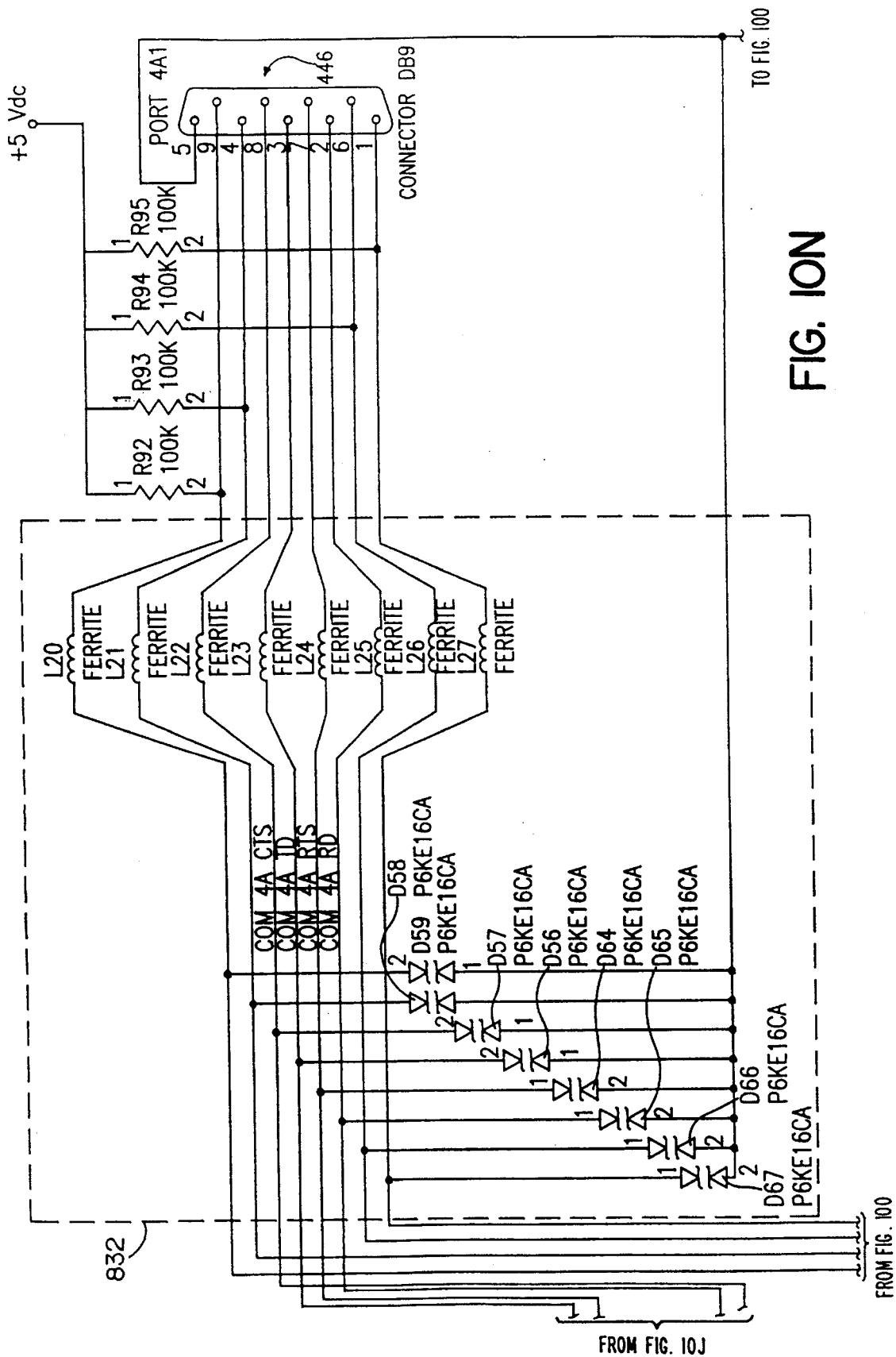
Figure 10O:
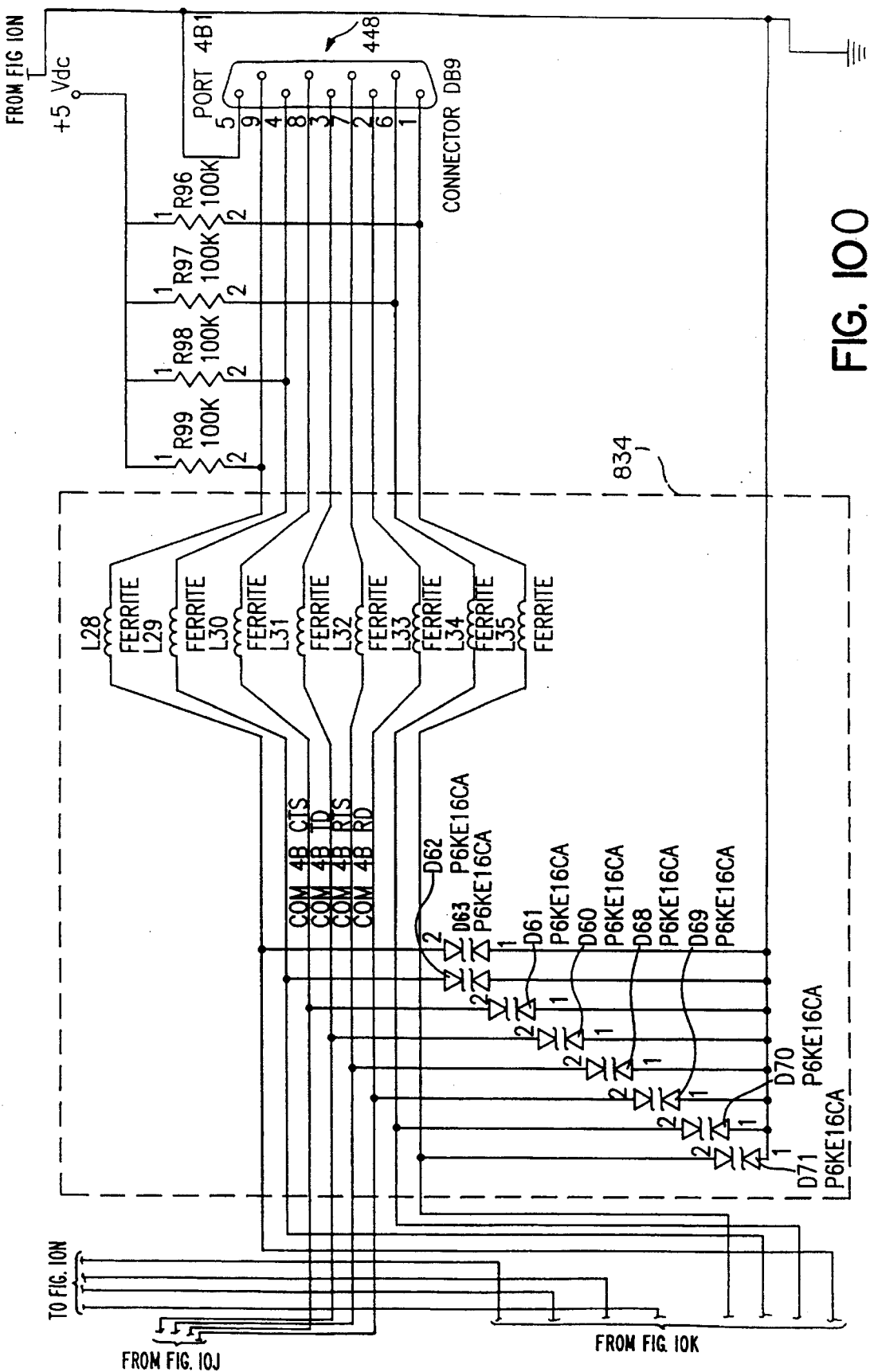

FIG. 8 is a schematic of the temperature and scale board 420. It comprises an analog-to-digital converter (ADC) 770, temperature signal procession 772 and a weight scale signal processor 774. As shown in FIG. 8, the ADC 770 accepts analog inputs from multiple channels. In the present embodiment, the ADC 770 accepts inputs from 3 channels. The low voltage sense signals from the RBU 150 enter the ADC 770 which converts the sense signals to digital form upon request by the CPU 412. The digitized values are read by the CPU 412 via a conventional data bus connecting the ADC 770 to the CPU 412.

As shown in FIG. 8, the temperature scale signal processor 772 is connected to an external temperature probe 124 (FIG. 4) via a connector 443 in the storage bay 440, and comprises a temperature probe presence detect signal line 776, an autocalibration circuit 778, a gain and offset circuit 780 and a filter 782. When the temperature probe 124 is plugged into the connector 443, the temperature presence detect signal line 776, which is read by the CPU 412 (FIG. 4), is grounded by the temperature probe 124, thereby indicating that the probe 124 is plugged in. A second signal is concurrently provided by the probe 124 to an autocalibration circuit 778, which calibrates the scale to be used in measuring the incoming signal. Calibration is performed by the software. The gain and offset circuit 780 then amplifies the signal from the temperature probe 124 so as to correspond to the range of the ADC 770, and offsets the signal to take full advantage of the ADC's range. The signal is then filtered through filter 782 to eliminate random noise and then provided to the ADC. The CPU 412 will then read the output of the ADC 770.

The weight scale signal processor 774 is also connected to an external weight scale 122 (FIG. 4), via connector 470. The processor 774 comprises a scale presence detect signal line 784, a scale gain potentiometer 786, a gain and offset circuit 788 and a filter 790. The scale presence detect signal line 784 detects the presence of an external scale 122 in the same manner as the temperature probe 124 presence detect signal line 776. A second signal provided by the scale 122 is concurrently provided to the scale gain potentiometer 786, which sets the signal range for proper digitization for the ADC 770. The signal is then provided to a gain and offset circuit 788. The gain and offset circuit 788 then amplifies the signal so as to correspond to the range of the ADC 770, and offsets the signal to take full advantage of the ADC's range. The signal is then filtered via filter 790 to eliminate random noise and then provided to the ADC 770. The CPU 412 will then read the output of the ADC 770.

FIG. 9 illustrates the Memory Interface Circuit 430 of the RBU 150 diagrammed in FIG. 4. The Memory Interface Circuit 430 comprises an address bus buffer 792, a boot microprocessor decoder 794, a ROM BIOS Hook 796, a data decoder 798, a run decoder 799, a data bus buffer 800, a memory module with 4 sets of memory 418a, 418b, 418c, 418d and a programmable configuration change circuit 810.

The memory module 418, connected to the CPU 412 (FIG. 4) via a conventional data bus, comprises 64 Kbytes of Read Only Memory (ROM) used for the Basic I/O System (BIOS), 1 Megabyte of ROM used for the operating system and applications software and up to 32 Megabytes of Random Access Memory (RAM).

Signals from the CPU 412 are provided to the address bus buffer 792 which provides a boost to signal strength along the address bus. The address bus buffer 792 then provides the signals to the boot microprocessor decoder 794 which decodes ROM addresses and enables the ROM BIOS hook 796. The ROM BIOS hook 796 provides a mechanism for allowing the software to be executed during the boot-up process. The signals are then provided to the data bus buffer 800 which ensures that the memory circuits are adequately driven and the programmable configuration change circuit 810 permits changes in configuration to be implemented. These signals are then provided to the memory modules 418 which reside on the same circuit board as the memory interface circuit 430.

Signals from the CPU 412 are also provided to the data decoder 798 which provides selection of the correct channels. These signals are then provided to the run decoder 799 which coordinates signal flow. Signals from the run decoder are then provided to the data bus buffer 800, which functions as described above and which provides the signals to the memory modules 418. Signal flow between the CPU 412 and the memory modules 418 via the memory interface board 430 is bi-directional. The components described above are well understood in the art.

As shown in FIG. 10, the Communications Interface Board 440 comprises an I/O Port Decode Circuit 820 implemented by two Universal Asynchronous Receiver/Transmitters 822, 824 (UART) as known in the technology. The UART provides clear-to-send and request-to-send processing used for data flow control. Multiplexers 826, 828 connected to each of the UARTs 822, 824 select microprocessor communication with communications ports 446, 448 and the event switch receptacle 444. The multiplexer 828 is connected via RS232 converter 830 which converts RS 232 voltages to transistor-to-transistor (TTL) voltage levels, as known in the art. The RS 232 converter 830 is connected to two EMI/ESD circuits 832, 834. The EMI/ESD circuits 832, 834 filter extraneous electromagnetic signals from the circuits and are connected to communications ports 446, 448.

Also illustrated in FIG. 10, the Hardware Watchdog Alarm 836 connected to the CPU 412 forces a system reset if the system is not triggered at a predetermined interval, as known in the technology. In the present embodiment, the predetermined interval is 30 seconds and serves to conserve power. The system reset is also announced by a 200 millisecond beep from a small piezoelectric speaker.

Figure 11A:
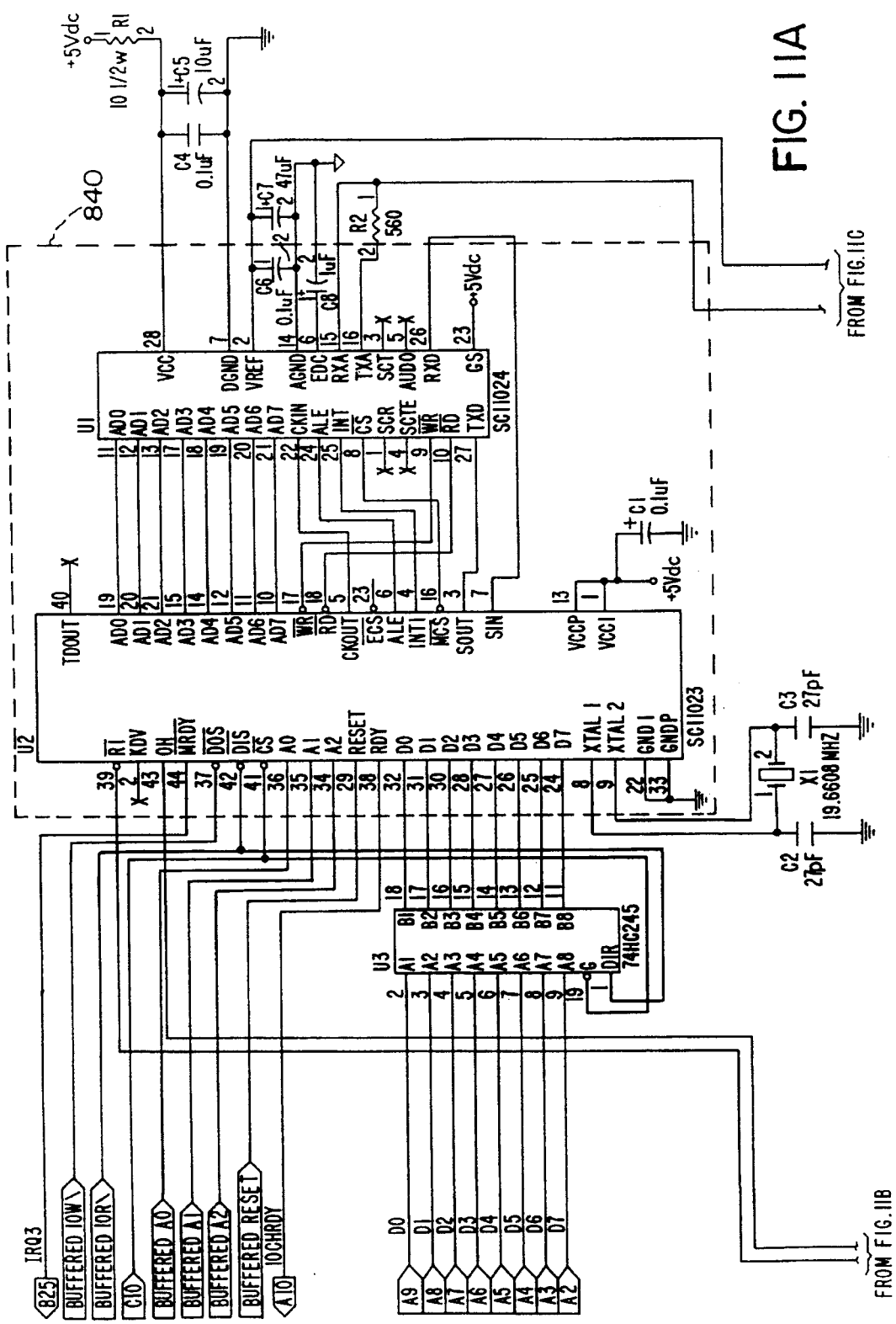
FIG. 11 is a schematic diagram of an exemplary Modem Circuit of the remote base unit of FIG. 4.
Figure 11B:
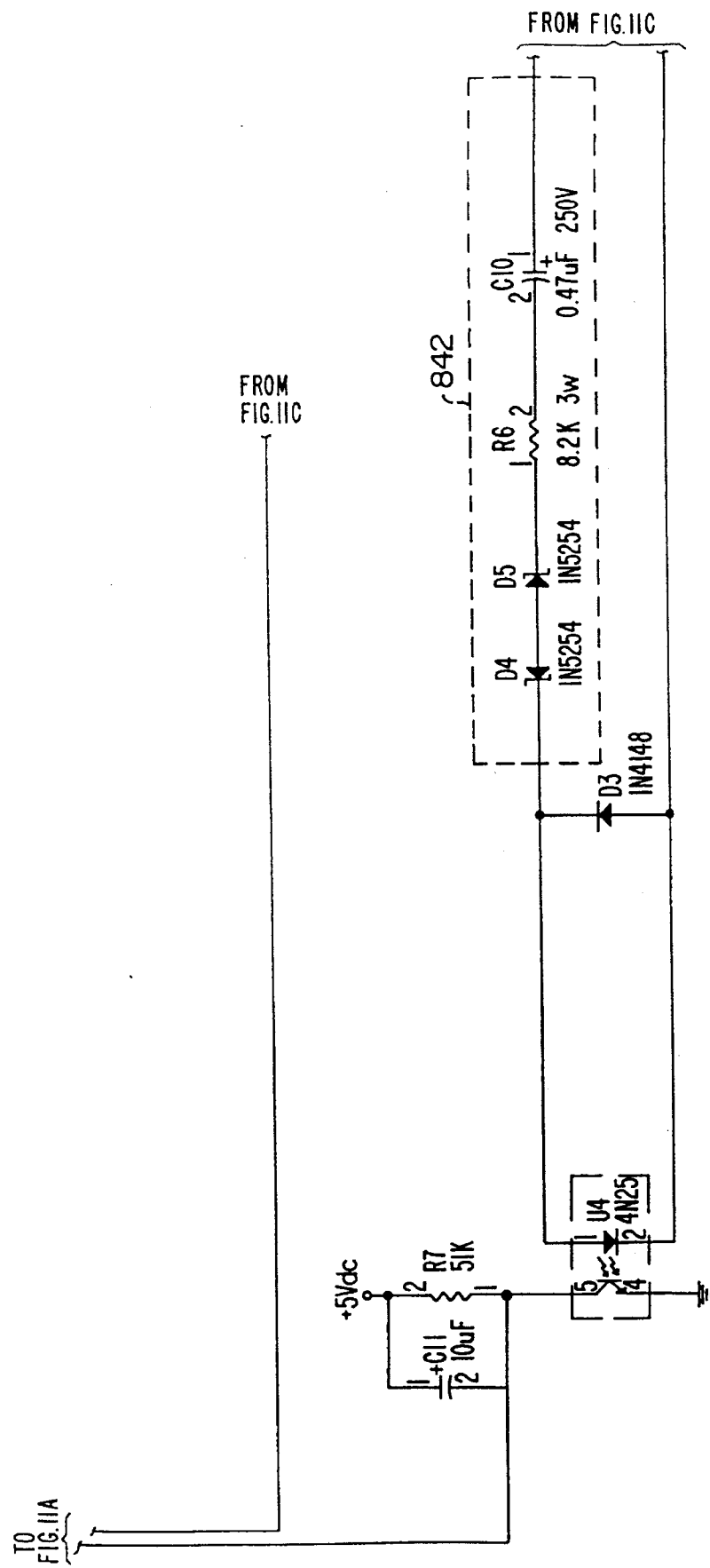
Figure 11C:
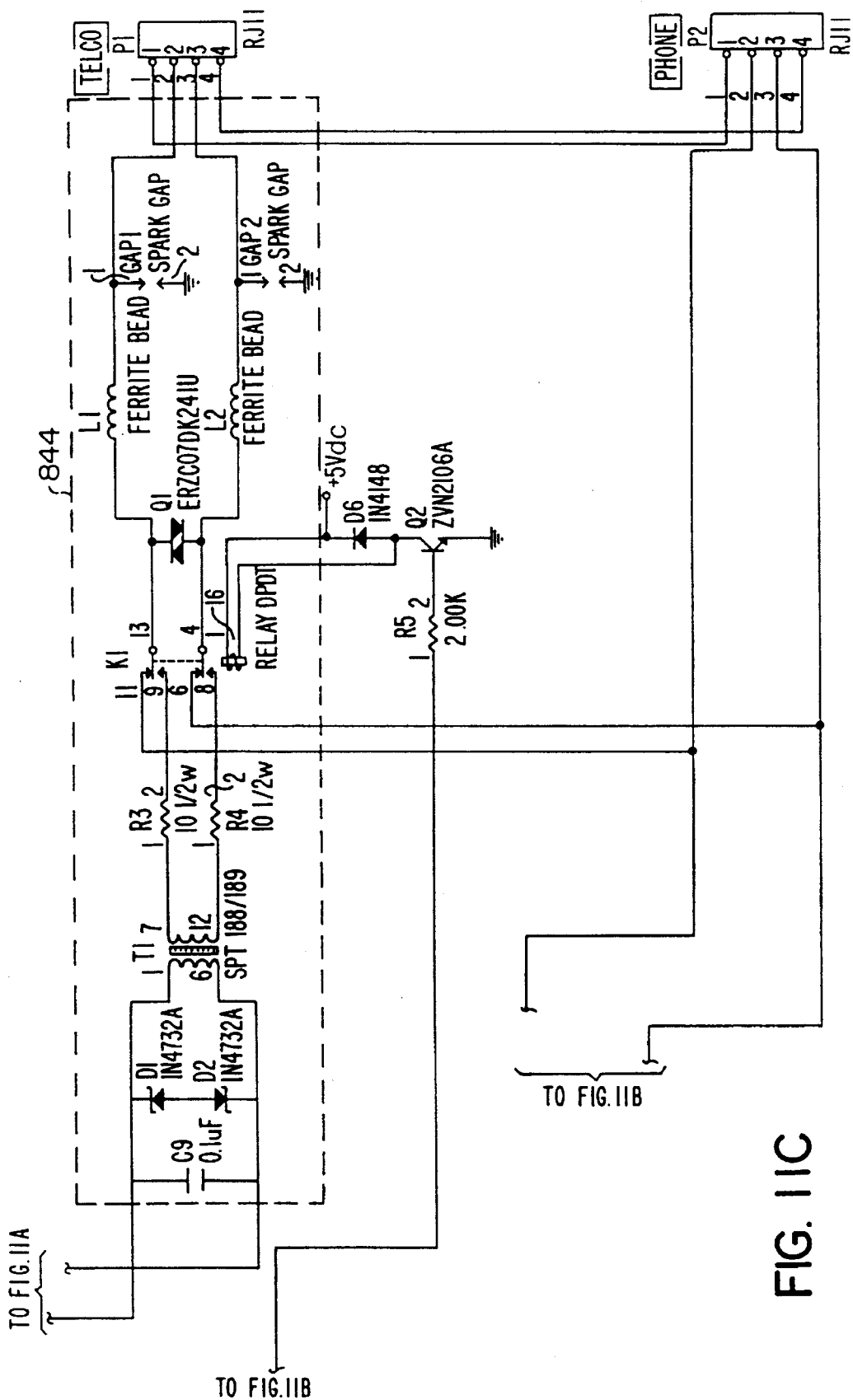
Figure 12A:
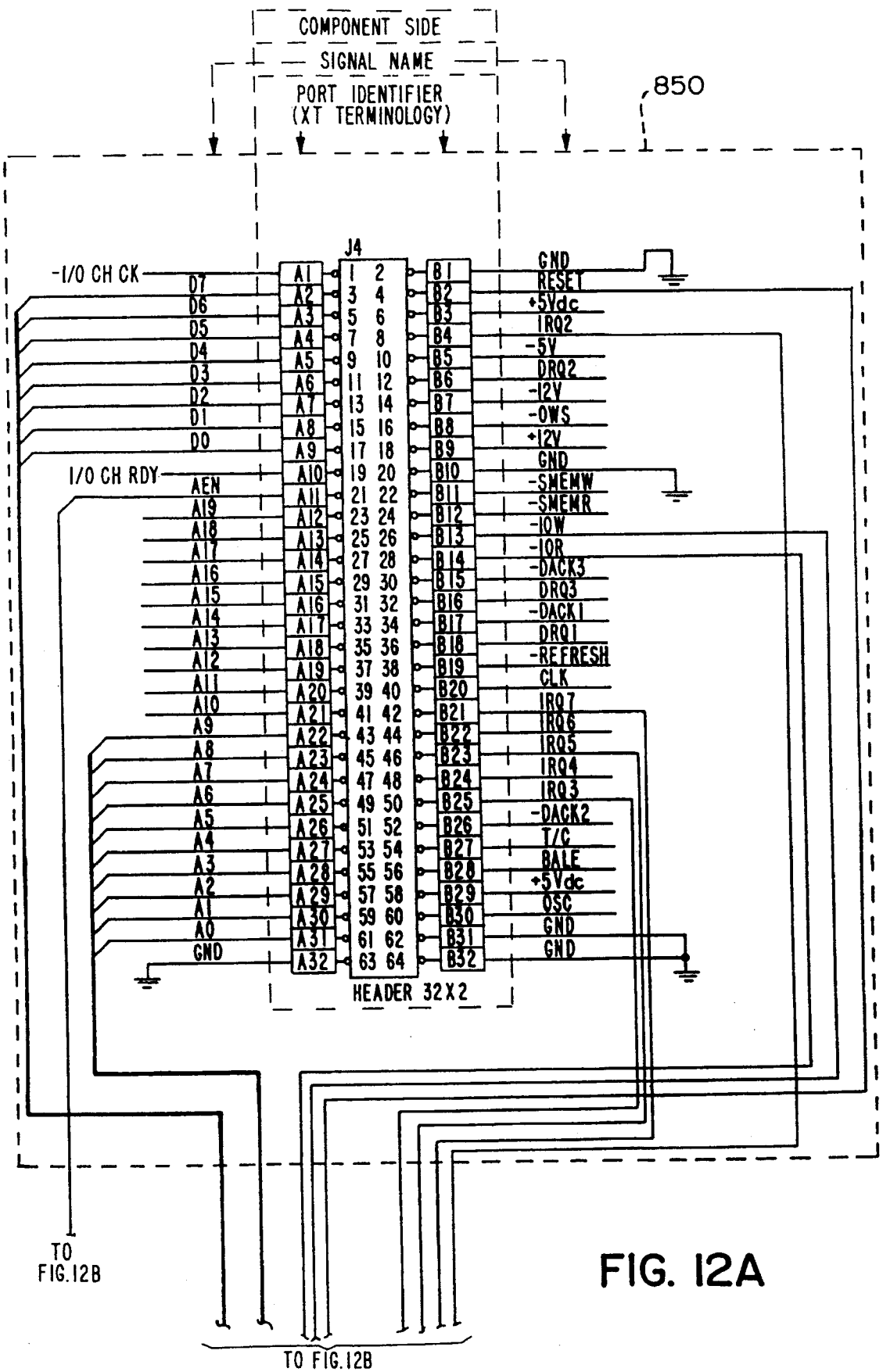
FIG. 12 is a schematic diagram of an exemplary Microprocessor Buffer Decode Circuit of the remote base unit of FIG. 4.
Figure 12C:
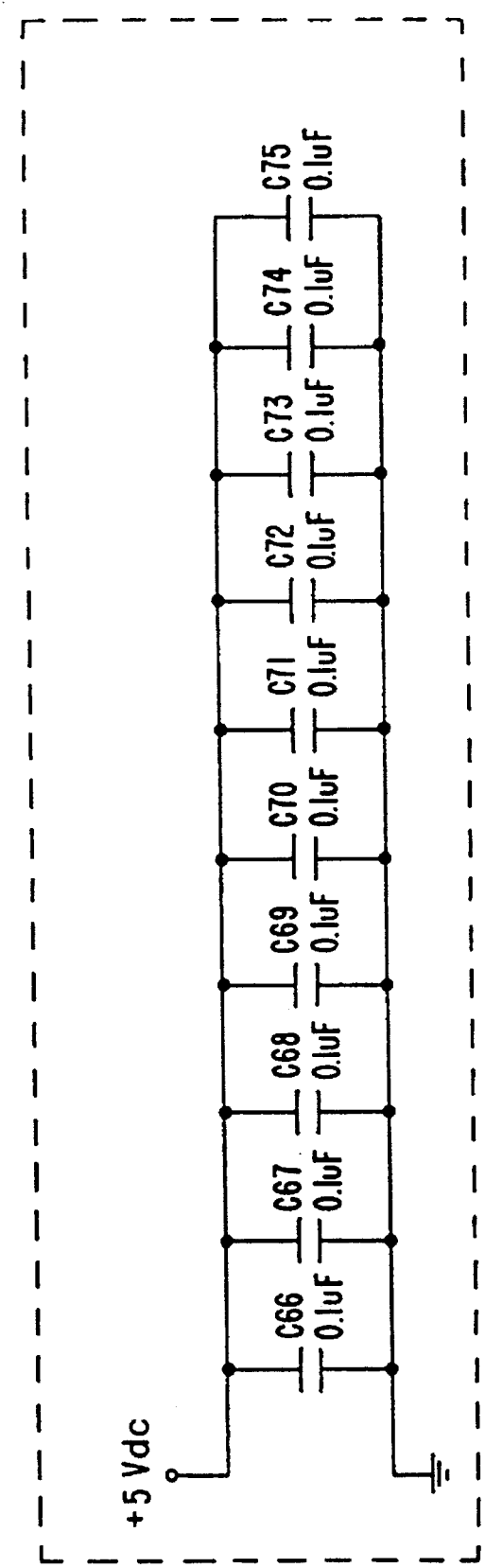
Figure 12D:
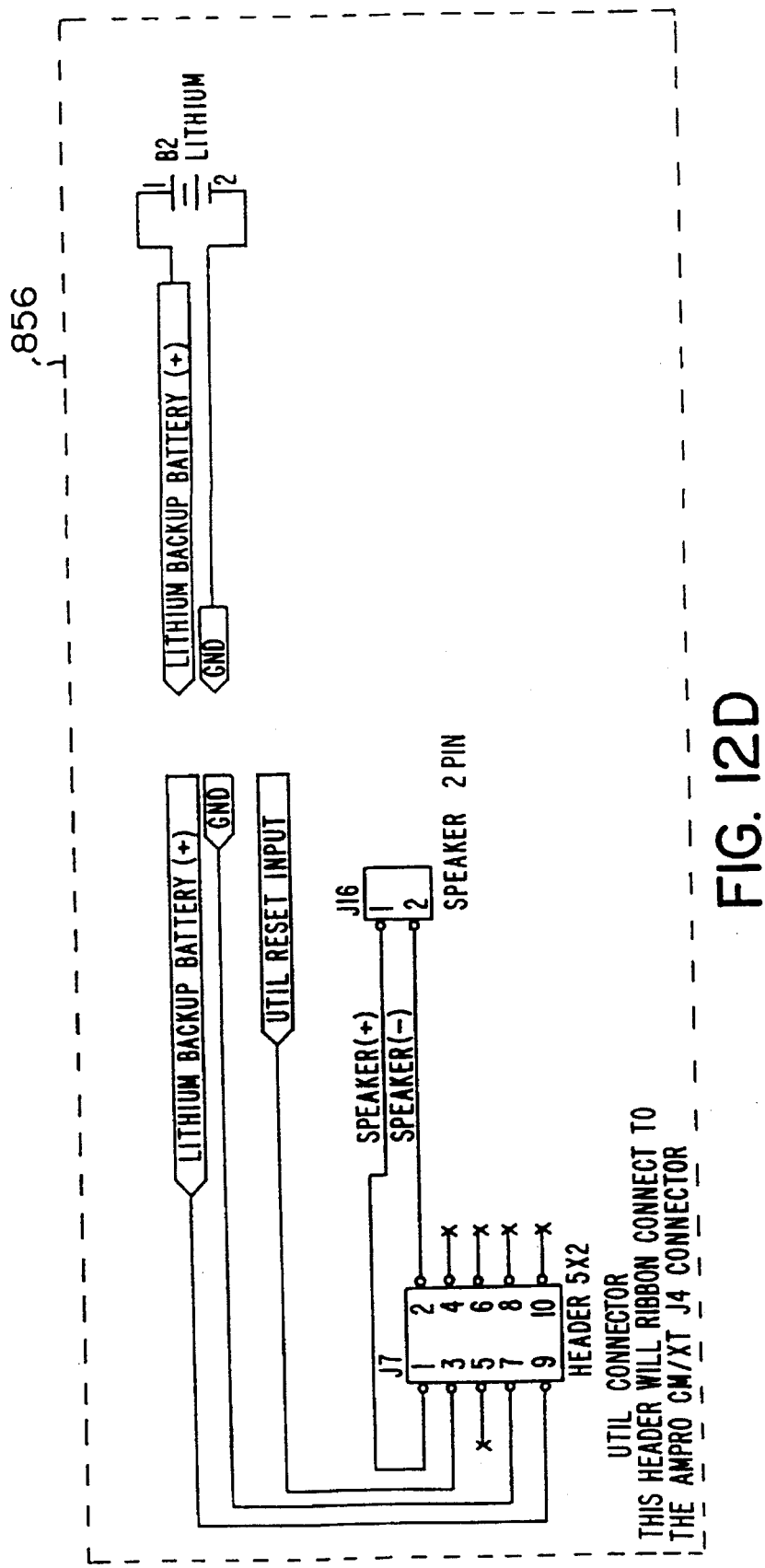
Figure 12E:
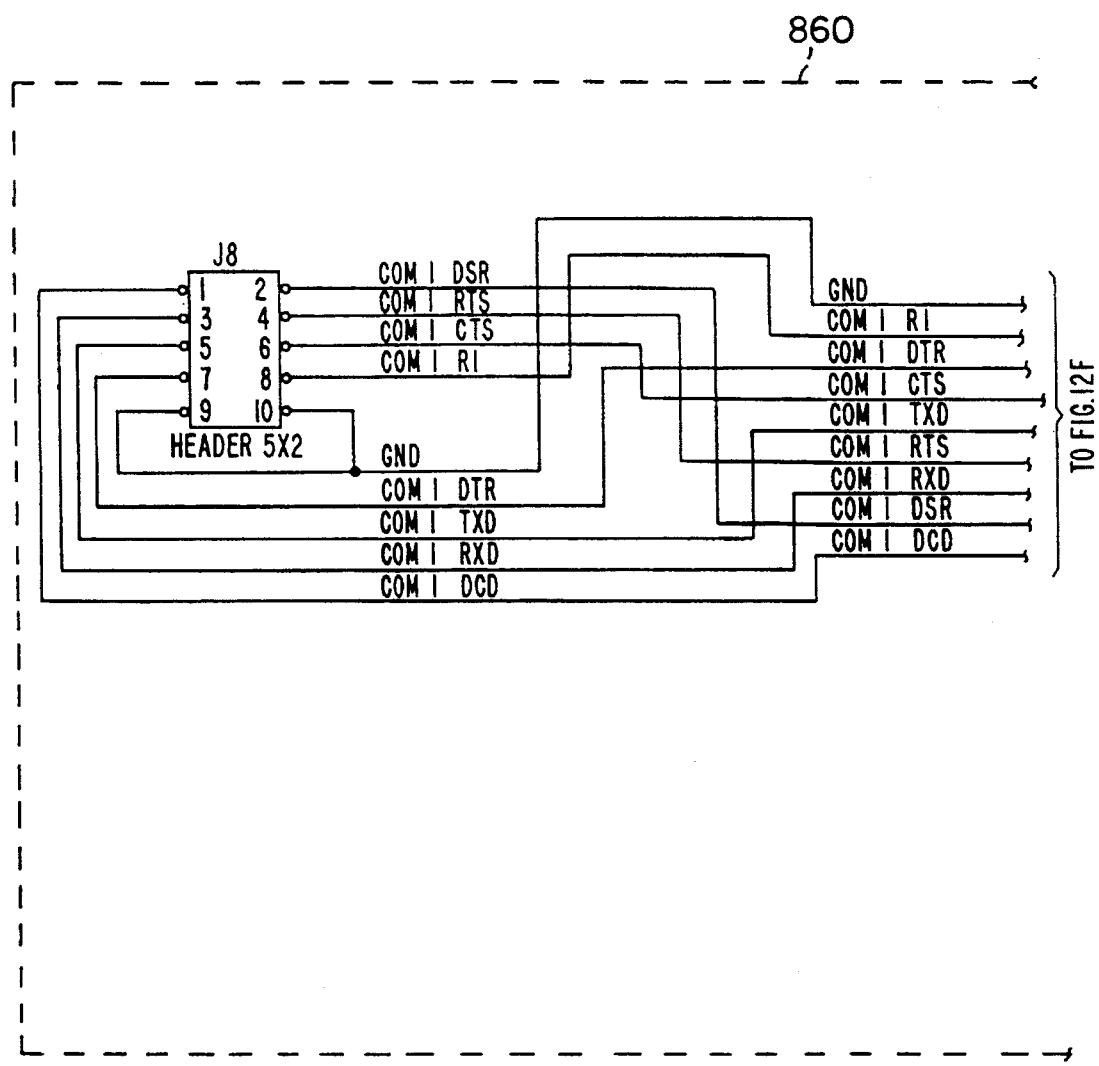
Figure 12F:
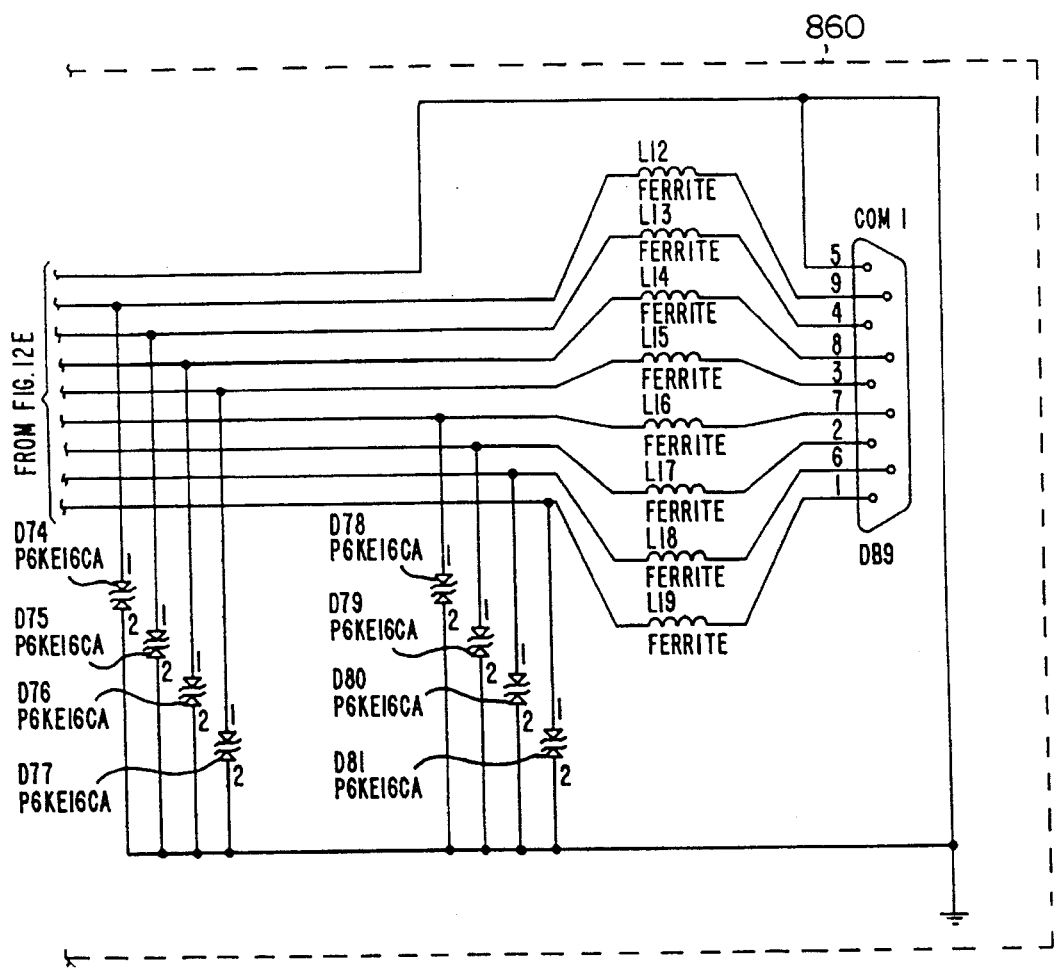
Figure 12G:
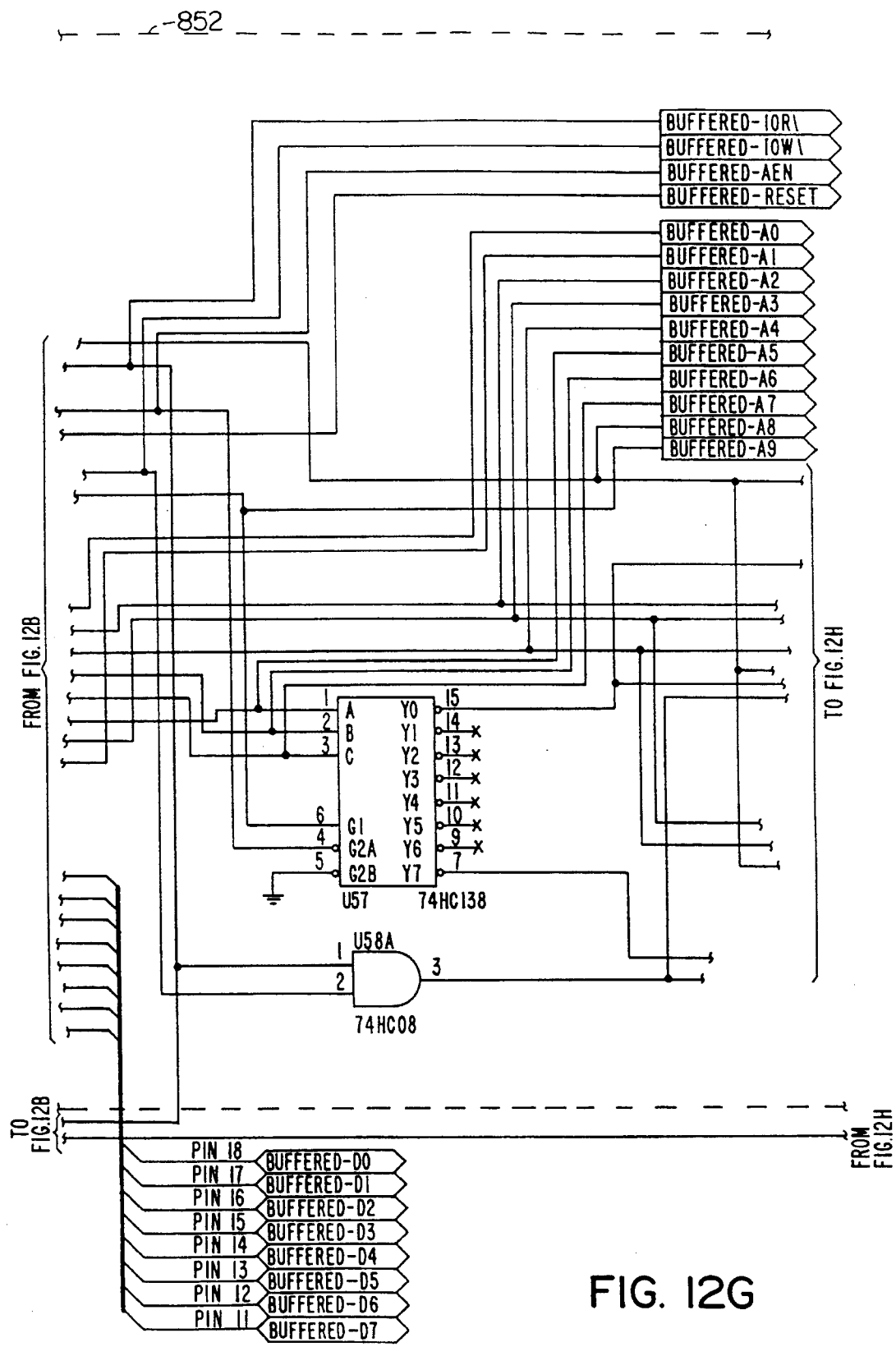
Figure 12H:
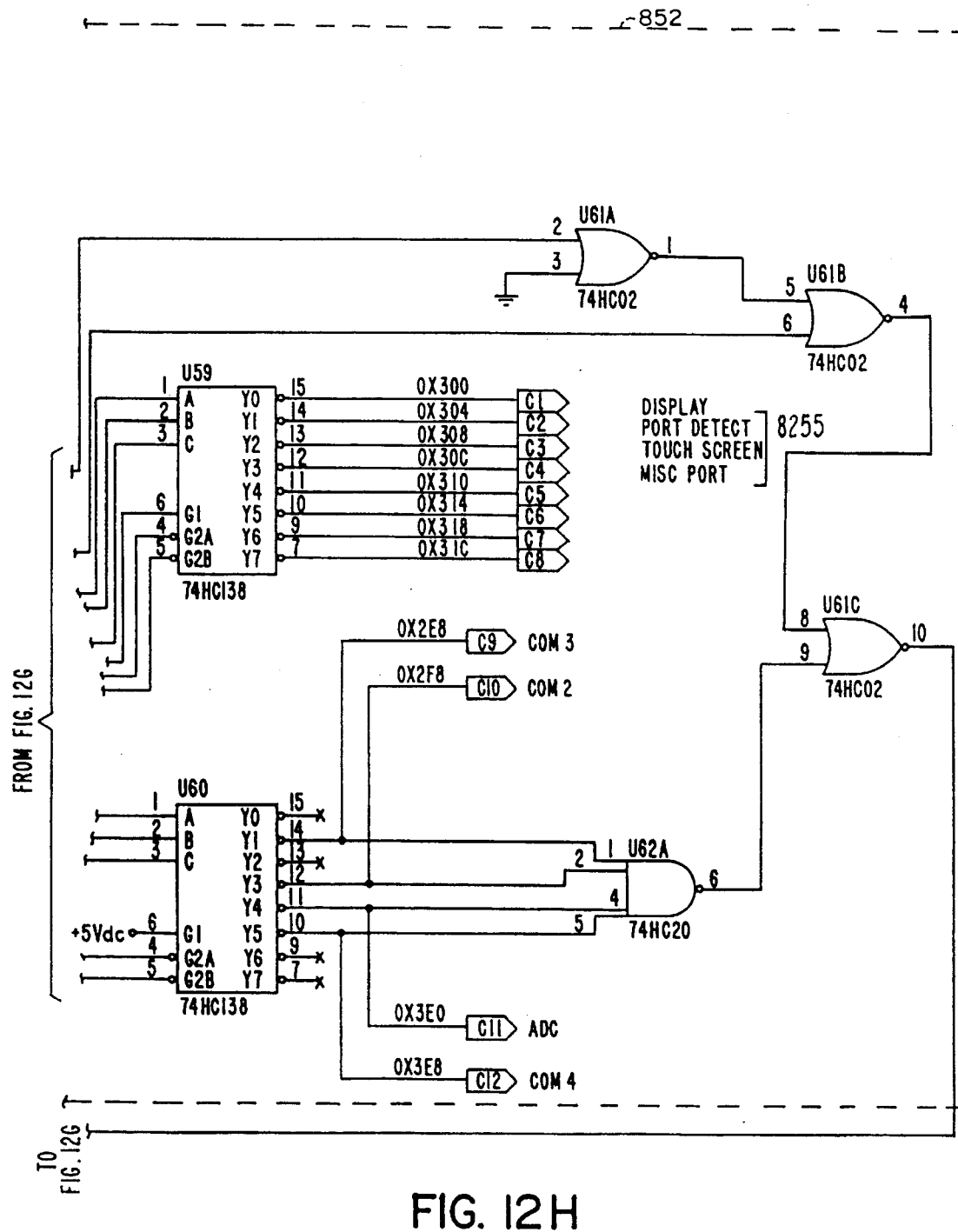
Figure 12I:
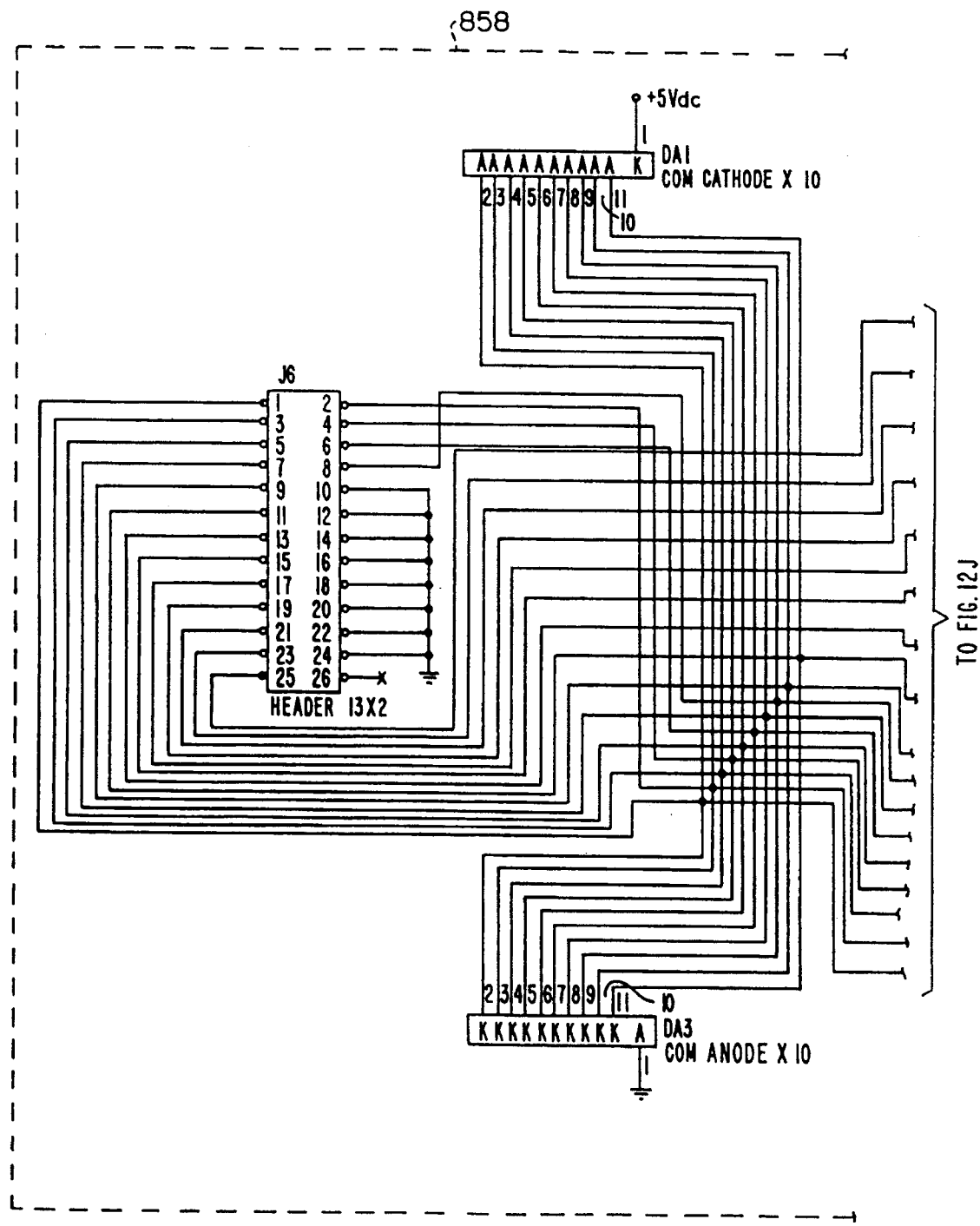
Figure 12J:
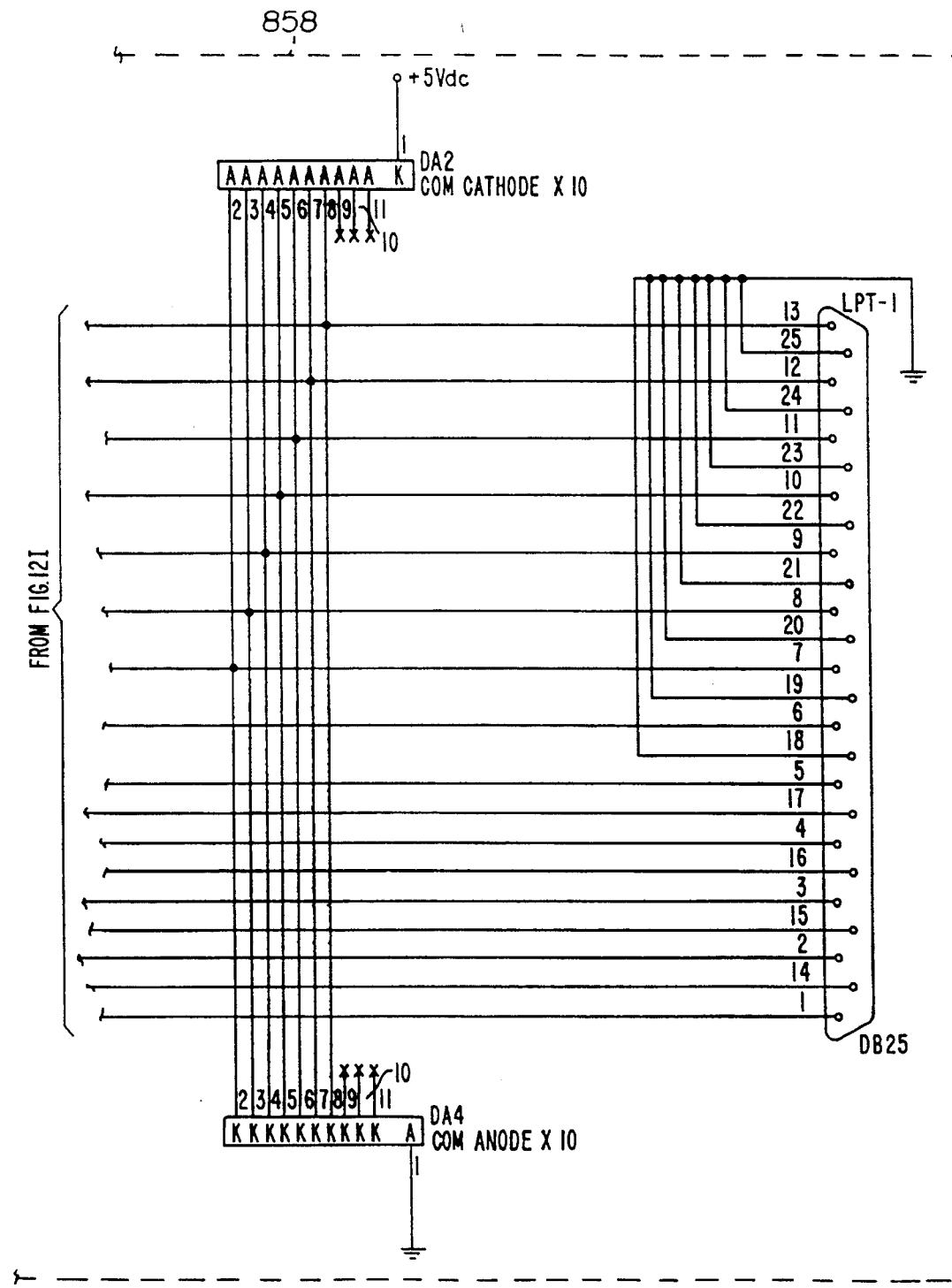
Figure 12K:
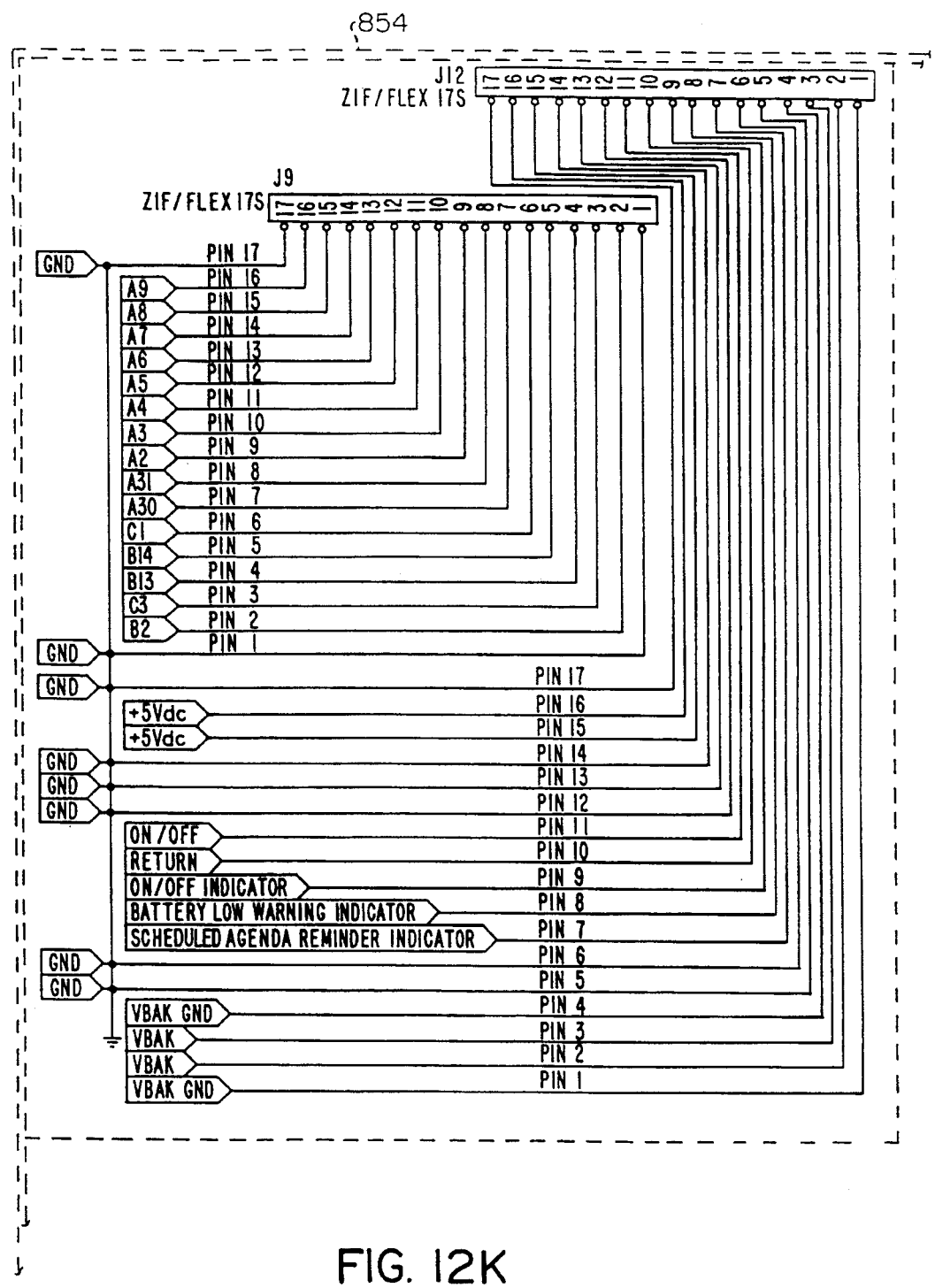
Figure 12L:
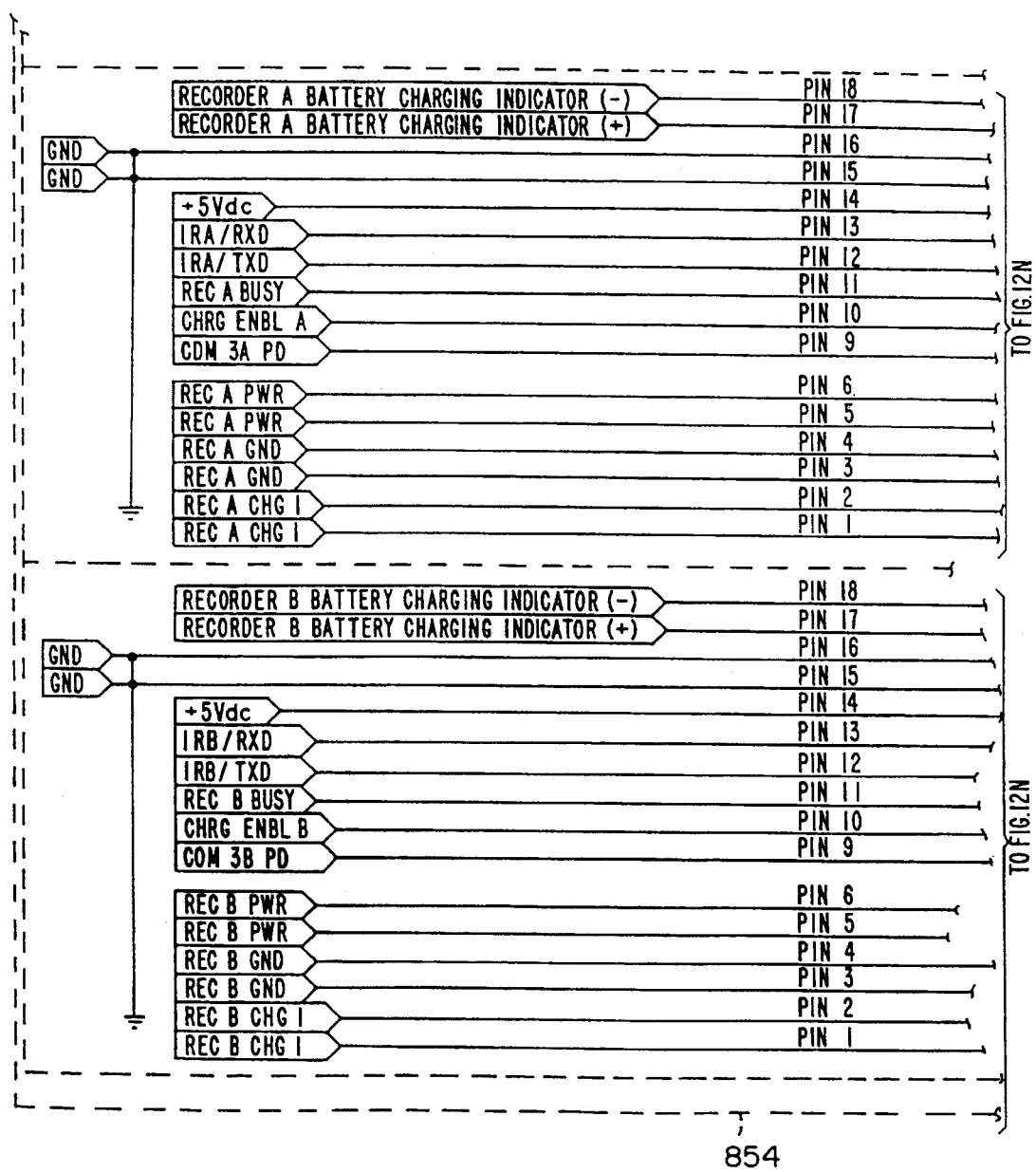
Figure 12N:
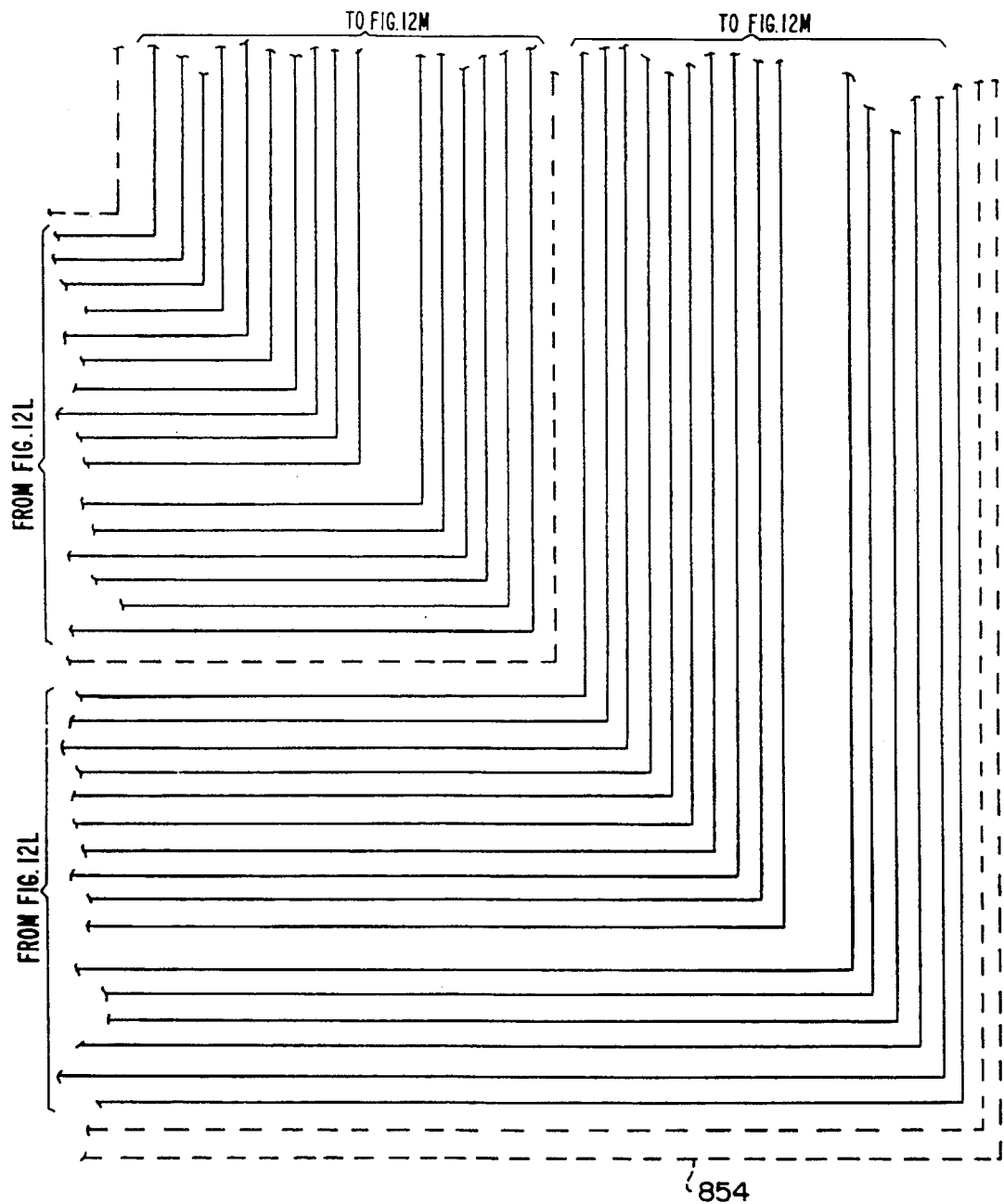
Figure 13A:
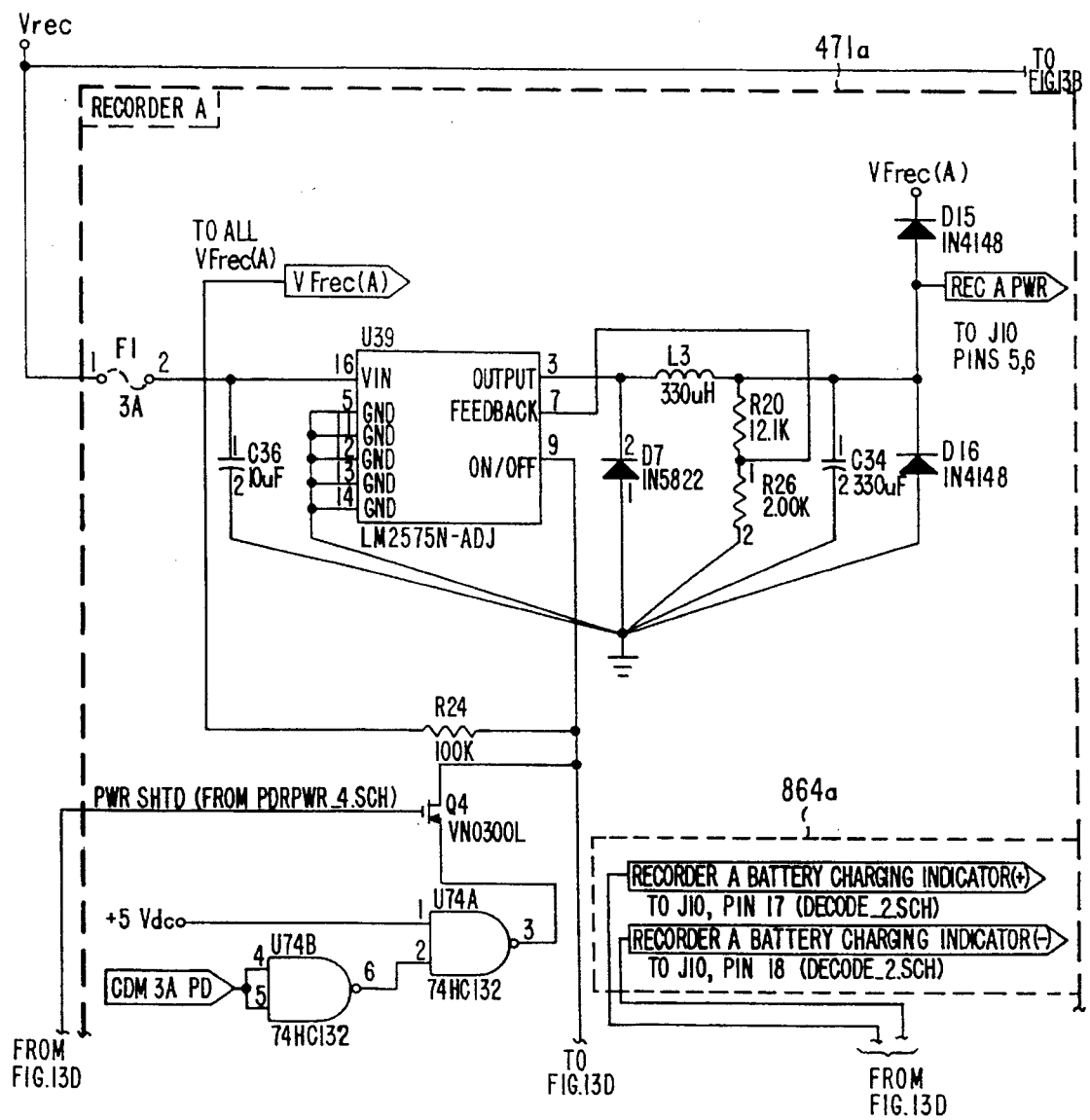
FIG. 13 is a schematic diagram of an exemplary Power Supply Circuit of the remote base unit of FIG. 4.
Figure 13B:
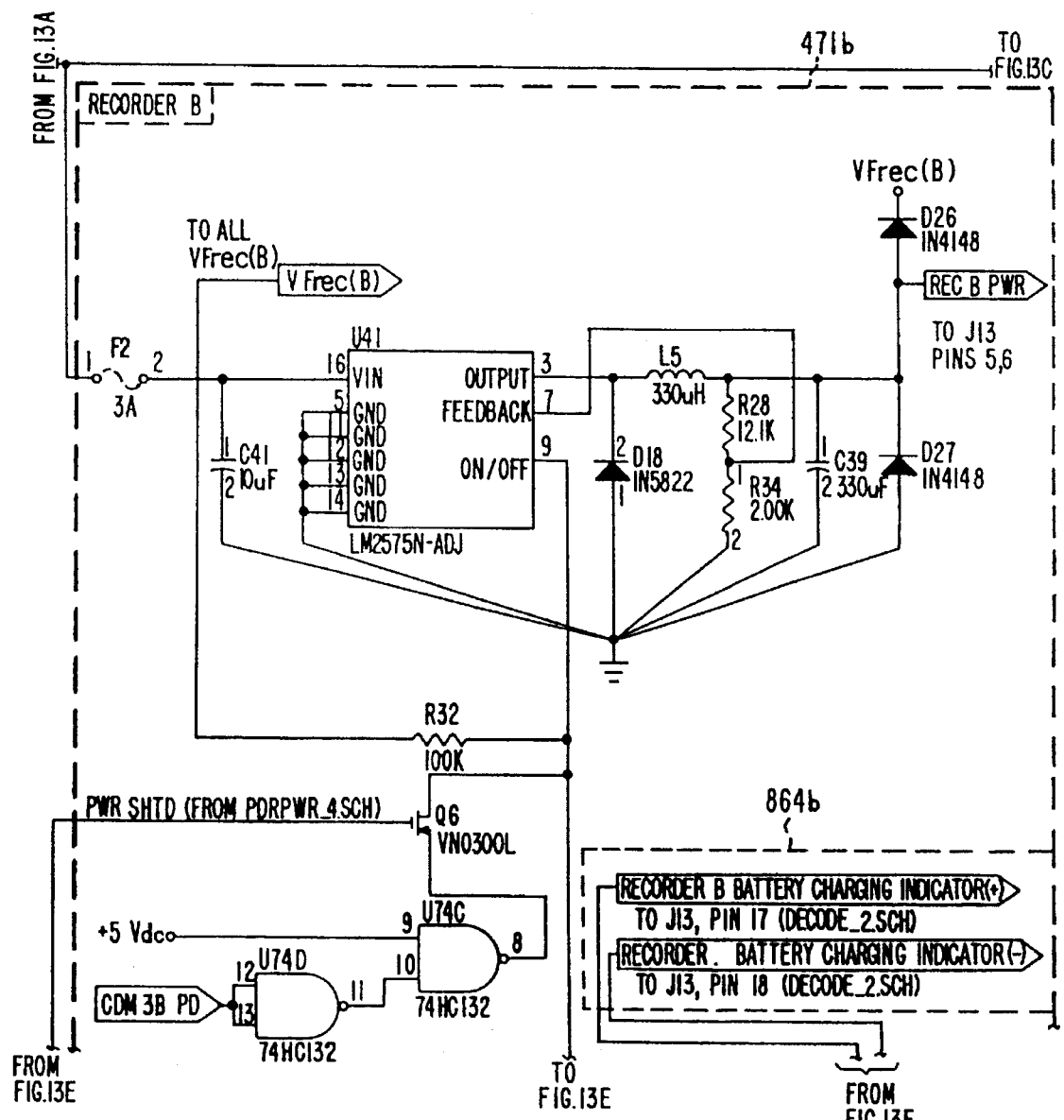
Figure 13C:
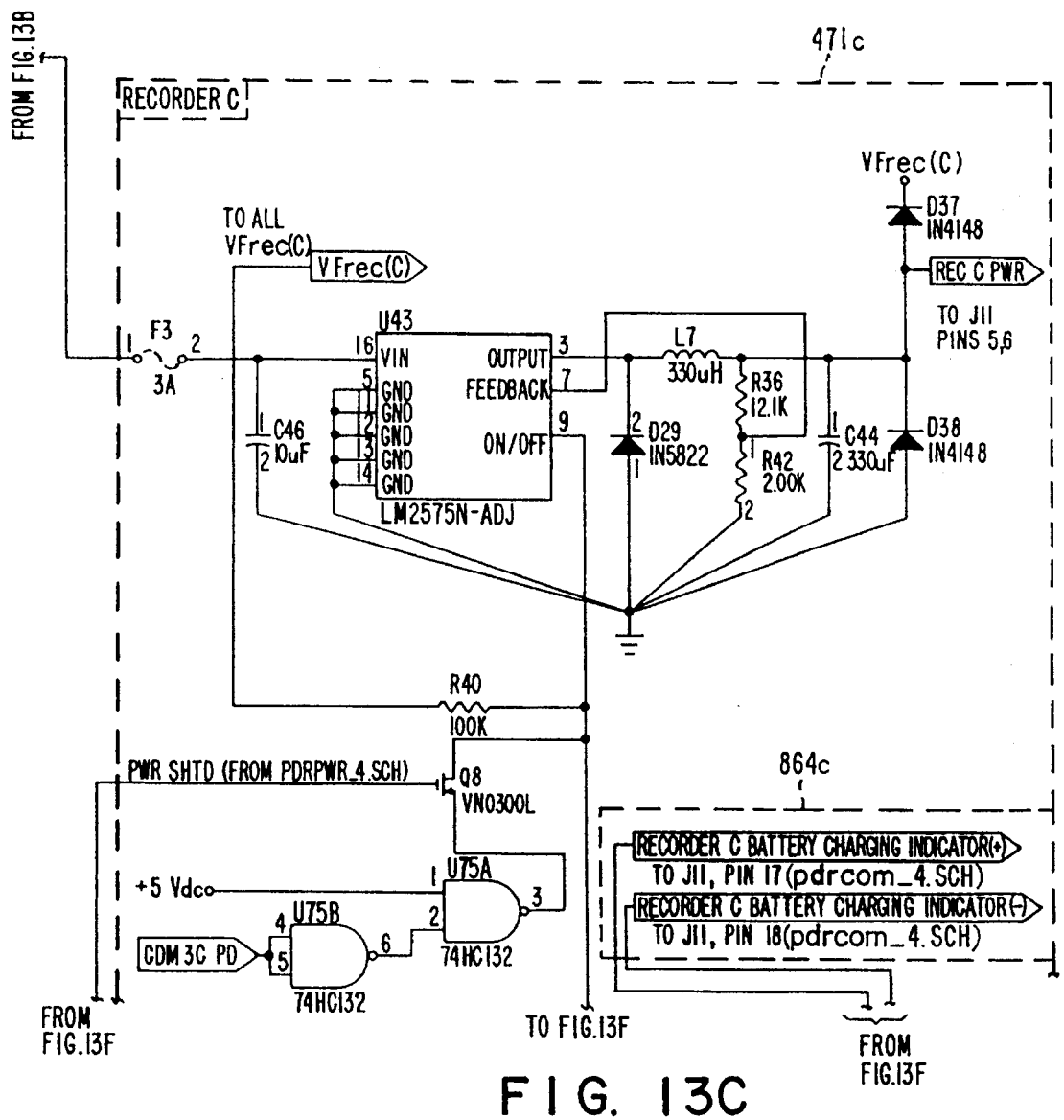
Figure 13D:
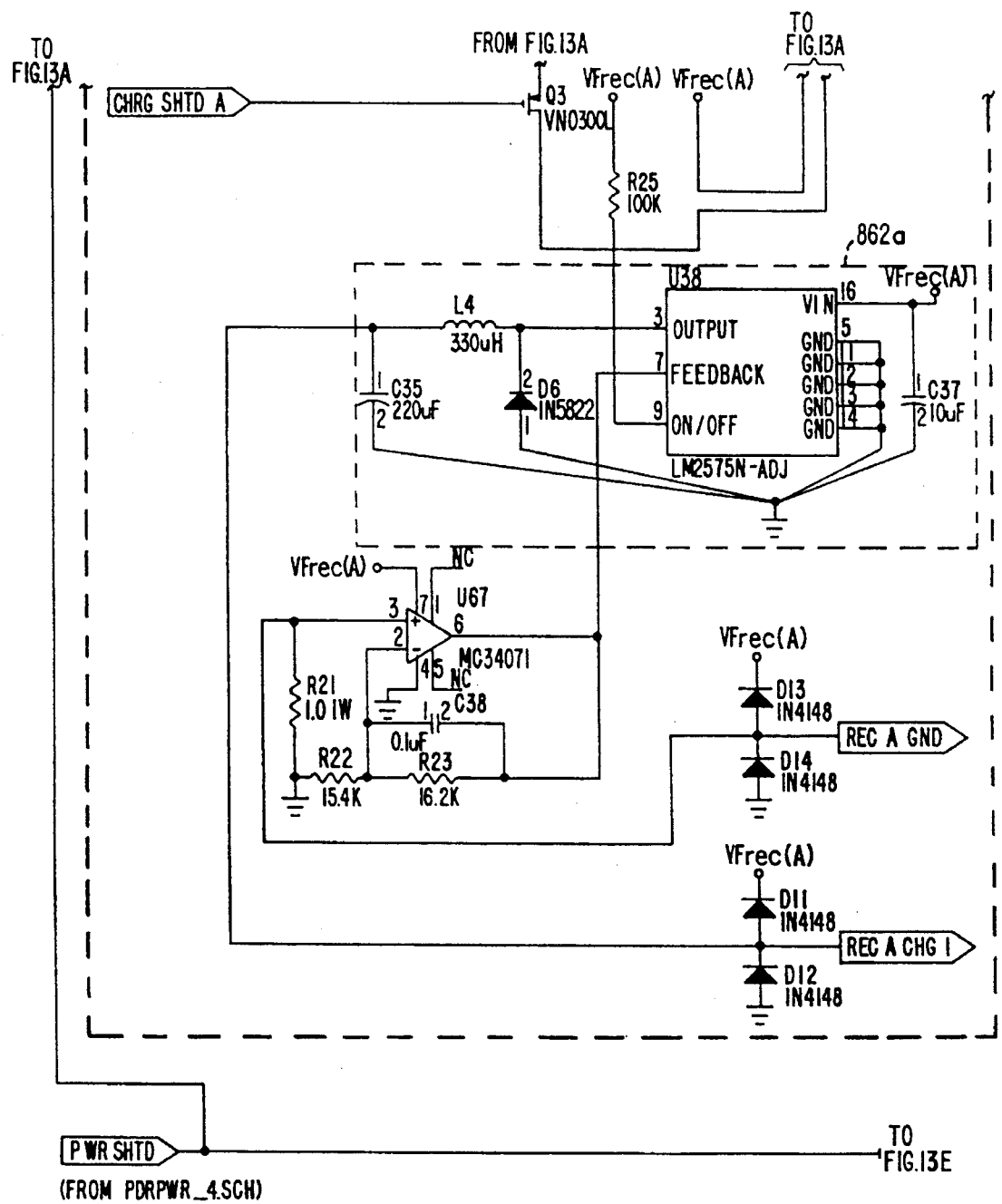
Figure 13E:
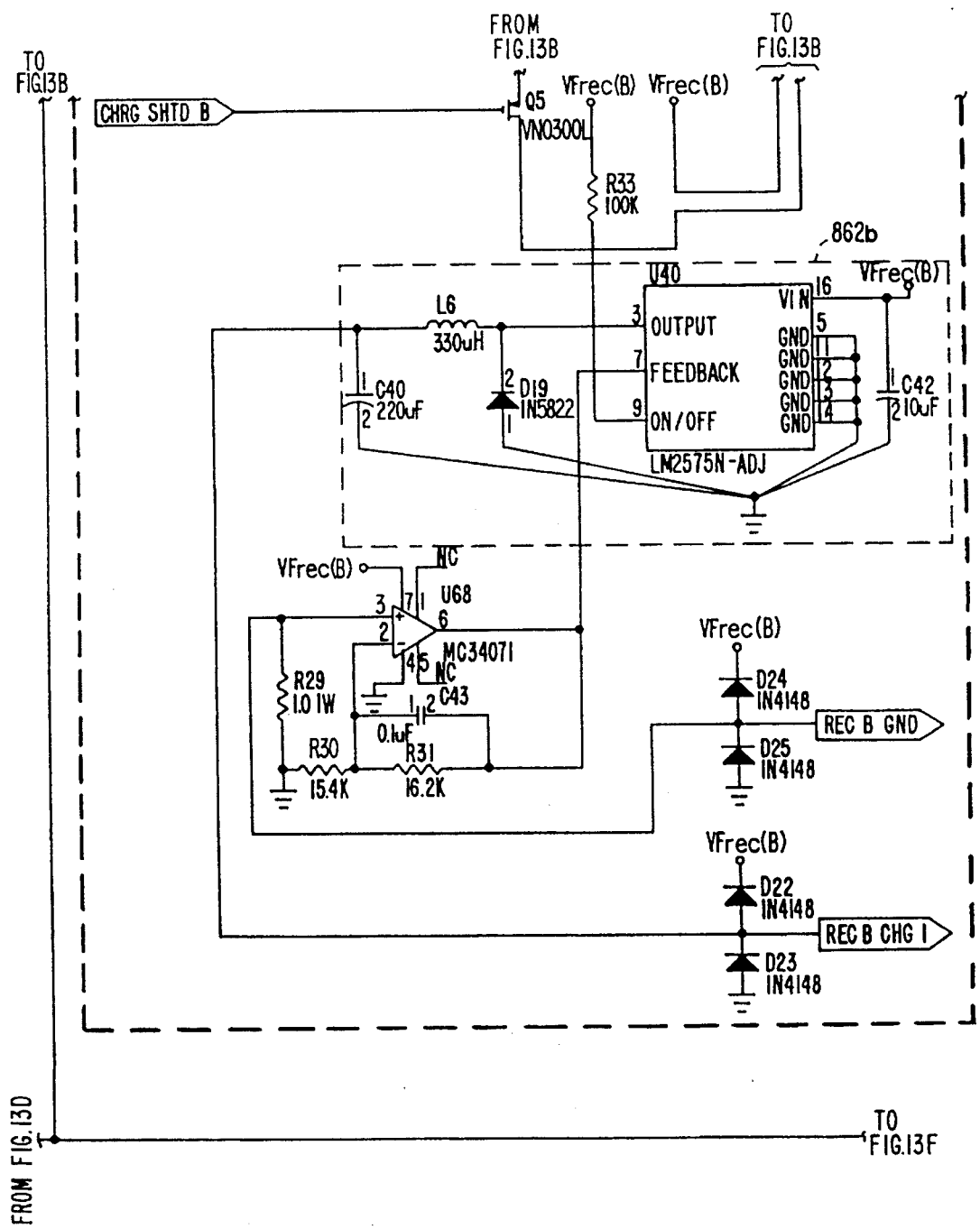
Figure 13F:
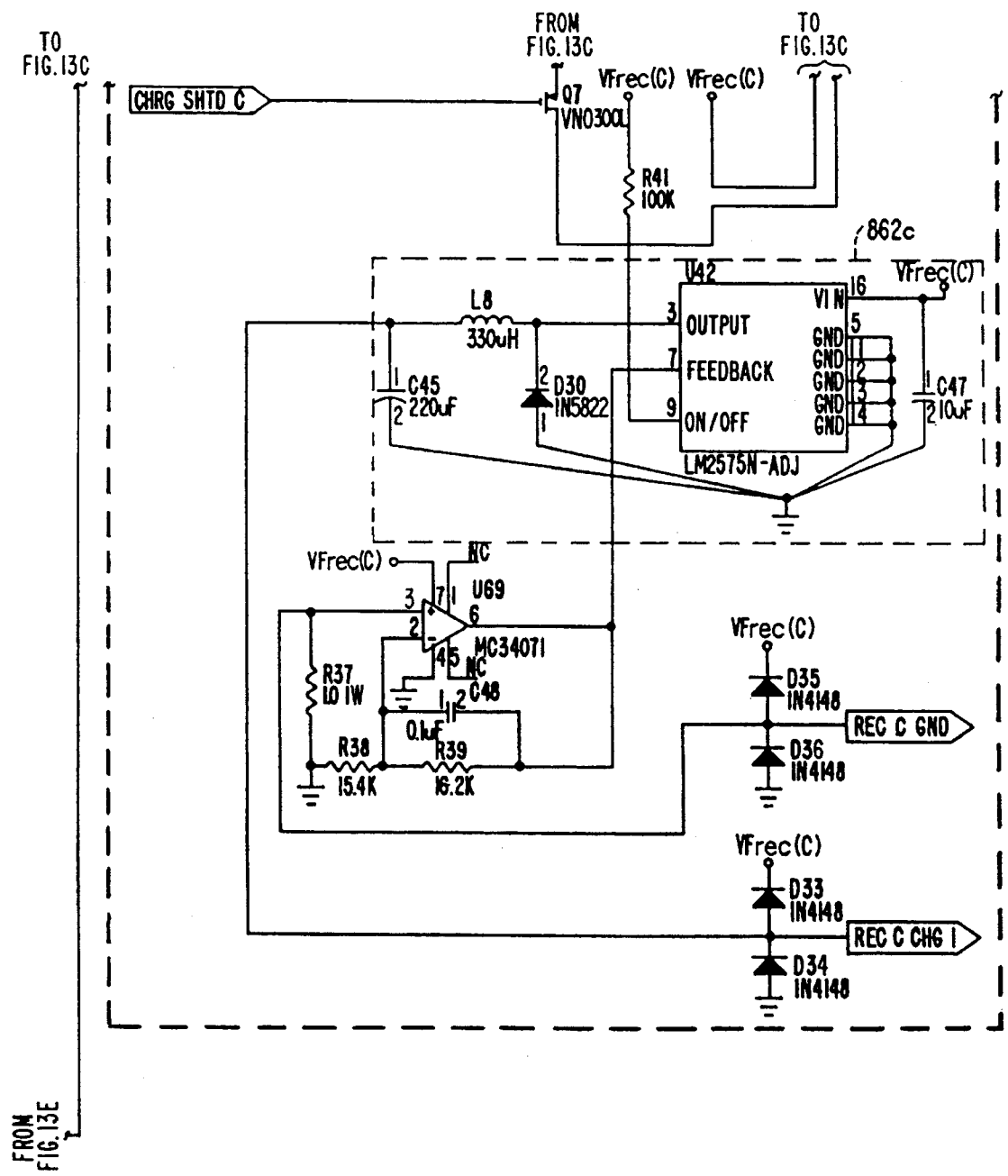
Figure 14A:
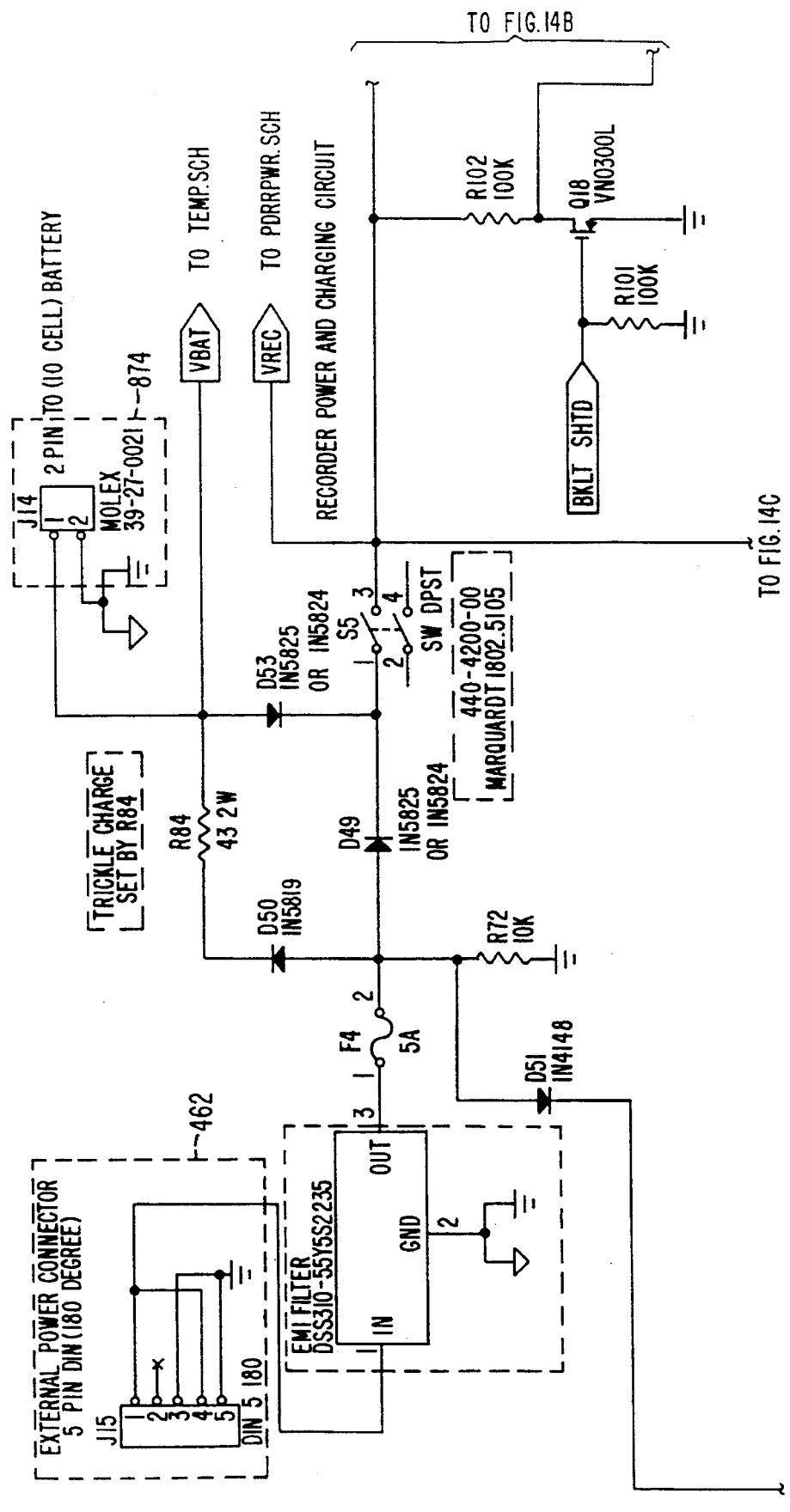
FIG. 14 is a schematic diagram of an exemplary Power Interface and Control Circuit of the remote base unit of FIG. 4.
Figure 14B:
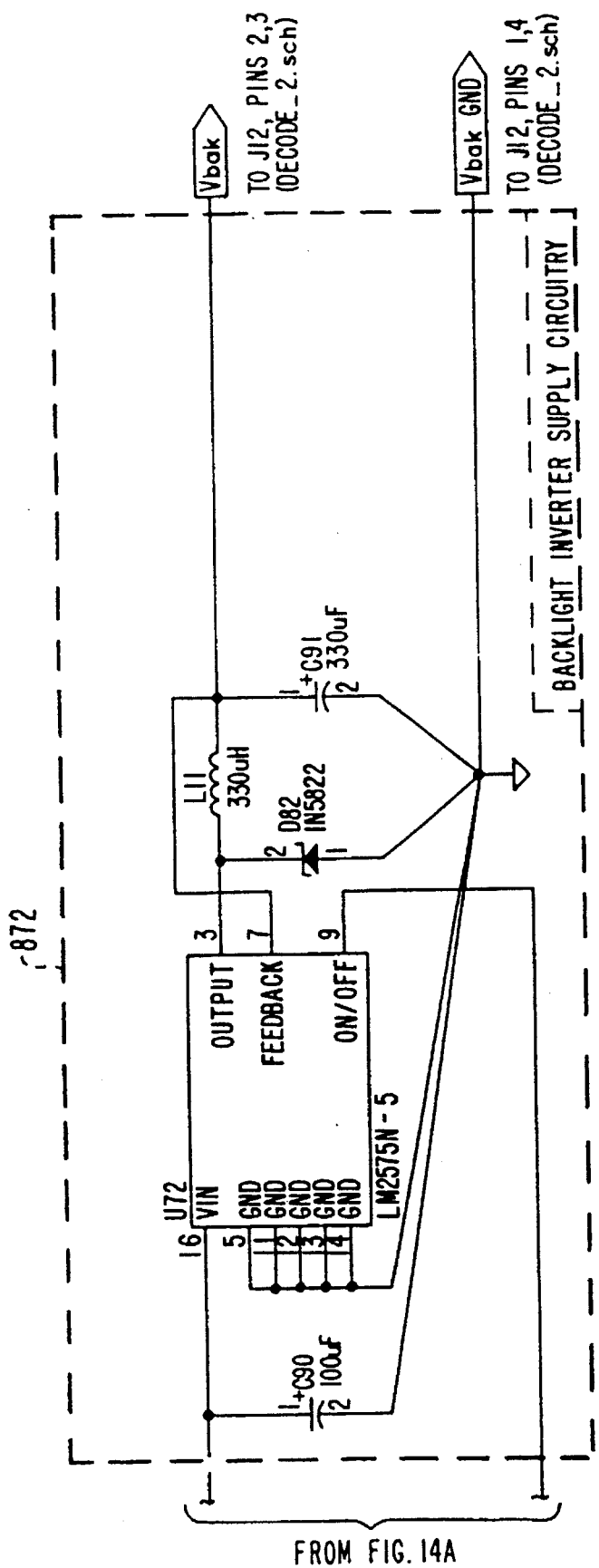
Figure 14C:
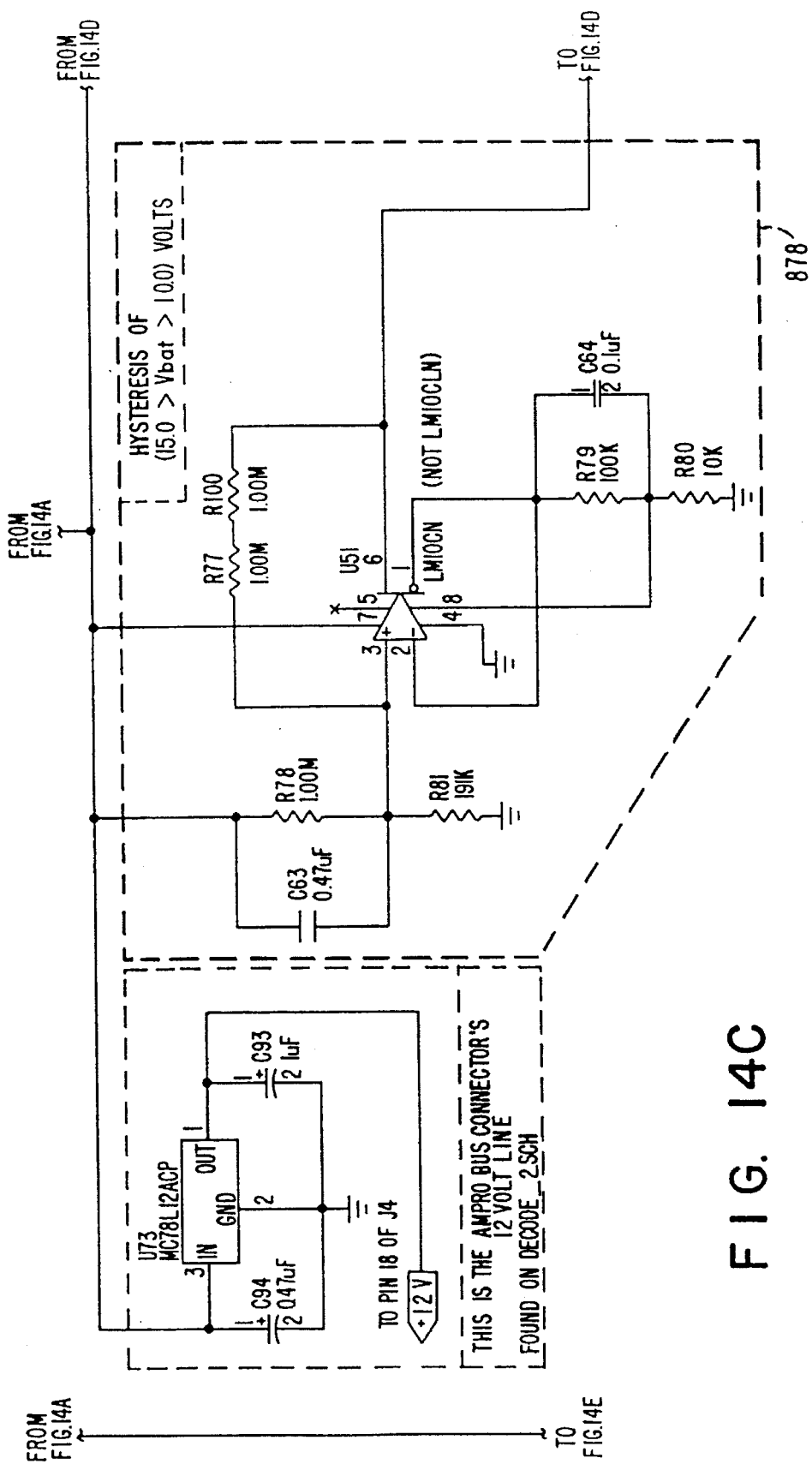
Figure 14D:
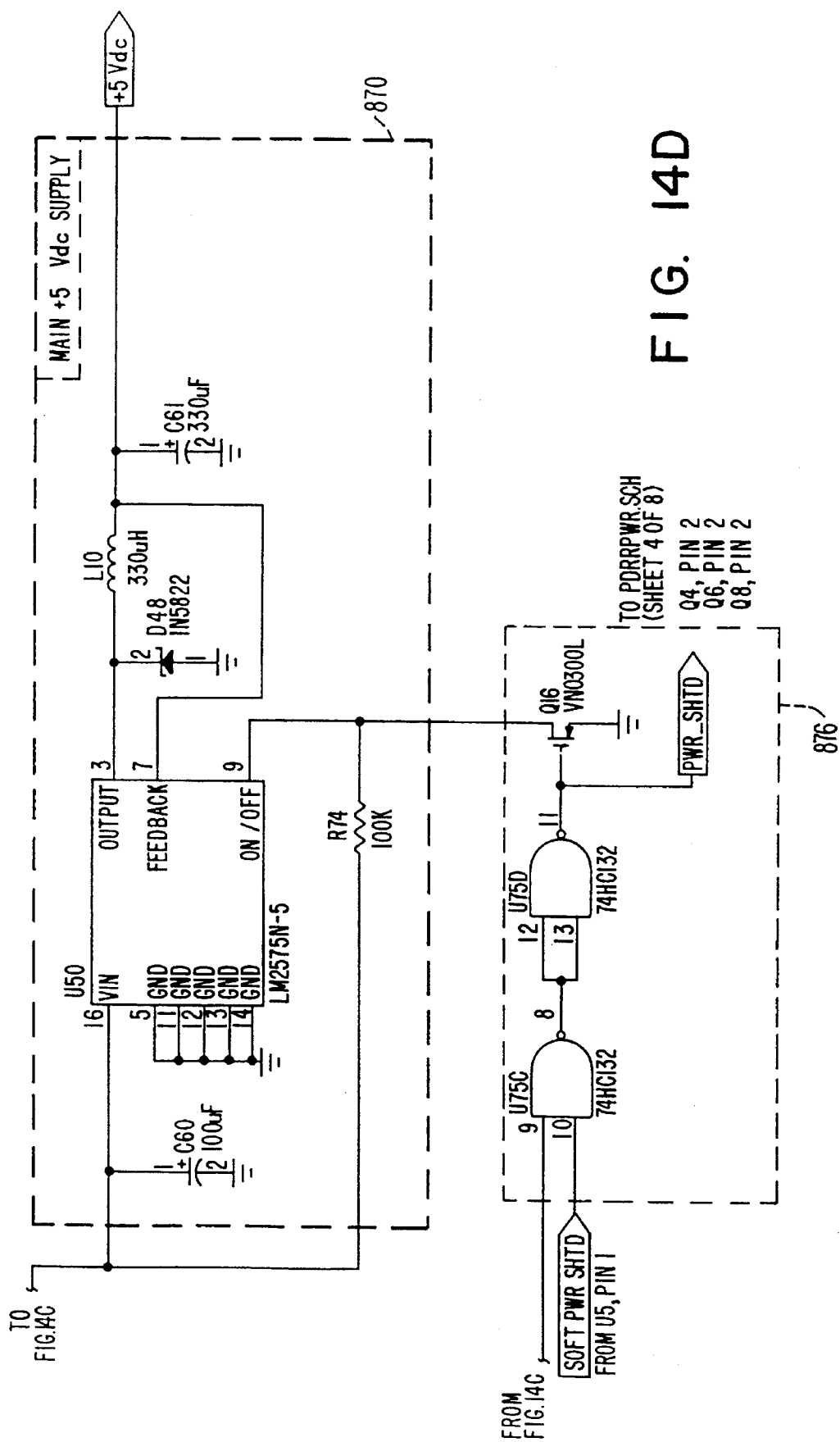
Figure 14E:
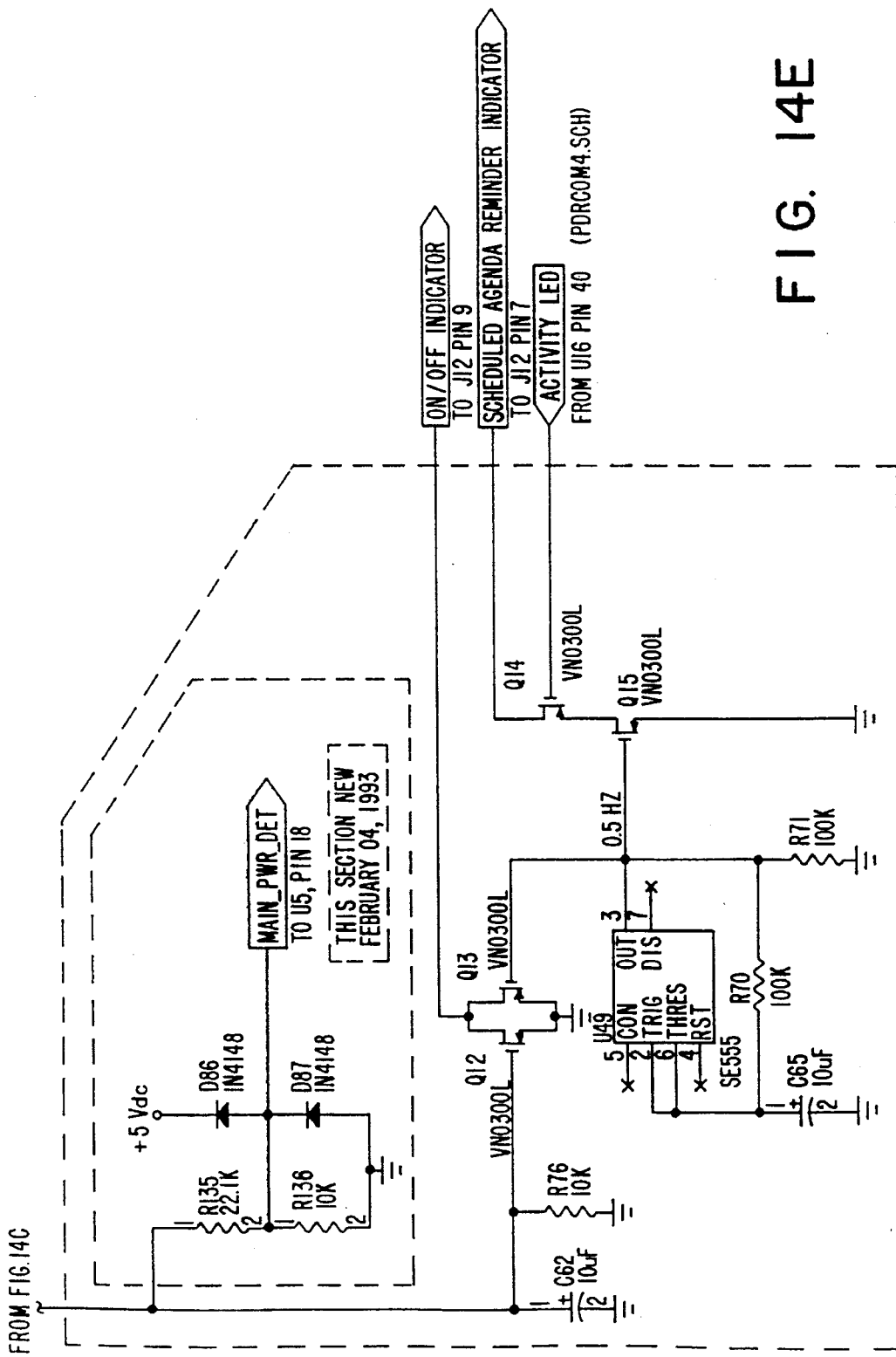

FIG. 11 depicts the Internal Modem Circuit 450 of the RBU 150. One serial interface of the communications interface circuit 440 is used to communicate to an internal modem 450, which in turn connects to a telephone line 134 (FIG. 4) via phone jack 478 to communicate with the care center 600. In the present embodiment, the internal modem 450 is a Hayes-compatible integrated circuit 840 which provides 2400 baud modulation and demodulation for direct telephone line connection. Alternatively, the serial interface is used to communicate to a radio interface (not shown) which in turn connects to a radio (not shown) to communicate with the care center 600. Those skilled in the relevant technology will appreciate that other communications links may also be used. The internal modem circuit 450 also has a ring detect circuit 842 which indicates when a message is received. Finally, the circuit 450 has a line interface circuit 844 which provides the necessary interface from the modem circuit 840 to the connector 478 and the ring detect circuit 842.

FIG. 12 is a schematic diagram of the Microprocessor Buffer Decode Circuit 461 of the RBU 150 diagrammed in FIG. 4. This circuit provides a buffer for the CPU 412 and permits the CPU 412 to select the device it is reading from or to. The microprocessor of the CPU 412 fits into the connector 850 on the microprocessor buffer decode circuit 461. The connector connects to a microprocessor buffer decode circuit 852 which provides a buffer for the CPU 412 as known in the art. The buffer decode circuit 852 is connected to flex cables 854 which connect the base assembly board 410 to the lid assembly board 340. The communications interface circuit 858 connects the direct connector 474 to the CPU 412 and the ESD/EMI circuit 860 connects the printer connector 472 to the CPU 412.

As illustrated in FIG. 13, three identical power supplies each provide +8.75 volts DC to power each of the recorders 210, 220, 230 for data communications and operation. An additional lead 862a, 862b, 862c in each of the power supplies 471a, 471b, 471c provide a 600 mA constant current source to charge the battery pack. The power supplies 471a, 471b, 471c additionally controls the shutdown interlock via connections 864a, 864b, 864c.

As shown in FIG. 14, the Power Interface and Control Circuitry 480 provides an interface to external power and circuitry for control and monitoring of power. An external source 132 provides the +16 volts DC to the RBU's I/O bus via power connection 462. From the external power source 132, the control circuitry 870 derive +5 volts DC power necessary for other elements in the RBU 150. The control circuit 872 derives power for the LCD backlight 313 and the indicator lights 324, 326, 328. A separate battery-backed RAM 874 is provided to retain memory during power loss. Presently, nickel-cadmium batteries are used. The power interface and control circuit 480 also has a shutdown circuit 876 which shuts down the system in the event of a catastrophic circuit failure and a low power shutdown circuit 878 which provides for power shutdown when the battery voltage falls below the limit required for normal operations.

III. Functional Modules for Monitoring At-Risk Pregnancy

As shown in FIGS. 2 and 4, two types of modules 110 may be connected into the RBU 150: sensors 120 which may be plugged directly into the RBU 150, and recorders 160, which receive inputs from sensors 120, record the sensor information, and transmit the inputs to the RBU 150. The recorders 160 are completely portable and may be used remotely by the patient. The recorders 160 must however, be periodically placed into a docking port 350 in the RBU 150 so as to upload or download data or instructions and to charge its batteries.

In the present embodiment, the RBU 150 is configured to receive three recorders 210, 220, 230 for monitoring a the medical status or condition of a patient. In one embodiment, the medical condition monitored is an at-risk pregnancy. Advantageously, the recorders utilized to monitor this condition are: a combined fetal heart rate/uterine activity recorder 210, a blood pressure recorder 220 and a urinalysis recorder 230.

The fetal heart rate/uterine activity recorder 210 is a hand-held, completely self-contained ultrasound fetal heart rate monitor with uterine activity and event channels. The fetal heart rate/uterine activity recorder comprises a docking interface board (DIB) 414 and a fetal heart rate/uterine activity circuit board (not shown).

The DIB 414 comprises four infrared channels which provide logic levels to indicate that the recorder is busy with a measurement, to indicate that the battery pack is 10 degrees C above ambient (indicating full battery charge) and the third and fourth channels are used to transmit and receive data as discussed above.

An intrauterine sensor 214 is connected to the fetal heart rate/uterine activity board via a connector. A tokodynamometer as claimed in pending U.S. patent application Ser. No.

07/754,960 and assigned to the assignees of the present invention is preferably used as the intrauterine sensor 214 and is connected to the uterine activity recorder via a connector.

In the presently preferred embodiment, the fetal heart rate/uterine activity circuit board is model number 4220 provided by Seward Medical Ltd. in Newport, Wales. An ultrasound transducer 212, model 4220 provided by Seward Medical Ltd. is also connected to the fetal heart rate/uterine activity circuit board via a connector. The ultrasound transducer 212 monitors the fetal heart rate and provides the fetal heart rate to the fetal heart rate/uterine activity circuit board. The fetal heart rate/uterine activity circuit board utilizes continuous doppler shift ultrasound technology, as known in the relevant technology, to provide the fetal heart rate signals on the LCD 312 of the RBU 150. The fetal heart rate may be detected via headphones connected to the fetal heart rate circuit board. A programmable timer in the fetal heart rate/uterine activity circuit board controls the monitoring session length and overall exposure time to ultrasound energy.

The fetal heart rate/uterine activity recorder 210 is docked in the RBU 150 and the LCD 310 in the RBU 150 prompts the patient through the set-up procedure and monitoring session. Various warning prompts and an audible beeper alerts the patient to any problems during the session.

The blood pressure recorder 220 comprises an DIB 414 and a blood pressure circuit board. The DIB is substantially similar to the DIB described above. The blood pressure circuit board is model number 90207 provided by Spacelabs Medical Inc. from Redmond, Wash. A blood pressure cuff 222 with a pressure transducer is connected to the blood pressure recorder 220 and used to monitor blood pressure. One of four blood pressure cuff sizes may be selected, and these are model numbers SAD 4211, AD 4212, LAU 4213 and EXL 4214 provided by Spacelabs Medical Inc. The blood pressure recorder 220 is a battery-operated microprocessor-controlled non-invasive pressure monitor. The blood pressure recorder 220 automatically inflates and deflates a range of pressure cuffs described above. The blood pressure recorder 220 has two modes of operation: an ambulatory mode, where the patient wears the cuff 222 for an extended period and the RBU 150 automatically takes readings and a reminder mode where the unit alerts the patient that it is time for a reading. The blood pressure recorder 220 is placed in one of the RBU's docking ports 350 to charge its batteries and transfer its data. The RBU 150 may also reset the controls in the blood pressure recorder 220.

The urinalysis recorder 230 used in the present embodiment is disclosed in U.S. Pat. No. 5,182,707 assigned to the assignee of the present invention and is hereby incorporated by reference. The urinalysis recorder 230 additionally comprises an DIB 414 which is substantially identical to DIB 414 described above. The urinalysis recorder 230 is a battery-operated microprocessor-controlled device that permits a patient to visually match the results of a urine reagent strip 232 with color blocks printed on the top of the recorder 230. Each record is time and date stamped and stored in memory. When the urinalysis recorder is returned to the RBU 150, the data will be transferred to the RBU memory 418 via the infrared link 415. The LCD display 312 is employed to prompt the patient through the measurements. Additionally, the front panel overlay on the urinalysis recorder 230 can be changed to accommodate different combinations of reagent test pads.

The sensors 110 which are directly plugged into the RBU 150 to monitor at-risk pregnancy are: a temperature probe 124, a weight scale 122, an infusion pump 128, an event switch 126 and a glucometer 130.

In the present embodiment, the temperature probe 124 is of the thermistor variety. The thermistor is located at the end of a four-inch long shaft encased in an aluminum tube. The tip is isolated from the rest of the shaft via a plastic separator section with the rest of the shaft made of stainless steel. The opposite end of the shaft has a molded plastic grip that will also provide a cable strain relief. The cable connected to the probe is a three feet long coiled cord terminated at a connector that mates with the connector in the storage bay.

The weight scale 122 used in the present embodiment is a platform which connects via cable to the rear panel 460 of the RBU 150. The presently preferred scale utilizes a four load cell configuration for a measuring a maximum weight of 440 pounds, ±0.5 pounds. The platform is preferably covered with a molded plastic housing and provided with a bottom plate to protect the load cells. In the present embodiment, the platform is 11"×13"×2".

The infusion pump 128 used in the present embodiment is model 508 manufactured by Mini-Med Inc. of Sylmar, Calif. The infusion pump 128 contains a data interface and may be connected to serial ports 466 or 468 on the rear panel 460. The infusion pump 128 may be reprogrammed from the care center 600 and medical information stored in the pump's internal memory may be uploaded from the pump 128 to the care center 600. In the at-risk pregnancy configuration, the patient may, for example, be infused with trebutaline under certain conditions.

The event switch 126 used in the present embodiment is model 4201 manufactured by Switchcraft Co. The event switch 126 is mounted in a hand-grip housing with a thumb button at one end and six feet of cable at the other end. The event switch 126 provides a means of counting the kicks of the fetus when the fetal recorder 210 is not included with the system. Alternatively, the event switch 126 may be reconfigured to monitor the occurrence of any event.

The glucometer 130 utilized in the present embodiment is model PVD manufactured by Miles Diagnostic Inc. of Illinois. The glucometer 130 contains a data interface and is connected to either serial ports 466 or 468 on the rear panel 460 of the RBU 150. The results of the glucose measurements stored in the glucometer's internal memory is transferred into the memory of the RBU 150 and subsequently transmitted to the care center 600.

IV. Functional Modules Used in Monitoring of Other Disease States

The RBU 150 may also be reconfigured to monitor a variety of other medical conditions or therapies. These conditions may be monitored in conjunction with at-risk pregnancy to provide a more complete treatment tailored to a patient's particular needs. Alternatively, the RBU 150 may be configured to monitor other specific medical therapies for the treatment of specific medical conditions. The following sections will continue to refer to FIGS. 2 and 4 in discussing: A. Monitoring of Human Organ Flow; B. Monitoring of In Vivo Plasma Separation; C. Monitoring of Blood Cholesterol Exchange; and D. Monitoring of Gas Exchange. It should be noted that the RBU 150 may be similarly reconfigured to monitor other disease states.

A. Monitoring of Human Organ Flow

The RBU 150 may be reconfigured to monitor human organ flow. Treatment of various disease states, such as kidney failure or liver failure, requires therapy involving the monitoring of fluid flow.

1. Monitoring of Kidney Dialysis

The RBU 150 may be reconfigured to monitor kidney dialysis. A kidney dialysis recorder may be used in place of one of the recorders 160 described above for a patient with an at-risk pregnancy condition, or used in conjunction with fetal heart rate/uterine activity recorder 210, the blood pressure recorder 220, and urinalysis recorder 230.

The kidney dialysis apparatus disclosed in U.S. Pat. No. 5,151,082 and assigned to the assignee of the present invention, which is hereby incorporated by reference, may be used in place of one of the recorders 160. In the presently preferred embodiment, this kidney dialysis recorder additionally comprises an DIB 414, which is substantially identical to the DIB 414 described above, and which is used to facilitate data communications with the RBU 150.

2. Monitoring of Liver Support Therapy

The RBU 150 may also be reconfigured to monitor liver support. A liver support recorder may be used in place of one of the recorders 160 described above or used in conjunction with the blood pressure recorder 220, and urinalysis recorder 230 or any other recorder 160.

The apparatus for monitoring human organ flow disclosed in U.S. Pat. No. 5,151,082 and assigned to the assignee of the present invention, which is hereby incorporated by reference, is preferably used to monitor liver support. In the presently preferred embodiment, this liver support recorder additionally comprises an DIB 414, which is substantially identical to the DIB 414 described above, and which is used to facilitate data communications with the RBU 150.

Just as the infusion pump 128 may be reprogrammed from the care center 600, the kidney dialysis recorder and the liver support recorder may also be reprogrammed from the care center 600. Such reprogramming includes updated treatment schedules and updated medical procedures which reflect changes in the treatment of kidney dialysis. Medical information stored in the kidney dialysis recorder's memory and that stored in the liver support recorder's memory may be uploaded from the respective recorders 160 to the care center 600.

B. Monitoring of In Vivo Plasma Separation

The recorder 160 for monitoring in vivo plasma separation is disclosed in U.S. Pat. No. 4,950,224, assigned to the assignees of the present invention and hereby incorporated by reference. The recorder additionally comprises an DIB 414 as described above and is docked in the recorder docking port 350 in the same manner as the recorders 160 described above. A catheter, as claimed and described in pending U.S. application Ser. No. 07/229,138, assigned to the assignees of the present invention, and hereby incorporated by reference, is used to connect the recorder to the patient's vein. The RBU 150 may also reconfigure the settings of the in vivo plasma separation recorder.

C. Monitoring of Blood Cholesterol Exchange

The recorder 160 for monitoring blood cholesterol exchange is disclosed in U.S. Pat. No. 5,152,743, assigned to the assignees of the present invention and is hereby incorporated by reference. In the present preferred embodiment, this recorder additionally comprises an DIB 414 as described above, to facilitate data transmission with the RBU 150. A catheter, as claimed and described in pending U.S. application Ser. No. 07/229,138, assigned to the assignees of the present invention and hereby incorporated by reference, is used to connect the recorder to the patient's vein. The recorder is docked, and information between the recorder and the RBU 150 is transmitted and received in the same manner as for the recorders described above. The RBU 150 may also reconfigure the settings of the in blood cholesterol exchange recorder.

D. Monitoring of Gas Exchange

The recorder 160 for monitoring gas exchange is disclosed in pending U.S. patent application Ser. No. 07/745,912, assigned to the assignees of the present invention and hereby incorporated by reference. In the present preferred embodiment, this recorder additionally comprises a DIB 414 as described above. A catheter, as claimed and described in pending U.S. application Ser. No. 07/229,138, assigned to the assignees of the present invention and hereby incorporated by reference, is used to connect the recorder to the patient's vein. The recorder is docked, and information between the recorder and the RBU 150 is transmitted and received in the same manner as for the recorders described above. The RBU 150 may also reconfigure the settings of the in gas exchange recorder.

V. System Process Flow

Figure 15A:
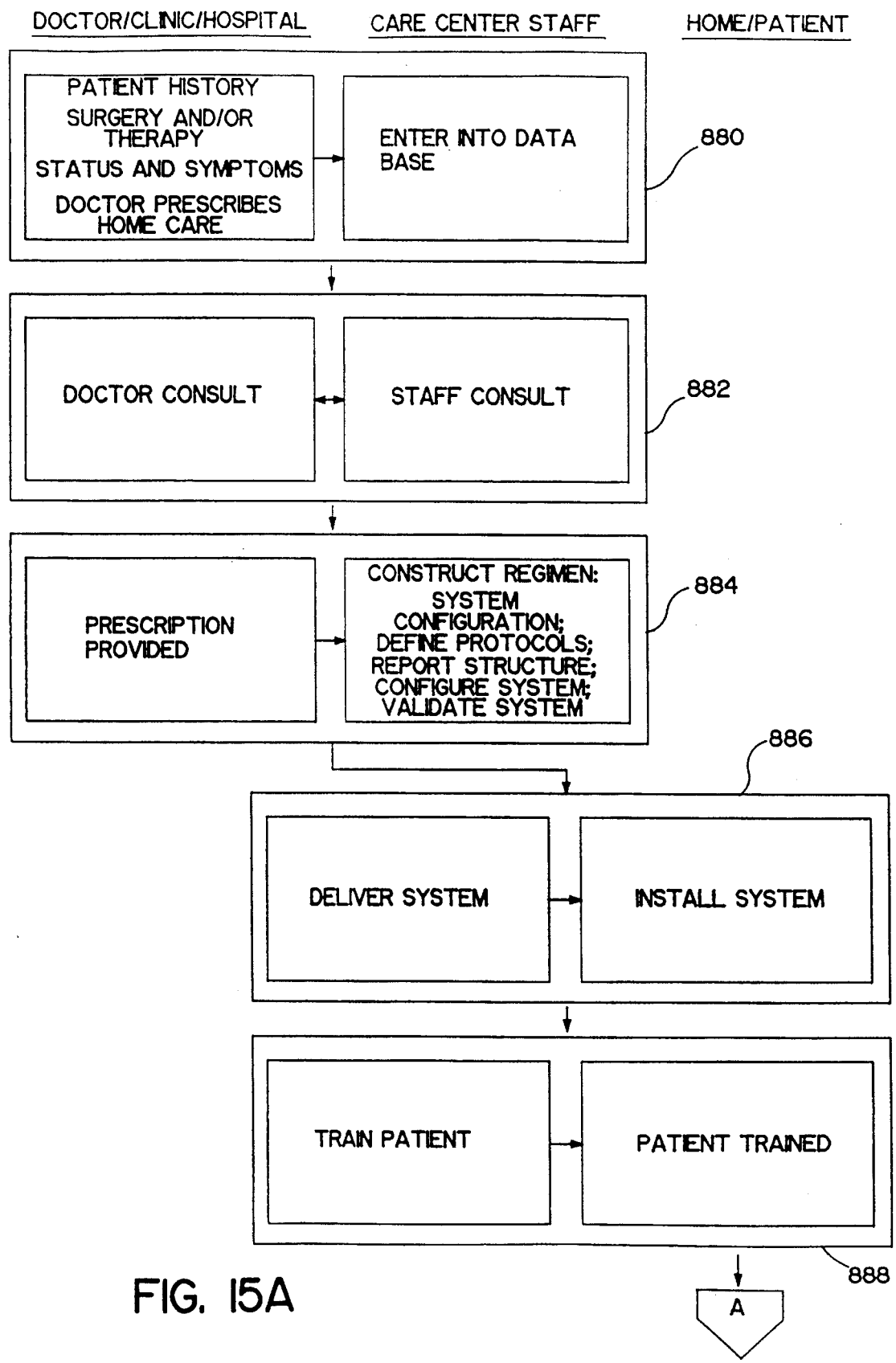
FIG. 15A is an operational flow diagram of the patient monitoring and support system of the present invention.
Figure 15B:
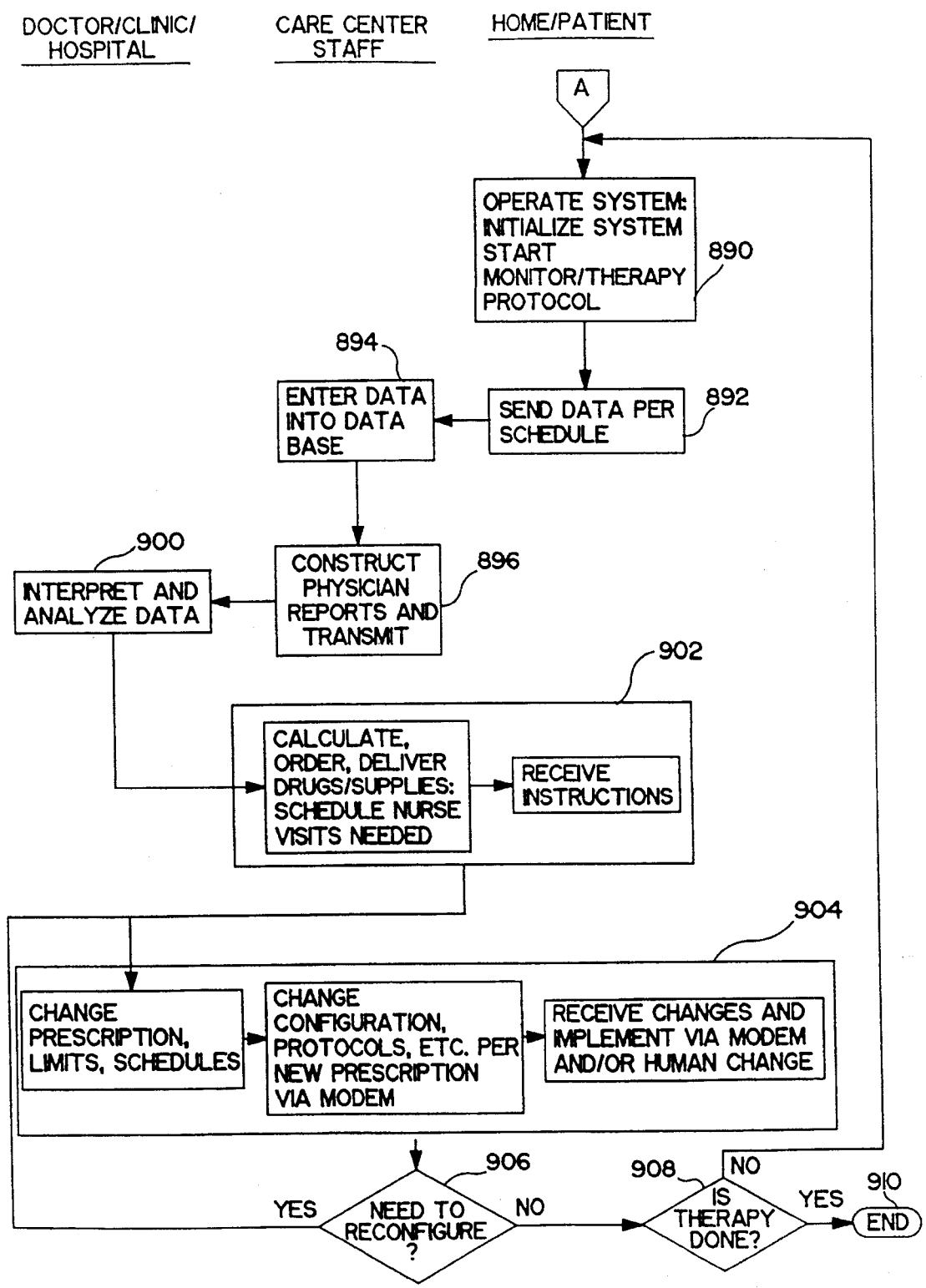
FIG. 15B is the continuation of the operational flow diagram of FIG. 15A.

FIG. 15 is an operational flowchart of the patient monitoring and support system 50 of the present invention. In general, the RBUs 150–150C acquire data representing the medical status and requirements of a patient and transmits the data to the care center. The care center 600 performs primarily the functions of obtaining data from the RBUs 150–150C and for communicating with the RBUs 150–150C. The care center 600 also accepts inputs from medical personnel monitoring the status of the patients at the care center 600 or from primary care physicians 710 on the LAN 700 and transfers the data to the RBU 150. It can also reconfigure the RBUs 150 based on the input provided at the care center 600.

With reference to state 880 in FIG. 15A, the primary care physician 710 or medical personnel from a clinic or hospital initially supplies individual patient history including surgery and/or therapy, the patient's medical status and symptoms to the care center 700 staff. Based on the patient's history and medical status, the doctor prescribes home care. The patient's personal data is entered into the database at the care center 600.

Next, as illustrated by state 882, the doctor and staff consults with each other and the doctor provides a prescription of the required therapy or treatment as shown in block 884. Based on the prescription, the care center staff constructs a regimen initially tailored for the patient. These include system configuration, the definition of protocols, developing a report of the structure, configuring the system and validating the system. The care center staff comprises a field nurse, a case nurse, a nutritionist, a therapist and other medical support personnel.

When the regimen is properly constructed, the system is delivered and installed in the patient's home as shown in state 886. Upon installation, a member of the care center staff trains the patient monitoring and status system 50 of the present invention, as shown in state 888.

When training is completed, the patient is ready to operate the system as shown in state 890. When a test or scheduled session has been completed, the medical data obtained is sent as depicted in state 892, to the care center staff who enters the data into the database, as shown in state 894. The staff then prepares the necessary physician reports and transmits them to the physician as shown in state 896.

Upon receipt of the data, the physician interprets and analyzes the data as shown in state 900. Based on the physician's analysis, the care center staff calculates, orders, delivers drugs or supplies and schedule nurse visits as required, as shown in state 902. These instructions are sent to the patient.

Based on the physician's analysis, the patient's prescription, visits and schedules are changed as shown in state 904. The care center staff accordingly changes the configuration, protocols, etc., according to the new prescription via modem. The patient receives the changes and implements the changes via modem or manually.

If configuration is required, the process in state 904 is repeated. If no configuration is necessary, operation of the system (state 890) is reinitiated and further therapy is obtained (state 908), otherwise, the session is terminated at state 910.

VI. Process Flow for Monitoring At-Risk Pregnancy

Figure 16:
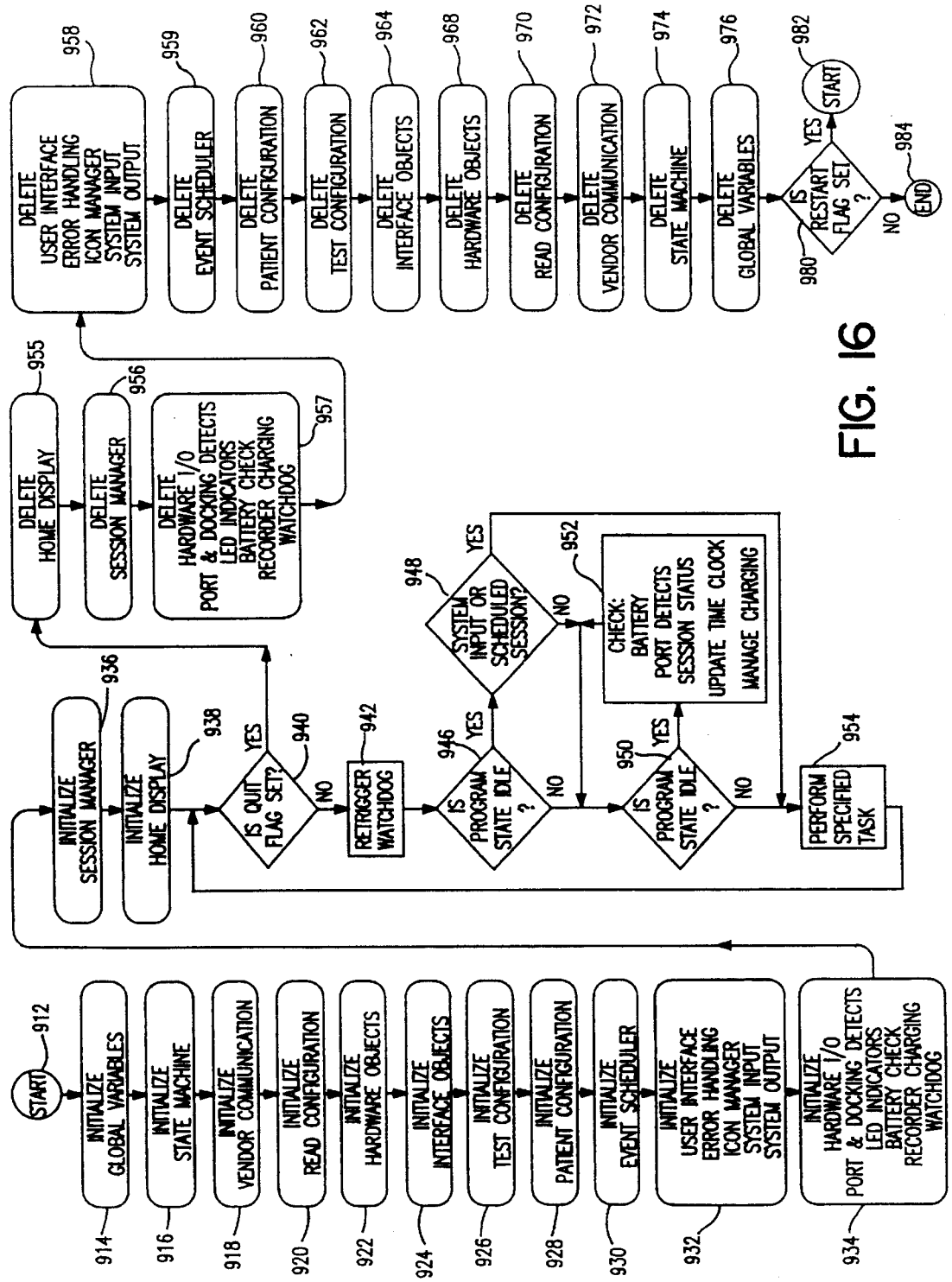
FIG. 16 is a top-level flow diagram of a preferred embodiment of the software for the remote base unit shown in FIG. 4.

FIG. 16 is a flow diagram of the at-risk pregnancy monitoring and support software of the present invention, which is located in the remote base unit 150. Software for the base unit 150 function is, in a presently preferred embodiment, written in the "C++" language. The software described herein, which is listed in the attached Microfiche Appendix, was translated from the source code into object code using a Borland "C++" compiler. Nonetheless, one skilled in the technology will recognize that the steps in the accompanying flowcharts can be implemented by using a number of different languages, language translators, computers and circuitries.

The RBU 150 comprises a microprocessor such as the AMPRO XT (CPU 412, FIG. 4) which executes a computer program. The computer program controls the operation of the system. At the start of the program, (state 912) initialization of variables, program data and device registers occurs.

Global variables which are common variables used by more than one function and/or object in the program are first initialized, as shown in state 914. The state machine is then initialized, as shown in state 916. This is a definition of process structure and starting point. Next, vendor communication is initiated at state 918. This is an initialization of the routines in communications software obtained from a third party; which make use of the modem and serial ports for data communications with the care center 600, the recorders 160 and other peripherals.

The Read Configuration file used to configure registers for the session program input/output, is then initialized (state 920). Next, hardware objects such as LCD control are initialized (state 922), followed by Interface objects (state 924) and Test Configuration (state 926) such as calibration settings. These are the software routines which control the hardware, interface data and test data.

Next, initialization of patient data configuration occurs (state 928). Patient Data includes the name, Patient identification, phone number of primary physician and care center and a list of their scheduled sessions.

The Event Schedule which handles the multitasking of the software objects is next initialized (state 930). Initialization of the User Interface Data follows (state 932). This includes initialization of Error Handling format, the Icon Manager and the System Input and Output.

The Hardware Input/Output registers are next initialized (state 934). These include initialization of the port and docking detects, the light indicators, the battery check register, the recorder charging register and the watchdog register.

Initialization of the Session Manager follows, as shown in state 936. The Session Manager schedules the sessions and updates all sessions displayed on the machine. Sessions here refer to the scheduled periods during which the patient monitors his medical condition. Variables in the Home Display are then initialized (state 938).

Upon completion of initialization, the program queries if the QUIT flag, a variable stored in RAM, is set as shown in state 940. If the flag is set, the program proceeds to delete the previously initialized values as shown in states 955–976. If the QUIT flag is not set, the program proceeds to the next state, state 942, which retriggers the hardware watchdog alarm. This process prevents the computer from being reset, and permits the program from continuing without interruption. The program then proceeds to examine if the program state is idle as shown in state 946. This state examines the reasons for inactivity.

If the program state is found to be idle, i.e., there is no activity in the base unit 150 indicated by the program, the program proceeds to state 948, which checks if there has been a system input by examining if a touchscreen 314 function key on the LCD 312 has been selected. The program also checks with the scheduler to examine if a session is scheduled. If either a key has been selected or a session has been scheduled, the program requests performance of the specified task as shown in state 954. For example, a session may be initiated, measurements such as blood pressure are taken and the data is transmitted from the base unit 150 to the care center 600. The human interface portion of the base unit 150 software will be described in some detail below with respect to FIGS. 18 to 22. If neither of these activities occurred, the program proceeds to examine if the program state is still idle as shown in state 950.

If the base unit 150 is idle, the program checks the test battery, the session controller and the recorder docking bays to see if a recorder is docked, it then updates the time clock, coordinates the charging of the recorder. If all these activities are not in error, the program returns to state 950 and checks if the base unit 150 is still idle. When the base unit 150 is no longer idle or if an error has been corrected, it proceeds to perform the task as specified by the patient or as scheduled (state 954).Upon completion of the task, the program checks the QUIT flag (state 940) and continues examination of the program state and performance of the specified tasks until request for termination is made. When termination of the program is requested, deletion of previously initialized values are deleted (states 955–976). Finally, the program examines if the restart flag is set as shown in state 980. If so, the program starts up again (state 982). If not, the program is terminated (state 984).

VII. Data Flow between the Remote Base Unit and the Care Center 600

A. Data Flow

Figure 17:
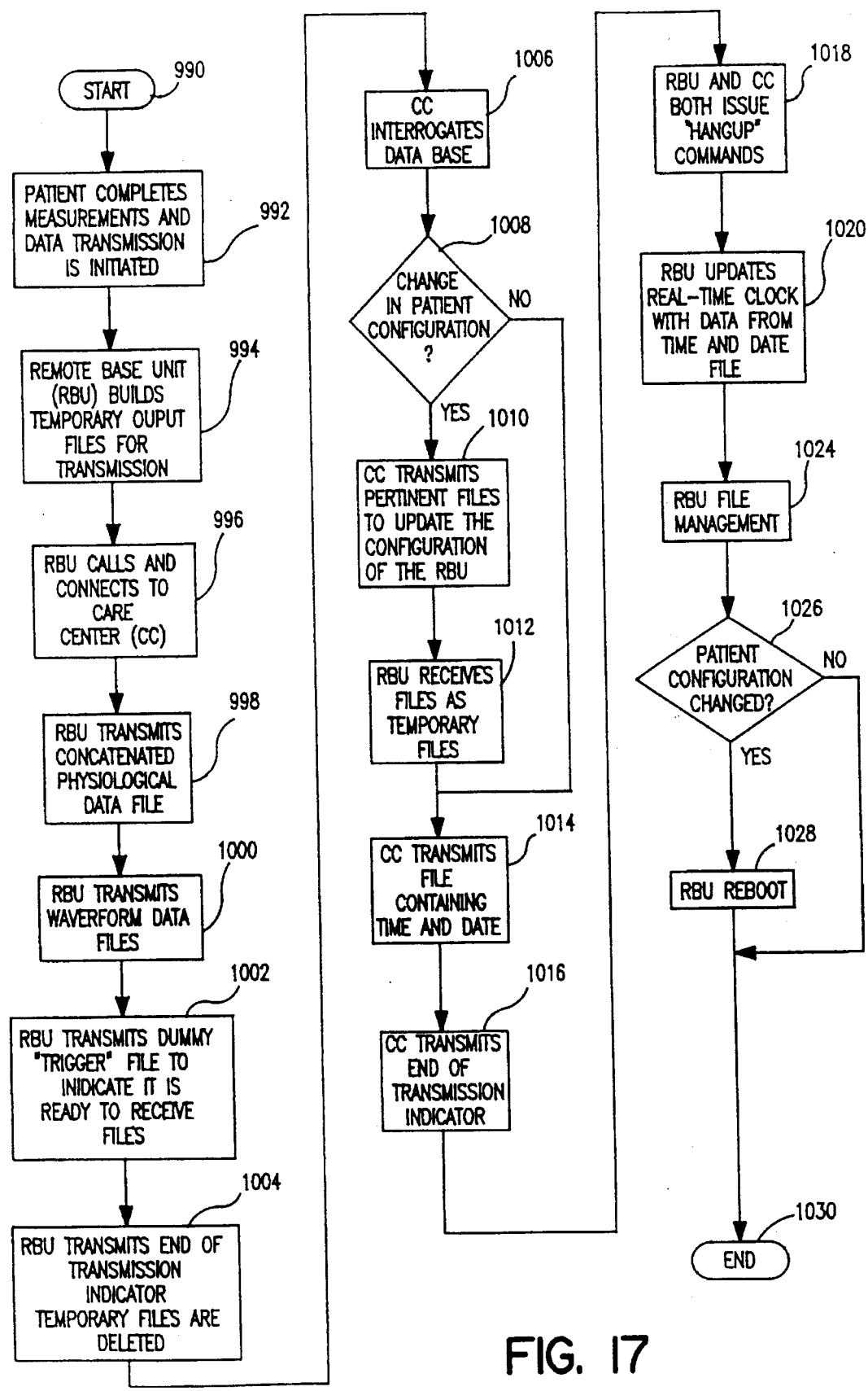
FIG. 17 is a flow diagram of the data communications between the presently preferred remote base unit and the care center shown in FIG. 4.

As shown in FIG. 17, the care center 600 functions as the system controller in the present embodiment and performs the following primary functions: poll the remote base units ("RBUs") 150 (FIG. 2) for data, provides the data received to a member of the medical staff, stores information obtained from the RBUs 150 in a central database managed by or maintained on the facility's patient database computer 660 (FIG. 1), transmits information such as instructions, medical procedures and scheduling of appointments to the RBUs 150. In the present embodiment, a South Mountain Communication Board with 8 channels is used. The patient database computer is preferably a VAX with 10 Gigabytes of memory.

The care center 600 is typically connected to the facility's existing Local Area Network ("LAN") 700. This facility may be a hospital, a service center or a clinic. One example of the LAN system is the Novell Operating System. Thus, the information collected by the care center 600 is accessible from any workstation 650 on the LAN 700. In this configuration, the primary care physician located at the remote site 710 can access information collected on each patient monitored by the care center 600.

Data transmission from the RBU 150 to the care center 600 is initiated in one of three ways. First, the user may request transmission. Second, transmission may be initiated at the end of a scheduled session. Third, transmission may be initiated by the care center 600 at a specified time. The second technique is represented by state 992 in FIG. 17.

When data transmission is initiated, the RBU 150 constructs a temporary output file or output files for transmission on the RAM drive, as shown in state 994. The RBU 150 then calls the care center 600 via the communications link 500 previously described and connects with the care center 600 as depicted in state 996. All available data is then transmitted by the RBU 150, as shown in state 998. This includes all concatenated physiological data files (state 998), for example, weight and temperature measurements, and the waveform data files (state 1000), for instance, contractions. Each session will be sent as a separate file with specific names. Examples of files that are sent are patient identification, data identification # where "TP" represents tocolytic data, "FH" represents fetal heart rate and "FA" represents fetal assessment. The "#" sign represents the characters 0 through 9 or A through F, which represent the hexadecimal value of the session number.

Next, a "trigger" file is sent, as depicted in state 1002. This file triggers the care center 600 to take an action. Specifically, the RBU 150 transmits a dummy file to the care center 600 to indicate that it is ready to receive files from the care center 600. The RBU 150 then indicates the end of its transmit phase, as illustrated in state 1004. The RAM drive files such as session data, are then temporarily deleted.

Upon receipt of the "trigger" file, the care center 600 prepares to transmit data to the RBU 150. The care center 600 first interrogates its data base (state 1006) to determine if there has been any change in patient configuration requiring an update of the RBU 150, as shown in state 1008. If no change is required, the care center 600 proceeds to transmit the time and date, as shown in state 1014. If there is a change in patient configuration, updated files are transmitted, as indicated in state 1010. Basically, the care center 600 transmits all pertinent files to update the RBU's configuration. The RBU 150 receives these files as temporary files and stores them on the RAM drive (state 1012).

The care center 600 then proceeds to send its current time and date, as indicated in state 1016. The end of the care center 600 transmit phase is then indicated (state 1016) and the call is terminated through issuing of hangup commands by both the RBU 150 and the care center 600, as depicted in state 1018.

Upon termination of the call, the RBU 150 updates its time clock from data received from the care center 600 (state 1020). File management in the RBU 150 then takes place at state 1024. If data transmission was successful, all measurement data files are deleted. If file reception was successful, the received files are distributed to the addressed locations. The remaining received files are then deleted. The RBU 150 then tests if any patient configuration, such as test schedules, medical procedures,etc., has changed (state 1026). If not, the present sequence ends and normal patient monitoring resumes (state 1030). If patient configuration has changed, the RBU 150 reboots itself, as indicated in state 1028. Upon rebooting, the present sequence ends and normal patient monitoring resumes (state 1030).

B. Remote Base Unit File Structures

The design of the files structures for the RBU is based on C++ computer language. The source code is used by both receiving and transmitting programs. All data is stored in separate files on the RBU. Each measurement taken is appended to a file named for the measurement, for instance, weight data, temperature date, etc. All data storage files consists of the data records only, without file headers or data header lines.

1. Physiological Data

Prior to transmission, all data contained in these files are concatenated into a single file for transmittal, with a File Header at the beginning of the file and a Data Header preceding each set of data. The filename of the concatenated files are derived from the patient identification with a "PHY" extension. Individual data structures or records have comma delimited fields and carriage return delimited records, with all data initially being in ASCII for development purposes.

2. Waveform Data

Each session of waveform data collection is stored in separate files on the RBU with a daily session number as part of the extension. All data storage files consists of the Data Headers and Data Records only. At the time for transfer of data, this data is prefixed with the File Header data and transmitted as separate files. Individual data structures or records have comma delimited fields, except for the waveform data itself, and carriage return delimited records, with all data initially in ASCII for development purposes.

VIII. Data Flow Between the Remote Base Unit and the Recorders

The recorders have certain parameters that can be configured by the nursing personnel at the care center 600, which may be transferred to the recorder via the RBU. In the present embodiment, the RBU is programmed to prompt the patient to collect data at predetermined intervals, as described below.

A. Infrared and Power Link

A serial data link via infrared (IR) transmitters and receivers permits data transfer from the recorder to the RBU after the recorder is placed in the RBU 150 docking port. The RBU 150 detects when the recorder has been placed in the docking port and queries the recorder for status. When communications is established, the RBU 150 accepts recorded data or transfers new programming information to the recorder. A data format of 9600 bits per second, with 8 data bits and one stop bit is preferably used. The first of four IR channels per docking port provides logic levels to indicate that the recorder is Busy with a measurement. The second IR channel indicates that the battery pack has a full charge, and the third and fourth IR channels are for transmit and receive data connections.

B. Recorder to Remote Base Unit Operation

Figure 18A:
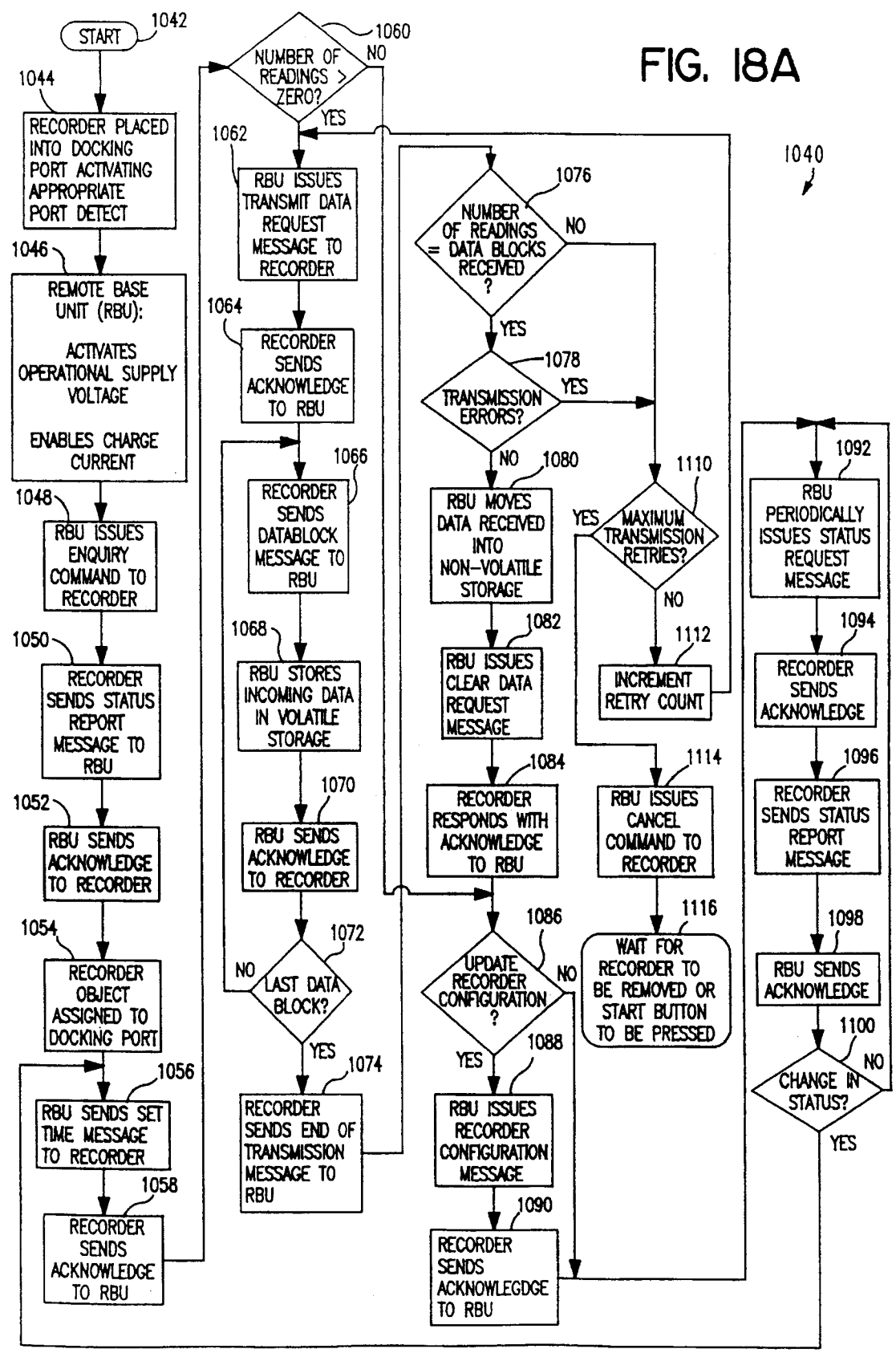

The flow diagram of FIG. 18 is a description of the communication process 1040 between the remote base unit (RBU) 150 and a recorder 160 (FIG. 2). Beginning at a start state 1042 of FIG. 18a, the process 1040 moves to a state 1044 wherein the recorder 160 is placed into one of the docking ports on the RBU 150, thereby activating the interlock switch 178 (FIG. 3C), which indicates that a recorder 160 is docked. Moving to state 1046, when the recorder 160 is docked, the RBU 150 provides a +8.75 Volt DC source via a power lead to power the recorder 160 for data communications and operation. The recorder 160 is in a reduced power mode. An additional power lead provides a 600 mA constant current source to charge the battery pack of the recorder. A third lead provides a ground return path. The four Infrared (IR) channels are for receiving data, transmitting data, indicating that the RBU 150 is busy processing a request or previously sent data, and indicating full battery charge. When the recorder 160 is placed in the docking port 350, the presence of the +8.75 Volts from the base unit alerts the recorder 160 that it is docked. The RBU 150 then checks to determine if the Full Charge line is low and attempts to charge the battery if it is low. The RBU 150 charges the battery until the Full Charge line is true.

The process 1040 moves on to state 1048 wherein the RBU 150 polls the recorder 160 to obtain status available by use of an Enquiry command. At state 1050, the recorder 160 responds with a Status Response message. The format of the Status Response is as follows:

<Recorder ID><Serial Number><Hardware Revision><Software Revision><BatteryType><BatteryStatus> <DataStatus><Recorder Status><Date><Time>.

The Data Status field in the Status Response indicates a number of readings value stored in the recorder. Moving to state 1052, the RBU 150 sends an Acknowledge signal to the recorder 160 to indicate reception of the status response. At state 1054, the process 1040 assigns a recorder object to the docking port 350 of the recorder 160. The recorder object includes a collection of functions specific to the type of recorder 160 and causes an icon, corresponding to the specific recorder type, to be displayed on the LCD screen 314 of the RBU 150. Moving to state 1056, the RBU 150 sends a Set Time message to the recorder 160 to synchronize the internal clock to the RBU 150. At state 1058, the recorder 160 sends an Acknowledge signal back to the RBU 150 to indicate reception of the message.

The process 1040 moves to a decision state 1060 to determine if the number of readings value from the Status Report message is greater than zero, i.e., the recorder has data available. If so, the following sequence of states describes the transfer of data to the RBU 150. However, if the decision state 1060 proves to be false, the process continues at a decision state 1086. Moving from decision state 1060 to state 1062, the RBU 150 issues a Transmit Data Request message to the recorder 160 to initiate the data transfer. At state 1064, the recorder 160 sends an Acknowledge signal back to the RBU 150 to indicate reception of the message. Then at state 1066, the recorder 160 sends a Data Block message to the RBU 150. With the exception of Waveform data, each reading stored in the recorder is sent to the RBU 150 in a separate Data Block message having incrementing block numbers. A format is defined for data messages exchanged between the RBU 150 and the recorder 160. This format includes a message identification, message content and a cyclic redundancy checksum (CRC) for detecting error. Moving to state 1068, the RBU 150 stores the incoming Data Block message in volatile storage, such as a Ram disk file. The RBU 150 responds to the recorder 160 at state 1070 with an Acknowledge signal to indicate reception of the data. Moving to a decision state 1072, a determination is made whether the number of readings value equals the Data Block number, i.e., whether all Data Blocks have been sent by the recorder. If not, the process 1040 loops back to state 1066 to retrieve the next Data Block.

When the last Data Block is sent to the RBU 150, as determined by decision state 1072, the recorder 160 sends an End of Transmission (EOT) message to the RBU 150. Moving to a decision state 1076, the process 1040 determines whether the maximum Data Block number equals the number of readings value. If not, the process 1040 moves to a decision state 1110 for error handling that will be described hereinbelow. If the decision state 1076 proves true, the process 1040 moves to a decision state 1078 to determine if any errors occurred during transmission or transferal of data. The CRC is utilized at state 1078. If an error is detected, the process 1040 moves to the decision state 1110 for error handling. If no errors are detected at decision state 1078, the process 1040 continues at state 1080 wherein the data temporarily stored in the volatile storage, e.g., Ram disk file, is transferred to non-volatile storage, and the file is deleted. Moving to state 1082, the RBU 150 issues a Clear Data Request message to command the recorder 160 to delete all its stored data. At state 1084, the recorder 160 sends an Acknowledge signal back to the RBU 150 to indicate reception of the message. The data transfer sequence of states is now completed.

Moving to a decision state 1086, the process 1040 determines if an update of the recorder configuration is required. The recorder configuration may be changed, for example, to modify the frequency that a measurement is performed. A nurse or doctor transmits information necessary for states 1086 and 1088 to the RBU 150. Based on this information, if an update is required, the process 1040 moves to state 1088 wherein the RBU 150 issues a Recorder Configuration message to the recorder 160. At state 1090, the recorder sends an Acknowledge signal back to the RBU 150 to indicate reception of the message.

At the completion of state 1090 or if decision state 1086 proves to be false, the process 1040 moves to state 1092 to begin an idle loop, through state 1100, that polls to see if new data has been collected. At state 1092, the RBU 150 issues a Status Request message to the recorder 160. This request is made periodically at predetermined time intervals, as dictated by the session protocol. Moving to state 1094, the recorder 160 sends an Acknowledge signal back to the RBU 150 to indicate reception of the message. Continuing at state 1096, the recorder 160 sends the Status Report message back to the RBU 150 to which the RBU 150 responds at state 1098 with an Acknowledge signal back to the recorder to indicate reception of the message. Moving to a decision state 1100, the process 1040 determines if the Status Report indicates new status, such as the collection of new data. If not, the process 1040 loops back to state 1092 to repeat the idle loop. However, if the decision state 1100 determines that a change in status has occurred, the process 1040 moves to state 1056 to repeat part of the previously described sequence of states.

If an error is detected by either of the decision states 1076 or 1078, the process 1040 moves to decision state 1110 to determine if the maximum number of transmission retries has been reached. The maximum number of retries is a predetermined number, typically three, that indicates the number of times the process 1040 directs the RBU 150 to attempt the data transfer from the recorder 160. If the maximum number is not reached, the process 1040 moves to state 1112 and increments the retry count by one, and then loops back to state 1062 wherein another Data Request message is sent to the recorder 160. If the maximum number of retries is reached, as determined at decision state 1110, the RBU 150 issues a Cancel command to the recorder 160 at state 1114. Further data transmission attempts from the recorder 160 are canceled at this time. Moving to state 1116, the process 1040 waits for an asynchronous interrupt to indicate that the recorder 160 is removed from the docking port 350 of the RBU 150, or that the start button of the recorder 160 is pressed while the recorder 160 is in the docking port 350. Because these two activities occur asynchronously, the process 1040 periodically checks for the corresponding interrupt and initiates an appropriate task as will be shown in FIGS. 18b and 18d.

Referring to FIG. 18b, the asynchronous task 1128 that is performed in response to the interrupt for when a user presses the start button while the recorder 160 is in the docking port 350 will be described. Beginning at a start state 1130, the task 1128 moves to state 1132 wherein the user initiates a measurement cycle by pressing the start button on the recorder 160. Alternatively, the recorder 160 begins a scheduled session. Moving to state 1134, the recorder asserts a Busy signal during the measurement. The Busy signal alerts the RBU 150 that the recorder is busy. Proceeding to state 1136, the RBU 150 charge current to the recorder 160 is removed, if previously applied. Charging is suspended during the time of measurement. Continuing at state 1138, periodic communication between the RBU 150 and the recorder 160 is suspended until the Busy signal is deasserted. Because of the Busy signal, the RBU 150 does not post an error message when the Status Response is not received from this docking port 350 during an idle loop poll (state 1092). The measurement is now taken by the recorder 160. Moving to state 1140, when the measurement is complete, the recorder 160 deasserts the Busy signal. At state 1142, the RBU 150 reestablishes the charging and polling operations with the recorder 160. The task 1128 ends at state 1144. The recorder 160 waits for the next poll from the RBU 150. The RBU 150 will then extract the data from the recorder 160. The data from the recorder 160 is then stored in RBU 150 memory and may be transmitted at the end of a scheduled session or when the patient indicates transmission to the care center 600.

Referring to FIG. 18d, the asynchronous task 1168 that is performed in response to the interrupt for when the recorder 160 is removed from the docking port 350 will be described. Beginning at a start state 1170, the task 1168 moves to state 1172 wherein the port detect is deactivated by the removal of the recorder 160 from the docking port 350, as previously described. Proceeding at state 1174, all communication between the recorder 160 and the RBU 150 is halted. Continuing at state 1176, the RBU 150 charge current, if applied, is removed from the recorder 160 along with the operational supply voltage. The task 1168 ends at state 1178.

Referring to FIG. 18c, a background task 1148 for the charge current will be described. Task 1148 utilizes the temperature of the recorder battery pack and the ambient temperature to determine when the battery pack is fully charged. Task 1148 is repeated every 24 hours, although other time intervals may be used in other embodiments. Beginning at a start state 1150, task 1148 moves to state 1152 wherein the recorder deactivates the Charge Enable signal when, in the preferred embodiment, the temperature of the recorder battery pack is ten degrees Celsius above the ambient temperature. Proceeding to state 1154, the RBU 150 responds by removing the charge current to the recorder 160 and then waiting 24 hours at state 1156. After the 24 hour interval, the task 1148 continues at state 1158 wherein the RBU 150 reapplies the charge current to the recorder battery pack and repeats the charging cycle. The task 1148 continues by looping back to state 1152 wherein the Charge Enable signal is deactivated at the appropriate time.

IX. Human Interface Process Flow

A. Session Procedure Flow

Figure 19:
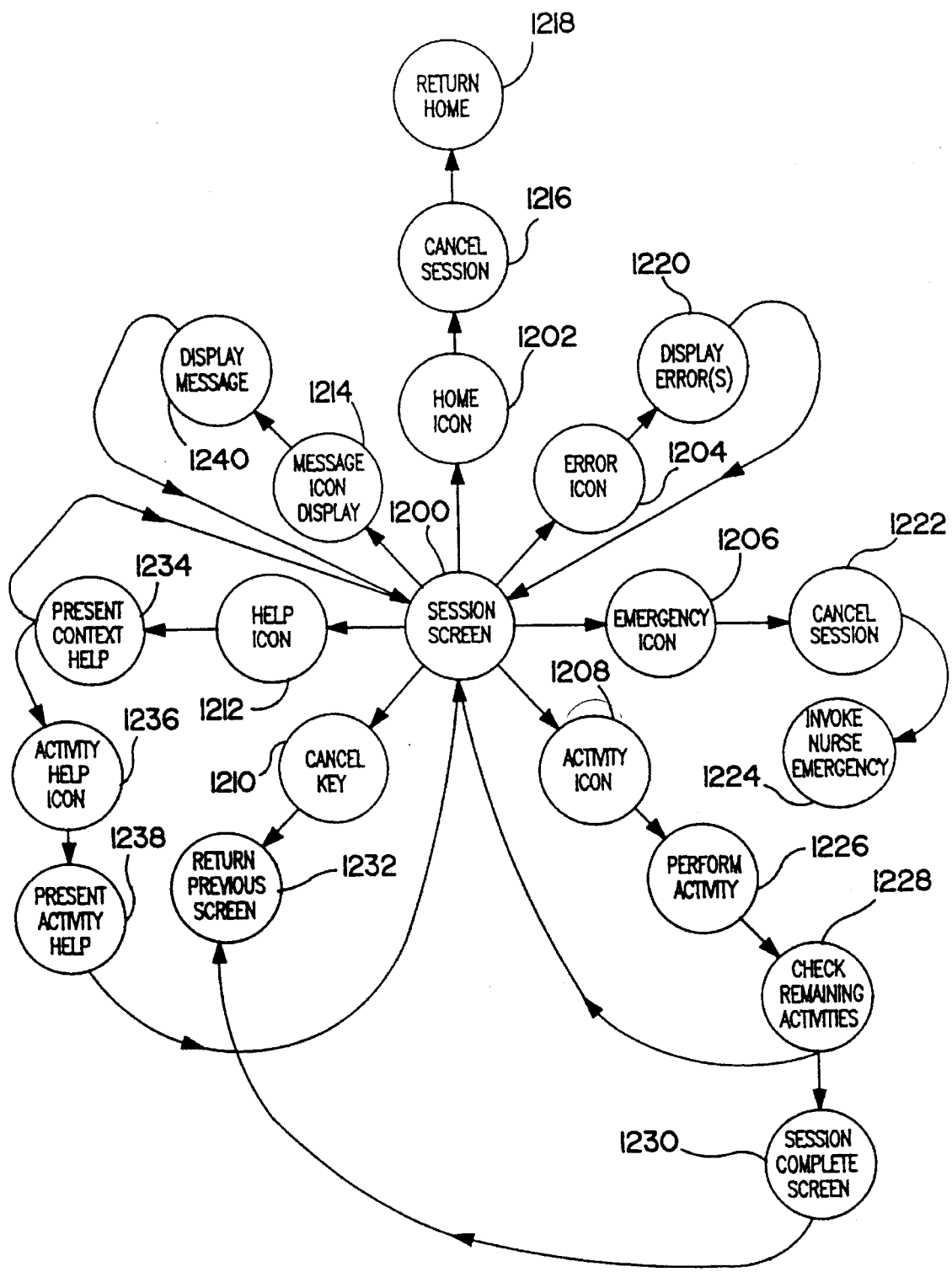
FIG. 19 is a state diagram of the Session Procedure Flow of the Perform Specified Task Function shown in FIG. 16.

FIG. 19 is a state diagram of the Session Procedure Flow of the Perform Specified Task Function shown in FIG. 16. A session is initiated when the patient presses the SESSION icon on the touch screen 314 of the RBU 150 and runs a session through selection of an item on the session screen in state 1200.

When the session screen in state 1200 is selected, a number of icons are illustrated on the screen. Each of the states 1212, 1214, 1202, 1204, 1206 and 1208 represents an icon. As shown in FIG. 19, state 1212 represents the Help icon, state 1214 represents the Message Display icon, state 1202 represents the Home icon, state 1204 represents the Error icon, state 1206 represents the Emergency icon and state 1208 represents the Activity icon. The CANCEL key represented in state 1210 may also be selected to return to the previous screen as shown in state 1232.

By selecting one of the icons, an associated session is stared. The session will end or be ended if any of the following occurs: the patient completes all activities; the CANCEL key in state 1212 is pressed while in the session screen 1200; the HOME icon in state 1202 is pressed; the EMERGENCY icon is pressed; or a timeout occurs due to patient inactivity.

The Activity icon in state 1208 is the mechanism by which all tests within a session are invoked. Each of the icons displayed must be pressed and the subsequent test performed, as shown in state 1226, before remaining activities are checked (state 1228). Upon checking the remaining activities (state 1228), the user may return to the session screen 1200, or declare a session completed (state 1230) and return to a previous screen (state 1232). As each scheduled test is performed, the associated activity icon will be removed.

The Error icon shown in state 1204 is active only when a system error has occurred within the RBU 150, such as a recorder 160 communication failure. Pressing this icon will invoke a text display to prevent the error message (state 1220) and, where possible, a solution to the problem.

The Home icon shown in state 1202 is always active. Pressing this while a session is in progress will cancel the session (state 1216) and return the user to the HOME screen (state 1218).

The Emergency icon shown in state 1206 is always active. Pressing this icon while a session is in progress will cancel the session (as shown in state 1222), and then invoke the Nurse Emergency Routine shown in state 1224.

The Message icon shown in state 1214 is active only when there is an unread message from the care center 600. Pressing this icon will invoke a text display to present the message, as shown in state 1240. After displaying the message, the user may return to the Session Screen 1200.

The Help icon in state 1212, when selected, will present a listing of the type of help required, as shown in state 1234. The user may select from the following types of assistance:

Should I call my Doctor?

Activity Help

Base Unit Tutorial

Information Library

Figure 20:
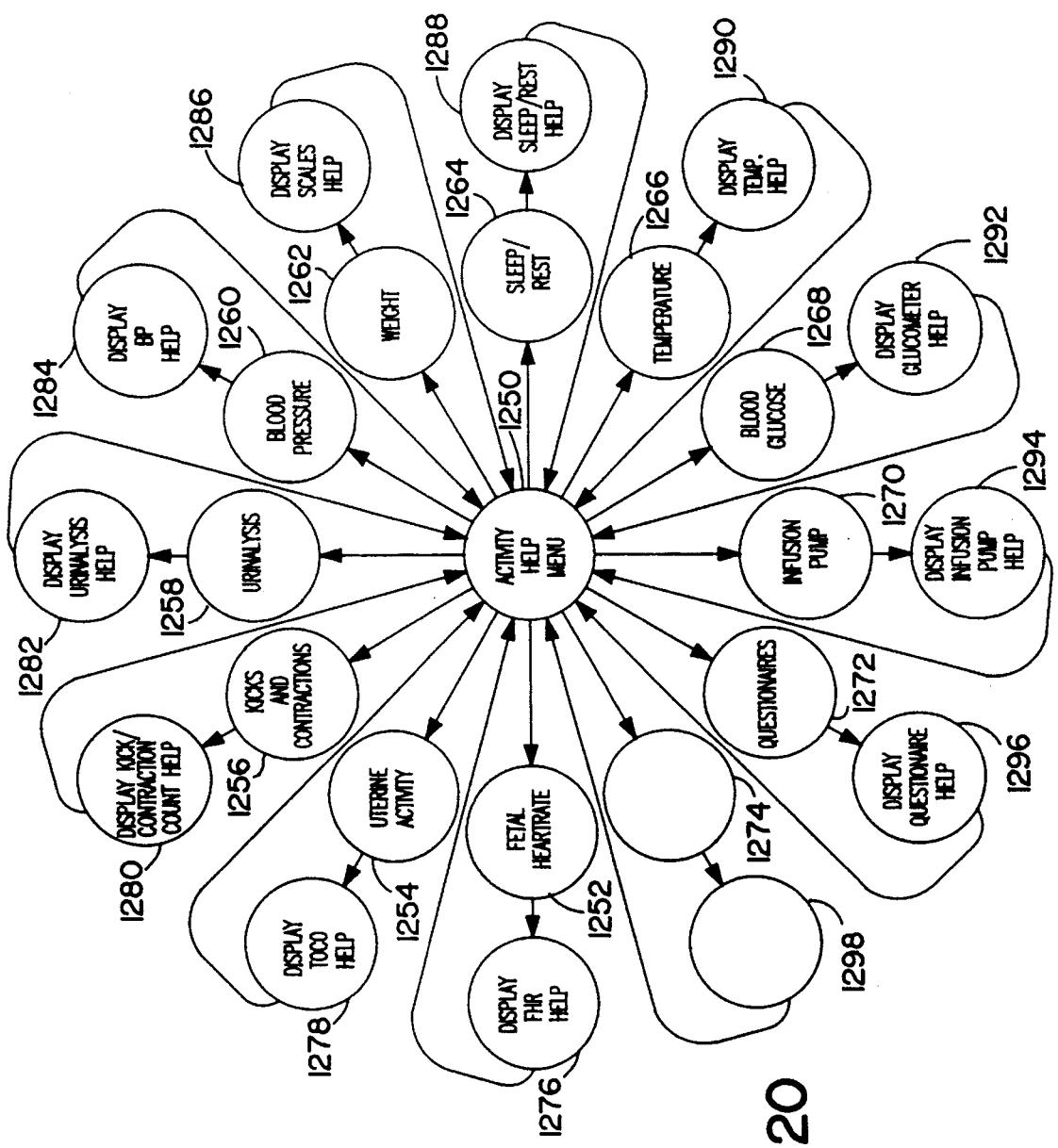
FIG. 20 is a state diagram of the Activity Help Menu Flow of the Perform Specified Task Function shown in FIG. 16.

Upon selecting one of the above, information will be provided to the user. For example, when the Activity Help icon is pressed as shown in state 1236, the Activity Help Menu is presented (stated 1238). This menu is illustrated in FIG. 20 and discussed in the following text section. At any given time, the user may return to the Session Screen 1200.

B. Activity Help Function & Flow

FIG. 20 is a state diagram of the Activity Help Menu Flow of the Perform Human Interface Function shown in FIG. 6. As illustrated, the Activity Help Menu 1250 provides a listing of the instructions available for each of the tests to be conducted in monitoring and support treatment of at-risk pregnancy. In the present embodiment, the patient may select instructions for performing the tests required to monitor fetal heart rate 1252, uterine activity 1254, blood pressure 1260, urinalysis 1258, body temperature 1266, body weight 1262, kicks and contractions 1256 and blood glucose 1268. The patient may also obtain instructions regarding the use of the infusion pump 1270, his sleep or rest schedule 1264 and answering of the questionnaires 1272. Option tests may be listed on the Activity Menu 1250, as indicated by Circle 1274.

By selecting one of the listed items on the Activity Help Menu 1250, they user will access test instructions corresponding to the listed tests/questionnaire/schedules 1252–1274.

For instance, when the user selects the fetal heart rate test instructions 1252 from the Activity Help Menu 1250, a display of the fetal heart rate help instructions 1276 will be illustrated on the LCD screen of the RBU 150. Likewise, instructions 1278–1298 corresponding to the other tasks 1254–1274 may be obtained.

Examples of the test instructions are listed below.

1. Fetal Monitor (both UA and FHR) 1252

I will record your uterine activity and your baby's heart rate for 60 minutes. You will be letting me know when your baby moves by pressing KICK and when you feel a contraction by pressing CONTRACTION. If you need to interrupt me, please press PAUSE. Be sure to start again within 15 minutes or I will need to restart my clock at 60 minutes.

Let's start by plugging the uterine activity and fetal heart rate sensors into my fetal monitor recorder. Now you can get into a comfortable reclining position, tilted to one side. A pillow under your hip can make it easy! Your baby would like you to stay tilted when you are lying down—not flat on your back.

Watch the displays on my recorder's screen. I will help you with every step!

2. Fetal Monitor Recorder (UA only) 1254

I will record your uterine activity for 60 minutes. You will be letting me know when you feel a contraction by pressing CONTRACTION. If you need to interrupt me, please press PAUSE. Be sure to start again within 15 minutes or I will need to restart my clock at 60 minutes.

Let's start by plugging the uterine activity sensor into my fetal monitor recorder. Now you can get into a comfortable reclining position, tilted to one side. A pillow under your hip can make it easy! Your baby would like you to stay tilted when you are lying down—not flat on your back.

Watch the displays on my recorder's screen. I will help you with every step

3. Fetal Kick Count 1256

I will record your baby's movements. You will let me know when your baby moves by press the event switch each time. I will let you know when I am finished. If your baby does not move at all during the next hour please call your HPS nurse.

4. Blood Pressure Recorder 1260

I will be recording your blood pressure and pulse rate. Be sure that you refrain from extreme exertion, eating, smoking, and extreme heat and cold for 15 minutes prior to each recording.

Let's start by plugging the cuff into my blood pressure recorder. Now you can get into a comfortable position, tilted to your left side. A pillow under your hip can make it easy! Use the arm that is on top of your body. All tight clothing should be removed from that arm. Slide your arm into the cuff so that the bottom of the cuff is 1–2 inches above your elbow at about the level of your heart.

Tighten the cuff securely. Support your arm on your lap, table, or chair armrest. Be as still as possible during the recording!

Watch the displays on my recorder's screen. I will help you with every step

5. Urinalysis Recorder 1258

I will be analyzing your urine for the presence of several substances. It is best to use the first urine of the morning for this test. To obtain a midstream urine sample, begin to urinate, stop the flow for a second, then begin the collection.

Make sure to have your bottle of urine strips handy. Watch the displays on my recorder's screen. I will help you with every step 6. Temperature 1266

I will be recording your body's temperature. Be sure that you do not eat, drink or smoke for 15 minutes prior to taking your temperature.

Let's start by putting a sheath on the temperature probe. Then place the probe in your mouth under your tongue. I will let you know when I have finished by displaying your temperature.

7. Weight/Scales 1262

I will be recording your body weight. Be sure that you weigh yourself at the same time each day wearing the same amount of clothing.

Step up onto the scale pad. I will let you know when I have finished by displaying your weight.

C. User Initiated Testing Flow

Figure 21:
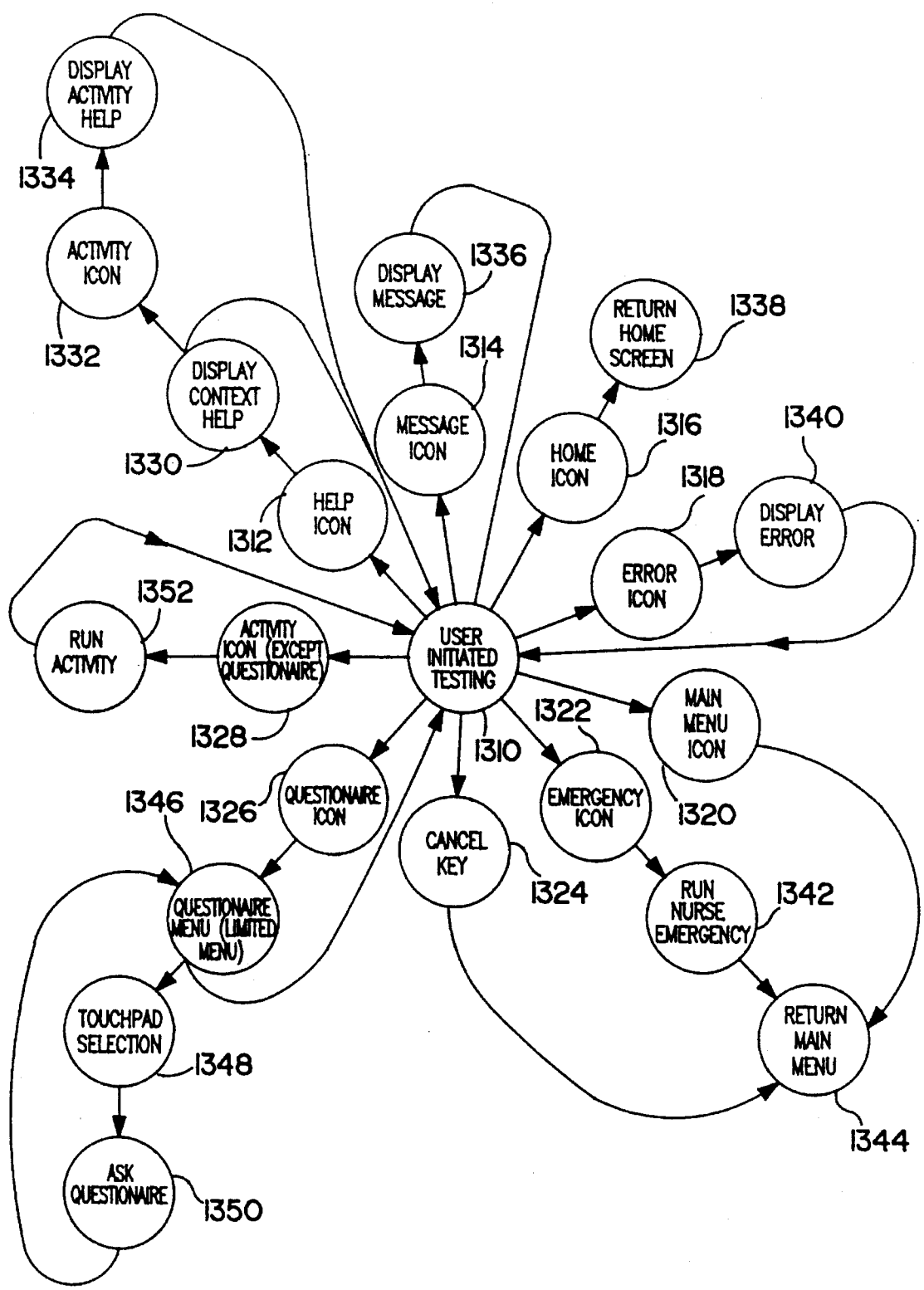
FIG. 21 is a state diagram of the User Initiated Testing Flow of the Perform Specified Task Function shown in FIG. 16.

FIG. 21 is a state diagram of User Initiated Testing Method of the Perform Human Interface Function shown in FIG. 16. As illustrated, the user may initiate the performance of a range of tests.

User Initiated Testing (state 1310) is the mechanism by which a patient can perform any test function manually. It is similar in look and feel to the Session Screen (FIG. 19) in that the Activity Icons displayed across the top of the screen are used to initiate the tests. User initiated testing does not operate as a menu. General Icon functions are limited or modified in order to control system access. The Activities themselves are shown in FIG. 20 and the corresponding text sections.

When User Initiated Testing is selected (state 1310), the user may access the Activity Icon (except the Questionnaire) (state 1328), the Help Icon (state 1312), the Message Icon (state 1314), the Home Icon (state 1316), the Error Icon (state 1318), the Main Menu Icon (state 1320), the Cancel Key (state 1324), and the Questionnaire Icon (state 1326).

The Help Icon (state 1312), Message Icon (state 1314), Home Icon (state 1316), Error Icon (state 1318), Cancel Key (state 1324) are similar to those available in the Session Screen feature discussed above.

The Activity Icon (state 1328) invokes all tests (state 1352), except for the Questionnaire, which is accessed by pressing the Questionnaire Icon (state 1326). Pressing the Questionnaire Icon as shown in state 1326 invokes the Questionnaire Menu (state 1346). Once in the Questionnaire Menu, the user first selects the type of Questionnaire he wants to respond to, as indicated by state 1348. He then answers each question (state 1350) and may return to the Questionnaire Menu (state 1346) to answer more questions by touching the touch screen 314 (state 1348).

X. Exemplary Demonstration Sequence

Figure 22:
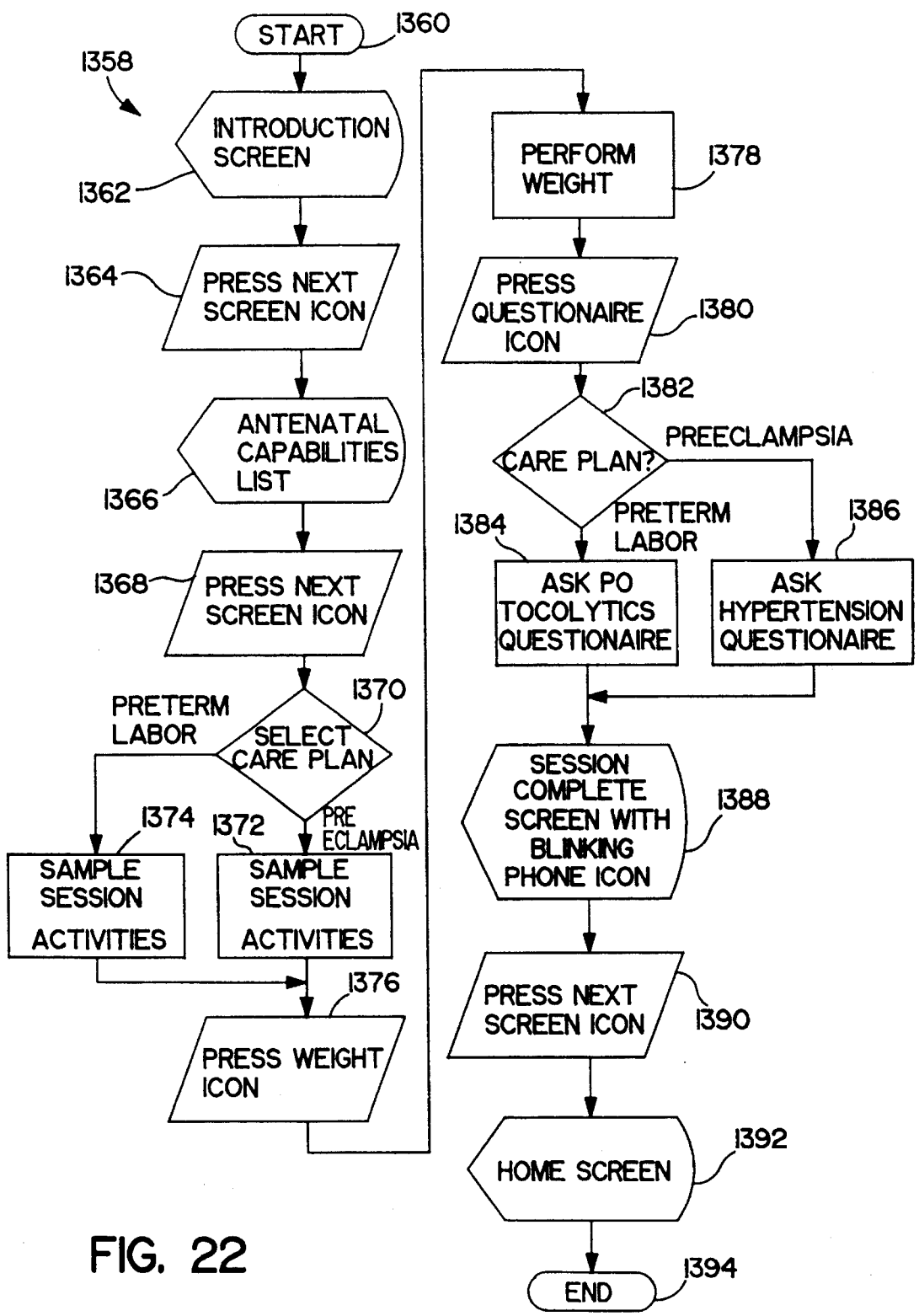
FIG. 22 is a flow diagram of an exemplary demonstration sequence of the patient monitor and support system of the present invention, configured for monitoring at-risk pregnancies.

FIG. 22 is a flow diagram of an exemplary demonstration sequence of the patient monitor and support system of the present invention, configured for monitoring at-risk pregnancies. The sequence 1358 is used to illustrate typical steps of interaction between a user and the remote base unit (RBU) 150, but is not intended to show an actual set of steps. The sequence 1358 is also an example of the manual user initiated testing described above.

Beginning at a start state 1360, the sequence 1358 moves to state 1362 wherein an introduction screen is presented to the user of the system on the LCD 312 of the RBU 150 (FIG. 4.) This screen has instructions to the user of the system. The actual system software produces a set of introductory screens. For example, in the demonstration of the system 50 being used to monitor high risk pregnancy, the following text may be provided:

ANTENATAL (OB1) TUTORIAL

I am your OB1 system.
You can interact with me by pressing
or touching the screen lightly.
When you plug the system into the
outlet (110 Volts) you have given
power to my system.
Please place all of the Recorder
units into the base.
Once the system has power, the
system will display your name and
the time.
You will have a HOME screen which
will be the starting point for all
functions I need to perform with
you.
You will always be able to return to
the Home screen. The Home screen
will display your next Scheduled
Session time.
A "Session" is the activities and
monitoring tests which have been
prescribed by your doctor.
Your doctor has set up a schedule of
monitoring tests for you and your
baby.
When it is time for your session, I
will alert you with an alarm. The
alarm will give you a warning period
to begin your session.
After pressing the Session button,
the activity test buttons will be
displayed. You will need to press
the button which is blinking.
To complete your session you must
push the test buttons until they
have all disappeared.
Once you finish your session's
activities, you will return to the
HOME screen.
The HOME screen will now show the
next scheduled session time.
If you have any questions please
press the Main Menu button. The
Main Menu provides access to all of
the system help.
The Main Menu provides access to:
Schedules Sessions
User Initiated Testing
Help Menu
System Menu
Please refer to the Main Menu to
access these programs to assist you.
You will always have the Emergency
button on the lower right corner of
the screen. If you press this
button, you will get phone numbers
to:
   Your doctor,
   Your Healthdyne Center, and
   Your local Hospital.
If you have any questions. Please
press the Main Menu button. The
Main Menu provides access to all of
the system help.

After the introductory screen has been displayed, the sequence 1358 moves to state 1364 wherein the user lightly presses the next screen icon on the LCD display to advance to the next screen of information. At state 1366, a list of antenatal capabilities, such as oral maternal temperature, uterine contractions, maternal weight, maternal blood pressure, fetal heart rate, and other capabilities, are displayed for the user. Moving to state 1368, the user presses the next screen icon to advance to a screen wherein a choice of care plans is presented to the user. Decision state 1370 determines whether the user selects the preeclampsia care plan at state 1372 or the preterm labor plan at state 1374. States 1372 and 1374 display screens corresponding to the selected care plan with the associated activity test buttons. The user presses the test button that is blinking to perform the monitoring test or activity corresponding to the test button. When a test is completed, the next test button blinks. The user then presses the next blinking test button to perform the next test and so forth until all test buttons have been pressed.

When the sample session activities have been completed at either state 1372 or 1374, the sequence 1358 continues at state 1376 wherein the user presses the weight icon. Moving to state 1378, the maternal weight measurement is performed by use of a load cell scale connected to the RBU 150. Proceeding to state 1380, the user presses the questionnaire icon. Depending on the selection determined at decision state 1370, the sequence 1358 determines the corresponding care plan questionnaire at state 1382. If preterm labor is selected, the sequence 1358 moves to state 1384 wherein a PO Tocolytics questionnaire is displayed for the user to answer. The questionnaire is similar to the following:

PO TOCOLYTIC PATIENTS

| | |
|---|---|
| Cramping? | Pelvic Pressure. |
| 1   Yes   2   No | 1   Yes   2   No |
| Backache? | Discharge? |
| 1   Yes   2   No | 1   Yes   2   No |
| Is uterine irritability present? | Shortness of breath? |
| 1   Yes   2   No | 1   Yes   2   No |
| Jitters? | |
| 1   Yes   2   No | |

If preeclampsia is selected, the sequence 1358 moves to state 1386 wherein a hypertension (or preeclampsia) questionnaire is displayed for the user to answer. The hypertension questionnaire is similar to the following:

HYPERTENSION PATIENTS

Edema?
1   Yes   2   No
Headache?
1   Yes   2   No
Epigastric pain?
1   Yes   2   No
Visual disturbances?
1   Yes   2   No When either of the questionnaires at state 1384 or 1386 is completed, the sequence 1358 moves to state 1388 wherein a session complete screen is displayed, including a blinking telephone icon to simulate data transmission to the care center. Moving to state 1390, the user presses the next screen icon to advance to the next screen. At state 1392, the Home screen is displayed which has the capabilities listed. The sequence 1358 ends at state 1394.

The unique features and functions of the patient monitor and support system 50 provide quality medical care to a plurality of patients with improved cost effectivity and outcomes. This is accomplished through comprehensive managed care, tailored to the patients' specific and individual medical history, and acute clinical needs. The present system 50 enables more patients to be treated per medical case infrastructure unit and thereby provides an increase in the productivity of medical and paramedical personnel.

In addition, the system 50 can be configured to monitor a variety of medical conditions and treatments, including hypertension, at-risk pregnancies, human organ flow such as kidney dialysis and liver support, cardiovascular diseases and immune system diseases. It can also monitor specific disease states, including parameters, subsystem component hardware, software, instructions, schedules, communication protocols, medication protocols, therapeutic devices, etc.

Moreover, the system 50 provides improved patient care and outcomes because of the same specific assigned team of physicians, nurses, and paramedical personnel to the individual throughout the course of care which reduces the learning factor involved with new or changing personnel., i.e., hospital shifts.

In summary, the patient monitor and support system 50 includes a number of patient sites 100 which are individually connected via a set of communications links 500 to a care center 600. A subsystem at each of the patient sites 100 has control and data acquisition capabilities and may be configured to automatically transfer patient communications and data to the care center 600. The subsystem is controlled by a remote base unit 150 which can down load from the care center 600 computer Patient Identification and Operating files to the base unit 150 in the home initialization and operating protocol files specific to that particular patient. Examples of these files include: medication schedules, blood pressure protocols, patient identification data, patient logistical data, parameter thresholds, auto dial phone numbers and schedules, call-in schedule, infusion pump settings and patient specific qualitative data questionnaires (relating to her present progress).

The base unit 150 at the patient sites 100 auto-dials the care center 600 on scheduled intervals and sends data to auto-receiving units which operate unattended. This ability provides for substantial savings in phone costs as well as human labor costs. The auto receiving units make the latest data available to the computer at the work station 650 which, among other capabilities:

a. Provides for qualified clinical reading and interpretation of data;

b. Provides for LAN 700 (local area network) communication with the center computer 660 for the purpose of updating the patients file and permanent record with both qualitative and quantitative data;

c. Provides for compilation, printing, and/or transmission of the patients record to the physician at appropriate intervals;

d. Provides the mechanism for special patient communications and instructions as well as instrumentation settings via the modem down link to the home base unit 150;

e. Provides the vehicle for recording and implementing physician instructions and changes in protocol.

The patient monitor and support system 50 is human engineered to make all operations as simple and user friendly as possible. The LCD display 312 on the home base unit 150 provides a communicative means to insure patient compliance with nor only the measurement regimes but other physician directed activities and therapy such as medication, diet and nutrition, exercise, sleep and rest periods, etc.

Finally, the care center database 600 provides information for medical research, supportive records for medico-legal purposes, and most importantly a tool for comparative analysis of patient progress against peer cases.

Although the preferred embodiment of the present invention has been described and illustrated above, those skilled in the art will appreciate that various changes and modifications to the present invention do not depart from the spirit of the invention. Accordingly, the scope of the present invention is limited only by the scope of the following appended claims.

What is claimed is:

1. A system for monitoring and responding to the health and medical condition of a patient, comprising:

a sensor for monitoring the patient's medical condition, the sensor generating a parameter indicative of the patient's medical condition;

a data base located at a remote location from the sensor for storing the sensor parameter, said data base comprising at least one record specific to the patient, the record including the sensor parameter;

means for communicating the parameter to the data base;

means for retrieving the parameter from the data base; and a software function executing on a processor for directing one or more medical procedures or activities to be carried out by the patient in response to the retrieved parameter.

2. The system of claim 1 wherein said function for directing comprises means for dispensing medicine to the patient.

3. The system of claim 2, wherein the medicine is dispensed through an infusion pump.

4. The system of claim 1, further comprising means for monitoring the parameters associated with a plurality of patients where the parameters of each patient are stored in the same data base.

5. The system of claim 1, further comprising a recorder for storing the parameters provided by the sensor.

6. The system of claim 5, wherein the recorder is selected from the group consisting of: a fetal heart rate recorder, a uterine activity recorder, a blood pressure recorder, a urinalysis recorder, a multi-sensor recorder, a maternal cardiac recorder and a cardio/pulmonary recorder.

7. The system of claim 1, wherein a plurality of sensors monitors the medical condition of the patient.

8. The system of claim 7, further comprising a plurality of recorders for storing the parameters provided by the sensors, each selected one of the recorders connected to the selected one of the sensors.

9. The system of claim 8, wherein the recorders are selected from the group consisting of: a fetal heart rate recorder, a uterine activity recorder, a blood pressure recorder, a urinalysis recorder, a multi-sensor recorder, a maternal cardiac recorder and a cardio/pulmonary recorder.

10. The system of claim 1, wherein the data base is located in a computer.

11. The system of claim 1, wherein the system is configured to monitor the prenatal condition of the patient.

12. The system of claim 11, wherein the medical procedure comprises a prescribed maternal diet or medication.

13. The system of claim 11, wherein the system is further configured to monitor the prenatal condition selected from the group consisting of: fetal heart rate, prenatal infections, genetic disorders of the fetus and environmental fetal damage.

14. The system of claim 1, wherein the system is configured to monitor cancer therapy.

15. The system of claim 1, wherein the system is configured to monitor human organ flow.

16. The system of claim 1, wherein the system is configured to monitor kidney failure.

17. The system of claim 1, wherein the system is configured to monitor liver support.

18. The system of claim 1, wherein the system configured to monitor cardiovascular disease.

19. The system of claim 1, wherein the system is configured to monitor immune system disease.

20. The system of claim 1, wherein the sensor is one of: an ultrasound sensor, a uterine contraction transducer, a temperature probe, an event switch, a weight scale, a glucometer, a plurality of reagent strips, and a blood pressure sensor.

21. The system of claim 1, wherein the health and medical requirements of the patient are monitored at predetermined intervals.

22. The system of claim 1, wherein the database is located in a workstation.

23. The system of claim 1, wherein the medical condition of the patient is selected from the group consisting of: hypertension, preeclampsia, maternal diabetes, risk of premature delivery, and risk of premature rupture of membranes.

24. The system of claim 1 wherein said software function for directing one or more medical procedures includes processes for directing specified patient task functions in response to a sensed parameter indicative of the patient's medical condition.

25. The system of claim 24 wherein said function for directing specified patient task functions includes a process for directing utilization of an infusion pump.

26. The system of claim 24 wherein said function for directing specified patient task functions includes means for dispensing medicine to the patient.

27. The system of claim 24 including patient communication means for communicating questions to the patient regarding the patient's medical condition.

28. The system of claim 27 wherein said patient communication means includes input means for patient response to questions communicated to the patient therefrom.

29. The system of claim 1 including patient communication means for communicating questions to the patient regarding the patient's medical condition.

30. The system of claim 29 wherein said patient communication means includes input means for patient response to questions communicated to the patient therefrom.

31. The system of claim 30 wherein said software function for directing one or more medical procedures or activities includes processes for directing specified patient task functions in response to a sensed parameter indicative of the patient's medical condition.

32. The system of claim 1 wherein said software function for directing one or more medical procedures or activities includes means for directing the patient to use the sensor.

33. The system of claim 1, wherein the data base record includes a plurality of fields, including fields for patient medical history, symptoms, and patient responses.

34. The system of claim 1, wherein the parameter indicative of the patient's medical condition is selected from the group consisting of fetal heart rate, uterine activity, blood pressure, urinalysis, weight, temperature, contractions, and glucose levels.

35. The system of claim 1, wherein the patient medical condition is selected from the group consisting of hypertension, at-risk pregnancies, human organ flow, cardiovascular diseases, cancer and immune system diseases.

36. The system of claim 35, wherein the human organ flow comprises kidney failure.

37. The system of claim 1, wherein the human organ flow comprises liver failure.

38. The system of claim 1, wherein the data base stores the parameters, a subsystem component hardware configuration, a set of patient instructions, a schedule, a communication protocol, and a medication protocol.

39. A system for monitoring the prenatal health and medical requirements of a patient, comprising:

a sensor for monitoring the patient's prenatal health and medical state, the sensor generating a parameter indicative of the patient's prenatal requirements;

a data base located at a remote location from the sensor for storing the patient's prenatal medical state;

means for communicating the parameter to the data base;

means for retrieving the parameter from the data base; and means for providing medical procedure to the patient in response to the retrieved parameter.

40. The system of claim 39, wherein the prenatal medical state of the patient is hypertension, preeclampsia, maternal diabetes, risk of premature delivery, or risk of premature rupture of membranes.

41. The system of claim 39, wherein the system is further configured to monitor fetal heart rate, prenatal infections, genetic disorders of the fetus, or environmental fetal damage.

42. The system of claim 39, further comprising means for dispensing medicine to the patient.

43. The system of claim 42, wherein the medicine is dispensed through an infusion pump.

44. The system of claim 39, further comprising means for monitoring the parameters associated with a plurality of patients where the parameters of each patient are stored in the same data base.

45. The system of claim 39, further comprising a recorder for storing the parameters provided by the sensor.

46. The system of claim 45, wherein the recorder is a fetal heart rate recorder, a uterine activity recorder, a blood pressure recorder, a urinalysis recorder, a multi-sensor recorder, a maternal cardiac recorder or a cardio/pulmonary recorder.

47. The system of claim 39, further comprising a plurality of sensors for monitoring the medical states of the patient.

48. The system of claim 47, further comprising a plurality of recorders for storing the parameters provided by the sensors.

49. The system of claim 48, wherein the recorders are selected from the group consisting of: a fetal heart rate recorder, a uterine activity recorder, a blood pressure recorder, a urinalysis recorder, a multi-sensor recorder, a maternal cardiac recorder or a cardio/pulmonary recorder.

50. The system of claim 48, wherein the data base is located inside a computer.

51. The system of claim 39, wherein the medical procedure is prescribed maternal diet or medication.

52. The system of claim 39, wherein the sensor is an ultrasound sensor, an uterine contraction transducer, a temperature probe, an event switch, a weight scale, a glucometer, a plurality of reagent strips, or a blood pressure sensor.

53. The system of claim 21, wherein the health and medical requirements of the patient are monitored at predetermined intervals.

54. In a network comprising a processor, a remotely located sensor, in communication with the processor, which generates a parameter indicative of a patient's medical condition and a database for storing the parameter, a method of monitoring and responding to the health and medical condition of a patient, comprising:

monitoring the patient's medical condition;

generating a parameter indicative of the patient medical condition;

communicating the parameter to the data base;

retrieving the parameter from the data base; and executing a network software function on the processor to provide medical procedure to the patient in response to the retrieved parameter.

55. The method of claim 54, further comprising dispensing medicine to the patient.

56. The method of claim 55, wherein the medicine is dispensed through an infusion pump.

57. The method of claim 54, further comprising monitoring the parameters associated with a plurality of patients where the parameters of each patient are stored in the same data base.

58. The method of claim 54, wherein the medical state of the patient is indicative of a prenatal condition.

59. The method of claim 54, wherein the medical state of the patient is indicative of cancer.

60. The method of claim 54, wherein the patient's medical condition is indicative of the patient's organ flow.

61. The method of claim 54, wherein the patient's medical state is indicative of the patient's kidney failure.

62. The method of claim 54, wherein the patient's medical state is indicative of the patient's liver condition.

63. The method of claim 54, wherein the patient's medical state is indicative of the patient's cardiovascular disease.

64. The method of claim 54, wherein the patient's medical state is indicative of the patient's immune system disease.

65. The method of claim 54 including directing the patient to perform one or more specified procedures or activities in response to the retrieved parameter.

66. The method of claim 54 including requesting information from the patient regarding the medical procedure.

67. The method of claim 66 including inputting patient response to the information request, and recording the patient response in the data base.

68. The method of claim 67 including directing the patient to accomplish one or more activities or dispense medication based on the patient response.

69. The system of claim 54, wherein the patient medical condition is selected from the group consisting of hypertension, at-risk pregnancy, human organ flow, cardiovascular diseases, cancer, and immune system diseases.

70. In a network comprising a remotely located sensor which generates a parameter indicative of a patient's prenatal medical condition and a database for storing the parameter, a method of monitoring and responding to the prenatal health and medical condition of the patient, comprising:

monitoring the patient's prenatal health and medical condition;

generating a parameter indicative of the patient prenatal medical condition;

communicating the parameter to the data base;

retrieving the parameter from the date base; and executing a network software function on a processor to provide medical procedure to the patient in response to the retrieved parameter.

71. The method of claim 70 wherein the prenatal medical state of the patient is hypertension, preeclampsia, maternal diabetes, risk of premature delivery, or risk of premature rupture of membranes.

72. The method of claim 70, wherein the parameter is indicative of fetal heart rate, prenatal infections, genetic disorders of the fetus, or environmental fetal damage.

73. The method of claim 70, further comprising the step of monitoring the parameters associated with a plurality of patients where the parameters of each patient are stored in the same data base.

74. The method of claim 70 including directing the patient to perform one or more specified procedures or activities in response to the retrieved parameter.

75. The method of claim 70 including requesting information from the patient regarding the medical procedure.

76. The method of claim 75 including inputting patient response to the information request, and recording the patient response in the data base.

77. The method of claim 76 including directing the patient to accomplish one or more activities or dispense medication based on the patient response.

78. The system of claim 70, wherein the parameter indicative of the patient's medical condition is selected from the group consisting of fetal heart rate, uterine activity, blood pressure, urinalysis, weight, temperature, contractions, and glucose levels.

79. The system of claim 70, wherein the patient medical condition comprises an at-risk pregnancy.

80. The system of claim 70, wherein the data base stores the parameter, a subsystem component hardware configuration, a set of patient instructions, a schedule, a communication protocol, and a medication protocol for an at-risk pregnancy.

81. A system for monitoring and responding to the health and medical condition of a patient, comprising:

a first sensor for monitoring the patient's medical condition, the first sensor generating a first parameter indicative of the patient's medical condition;

a second sensor for monitoring the patient's medical condition, the second sensor generating a second parameter indicative of the patient's medical condition;

a recorder for storing the second parameter generated by the second sensor;

a base unit for storing the parameters generated by the first sensor and the recorder;

a data base located at a remote location from the first and second sensors and the recorder, for storing parameters indicative of the patient's medical condition, said data base comprising at least one record specific to the patient, the record including the sensor parameters;

a communications subsystem to transfer the parameters from the base unit to the data base;

a process to retrieve the parameters from the data base; and a software function executing on a processor for directing one or more medical procedures or activities to be carried out by the patient in response to the retrieved parameters.

82. The system of claim 81 wherein said software function for directing one or more medical procedures or activities includes processes for directing specified patient task functions in response to a sensed parameter indicative the patient's medical condition.

83. The system of claim 82 wherein said software function for directing specified patient task functions includes means for directing utilization of an infusion pump.

84. The system of claim 82 wherein said function for directing specified patient task functions includes means for dispensing medicine to the patient.

85. The system of claim 81 including patient communication means for communicating questions to the patient regarding the patient's medical condition.

86. The system of claim 85 wherein said patient communication means includes input means for patient response to questions communicated to the patient therefrom.

87. The system of claim 86 wherein said software function for directing one or more medical procedures or activities includes processes for directing specified patient task functions in response to a sensed parameter indicative the patient's medical condition.

88. The system of claim 85 including patient communication means for communicating questions to the patient regarding the patient's medical condition.

89. The system of claim 88 wherein said patient communication means includes input means for patient response to questions communicated to the patient therefrom.

90. The system of claim 81, wherein the data base record includes a plurality of fields, including fields for patient medical history, symptoms, and patient responses.

91. A medical monitoring system, comprising:
a care center, comprising:
means for configuring medical sensors with parameter data;
a database for storing medical data indicative of a plurality of patients; and
means, responsive to the configuring means and the database, for communicating data;
a plurality of patient sites, each patient site remotely located from the care center and comprising:
a base unit comprising means for communicating data and means for storing parameter and medical data, the data indicative of the patient located at the patient site; and
a plurality of medical sensors, each sensor connected to the base unit, receiving parameter data from the configuring means and providing medical data to the database under control of the base unit.

92. The system defined in claim 91, wherein the parameter data includes a measurement time.

93. The system defined in claim 91, wherein the medical data includes temperature.

94. The system defined in claim 91, wherein one of the sensors comprises a weight scale.

95. The system defined in claim 91, wherein at least one sensor stores medical data in a recorder.

96. The system defined in claim 91, additionally comprising means, connected to the base unit, for providing medication to the patient, wherein the providing means receives parameter data from the care center.

97. The system defined in claim 96, wherein the providing means comprises an infusion pump.

98. The system defined in claim 91, additionally comprising a plurality of doctor sites in data communication with the care center.

99. The system defined in claim 91, wherein the care center communicating means and the patient site communicating means include modems.

* * * * *